United States Patent
Lim et al.

(10) Patent No.: US 10,494,417 B2
(45) Date of Patent: Dec. 3, 2019

(54) PEPTIDE INHIBITORS OF BCR-ABL OLIGOMERIZATION

(71) Applicant: University of Utah Research Foundation, Salt Lake City, UT (US)

(72) Inventors: Carol Lim, Salt Lake City, UT (US); Benjamin J. Bruno, Salt Lake City, UT (US); Geoffrey D. Miller, Salt Lake City, UT (US); Andrew S. Dixon, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/128,642

(22) PCT Filed: Mar. 25, 2015

(86) PCT No.: PCT/US2015/022417
§ 371 (c)(1),
(2) Date: Sep. 23, 2016

(87) PCT Pub. No.: WO2015/148620
PCT Pub. Date: Oct. 1, 2015

(65) Prior Publication Data
US 2017/0174750 A1 Jun. 22, 2017

Related U.S. Application Data

(60) Provisional application No. 61/970,329, filed on Mar. 25, 2014.

(51) Int. Cl.
*A61K 38/00* (2006.01)
*C07K 14/82* (2006.01)
*A61K 31/5025* (2006.01)
*A61K 31/506* (2006.01)
*A61K 38/17* (2006.01)

(52) U.S. Cl.
CPC ............ *C07K 14/82* (2013.01); *A61K 31/506* (2013.01); *A61K 31/5025* (2013.01); *A61K 38/17* (2013.01); *A61K 38/00* (2013.01)

(58) Field of Classification Search
None
See application file for complete search history.

(56) References Cited

U.S. PATENT DOCUMENTS

| 2003/0064061 | A1* | 4/2003 | Zhao | C07K 14/82 424/94.1 |
| 2010/0029676 | A1* | 2/2010 | Sawyers | C12Q 1/6886 514/252.19 |
| 2014/0005118 | A1 | 1/2014 | Verdine et al. | |

FOREIGN PATENT DOCUMENTS

| AU | PCT/US2015/022417 | 3/2015 |
| CA | PCT/US2015/022417 | 3/2015 |
| EP | 15768071.1 | 3/2015 |
| WO | WO-96/25520 A1 | 8/1996 |
| WO | WO-2012/142604 A2 | 10/2012 |
| WO | PCT/US2015/022417 | 3/2015 |
| WO | WO-2015/148620 A2 | 10/2015 |

OTHER PUBLICATIONS

The Medical Dictionary, "moiety", https://medical-dictionary.thefreedictionary.com/moiety; visited May 8, 2018.*
U.S. Appl. No. 61/970,329, filed Mar. 25, 2014, Lim et al.
Argmann, C.A. and J. Auwerx (2006) Collection of blood and plasma from the mouse. Curr. Protoc. Mol. Biol. Chapter 29, p. Unit 29A 3.
Bartram, C.R., et al. (1983) Translocation of c-ab1 oncogene correlates with the presence of a Philadelphia chromosome in chronic myelocytic leukaemia. Nature 306(5940): 277-280.
Baskiewicz-Masiuk, M. and Machalinski, B. (2004) The role of the STAT5 proteins in the proliferation and apoptosis of the CML and AML cells. Eur. J. Haematol. 72(6): 420-429.
Beissert, T., et al. (2008) Targeting of the N-terminal coiled coil oligomerization interface by a helix-2 peptide inhibits unmutated and imatinib-resistant BCR/ABL. Int. J. Cancer 122(12): 2744-2752.
Ben-Neriah, Y., et al. (1986) The chronic myelogenous leukemia-specific P210 protein is the product of the bcr/abl hybrid gene. Science 233(4760): 212-214.
Bernal, F., et al. (2007) Reactivation of the p53 Tumor Suppressor Pathway by a Stapled p53 Peptide. J. Am. Chem. Soc. 129, 2456-2457.
Bird, G.H., et al. (2008) Synthesis and biophysical characterization of stabilized a-helices of BCL-2 domains. Methods Enzymol. 446, 369-386.
Bird, G.H., et al. (2010) Hydrocarbon double-stapling remedies the proteolytic instability of a lengthy peptide therapeutic. PNAS USA 107: 14093-14098.
Bradeen, H.A., et al. (2006) Comparison of imatinib mesylate, dasatinib (BMS-354825), and nilotinib (AMN107) in an N-ethyl-N-nitrosourea (ENU)-based mutagenesis screen: high efficacy of drug combinations. Blood 108(7): 2332-2338.
Branford, S., et al. (2003) Detection of BCR-ABL mutations in patients with CML treated with imatinib is virtually always accompanied by clinical resistance and mutations in the ATP phosphate-binding loop (P-loop) are associated with a poor prognosis. Blood 102(1): 276-283.

(Continued)

*Primary Examiner* — Jeanette M Lieb
(74) *Attorney, Agent, or Firm* — Ballard Spahr LLP

(57) ABSTRACT

In one aspect, the invention relates to peptides comprising the Bcr-Abl coiled-coil oligomerization domain and an alpha helix stabilizing moiety, mutant forms thereof, truncated forms thereof, derivatives thereof, and related peptides, which are useful as inhibitors of the Bcr-Abl chimeric protein; pharmaceutical compositions comprising the compounds; and methods of treating hyperproliferative disorders associated with Bcr-Abl using the compounds and compositions. This abstract is intended as a scanning tool for purposes of searching in the particular art and is not intended to be limiting of the present invention.

21 Claims, 72 Drawing Sheets

Specification includes a Sequence Listing.

(56) References Cited

OTHER PUBLICATIONS

Bruno, B.J., et al. (2013) Basics and recent advances in peptide and protein drug delivery. Therapeutic Delivery 4(11):1443-1467.
Calabretta, B., and Perrotti, D. (2004) The biology of CML blast crisis. Blood 103(11): 4010-4022.
Cancer.org. (2013) What are the key statistics about chronic myeloid leukemia? Available from: http://www.cancer.org/cancer/leukemia-chronicmyeloidcml/detailedguide/leukemia-chronic-myeloid-myelogenous-key-statistics.
Carella, A.M., et al. (2010) Kinase domain mutations of BCR-ABL identified at diagnosis before imatinib-based therapy are associated with progression in patients with high Sokal risk chronic phase chronic myeloid leukemia. Leuk. Lymphoma 51(2): 275-278.
Cassuto, 0., et al. (2012) All tyrosine kinase inhibitor-resistant chronic myelogenous cells are highly sensitive to Ponatinib. Oncotarget. 3(12): 1557-1565.
Cerutti, D.S., et al. (2009) Staggered Mesh Ewald: An extension of the Smooth Particle-Mesh Ewald method adding great versatility. J. Chem. Theory Comput. 5(9): 2322.
Chang, Y.S., et al. (2013) Stapled a-helical peptide drug development: a potent dual inhibitor of MDM2 and MDMX for p53-dependent cancer therapy. PNAS USA 110(36):E3445-3454.
Cohen, N.A., et al. (2012) A competitive stapled peptide screen identifies a selective small molecule that overcomes MCL-1-dependent leukemia cell survival. Chem. Biol. 19(9):1175-1186.
Constance, I.E., et al. (2012) Enhanced and selective killing of chronic myelogenous leukemia cells with an engineered BCR-ABL binding protein and imatinib. Mol. Pharmaceutics, 2012,9 (11): 3318-3329.
Constance, I.E., et al. (2012) Selective targeting of c-Abl via a cryptic mitochondrial targeting signal activated by cellular redox status in leukemic and breast cancer cells. Pharm. Res. 29(8): 2317-2328.
Cortes, I.E., et al. (2012) Ponatinib in Refractory Philadelphia Chromosome-Positive Leukemias. N Engl. J. Med. 367: 2075-88.
Daley, G.Q., et al. (1991) Blast crisis in a murine model of chronic myelogenous leukemia. PNAS USA. 88(24): 11335-11338.
Demehri, S., et al. (2010) The function of the pleckstrin homology domain in BCR-ABL-mediated leukemogenesis. Leukemia 24(1): 226-229.
Dexter, T.M., et al. (1980) Growth of factor-dependent hemopoietic precursor cell lines. J. Exp. Med. 152(4):1036-1047.
Dixon et al. (2012) "Improved coiled-coil design enhances interaction with Bcr-Abl and induces apoptosis" Mol Pharm. 9(1): 187-195.
Dixon, A. S., et al. (2012) Changing the subcellular location of the oncoprotein Bcr-Abl using rationally designed capture motifs. Pharm. Res. 29(4): 1098-1109.
Dixon, A.S., et al. (2011) Disruption of Bcr-Abl coiled coil oligomerization by design. J. Biol. Chem. 286(31): 27751-27760.
Druker, B.J., et al. (1996) Effects of a selective inhibitor of the Abl tyrosine kinase on the growth of Bcr-Abl positive cells. Nat. Med. 2(5): 561-566.
Duan, Y., et al. (2003) A point-charge force field for molecular mechanics simulations of proteins based on condensed-phase quantum mechanical calculations. J. Comput. Chem. 24(16): 1999-2012.
Eide, C.A., et al. (2011) Resistance Profiling of BCR-ABL Compound Mutations Linked to Tyrosine Kinase Inhibitor Therapy Failure in Chronic Myeloid Leukemia [abstract]. Blood (ASH Annual Meeting Abstracts) 118, 1416.
Fleischman, A.G., et al. (2011) TNFa facilitates clonal expansion of JAK2V617F positive cells in myeloproliferative neoplasms. Blood 118(24): 6392-6398.
Garner, A.P., et al. (2013) Ponatinib, a pan-BCR-ABL inhibitor, potently inhibits key activating and drug-resistant KIT mutants found in GIST [Abstract 3394]. AACR Annual Meeting Abstracts.
Gentilucci, L., et al. (2010) Chemical modifications designed to improve peptide stability: incorporation of non-natural amino acids, pseudo-peptide bonds, and cyclization. Curr. Pharm. Des. 16(28): 3185-3203.
Gozgit, J.M., et al. (2011) Potent activity of ponatinib (AP24534) in models of FLT3-driven acute myeloid leukemia and other hematologic malignancies. Mol. Cancer Ther. 10(6): 1028-1035.
Grant, B.J., et al. (2010) Large conformational changes in proteins: signaling and other functions. Curr. Opin. Struct. Biol. 20(2): 142-147.
Grimley, P.M., et al. (1999) Stat5a and Stat5b: fraternal twins of signal transduction and transcriptional activation. Cytokine Growth Factor Rev. 10(2):131-157.
Guo et al. (1998) "Peptide containing the BCR oligomerization domain (AA 1-160) reverses the transformed phenotype of p210bcr-abl positive 32D myeloid leukemia cells" Oncogene 17(7):825-833.
Hanfstein, B., et al. (2012) Early molecular and cytogenetic response is predictive for long-term progression-free and overall survival in chronic myeloid leukemia (CML). Leukemia 26(9): 2096-2102.
Hantschel, O., et al. (2004) Regulation of the c-Abl and Bcr-Abl tyrosine kinases. Nat. Rev. Mol. Cell Biol. 5, 33-44.
Hantschel, O., et al. (2005) Structural basis for the cytoskeletal association of Bcr-Abl/c-Abl. Mol. Cell 19(4): 461-473.
Hazlehurst, L.A., et al. (2009) Signaling networks associated with BCR-ABL-dependent transformation. Cancer Control 16(2):100-107.
Hehlmann, R., et al. (1993) Randomized comparison of busulfan and hydroxyurea in chronic myelogenous leukemia: prolongation of survival by hydroxyurea. Blood 82(2):398-407.
Hehlmann, R., et al. (2011) Tolerability-adapted imatinib 800 mg/d versus 400 mg/d versus 400 mg/d plus interferon-a in newly diagnosed chronic myeloid leukemia. J. Clin. Oncol. 29(12):1634-1642.
Henchey, L.K., et al. (2008) Contemporary Strategies for the Stabilization of Peptides in the a-Helical Conformation. Curr. Opin. Chem. Biol. 12(6):692-697.
Hochhaus, A., et al. (2007) Dasatinib induces notable hematologic and cytogenetic responses in chronic-phase chronic myeloid leukemia after failure of imatinib therapy. Blood 109(6): 2303-2309.
Huang, W. S. et al. (2010) Discovery of 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a potent, orally active pan-inhibitor of breakpoint cluster region-abelson (BCR-ABL) kinase including the T315l gatekeeper mutant. J. Med. Chem. 53(12):4701-4719.
Huo, S., I. et al. (2002) Computational alanine scanning of the 1:1 human growth hormone-receptor complex. J. Comput. Chem. 23(1):15-27.
Inman, S. Late-stage ponatinib study discontinued. 2013; available from: http://www.onclive.com/web-exclusives/Frontline-Late-Stage-Ponatinib-Study-Discontinued.
Jabbour, E., and Kantarjian, H. (2012) Chronic myeloid leukemia: 2012 update on diagnosis, monitoring, and management. Am. J. Hematol. 87(11):1037-1045.
Jabbour, E., et al. (2010) Choosing the best treatment strategy for chronic myeloid leukemia patients resistant to imatinib: weighing the efficacy and safety of individual drugs with BCR-ABL mutations and patient history. Leukemia 24(1): 6-12.
Kelly, S.M. and N.C. Price (2000) The use of circular dichroism in the investigation of protein structure and function. Current Protein and Peptide Science 1, 349-384.
Khorashad, J.S., et al. (2013) BCR-ABL1 compound mutations in tyrosine kinase inhibitor-resistant CML: frequency and clonal relationships. Blood 121(3):489-498.
Kim, Y.W., et al. (2010) Introduction of All-Hydrocarbon i,i+3 Staples into a-Helices via Ring-Closing Olefin Metathesis. Org. Lett. 12(13):3046-3049.
Kim, Y.W., et al. (2011) Synthesis of all-hydrocarbon stapled a-helical peptides by ring-closing olefin metathesis Nat. Protoc. 6(6): 761-771.
Kin, Y., et al. (2001) The Dbl homology domain of BCR is not a simple spacer in P210BCR-ABL of the Philadelphia chromosome. J. Biol. Chem. 276(42): 39462-39468.

(56) References Cited

OTHER PUBLICATIONS

Kinstrie, R. and M. Copland (2013) Targeting chronic myeloid leukemia stem cells. Curr Hematol Malig Rep. 8(1):14-21.

Klamova, H., et al. (2010) Dasatinib in Imatinib-Resistant or -Intolerant CML Patients: Data From the Clinical Practice of 6 Hematological Centers in the Czech Republic. Neoplasma 57(4): 355-359.

Klepeis, J.L., et al. (2009) Long-timescale molecular dynamics simulations of protein structure and function. Curr. Opin. Struct. Biol. 19, 120-127.

Kollman, P.A., et al. (2000) Calculating structures and free energies of complex molecules: combining molecular mechanics and continuum models. Ace. Chem. Res. 33, 889-897.

Koren-Michowitz, M., et al. (2010) Activity and tolerability of nilotinib: a retrospective multicenter analysis of chronic myeloid leukemia patients who are imatinib resistant or intolerant. Cancer 116, (19): 4564-4572.

La Rosee, P., et al. (2002)Activity of the Bcr-Abl kinase inhibitor PD180970 against clinically relevant Bcr-Abl isoforms that cause resistance to imatinib mesylate (Gleevec, STI571). Cancer Res. 62(24):7149-7153.

Le Coutre, P., et al. (2008) Nilotinib (formerly AMN107), a highly selective BCR-ABL tyrosine kinaseinhibitor, is active in patients with imatinib-resistant or -intolerant accelerated-phase chronic myelogenous leukemia. Blood 111, 1834-1839.

Lee, E.H., et al. (2009) Discovery through the computational microscope. Structure 17(10):1295-1306.

Lee, J.C., et al. (1982) Constitutive production of a unique lymphokine (IL 3) by the WEHI-3 cell line. J. Immunol. 128(6): 2393-2398.

Maru, Y.; Witte, 0. N. (1991) The BCR gene encodes a novel serine/threonine kinase activity within a single exon. Cell 67(3): 459-468.

Mauro, M.J. and B.J. Druker (2001) STI571: targeting BCR-ABL as therapy for CML. Oncologist 6(3):233-238.

McWhirter, J.R., et al. (1993) A coiled-coil oligomerization domain of Bcr is essential for the transforming function of Bcr-Abl oncoproteins. Mol. Cell Biol. 13(12): 7587-7595.

Mian, A.A., et al. (2009) Oligomerization inhibition, combined with allosteric inhibition, abrogates the transformation potential of T315I-positive BCR/ABL. Leukemia 23, 2242-2247.

Mian, A.A., et al. (2009) The gatekeeper mutation T315I confers resistance against small molecules by increasing or restoring the ABL-kinase activity accompanied by aberrant transphosphorylation of endogenous BCR, even in loss-of-function mutants of BCR/ABL. Leukemia 23(9):1614-1621.

Miao, Y. J. and Wang, J. Y. (1996) Binding of A/T-rich DNA by three high mobility group-like domains in c-Abl tyrosine kinase. J. Biol. Chem. 271(37): 22823-22830.

Miller, G.D., et al. (2013) Multidomain Targeting of Bcr-Abl by Disruption of Oligomerization and Tyrosine Kinase Inhibition: Toward Eradication of CML. Mol. Pharm. 10(9): 3475-3483.

Mulcahy, N. (2013) Leukemia drug ponatinib (Iclusig) pulled from market. Available from: http://www.medscape.com/viewarticle/813531.

Naldini, L., et al. (1986) Phosphotyrosine antibodies identify the p210c-abl tyrosine kinase and proteins phosphorylated on tyrosine in human chronic myelogenous leukemia cells. Mol. Cell Biol. 6(5):1803-1811.

Natalello, A., et al. (2012) Biophysical Characterization of Met-G-CSF: Effects of Different Site-Specific Mono-Pegylations on Protein Stability and Aggregation. PLoS One 7, e42511.

Neelakantan, P., et al. (2012) Platelet dysfunction associated with ponatinib, a new pan BCR-ABL inhibitor with efficacy for chronic myeloid leukemia resistant to multiple tyrosine kinase inhibitor therapy. Haematologica 97(9):1444.

O'Brien, S., et al. (2011) NCCN Task Force report: tyrosine kinase inhibitor therapy selection in the management of patients with chronic myelogenous leukemia. J Natl Compr Canc Netw. 9 Suppl 2:S1-25.

O'Hare, T., et al. (2004) Inhibition of wild-type and mutant Bcr-Abl by AP23464, a potent ATP-based oncogenic protein kinase inhibitor: implications for CML. Blood 104(8): 2532-2539.

O'Hare, T., et al. (2007) Bcr-Abl kinase domain mutations, drug resistance, and the road to a cure for chronic myeloid leukemia. Blood 110(7):2242-2249.

O'Hare, T., et al. (2009) AP24534, a pan-BCR-ABL inhibitor for chronic myeloid leukemia, potently inhibits the T315I mutant and overcomes mutation-based resistance. Cancer Cell 16, 401-412.

O'Hare, T., et al. (2012) Pushing the limits of targeted therapy in chronic myeloid leukemia. Nat. Rev. Cancer 12(8): 513-526.

Ohnishi, K., et al. (1995) a randomized trial comparing interferon-alpha with busulfan for newly diagnosed chronic myelogenous leukemia in chronic phase. Blood 86(3):906-916.

Preyer, M., et al. (2011) Interplay between Kinase Domain Autophosphorylation and F-Actin Binding Domain in Regulating Imatinib Sensitivity and Nuclear Import of BCR-ABL. PloS One 6(2): e17020.

Razzak, M. (2013) Haematology: Ponatinib: the next TKI challenge. Nat. Rev. Clin. Oncol. 10, 65.

Ren, R. (2002) The molecular mechanism of chronic myelogenous leukemia and its therapeutic implications: studies in a murine model. Oncogene 21(56): 8629-8642.

Rowley, J.D. (1973) Letter: A new consistent chromosomal abnormality in chronic myelogenous leukemia identified by quinacrine fluorescence and Giemsa staining. Nature 243(5405):290-293.

Sawyers, C.L., et al. (2002) Imatinib induces hematologic and cytogenetic responses in patients with chronic myelogenous leukemia in myeloid blast crisis: results of a phase II study. Blood 99, 3530-3539.

Schafmeister, C.E., et al. (2000) An all-hydrocarbon cross-linking system for enhancing the helicity and metabolic stability of peptides. J. Am. Chem. Soc. 122(24):5891-5892.

Schaller-Schoenitz, M., et al. (2011) Function of Stats Isoforms in Bcr-Abl Positive Cells. ASH Annual Meeting Abstracts.

Shami, P.J. and M. Deininger (2012) Evolving treatment strategies for patients newly diagnosed with chronic myeloid leukemia: the role of second-generation BCR-ABL inhibitors as first-line therapy. Leukemia 26(2): 214-224.

Sherbenou, D.W., et al. (2008) Characterization of BCR-ABL deletion mutants from patients with chronic myeloid leukemia. Leukemia 22(6):1184-1190.

Sierra, J.R., et al. (2010) Molecular mechanisms of acquired resistance to tyrosine kinase targeted therapy. Mol. Cancer 9:75.

Steinbrecher, T. and A. Labahn (2010) Towards accurate free energy calculations in ligand protein-binding studies. Curr. Med. Chem. 17, 767-785.

Van Etten, R.A., et al. (1994) The COOH terminus of the c-Abl tyrosine kinase contains distinct F-and G-actin binding domains with bundling activity. J. Cell Biol. 124(3):325-340.

Verdine, G.L. and G.J. Hilinski (2012) Stapled peptides for intracellular drug targets. Methods Enzymol. 503: 3-33.

Walensky, L.D., et al. (2004) Activation of apoptosis in vivo by a hydrocarbon-stapled BH3 helix. Science 305(5689)1466-1470.

Walensky, L.D., et al. (2006) A stapled BID BH3 helix directly binds and activates BAX. Mol. Cell 24(2): 199-210.

Wetzler, M., et al. (1993) Subcellular localization of Bcr, Abl, and Bcr-Abl proteins in normal and leukemic cells and correlation of expression with myeloid differentiation. J. Clin. Invest. 92(4):1925-1939.

Woessner, D.W. and C.S. Lim (2013) Disrupting BCR-ABL in combination with secondary leukemia-specific pathways in CML cells leads to enhanced apoptosis and decreased proliferation. Mol. Pharm. 10(1): 270-277.

Woessner, D.W., et al. (2011) Development of an effective therapy for chronic myelogenous leukemia. Cancer J. 17(6): 477-486.

Zhang, J., et al. (2009) Targeting cancer with small molecule kinase inhibitors. Nat. Rev. Cancer 9(1): 28-39.

Zhao, X. et al.(2002) Structure of the Bcr-Abl oncoprotein oligomerization domain. Nat. Struct. Biol. 9, 117-20.

International Search Report was dated Oct. 13, 2015 by the International Searching Authority for Application No. PCT/US2015/022417, which was filed on Mar. 25, 2015 and published as

(56) References Cited

OTHER PUBLICATIONS

WO/2015/148620 on Oct. 1, 2015 (Applicant—University of Utah Research Foundation; Inventor-Lim et al) (6 pages).

Written Opinion dated Oct. 13, 2015 by the International Searching Authority for Application No. PCT/US2015/022417, which was filed on Mar. 25, 2015 and published as WO/2015/148620 on Oct. 1, 2015 (Applicant—University of Utah Research Foundation; Inventor-Lim et al) (7 pages).

International Preliminary Report on Patentability dated Sep. 27, 2016 by the International Searching Authority for Application No. PCT/US2015/022417, which was filed on Mar. 25, 2015 and published as WO/2015/148620 on Oct. 1, 2015 (Applicant—University of Utah Research Foundation; Inventor-Lim et al) (8 pages).

European Search Report dated Sep. 8, 2017 by the European Patent Office for EP Application No. 15768071.1, which was filed on Mar. 25, 2015 (Applicant—University of Utah Research Foundation)(8 pages).

* cited by examiner

PEPTIDE INHIBITORS OF BCR-ABL OLIGOMERIZATION

CROSS-REFERENCE TO RELATED APPLICATIONS

This application claims benefit of and priority under 35 U.S.C. § 371 of PCT/US2015/022417, filed Mar. 25, 2015, which claims the benefit under 35 U.S.C. § 119(e) of U.S. Provisional Application No. 61/970,329, filed Mar. 25, 2014, which are incorporated herein by reference in their entirety.

STATEMENT REGARDING FEDERALLY SPONSORED RESEARCH

This invention was made with government support under Grant Number CA129528 awarded by the National Institutes of Health. The government has certain rights in this invention.

REFERENCE TO SEQUENCE LISTING

The Sequence Listing submitted "21101_0298U2_Sequence_Listing.txt," created on Sep. 23, 2016, and having a size of 10,782 bytes is hereby incorporated by reference pursuant to 37 C.F.R. § 1.52(e)(5).

BACKGROUND

Each year, nearly 6,000 new cases of chronic myeloid leukemia (CML) are diagnosed in the United States (Cancer.org. (2013) Available from: cancer.org/cancer/leukemia-chronicmyeloidcml/detailedguide/leukemia-chronic-myeloid-myelogenous-key-statistics). The fusion oncoprotein Bcr-Abl, the product of t(9;22)(q34;q11), is the causative agent of chronic myeloid leukemia (CML) (Nowell, P. C. (1962) Blut. 8, 65-66; Bartram, C. R., et al. (1983) Nature 306, 277-280; Ren, R. (2002) Oncogene 21, 8629-8642). BCR-ABL1 is a constitutively active tyrosine kinase and the target of small molecule therapeutics for the disease including the first inhibitor of its kind, imatinib (Druker, B. J., et al. (1996) Nat. Med. 2, 561-566; Naldini, L., et al. (1986) Mol. Cell Biol. 6, 1803-1811; Evans, J. P., et al. (1987) Leukemia 1, 524-525). Overall, imatinib has displayed considerable efficacy in CML, with high rates of complete hematologic (CHR) and cytogenetic response (CCyR) that have translated into improved progression-free and overall survival compared to non-TKI therapies (Hanfstein, B., et al. (2012) Leukemia 26:2096-2102; Sawyers, C. L., et al. (2002) Blood 99, 3530-3539; Hochhaus, A., et al. (2007) Blood 109, 2303-2309; Le Coutre, P., et al. (2008) Blood 111, 1834-1839; Hehlmann, R., et al. (1993) Blood 82, 398-407; Ohnishi, K., et al. (1995) Blood 86, 906-916). Although many imatinib responses are durable, some patients acquire kinase domain mutations that confer BCR-ABL1-dependent resistance and are associated with clinical relapse (Branford, S., et al. (2003) Blood 102, 276-283).

To overcome this type of resistance, second-generation TKIs dasatinib, nilotinib, and bosutinib, and most recently the pan-BCR-ABL inhibitor ponatinib, were developed Cassuto, O., et al. (2012) Oncotarget 3, 1557-1565). Second generation TKIs are active in imatinib-resistant patients with or without BCR-ABL1 mutations, but have no activity in patients with the T315I mutation in the gatekeeper position of the kinase (O'Brien, S., et al. (2011) J. Natl. Compr. Canc. Netw. 9 Suppl. 2:S1-25; Mian, A. A., et al. (2009) Leukemia 23, 614-1621). In contrast to the first and second generation TKIs, ponatinib is effective against the T315I mutant, representing a major therapeutic breakthrough (Burke, A. C., et al. (2011) Expert Opin. Emerg. Drugs 16, 85-103). Thus far no single mutation has been shown to confer resistance to ponatinib, but multiple mutations in the same BCR-ABL1 molecule, referred to as compound mutations, can confer resistance to ponatinib in vitro and possibly in vivo.

Second and third generation tyrosine kinase inhibitors (nilotinib, dasatinib, bosutinib, ponatinib) have been developed to cover a more broad range of Bcr-Abl kinase domain mutations, leading to greater success in CML therapy and in all cases showing higher potency (O'Hare, T., et al. (2012) Nat. Rev. Cancer 12, 513-526). This broader range of coverage and enhanced potency, especially with the third generation ponatinib, also leads to inhibition of other tyrosine kinases, namely FLT3, KIT, and VEGFR, to name a few (Garner, A. P., et al. (2013) AACR Annual Meeting Abstracts; Gozgit, J. M., et al. (2011) Mol. Cancer Ther. 10, 1028-1035). Inhibition of off-target kinases in many patient cases has led to the appearance of toxic side effects, including thrombocytopenia, rash, arthralgia, and serious blood clotting (Neelakantan, P., et al. (2012) Haematologica 97, 1444; Cortes, J. E., et al. (2012) N Engl. J. Med. 367, 2075-2088). In fact, the recently FDA-approved ponatinib (Iclusig), the first TKI able to target the long sought-after "gate-keeper" T315I point mutation in Bcr-Abl, had been in a Phase III trial for first-line therapy in CML patients. This trial has since been discontinued due to the serious side effects seen in nearly 12% of patients (Inman, S. (2013) Late-stage ponatinib study discontinued), presumably due to its broad specificity and potency, and further resulting in the complete withdrawal of ponatinib from the market as of October 2013 (Mulcahy, N. (2013) Leukemia drug ponatinib (Iclusig) pulled from market). In addition to showing toxic side effects, consecutive treatment with multiple TKIs has shown to allow for compound mutations, or multiple Bcr-Abl point mutations in a single molecule, to arise (Eide, C. A., et al. (2011) Blood (ASH Annual Meeting Abstracts) 118, 1416). Despite certain TKI success against a variety of single point mutations, many of these compound mutations still show a high level of resistance against all currently available TKIs, leaving no treatment for this increasing subset of patients (Khorashad, J. S., et al. (2013) Blood 121, 489-498).

Rational therapy of CML has thus far focused on targeting the BCR-ABL1 catalytic site, but as described above, kinase domain mutations that impair or block drug binding limit the scope of this approach (Zhang, J., et al. (2009) Nat. Rev. Cancer 9, 28-39). Kinase activity requires transactivation of BCR-ABL1 following an oligomerization event. The domain responsible and necessary for oligomerization is the coiled-coil (CC) domain in the N-terminus of BCR, and this domain has been shown to be critically important for BCR-ABL1. In order to aberrantly activate the downstream signaling characteristic of this disease, Bcr-Abl must homo-oligomerize via a coiled-coil domain located at its N-terminus (Hazlehurst, L. A., et al. (2009) Cancer Control 16, 100-107; Zhao, X., et al. (2002) Nat. Struct. Biol. 9, 117-120). Removing this domain, or simply disrupting oligomerization, eliminates the oncogenic activity of Bcr-Abl (McWhirter, et al. (1993) Mol. Cell Biol. 13:7587-95; and Dixon, A. S., et al., (2011) J. Biol. Chem. 286:27751-60). Thus, this domain could thus represent an alternative target (Zhao, X., et al. (2002) Nat. Struct. Biol. 9, 117-120; McWhirter, J. R., et al. (1993) Mol. Cell Biol. 13, 7587-7595). A peptidomemetic to block dimerization were explored by several groups. For example, Ruthardt et al. reported that introduction of a peptidomemetic of helix α2 of the dimerization region of the coiled-coil of BCR reduced BCR-ABL1 phosphorylation and inhibited the proliferation of cells expressing wild-type and mutant BCR-ABL1 variants (Beissert, T., et al. (2008) *Int. J. Cancer* 122, 2744-2752). However, the isolated wild-type helix 2 alone was inactive in cells expressing the T315I mutant (Beissert, T., et al. (2008) *Int. J. Cancer* 122, 2744-2752; Mian, A. A., et al. (2009) *Leukemia* 23, 2242-2247).

Thus, there remains a need for effective, safe, and selective Bcr-Abl inhibitors, particularly Bcr-Abl inhibitors that do not target the catalytic kinase domain of the protein and that are effective against mutant forms of Bcr-Abl or cancers that are refractory to treatment with currently available Bcr-Abl inhibitors. Therefore, there remains a need for methods and compositions that overcome these deficiencies and that effectively provide Bcr-Abl inhibitors.

BRIEF SUMMARY

In accordance with the purpose(s) of the invention, as embodied and broadly described herein, the invention, in one aspect, relates to peptide compositions useful as inhibitors of Bcr-Abl, pharmaceutical compositions comprising same, and methods of treating hyperproliferative disorders, e.g. leukemias, and other disorders associated with Bcr-Abl.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety.

Also disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide.

Disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety.

Also disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide.

Disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety.

Also disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety; and wherein the peptide comprises a cell-penetrating peptide.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair.

Disclosed are pharmaceutical compositions comprising a disclosed peptide, or a pharmaceutically acceptable salt or solvate thereof, and a pharmaceutically acceptable carrier, buffer, or diluent.

Disclosed are pharmaceutical compositions comprising a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; or a pharmaceutically acceptable salt or solvate thereof; and a pharmaceutically acceptable carrier, buffer, or diluent.

Also disclosed are pharmaceutical compositions comprising a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof; and a pharmaceutically acceptable carrier, buffer, or diluent.

Disclosed are pharmaceutical compositions comprising a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof, and a pharmaceutically acceptable carrier, buffer, or diluent.

Also disclosed are pharmaceutical compositions comprising a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof, and a pharmaceutically acceptable carrier, buffer, or diluent.

Disclosed are pharmaceutical compositions comprising a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety, or a pharmaceutically acceptable salt or solvate thereof, and a pharmaceutically acceptable carrier, buffer, or diluent.

Also disclosed are pharmaceutical compositions comprising a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof, and a pharmaceutically acceptable carrier, buffer, or diluent.

Disclosed are uses of a disclosed peptide, or a pharmaceutically acceptable salt or solvate thereof, in the preparation of a medicament for the treatment of cancer.

Disclosed are uses of a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof, in the preparation of a medicament for the treatment of cancer.

Also disclosed are uses of a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof, in the preparation of a medicament for the treatment of cancer.

Disclosed are uses of a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof, in the preparation of a medicament for the treatment of cancer.

Also disclosed are uses of a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof, in the preparation of a medicament for the treatment of cancer.

Disclosed are uses of a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety, or a pharmaceutically acceptable salt or solvate thereof, in the preparation of a medicament for the treatment of cancer.

Also disclosed are uses of a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof, in the preparation of a medicament for the treatment of cancer.

Also disclosed are nucleic acid sequences capable of encoding the peptides of any of SEQ ID NO:4, SEQ ID NO:5, or SEQ ID NO:6; or active fragments thereof.

Also disclosed are vectors comprising nucleic acid sequences capable of encoding the peptides of any of SEQ ID NO:4, SEQ ID NO:5, or SEQ ID NO:6; or active fragments thereof.

Also disclosed are recombinant cells comprising nucleic acid sequences capable of encoding the peptides of any of SEQ ID NO:4, SEQ ID NO:5, or SEQ ID NO:6; or active fragments thereof.

Also disclosed are recombinant cells comprising vectors comprising nucleic acid sequences capable of encoding the peptides of any of SEQ ID NO:4, SEQ ID NO:5, or SEQ ID NO:6; or active fragments thereof.

Also disclosed are recombinant cells comprising a disclosed peptide.

Also disclosed are recombinant cells comprising a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof.

Also disclosed are recombinant cells comprising a peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the peptide comprises a cell-penetrating peptide.

Also disclosed are recombinant cells comprising a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1.

Also disclosed are recombinant cells comprising a peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the peptide comprises a cell-penetrating peptide.

Also disclosed are recombinant cells comprising a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4.

Also disclosed are recombinant cells comprising a peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the peptide comprises a cell-penetrating peptide.

Also disclosed are monoclonal antibodies that specifically bind the disclosed peptides described herein.

Disclosed are methods of treating a hyperproliferative disorder in a mammal, comprising the step of administering to the mammal an effective amount of at least one of the disclosed peptides.

Disclosed are methods of treating a hyperproliferative disorder in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof, wherein the Bcr-Abl coiled-coil oligomerization domain comprises at least one alpha helix stabilizing moiety, or a pharmaceutically acceptable salt or solvate thereof.

Disclosed are methods of treating a hyperproliferative disorder in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of treating a hyperproliferative disorder in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods of treating a hyperproliferative disorder in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr- Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of treating a hyperproliferative disorder in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods of treating a hyperproliferative disorder in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods of treating cancer in a mammal, comprising the step of administering to the mammal an effective amount of at least one of the disclosed peptides.

Disclosed are methods of treating cancer in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Disclosed are methods of treating cancer in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of treating cancer in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods of treating cancer in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of treating cancer in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods of treating cancer in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods of inducing apoptosis in a mammal, comprising the step of administering to the mammal an effective amount of at least one of the disclosed peptides.

Disclosed are methods of inducing apoptosis in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Disclosed are methods of inducing apoptosis in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inducing apoptosis in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods of inducing apoptosis in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inducing apoptosis in a mammal, the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods of inducing apoptosis in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods of inhibiting Bcr-Abl activity in a mammal, comprising the step of administering to the mammal an effective amount of at least one of the disclosed peptides.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods of inhibiting Bcr-Abl activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods for suppressing tumor activity in a mammal, comprising the step of administering to the patient an effective amount of at least one of the disclosed peptides.

Disclosed are methods for suppressing tumor activity in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Disclosed are methods for suppressing tumor activity in a mammal, comprising the step of administering to the mammal an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods for suppressing tumor activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods for suppressing tumor activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods for suppressing tumor activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods for suppressing tumor activity in a mammal, comprising the step of administering to the mammal an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods of inhibiting Bcr-Abl activity in at least one cell, comprising the step of contacting the cell with an effective amount of at least one of the disclosed peptides.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Disclosed are methods of inhibiting Bcr-Abl activity in at least one cell, comprising the step of contacting the cell with an effective amount of at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Also disclosed are kits comprising at least one of the disclosed peptides.

Also disclosed are kits comprising at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety, or a pharmaceutically acceptable salt or solvate thereof.

Also disclosed are kits comprising at least one peptide, wherein the peptide comprises a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Also disclosed are kits comprising at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety, or a pharmaceutically acceptable salt or solvate thereof.

Also disclosed are kits comprising at least one peptide, wherein the peptide comprises a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr- Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide; or a pharmaceutically acceptable salt or solvate thereof.

Also disclosed are kits comprising at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety; or a pharmaceutically acceptable salt or solvate thereof.

Also disclosed are kits comprising at least one peptide, wherein the peptide comprises a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety, and wherein the peptide comprises a cell-penetrating peptide; or a pharmaceutically acceptable salt or solvate thereof.

Disclosed are methods of making a peptide comprising at least one hydrocarbon staple pair comprising the step of reacting a peptide comprising at least one hydrocarbon staple precursor pair in the presence of a catalyst for ring-closing olefin metathesis, thereby providing a disclosed peptide comprising at least one hydrocarbon staple.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 2A (top) shows a representative illustration of the wild-type Bcr-Abl coiled-coil oligomerization domain showing the peptide sequence and location of the two alpha helices in the coiled-coil domain, helix 1 and helix 2, and flanking regions. FIG. 2B (bottom) shows a representative illustration of a peptide sequence comprising helix 2 comprising C38A, K39E, S41R, L45D, E48R, and Q60E mutations (starred) designed to improve hetero-dimerization with wild-type Bcr-Abl coiled-coil oligomerization domain.

FIG. 10A shows that Ba/F3 cells parental cells were not affected by expression of the $CC^{mut3}$ compared to empty vector (EV) control. FIG. 10B shows that $CC^{mut3}$ treatment of Ba/F3 p210 cells significantly reduced proliferation at 96 h compared to EV control. FIG. 10C shows that $CC^{mut3}$ but not EV expression results in significant reduction of single Ba/F3 p210 mutant E255V proliferative capacity. FIG. 10D shows that $CC^{mut3}$ but not EV expression results in significant reduction of single Ba/F3 p210 mutant T315I proliferative capacity. FIG. 10E shows that Ba/F3 cells expressing p210 Bcr-Abl1$^{E255V/T315I}$ demonstrate significant growth reduction at 96 h.

FIG. 12A shows that Ba/F3 parental cells are not affected by overexpression of the $CC^{mut3}$ compared to EV control. FIG. 12B shows representative data demonstrating that the transformative ability of Ba/F3 cells expressing p210 Bcr-Abl1 is greatly reduced in the $CC^{mut3}$ treatment group. FIGS. 12C and 12D show representative data demonstrating that the transformative ability of Ba/F3 p210 mutants E255V (12C) and T315I (12D) is more than 10-fold reduced in the $CC^{mut3}$ group. FIG. 12E shows that colonies per area are reduced in the compound mutant cell line (Ba/F3 p210-E255V/T315I) by $CC^{mut3}$ compared to EV control.

FIG. 13A shows representative data demonstrating that $CC^{mut3}$ induces apoptosis in Bcr-Abl1-expressing K562 cells. FIG. 13B shows representative images of $CC^{mut3}$ causing apoptosis via nuclear segmentation, with cells containing segmented nuclei pointed out by the arrows.

FIG. 14A shows that Ba/F3 parental cells are not affected by overexpression of the $CC^{mut3}$ compared to EV control. FIG. 14B shows that Ba/F3 p210 cells have a more than 30% increase in apoptotic population when treated with $CC^{mut3}$ versus EV control. Single Ba/F3 p210 mutants E255V (14C) and T315I (14D) display a significant shift toward the apoptotic fraction when expressing $CC^{mut3}$ compared to EV control. FIG. 14E shows that the Ba/F3 p210 compound mutant E255V/T315I line is significantly more apoptotic when treated with $CC^{mut3}$.

FIG. 27A shows representative data pertaining to the effect of $CC^{mut3}$ on cell growth compared to EV control. FIGS. 27B and 27C show representative data pertaining to the effect of $CC^{mut3}$ on colony formation compared to EV control.

FIG. 28A shows representative data pertaining to the effect of $CC^{mut3}$ or ponatinib on transduction in a single patient compared to EV control. FIG. 28B shows representative data pertaining to the effect of $CC^{mut3}$ or ponatinib on transduction in the same patient (now in blast crisis stage) compared to EV control. FIG. 28C shows representative data pertaining to the effect of $CC^{mut3}$ or increasing concentrations of ponatinib on transduction.

FIG. 30A shows a ribbon diagram of the WT Brc-Abl homo-dimer. FIG. 30B shows a ribbon diagram of the truncated $CC^{mut3}$-Bcr-Abl hetero-dimer. FIG. 30C shows a ribbon diagram of the truncated $CC^{mut3}$-Bcr-Abl hetero-dimer, with a G29 and E36 stable. FIG. 30D shows a ribbon diagram of the truncated $CC^{mut3}$-Bcr-Abl hetero-dimer, with a N50 and 157 staple. FIG. 30E shows a ribbon diagram of a double-stapled peptide.

Figure 1:
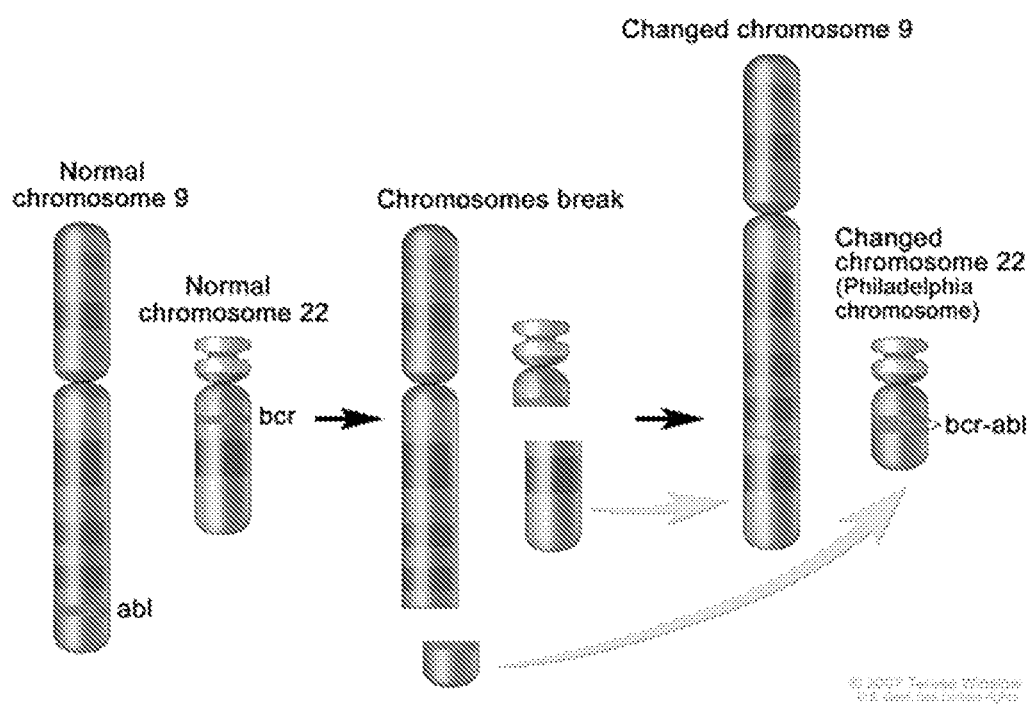
FIG. 1 shows a representative cartoon illustrating the chromosomal translocation of Bcr (22) and Abl (9), leading to the Bcr-Abl fusion protein.
Figure 2:
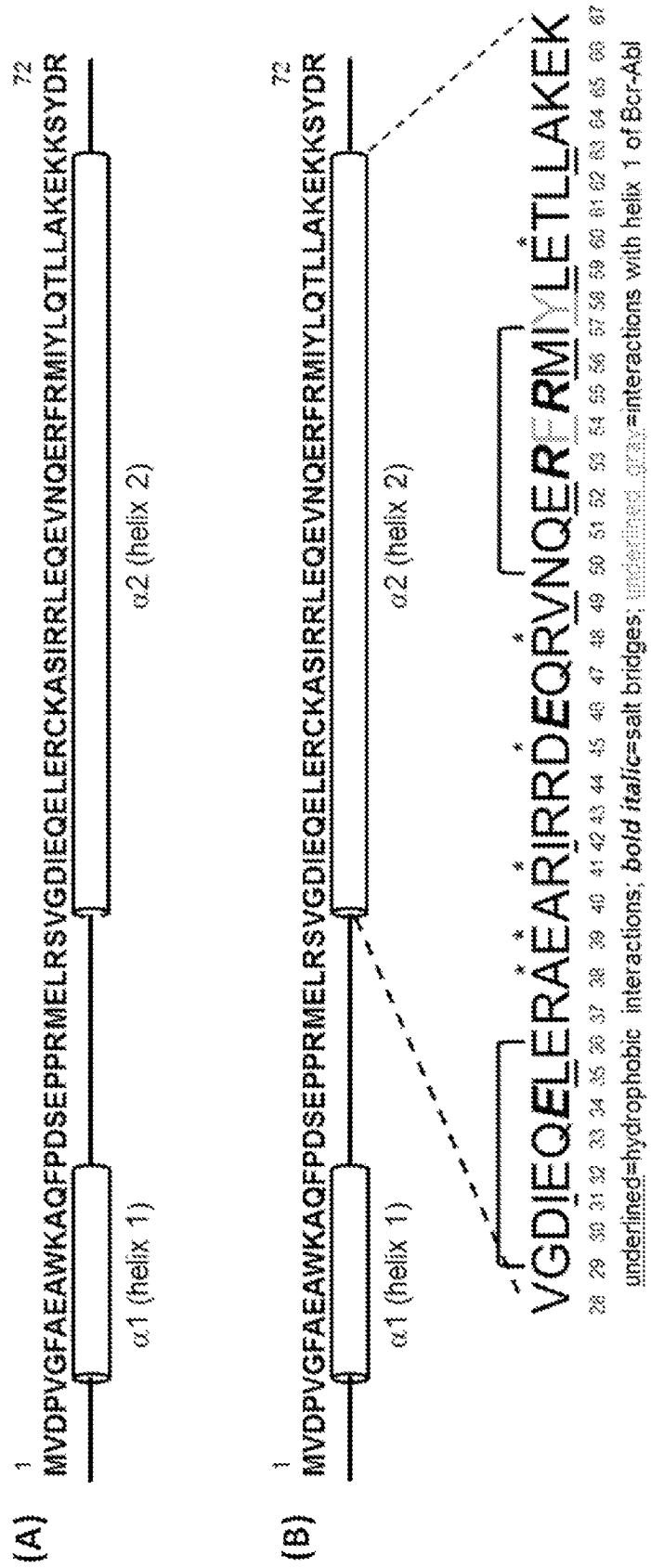
FIGS. 2A and 2B show peptide sequences.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims. As used herein, nomenclature for compounds, including peptides and nucleic acids, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like.

It must be noted that as used herein and in the appended claims, the singular forms "a", "an", and "the" include plural reference unless the context clearly dictates otherwise. Thus, for example, reference to "a peptide" includes a plurality of such peptides, reference to "the nucleic acid sequence" is a reference to one or more nucleic acid sequences and equivalents thereof known to those skilled in the art, and so forth.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments or aspects are explicitly disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, the term "amino acid sequence" refers to a list of abbreviations, letters, characters or words representing amino acid residues.

The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; X, represents a position wherein any amino acid can occur in the indicated position, unless otherwise explicitly limited to particular amino acids; Z, glutamine or glutamic acid. Alternatively, acid abbreviations used herein can use the convention three letter codes for amino acids and are expressed as follows: Ala, alanine; Asx, asparagine or aspartic acid; Cys, cysteine; Asp, aspartic acid; Glu, glutamic acid; Phe, phenylalanine; Gly, glycine; His, histidine; Ile, isoleucine; Lys, lysine; Leu, leucine; Met, methionine; Asn, asparagine; Pro, proline; Gln, glutamine; Arg, arginine; Ser, serine; Thr, threonine; Val, valine; Trp, tryptophan; Xaa, represents a position wherein any amino acid can occur in the indicated position, unless otherwise explicitly limited to particular amino acids; Tyr, tyrosine; and Glx, glutamine or glutamic acid.

By an "effective amount" of a compound, peptide, pharmaceutical composition, and the like as provided herein is meant a sufficient amount of the compound, peptide, pharmaceutical composition, and the like to provide the desired effect or to have an effect on an undesired condition. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "Bcr-Abl" can refer to the Bcr-Abl chimeric protein, the Bcr-Abl fusion gene, or collectively to both.

As used herein, "Bcr-Abl fusion gene" refers a fusion gene arising from a reciprocal translocation between chromosome 9 and 22, shown schematically in FIG. 1. The result is that a fusion gene is created by the juxtaposition of the Abl1 gene on chromosome 9 (region q34) to a part of the BCR ("breakpoint cluster region") gene on chromosome 22 (region q11). This is a reciprocal translocation, creating an elongated chromosome 9 (der 9), and a truncated chromosome 22 (the Philadelphia chromosome). In agreement with the International System for Human Cytogenetic Nomenclature (ISCN), this chromosomal translocation is designated as t(9;22)(q34;q11). It is found in most patients with chronic myelogenous leukemia (CML), and in some patients with acute lymphoblastic leukemia (ALL) or acute myelogenous leukemia (AML). Specifically, the translocation is found in 95% of people with chronic myelogenous leukemia (CML), 25-30% of adult cases and 2-10% of pediatric cases of acute lymphoblastic leukemia (ALL), and occasionally in acute myelogenous leukemia (AML).

As used herein, "Bcr-Abl chimeric protein" refers to a protein comprising coding segments of the two genes forming the Bcr-Abl chimeric gene. The Bcr-Abl chimeric protein is a tyrosine kinase that is constitutively active and has a molecular weight from about 185 to 210 kDa, depending upon the precise location of breakpoints given rise to the Bcr-Abl chimeric gene. Among the variant proteins comprising the Bcr-Abl are the three most clinically significant isoforms: p190, p210, and p230, referring respectively to their apparent molecular weights of 190 kDa, 210 kDa, and 230 kDa. These isoforms are generally associated with particular cancers: p190 is generally associated with ALL; p210 is generally associated with CML but can also be associated with ALL; and p230 is generally associated with CML. The Bcr-Abl chimeric protein can be alternatively referred to herein as the Bcr-Abl fusion protein, Bcr-Abl protein, or simply Bcr-Abl.

"Native Bcr" refers to the Bcr protein found in nature. For example, native Bcr refers to the Bcr found naturally in a subject.

"Native Abl" refers to the Abl protein found in nature. For example, native Abl refers to the Abl found naturally in a subject.

"Native Bcr-Abl" refers to the Bcr-Abl chimeric protein found in nature in subjects having a "Bcr-Abl fusion gene."

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

A "wild-type Bcr coiled-coil" refers to the coiled-coil domain present in wild-type or native Bcr. W.t. Bcr coiled-coil refers to the sequence of SEQ ID NO:1. The sequence of SEQ ID NO:1 is:

(SEQ ID NO: 1)
MVDPVGFAEAWKAQFPDSEPPRMELRSVGDIEQELERCKASIRRLEQEVN

QERFRMIYLQTLLAKEKKSY

Alternatively, the wild-type Bcr coiled-coil can be referred to using the synonyms "wild-type Bcr coiled-coil domain," "w.t. Bcr coiled-coil," "wt Bcr coiled-coil," or "$CC^{wt}$."

A "mutant Bcr coiled-coil" refers to the wild-type Bcr coiled-coil sequence of SEQ ID NO:1 having at least one amino acid mutation. For example, the mutated Bcr coiled-coil domain can have an Ala at position 38, an Arg at position 41, a Asp at position 45, an Arg at position 48, and a Glu at position 60 as shown for SEQ ID NO:2.

A "truncated Bcr coiled-coil" refers to the peptide consisting essentially of the alpha helix domain of the wild-type Bcr coiled-coil, i.e. a peptide comprising 35-40 amino acids in the region from about position 23 to about position 65, inclusive, of SEQ ID NO:1, SEQ ID NO:2, SEQ ID NO:3, or SEQ ID NO:7. Examples of suitable truncated Bcr coiled-coil peptides are given in SEQ ID NO:4, SEQ ID NO:5, SEQ ID NO:6, and SEQ ID NO:8.

"Peptide" as used herein refers to any polypeptide, oligopeptide, gene product, expression product, or protein. A peptide is comprised of consecutive amino acids. The term "peptide" encompasses recombinant, naturally occurring and synthetic molecules.

In addition, as used herein, the term "peptide" refers to amino acids joined to each other by peptide bonds or modified peptide bonds, e.g., peptide isosteres, etc. and may contain modified amino acids other than the 20 gene-encoded amino acids. The peptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given peptide. Also, a given peptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W. H. Freeman and Company, New York (1993); Posttranslational Covalent Modification of Proteins, B. C. Johnson, Ed., Academic Press, New York, pp. 1-12 (1983)).

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders associated with Bcr-Abl prior to the administering step. In some aspects of the disclosed method, the subject has been diagnosed with a need for inhibiting Bcr-Abl prior to the administering step. In some aspects of the disclosed method, the subject has been diagnosed with a need for treatment of a cancer. Typically, "subjects" are animals, including mammals such as humans and primates and the like.

By "treat" is meant to administer a compound or molecule of the invention to a subject, such as a human or other mammal (for example, an animal model), that has an increased susceptibility for developing a hyperproliferative disorder, or that has a hyperproliferative disorder, in order to prevent or delay a worsening of the effects of the disease or condition, or to partially or fully reverse the effects of the disease. For example, the hyperproliferative disorder can be cancer.

As used herein, the term "treatment" refers to the medical management of a patient with the intent to cure, ameliorate, stabilize, or prevent a disease, pathological condition, or disorder, e.g. a Hyperproliferative disorder, a cancer, or a disorder associated with Bcr-Abl. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibition of Bcr-Abl" means having been subjected to a physical examination by a person of skill, for example, a physician, and found to have a condition that can be diagnosed or treated by a compound, peptide, or composition that can inhibit Bcr-Abl. As a further example, "diagnosed with a need for inhibition of Bcr-Abl" refers to having been subjected to a physical examination by a person of skill, for example, a physician, and found to have a condition characterized by Bcr-Abl activity. Such a diagnosis can be in reference to a disorder, such as a hyperproliferative disorder, and the like, as discussed herein. For example, the term "diagnosed with a need for inhibition of Bcr-Abl activity" refers to having been subjected to a physical examination by a person of skill, for example, a physician, and found to have a condition that can be diagnosed or treated by inhibition of Bcr-Abl activity. For example, "diagnosed with a need for treatment of one or more hyperproliferative disorders associated with Bcr-Abl" means having been subjected to a physical examination by a person of skill, for example, a physician, and found to have one or more hyperproliferative disorders associated with Bcr-Abl.

As used herein, the phrase "identified to be in need of treatment for a disorder," or the like, refers to selection of a subject based upon need for treatment of the disorder. For example, a subject can be identified as having a need for treatment of a disorder (e.g., a disorder related to Bcr-Abl activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide and a cell, target Bcr-Abl, or other biological entity together in such a manner that the compound can affect the activity of the target (e.g., protein, cell, etc.), either directly; i.e., by interacting with the target itself, or indirectly; i.e., by interacting with another molecule, co-factor, factor, or protein on which the activity of the target is dependent.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neo-pentyl, hexyl, heptyl, octyl, nonyl, decyl, dodecyl, tetradecyl, hexadecyl, eicosyl, tetracosyl, and the like. It is understand that the alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. PEPTIDES

Disclosed are peptides comprising a Bcr coiled-coil domain.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety.

Disclosed are peptides comprising, a Bcr-Abl coiled-coil oligomerization domain comprising the sequence of SEQ ID NO:4, SEQ ID NO:5, or SEQ ID NO:6; or active fragments thereof; wherein the Bcr-Abl coiled-coil oligomerization domain comprises at least one alpha helix stabilizing moiety.

Disclosed are peptides comprising, a Bcr-Abl coiled-coil oligomerization domain comprising the sequence of SEQ ID NO:6; or active fragments thereof; wherein the Bcr-Abl coiled-coil oligomerization domain comprises at least one alpha helix stabilizing moiety.

Also disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide.

Also disclosed are peptides comprising, a Bcr-Abl coiled-coil oligomerization domain comprising the sequence of SEQ ID NO:4, SEQ ID NO:5, or SEQ ID NO:6; or active fragments thereof; wherein the Bcr-Abl coiled-coil oligomerization domain comprises at least one alpha helix stabilizing moiety; and wherein the peptide comprises a cell-penetrating peptide.

Also disclosed are peptides comprising, a Bcr-Abl coiled-coil oligomerization domain comprising the sequence of SEQ ID NO:6; or active fragments thereof; wherein the Bcr-Abl coiled-coil oligomerization domain comprises at least one alpha helix stabilizing moiety; and wherein the peptide comprises a cell-penetrating peptide.

Disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; and wherein the Bcr-Abl coiled-coil oligomerization domain comprises at least one alpha helix stabilizing moiety.

Disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein X at position 32 is E, K, R, or H; X at position 38 is C, G, A, or V; X at position 39 is K, E, D, Q, or N; X at position 41 is S, R, H, or K; X at position 45 is L, E, D, Q, or N; X at position 46 is E, K, R, or H; X at position 48 is E, R, H, or K; or X at position 60 is Q, E, D, or N; or combinations thereof; and wherein the Bcr-Abl coiled-coil oligomerization domain comprises at least one alpha helix stabilizing moiety.

Disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein X at position 38 is C; X at position 39 is E; X at position 41 is R; X at position 45 is D; X at position 48 is R; or X at position 60 is E; or combinations thereof; and wherein the Bcr-Abl coiled-coil oligomerization domain comprises at least one alpha helix stabilizing moiety.

Also disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide.

Also disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein the Bcr-Abl inhibitory activity of the Bcr-Abl coiled-coil oligomerization domain comprising the sequence of SEQ ID NO:7 is greater than that of SEQ ID NO:1; wherein X at position 32 is E, K, R, or H; X at position 38 is C, G, A, or V; X at position 39 is K, E, D, Q, or N; X at position 41 is S, R, H, or K; X at position 45 is L, E, D, Q, or N; X at position 46 is E, K, R, or H; X at position 48 is E, R, H, or K; or X at position 60 is Q, E, D, or N; or combinations thereof; wherein the Bcr-Abl coiled-coil oligomerization domain comprises at least one alpha helix stabilizing moiety; and wherein the peptide comprises a cell-penetrating peptide.

Also disclosed are peptides comprising, a Bcr-Abl coiled-coil oligomerization domain, wherein the Bcr-Abl coiled-coil oligomerization domain comprises the sequence of SEQ ID NO:7; or active fragments thereof; wherein one or more amino acid(s) of the Bcr-Abl coiled-coil oligomerization domain designated by X in SEQ ID NO:7 is an amino acid different from the corresponding amino acid of SEQ ID NO:1; wherein X at position 38 is C; X at position 39 is E; X at position 41 is R; X at position 45 is D; X at position 48 is R; or X at position 60 is E; or combinations thereof; wherein the Bcr-Abl inhibitory activity of the Bcr-Abl coiled-coil oligomerization domain comprising the sequence of SEQ ID NO:7 is greater than that of SEQ ID NO:1; wherein the Bcr-Abl coiled-coil oligomerization domain comprises at least one alpha helix stabilizing moiety; and wherein the peptide comprises a cell-penetrating peptide.

Disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety.

Disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein X at position 32 is E, K, R, or H; X at position 38 is C, G, A, or V; X at position 39 is K, E, D, Q, or N; X at position 41 is S, R, H, or K; X at position 45 is L, E, D, Q, or N; X at position 46 is E, K, R, or H; X at position 48 is E, R, H, or K; or X at position 60 is Q, E, D, or N; or combinations thereof; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety. It is understood that that position number in the foregoing refers to the corresponding or analogous sequence position in the non-truncated form of the peptide as described by SEQ ID NO:7.

Disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein X at position 38 is C; X at position 39 is E; X at position 41 is R; X at position 45 is D; X at position 48 is R; or X at position 60 is E; or combinations thereof; wherein the Bcr-Abl inhibitory activity of the Bcr-Abl coiled-coil oligomerization domain comprising the sequence of SEQ ID NO:8 is greater than that of SEQ ID NO:4; and wherein the Bcr-Abl coiled-coil oligomerization domain comprises at least one alpha helix stabilizing moiety. It is understood that that position number in the foregoing refers to the corresponding or analogous sequence position in the non-truncated form of the peptide as described by SEQ ID NO:7.

Also disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety; and wherein the peptide comprises a cell-penetrating peptide.

Also disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein X at position 32 is E, K, R, or H; X at position 38 is C, G, A, or V; X at position 39 is K, E, D, Q, or N; X at position 41 is S, R, H, or K; X at position 45 is L, E, D, Q, or N; X at position 46 is E, K, R, or H; X at position 48 is E, R, H, or K; or X at position 60 is Q, E, D, or N; or combinations thereof; wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety; and wherein the peptide comprises a cell-penetrating peptide. It is understood that that position number in the foregoing refers to the corresponding or analogous sequence position in the non-truncated form of the peptide as described by SEQ ID NO:7.

Also disclosed are peptides comprising, a Bcr-Abl coiled-coil oligomerization domain, wherein the Bcr-Abl coiled-coil oligomerization domain comprises the sequence of SEQ ID NO:8; or active fragments thereof; wherein one or more amino acid(s) of the Bcr-Abl coiled-coil oligomerization domain designated by X in SEQ ID NO:8 is an amino acid different from the corresponding amino acid of SEQ ID NO:4; wherein X at position 38 is C; X at position 39 is E; X at position 41 is R; X at position 45 is D; X at position 48 is R; or X at position 60 is E; or combinations thereof, wherein the Bcr-Abl inhibitory activity of the Bcr-Abl coiled-coil oligomerization domain comprising the sequence of SEQ ID NO:8 is greater than that of SEQ ID NO:4; wherein the Bcr-Abl coiled-coil oligomerization domain comprises at least one alpha helix stabilizing moiety; and wherein the peptide comprises a cell-penetrating peptide. It is understood that that position number in the foregoing refers to the corresponding or analogous sequence position in the non-truncated form of the peptide as described by SEQ ID NO:7.

In various aspects, the alpha helix stabilizing moiety for any of the preceding disclosed peptides is a hydrocarbon staple, an acetylenic crosslink, or a lactam bridge, or combinations thereof. In a further aspect, the alpha helix stabilizing moiety for any of the preceding disclosed peptides is a hydrocarbon staple.

In a further aspect, the hydrocarbon staple is in the i, i+3; i, 1+4; or i, i+7 configuration; wherein i is at any amino acid position from 28-69, 28-68, or 28-65 for the i, i+3; i, i+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, i+3; i+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein the hydrocarbon staple has the structure:

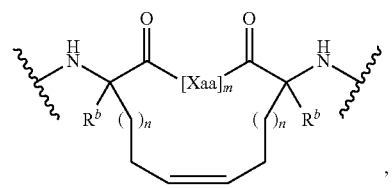

wherein m is 2, 3, or 6; wherein n is an integer between 1 and 10, inclusive; wherein $R^b$ is independently H or methyl; and wherein $[Xaa]_m$ represents 2, 3, or 6 contiguous amino acids of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 when m is 2, 3, or 6, respectively.

In a further aspect, the hydrocarbon staple is in the i, i+3; i, 1+4; or i, i+7 configuration; wherein i is at any amino acid position from 28-69, 28-68, or 28-65 for the i, i+3; i, i+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, 1+3; i+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein the hydrocarbon staple has the structure:

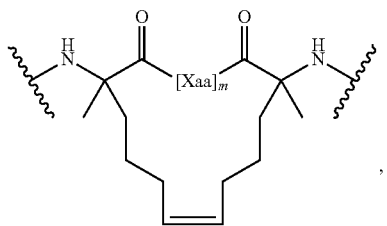

wherein m is 2, 3, or 6; and wherein [Xaa]$_m$ represents 2, 3, or 6 contiguous amino acids of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 when m is 2, 3, or 6, respectively.

In a further aspect, m is 2. In a still further aspect, m is 3. In a yet further aspect, m is 6.

In various aspects, m is 6; and i, i+7 corresponds to amino acid positions 29 and 36; 30 and 37; 33 and 40; 36 and 43; 37 and 44; 40 and 47; 44 and 51; 50 and 57; or 57 and 64 of SEQ ID NO:1, SEQ ID NO:2, SEQ ID NO:3, or SEQ ID NO:7, or non-overlapping combinations thereof.

In various aspects, m is 6; and i, i+7 corresponds to amino acid positions 2 and 9; 3 and 10; 6 and 13; 9 and 16; 10 and 17; 13 and 20; 17 and 24; 23 and 30; or 30 and 37 of SEQ ID NO:4, SEQ ID NO:5, SEQ ID NO:6; or SEQ ID NO:8, or non-overlapping combinations thereof. It is understood that these positions correspond to analogous or similar positions 29 and 36; 30 and 37; 33 and 40; 36 and 43; 37 and 44; 40 and 47; 44 and 51; 50 and 57; or 57 and 64 of SEQ ID NO:1, SEQ ID NO:2, SEQ ID NO:3, or SEQ ID NO:7, or non-overlapping combinations thereof, of SEQ ID NO:7.

In a further aspect, the peptide comprising a Bcr-Abl coiled-coil oligomerization domain and comprising at least one alpha helix stabilizing moiety in the i, i+7 configuration has the structure:

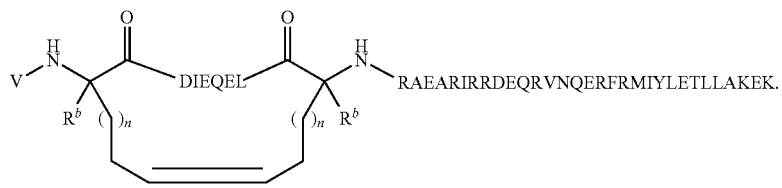

In a further aspect, the peptide comprising a Bcr-Abl coiled-coil oligomerization domain and comprising at least one alpha helix stabilizing moiety in the i, i+7 configuration has the structure:

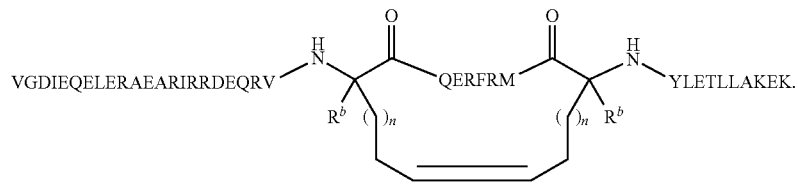

In a further aspect, the peptide comprising a Bcr-Abl coiled-coil oligomerization domain and comprising at least one alpha helix stabilizing moiety in the i, i+7 configuration has the structure:

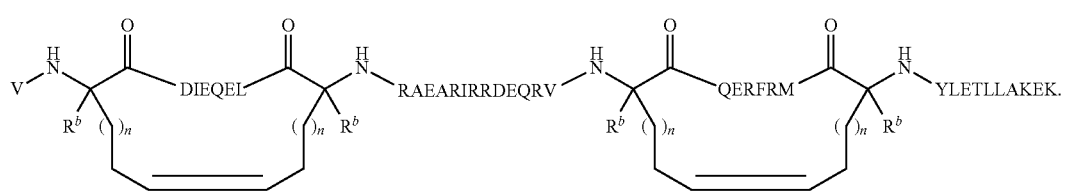

In various further aspects, the disclosed peptide, e.g. any of the preceding peptides described herein above, further comprises a cell-penetrating peptide. In a further aspect, the cell-penetrating peptide comprises the peptides of any of SEQ ID NO:9-SEQ ID NO:23. In a still further aspect, the cell-penetrating peptide comprises the peptides of SEQ ID NO:9 or SEQ ID NO:10. In a yet further aspect, the cell-penetrating peptide comprises the peptide of SEQ ID NO:9. In an even further aspect, the cell-penetrating peptide comprises the peptide of SEQ ID NO:10.

In a further aspect, the cell penetrating peptide is linked to the Bcr-Abl coiled-coil oligomerization domain. In some aspects, the cell-penetrating peptide is linked the N-terminus of the Bcr-Abl coiled-coil oligomerization domain. In alternative aspects, the cell-penetrating peptide is linked the C-terminus of the Bcr-Abl coiled-coil oligomerization domain.

In a further aspect, the peptide comprising the Bcr-Abl coiled-coil oligomerization domain, the alpha helix stabilizing moiety, and the cell-penetrating peptide shows enhanced cell internalization compared to the corresponding peptide without the cell-penetrating peptide. In the yet further aspect, comparative cell internalization is determined via FACS analysis of the peptide comprising a fluorescent label.

In various aspects, the disclosed peptides of the present invention are capable of triggering apoptosis. In a further aspect, the peptide has triggers apoptosis at a lower concentration compared to a peptide with SEQ ID NO:1. In a still further aspect, apoptosis is determined using an annexin V-based assay.

In various aspects, the disclosed peptides of the present invention retain Bcr-Abl binding activity. Although binding affinities and binding constants can be determined by a multitude of methods known to one skilled in the art, a preferred method is using a surface plasmon resonance assay. In a further aspect, preferred disclosed peptides of the present invention have a binding constant for Bcr-Abl about the same as the binding constant determined for SEQ ID NO:1. In a still further aspect, aspect, preferred disclosed peptides of the present invention have a higher affinity binding constant for Bcr-Abl about the same as the binding constant determined for SEQ ID NO:1.

In various aspects, the disclosed peptides can be modified by truncation of 1, 2, 3, 4, or 5 amino acids. In a further aspect, the truncation is at the N-terminus of the peptide. In a still further aspect, the truncation is at the C-terminus of the peptide. In a yet further aspect, the truncation is at both the N-terminus and C-terminus of the peptide; and wherein the aggregate total of amino acids truncated does not exceed 5 amino acids.

It is understood that the disclosed peptides of the present invention can further comprise pharmaceutically acceptable salts and solvates of the peptide.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair, wherein the peptide comprises at least one hydrocarbon staple precursor pair in the i, 1+3; i, i+4; or i, i+7 configuration; wherein i is at any amino acid position from 28-69, 28-68, or 28-65 for the i, i+3; i, i+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, 1+3; i, 1+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, 1+3; i, i+4; or i, i+7 of the peptide sequence; and wherein each α,α-disubstituted amino acid is a α-methyl, α-alkenylglycine or α-hydro, α-alkenylglycine residue having the structure:

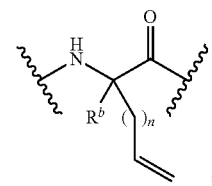

wherein n is an integer between 1 and 10, inclusive; and wherein $R^b$ is H or methyl.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair, wherein the peptide comprises at least one hydrocarbon staple precursor pair in the i, i+3; i, i+4; or i, i+7 configuration; wherein i is at any amino acid position from 28-69, 28-68, or 28-65 for the i, i+3; i, i+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, 1+3; i+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, 1+3; i, 1+4; or i, i+7 of the peptide sequence; and wherein each α,α-disubstituted amino acid having the structure:

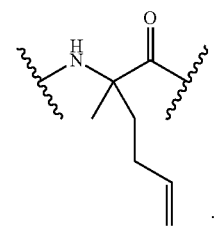 [SMILES: *NC(C)(CCC=C)C(*)=O]

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair, wherein the peptide comprises at least one hydrocarbon staple precursor pair in the i, i+7 configuration; wherein i is at any amino acid position from 28-65 for the i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-33 for the i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+7 of the peptide sequence; and wherein each α,α-disubstituted amino acid is a α-methyl, α-alkenylglycine or α-hydro, α-alkenylglycine residue having the structure:

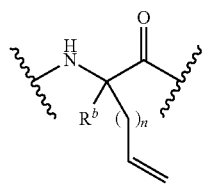

wherein n is an integer between 1 and 10, inclusive; and wherein $R^b$ is H or methyl.

Disclosed are peptides comprising, a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6; or active fragments thereof; wherein the Bcr-Abl coiled-coil oligomerization domain comprises at least one hydrocarbon staple precursor pair, wherein the peptide comprises at least one hydrocarbon staple precursor pair in the i, i+7 configuration; wherein i is at any amino acid position from 28-65 for the i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-33 for the i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+7 of the peptide sequence; and wherein each α,α-disubstituted amino acid having the structure:

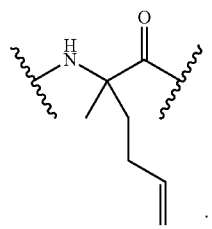

Also disclosed are the uses of the peptides described herein in the preparation of a medicament for the treatment of cancer.

C. METHODS OF MAKING PEPTIDES WITH A HYDROCARBON STAPLE

In one aspect, disclosed are methods of making a peptide comprising at least one hydrocarbon staple pair, the method comprising the step of reacting a peptide comprising at least one hydrocarbon staple precursor pair, as disclosed herein, in the presence of a catalyst for ring-closing olefin metathesis, thereby providing a peptide comprising at least one hydrocarbon staple as disclosed herein.

In a further aspect, the hydrocarbon staple precursor pair of the method comprises at least one hydrocarbon staple precursor pair in the i, i+3; i, i+4; or i, i+7 configuration; wherein i is at any amino acid position from 28-69, 28-68, or 28-65 for the i, i+3; i, 1+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, i+3; i, i+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+3; i, 1+4; or i, i+7 of the peptide sequence; and wherein each α,α-disubstituted amino acid is a α-methyl, α-alkenylglycine or α-hydro, α-alkenylglycine residue having the structure:

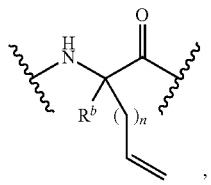

wherein n is an integer between 1 and 10, inclusive; and wherein $R^b$ is H or methyl.

In a further aspect, the hydrocarbon staple precursor pair of the method comprises at least one hydrocarbon staple precursor pair in the i, i+3; i, i+4; or i, i+7 configuration; wherein i is at any amino acid position from 28-69, 28-68, or 28-65 for the i, 1+3; i, 1+4; or i, i+7 configuration hydrocarbon staple, respectively, or the corresponding amino acid in an active fragment thereof, of SEQ ID NO:1, SEQ ID NO:2, SEQ ID NO:3, or SEQ ID NO:7; wherein i is at any amino acid position from 1-37, 1-38, or 1-33 for the i, i+3; i, i+4; or i, i+7 configuration hydrocarbon staple, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+3; i, i+4; or i, i+7 of the peptide sequence; and wherein each α,α-disubstituted amino acid has the structure:

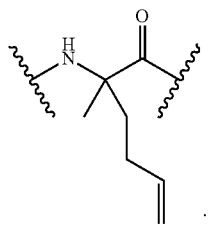 [SMILES: *NC(C)(CCC=C)C(*)=O]

In a further aspect, the hydrocarbon staple precursor pair of the method comprises at least one hydrocarbon staple precursor pair in the i, i+7 configuration; wherein i is at any amino acid position from 28-65, respectively, or the corresponding amino acid in an active fragment thereof, of SEQ ID NO:1, SEQ ID NO:2, SEQ ID NO:3, or SEQ ID NO:7;

wherein i is at any amino acid position from 1-33, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+7 of the peptide sequence; and wherein each α,α-disubstituted amino acid is a α-methyl, α-alkenylglycine or α-hydro, α-alkenylglycine residue having the structure:

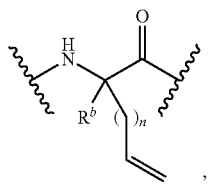

wherein n is an integer between 1 and 10, inclusive; and wherein $R^b$ is H or methyl.

In a further aspect, the hydrocarbon staple precursor pair of the method comprises at least one hydrocarbon staple precursor pair in the i, i+7 configuration; wherein i is at any amino acid position from 28-65, respectively, or the corresponding amino acid in an active fragment thereof, of SEQ ID NO:1, SEQ ID NO:2, SEQ ID NO:3, or SEQ ID NO:7; wherein i is at any amino acid position from 1-33, respectively, or the corresponding amino acid in an active fragment thereof, of SEQ ID NO:4, SEQ ID NO:5, SEQ ID NO:6; or SEQ ID NO:8; wherein a pair α,α-disubstituted amino acids replace the amino acids at the i, i+7 of the peptide sequence; and wherein each α,α-disubstituted amino acid has the structure:

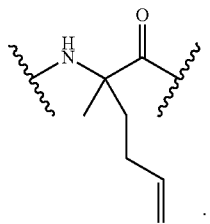 [SMILES: *NC(C)(CCC=C)C(*)=O]

In various aspects, the catalyst for ring-closing olefin metathesis is a Schrock catalyst or Grubbs' catalyst. In a still further aspect, the catalyst for ring-closing olefin metathesis is a Grubbs' catalyst.

D. NUCLEIC ACID SEQUENCES

Disclosed are nucleic acid sequences capable of encoding the peptides disclosed herein. Also disclosed are isolated nucleic acid sequences capable of encoding one or more of the peptides described herein. Nucleic acid sequences can comprise DNA, RNA, and/or cDNA.

Disclosed are nucleic acid sequences capable of encoding a peptide comprising a Bcr coiled-coil domain. In a further aspect, the present invention relates to nucleic acid sequences capable of encoding the peptides of any of SEQ ID NO:4, SEQ ID NO:5, or SEQ ID NO:6; or active fragments thereof. In a still further aspect, the present invention relates to vectors comprising the nucleic acid sequences capable of encoding the peptides of any of SEQ ID NO:4, SEQ ID NO:5, or SEQ ID NO:6; or active fragments thereof. In a yet further aspect, the vectors of the present invention are operably linked to a promoter. In some aspects, the vector is an inducible promoter. In alternative aspects, the vector is constitutive promoter.

In various aspects, the present invention relates to nucleic acid sequences capable of encoding the peptides of any of SEQ ID NO:4, SEQ ID NO:5, or SEQ ID NO:6; or active fragments thereof, wherein the nucleic acid sequence further comprises a nucleic acid sequence capable of encoding the peptides of SEQ ID NO:9-SEQ ID NO:23.

Also disclosed are the uses of the nucleic acid sequences described herein in the preparation of a medicament for the treatment of cancer.

E. VECTORS

Disclosed are vectors comprising the nucleic acids disclosed herein. For example, disclosed are vectors comprising a nucleic acid sequence, wherein the nucleic acid sequence is capable of encoding a peptide comprising a Bcr coiled-coil domain.

Also disclosed are vectors comprising a nucleic acid sequence, wherein the nucleic acid sequence is capable of encoding a peptide comprising a Bcr coiled-coil domain, wherein the Bcr coiled-coil domain is linked to the C' terminus of a cell-penetrating peptide sequence.

Also disclosed are vectors comprising a nucleic acid sequence, wherein the nucleic acid sequence is capable of encoding a peptide comprising a Bcr coiled-coil domain, wherein the Bcr coiled-coil domain is linked to the N' terminus of a cell-penetrating peptide sequence.

1. Viral and Non-Viral Vectors

The vectors disclosed herein can be viral or non-viral vectors. For example, the disclosed vectors can be viral vectors. Specifically, the disclosed vectors can be adenoviral vectors.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., *Science,* 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes or gene fragments into cells (e.g., a plasmid), or as part of a general strategy to deliver genes or gene fragments, e.g., as part of recombinant retrovirus or adenovirus (Ram et al. Cancer Res. 53:83-88, (1993)). For example, disclosed herein are expression vectors comprising a nucleic acid sequence capable of encoding one or more of the disclosed peptides operably linked to a control element.

The "control elements" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters (e.g., beta actin promoter). The early and late promoters of the SV40 virus are conveniently obtained as an SV40 restriction fragment, which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Additionally, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Optionally, the promoter or enhancer region can act as a constitutive promoter or enhancer to maximize expression of the polynucleotides of the invention. In certain constructs the promoter or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a marker product. This marker product is used to determine if the gene has been delivered to the cell and once delivered is being expressed. Preferred marker genes are the E. coli lacZ gene, which encodes β-galactosidase, and the gene encoding the green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, plasmid or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol., 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

F. COMPOSITIONS

Disclosed are compositions comprising one or more of the peptides or nucleic acid sequences described herein.

1. Compositions Comprising Peptides

Disclosed are compositions comprising a peptide comprising a Bcr coiled-coil domain.

Also disclosed are compositions comprising a peptide comprising a Bcr coiled-coil domain and further comprising an anti-cancer agent. For example, the anti-cancer agent can comprise paclitaxel. In some instances, the composition can further comprise carboplatin. Anti-cancer agents can include, but are not limited to, paclitaxel, carboplatin or a combination thereof. Anti-cancer agents are compounds useful in the treatment of cancer. Examples of anti-cancer agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-II (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CBl-TMl); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine (ELDISEME®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosf amide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

2. Compositions Comprising Nucleic Acid Sequences

Disclosed are compositions comprising a nucleic acid sequence, wherein the nucleic acid sequence is capable of encoding a peptide comprising a Bcr coiled-coil domain. In a further aspect, the nucleic acid is capable of encoding the peptides of any of SEQ ID NO:4, SEQ ID NO:5, SEQ ID NO:6, SEQ ID NO:7, or SEQ ID NO:8; or active fragments thereof.

In various aspects, the compositions comprise a vector comprising a nucleic acid sequence, wherein the nucleic acid sequence is capable of encoding a peptide comprising a Bcr coiled-coil domain. In a further aspect, the vector comprises nucleic acid is capable of encoding the peptides of any of SEQ ID NO:4, SEQ ID NO:5, SEQ ID NO:6, SEQ ID NO:7, or SEQ ID NO:8; or active fragments thereof. In a still further aspect, the vector comprises the nucleic acid operably linked to a promoter. In a yet further aspect, the vector comprises the nucleic acid operably linked to an inducible promoter. In an even further aspect, the vector comprises the nucleic acid operably linked to a constitutive promoter.

G. PHARMACEUTICAL COMPOSITIONS

In one aspect, the present invention relates to pharmaceutical compositions comprising any of the disclosed peptides described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides, nucleic acids, vectors and/or antibodies described herein can be used to produce a composition which can also include a carrier such as a pharmaceutically acceptable carrier. For example, disclosed are pharmaceutical compositions, comprising the peptides disclosed herein, and a pharmaceutically acceptable carrier. In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the invention also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, solvate, or polymorph thereof, a hydrate thereof, a solvate thereof, a polymorph thereof, or a stereochemically isomeric form thereof. In a further aspect, a disclosed compound, a product of a disclosed method of making, a pharmaceutically acceptable salt, solvate, or polymorph thereof, a hydrate thereof, a solvate thereof, a polymorph thereof, or a stereochemically isomeric form thereof, or any subgroup or combination thereof may be formulated into various pharmaceutical forms for administration purposes.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the disclosed compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The disclosed compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Thus, the pharmaceutical compositions of this invention can include a pharmaceutically acceptable carrier and a compound or a pharmaceutically acceptable salt of the compounds of the invention. By "pharmaceutically acceptable" is meant a material or carrier that would be selected to minimize any degradation of the active ingredient and to minimize any adverse side effects in the subject, as would be well known to one of skill in the art. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Because of the ease in administration, oral administration is preferred, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a peptide of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require positive allosteric modulation of metabotropic glutamate receptor activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

As already mentioned, the invention relates to a pharmaceutical composition comprising a therapeutically effective amount of a disclosed compound, a product of a disclosed method of making, a pharmaceutically acceptable salt, solvate, or polymorph thereof, a hydrate thereof, a solvate thereof, a polymorph thereof, and a pharmaceutically acceptable carrier. Additionally, the invention relates to a process for preparing a such pharmaceutical composition, characterized in that a pharmaceutically acceptable carrier is intimately mixed with a therapeutically effective amount of a compound according to the invention.

As already mentioned, the invention also relates to a pharmaceutical composition comprising a disclosed peptide, a pharmaceutically acceptable salt, solvate, or polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present invention also relates to a combination of disclosed peptides, a pharmaceutically acceptable salt, solvate, or polymorph thereof, and an anti-cancer therapeutic agent. In various further aspects, the present invention also relates to a combination of disclosed peptides, a pharmaceutically acceptable salt, solvate, or polymorph thereof, and an inhibitor of the kinase domain of Bcr-Abl. The present invention also relates to such a combination for use as a medicine. The present invention also relates to a product comprising (a) a disclosed peptide, a pharmaceutically acceptable salt, solvate, or polymorph thereof, and (b) an inhibitor of the kinase domain of Bcr-Abl, as a combined preparation for simultaneous, separate or sequential use in the treatment or prevention of a condition in a mammal, including a human. The different drugs of such a combination or product may be combined in a single preparation together with pharmaceutically acceptable carriers or diluents, or they may each be present in a separate preparation together with pharmaceutically acceptable carriers or diluents.

H. METHODS OF TREATING A HYPERPROLIFERATIVE DISORDER

In one aspect, disclosed are methods of treating a hyperproliferative disorder in a mammal, comprising the step of administering to the mammal an effective amount of at least one disclosed peptide. In a further aspect, the peptide administered further comprises a pharmaceutically acceptable salt or solvate thereof. In a yet further aspect, the peptide further comprises a cell-penetrating peptide.

In various aspects, the mammal the peptide is administered to is a human.

In a further aspect, the mammal has been diagnosed with a need for treatment of the disorder prior to the administering step. In a still further aspect, the method further comprises the step of identifying a mammal in need of treatment of the disorder.

In a further aspect, the hyperproliferative disorder is characterized by apoptosis, proliferation, transformative ability, gene expression profiling, or a dominant negative effect, or combinations thereof. In some aspects, the hyperproliferative disorder is a cancer. In a still further aspect, the cancer is a tumor. In a still further aspect, the tumor is a gastrointestinal stromal tumor ("GIST").

In a further aspect, the hyperproliferative disorder is a leukemia. In a still further aspect, the leukemia is chronic myelogenous leukemia. In a yet further aspect, the leukemia is a Philadelphia chromosome positive leukemia. In an even further aspect, the Philadelphia chromosome leukemia comprises a mutation in the kinase domain in the Bcr-Abl gene. In some aspects, the mutation in the kinase domain in the Bcr-Abl gene is a single mutation. In alternative aspects, the mutation in the kinase domain in the Bcr-Abl gene comprises at mutations at least at two positions in the gene. In a further aspect, when the mutation comprises at least two positions in the gene, it results in a mutation to at least two codons of the gene.

In various aspects, the Philadelphia chromosome positive leukemia comprises a mutation selected from H201L, Y232S, M237V, I242T, M244V, L248V, del248-274, G250E, G250V, Q252H, Y253F, Y253H, E255K, E255V, E258D, L273M, D276G, E279K, E281X, V289I, E292V, L298V, V299L, F311I, F311L, T315I, F317L, Y342H, M351T, E355G, F359C, F359I, F359V, D363Y, L364I, A365V, A366G, V379I, L384M, L387M, M388L, Y393C, H396P, H396R, A397P, S417Y, I418S, I418V, S438C, P441L, E450A, E450G, E450K, E450V, E453K, E453V, E459G, E459K, M472I, P480L, F486S, D504D, G514S, T240T, K247R, F311V, and E499E. In a further aspect, the Philadelphia chromosome positive leukemia comprises a T315I mutation.

In a further aspect, the Philadelphia chromosome positive leukemia comprises a mutation that results in the leukemia being refractory to treatment with a Bcr-Abl tyrosine kinase inhibitor. In a still further aspect, the Philadelphia chromosome positive leukemia comprises a mutation that results in the leukemia being refractory to treatment with a Bcr-Abl tyrosine kinase inhibitor is selected from bafetinib, bosutinib, dasatinib, imatinib, nilotinib, ponatinib, rebastinib, saracatinib, and tozasertib. In a yet further aspect, the Philadelphia chromosome positive leukemia comprises a mutation that results in the leukemia being refractory to treatment with imatinib. In an even further aspect, the Philadelphia chromosome positive leukemia comprises a mutation that results in the leukemia being refractory to treatment with dasatinib. In a still further aspect, the Philadelphia chromosome positive leukemia comprises a mutation that results in the leukemia being refractory to treatment with ponatinib.

In various aspects, the patient has been diagnosed with a Philadelphia chromosome positive leukemia that is refractory to treatment with a Bcr-Abl tyrosine kinase inhibitor. In a further aspect, the method further comprises identifying a patient with a Philadelphia chromosome positive leukemia that is refractory to treatment with a Bcr-Abl tyrosine kinase inhibitor.

In a further aspect, the method further comprises administration of a Bcr-Abl tyrosine kinase inhibitor. In some aspects, when the method further comprises administration of a Bcr-Abl tyrosine kinase inhibitor, the Bcr-Abl tyrosine kinase inhibitor is co-administered with the peptide. Alternatively, in alternative aspects, when the method further comprises administration of a Bcr-Abl tyrosine kinase inhibitor, the Bcr-Abl tyrosine kinase inhibitor is administered in a first period, and the peptide is administered in a second period. In a yet further alternative, when the method further comprises administration of a Bcr-Abl tyrosine kinase inhibitor, the Bcr-Abl tyrosine kinase inhibitor is administered in a first period, and the peptide is co-administered with the Bcr-Abl tyrosine kinase inhibitor in a second period.

The Bcr-Abl tyrosine kinase inhibitor that can be used with the present method is selected from bafetinib, bosutinib, dasatinib, imatinib, nilotinib, ponatinib, rebastinib, saracatinib, and tozasertib. In a further aspect, Bcr-Abl tyrosine kinase inhibitor that can be used with the present method is imatinib. In a still further aspect, Bcr-Abl tyrosine kinase inhibitor that can be used with the present method is dasatinib. In a yet further aspect, Bcr-Abl tyrosine kinase inhibitor that can be used with the present method is ponatinib.

In various aspects, co-administration of ponatinib and the peptide allows a decreased effective dose of ponatinib to be utilized, thus allowing for an improved side effect profile with ponatinib.

In a further aspect, the method further comprises administration of hormone therapy agent. In a still further aspect, the method further comprises administration of hormone therapy agent selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone.

In various aspects, the method further comprises administration of a chemotherapeutic agent selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the method further comprises administration of an antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin.

In a further aspect, the method further comprises administration of an antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine.

In a further aspect, the method further comprises administration of an alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin.

In a further aspect, the method further comprises administration of a mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide.

In a further aspect, the method further comprises administration of an mTor inhibitor agent is selected from one or more of the group consisting of everolimus, siroliumus, and temsirolimus.

Disclosed are methods of treating a hyperproliferative disorder in a patient comprising administering to the patient a composition comprising a disclosed peptide, wherein the hyperproliferative disorder is characterized by apoptosis, proliferation, transformative ability, gene expression profiling, and dominant negative effect.

Hyperproliferative disorders can include cancer and non-cancer hyperproliferative disorders. Cancers include, but are not limited to brain, lung, squamous cell, bladder, gastric, pancreatic, breast, head, neck, renal, kidney, ovarian, prostate, colorectal, endometrial, esophageal, testicular, gynecological and thyroid cancer. Non-cancer hyperproliferative disorders include, but are not limited to, benign hyperplasia of the skin (e.g., psoriasis), restenosis, or prostate (e.g., benign prostatic hypertrophy (BPH)), age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, an immunoproliferative disease or disorder, e.g., inflammatory bowel disease, rheumatoid arthritis, systemic lupus erythematosus (SLE), vascular hyperproliferation secondary to retinal hypoxia, or vasculitis.

Disclosed are methods of treating a hyperproliferative disorder in a patient comprising administering to the patient a composition comprising a peptide, wherein the peptide comprises a disclosed peptide, wherein the hyperproliferative disorder comprises cancer. For example, the cancer can comprise, but is not limited to, breast cancer, triple negative breast cancer, ovarian cancer, or any blood cancer.

I. METHODS OF SUPPRESSING TUMOR ACTIVITY

Disclosed are methods for suppressing tumor activity in a patient comprising administering one or more of the compositions disclosed herein.

Disclosed are methods for suppressing tumor activity in a patient comprising administering to the patient a composition comprising a peptide, wherein the peptide comprises at least one disclosed peptide, wherein tumor activity is measured by apoptosis, proliferation, transformative ability, gene expression profiling, and dominant negative effect.

Disclosed are methods for suppressing tumor activity in a patient comprising administering to the patient a composition comprising a peptide, wherein the peptide comprises at least one disclosed peptide, wherein the tumor comprises breast cancer, triple negative breast cancer, ovarian cancer or any blood cancer.

J. METHODS OF INHIBITING BCR-ABL ACTIVITY IN A MAMMAL

Disclosed are methods of inhibiting Bcr-Abl activity in a mammal, comprising the step of administering to the mammal an effective amount of at least one disclosed peptide. In a further aspect, the peptide further comprises a pharmaceutically acceptable salt or solvate thereof. In a still further aspect, the peptide comprises a cell-penetrating peptide. In various further aspects, the mammal is human. In a yet further aspect, the mammal has been diagnosed with a need for inhibiting Bcr-Abl activity prior to the administering step. In a still further aspect, the method further comprises the step of identifying a mammal in need of inhibiting Bcr-Abl activity.

K. METHODS OF TREATING CANCER

Disclosed are methods of treating cancer comprising administering to a patient one or more of the compositions disclosed herein.

Disclosed are methods of treating cancer comprising administering to a patient a composition comprising a disclosed peptide, wherein the composition further comprises an anti-cancer agent. For example, the anti-cancer agent can comprise paclitaxel, carboplatin or a combination thereof. Anti-cancer agents are compounds useful in the treatment of cancer. Examples of anti-cancer agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-II (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CBl-TMl); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosf amide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammall and calicheamicin omegall (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®), morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine (ELDISEME®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELB AN®); platinum; etoposide (VP-16); ifosf amide; mitoxantrone; vincristine (ONCOVIN®); oxaliplatin; leucovovin; vinorelbine (NAVELBINE®; novantrone; edatrexate; daunomycin; aminopterin; ibandronate; topoisomerase inhibitor RFS 2000; difluorometlhylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

In some instances, the peptide, as disclosed herein, is in a separate composition from an anti-cancer agent. For example, disclosed are methods of treating cancer comprising administering to a patient a first composition comprising the disclosed peptide and a second composition comprising an anti-cancer agent. The first composition can be one or more of the compositions disclosed herein. The first and second compositions can be administered together or consecutively. Administering the compositions together includes mixing the two compositions just prior to administration. Administering together also includes administering the separate compositions within one, two, three, four, five, six, seven, eight, nine or ten minutes of each other. Consecutive administration refers to administering the compositions at separate times greater than 10 minutes apart. For example, consecutive administration includes administering one composition at least 10, 15, 20, 25, 30, 60, 120 minutes after the administration of the other composition. In some instances, one composition can be administered 1, 2, 3, 4, 5, 6, 7, 8, 9, 10, 15, 20, 24 hours after administration of the other composition. In some instances, one composition can be administered 1, 2, 3, 4, 5, 6, 7, 8, 9, 10, 11, 12, 13, 14, 21, 28, 29, 30, or 31 days after administration of the other composition. In some instances, one composition can be administered 1, 2, 3, 4, 5, 6, 7, 8, 9, 10, 11, or 12 months after administration of the other composition.

L. INHIBITING BCR-ABLE ACTIVITY IN AT LEAST ONE CELL

In one aspect, disclosed herein methods of inhibiting Bcr-Abl activity in at least one cell, comprising the step of contacting the cell with an effective amount of at least one disclosed peptide. In a further aspect, the peptide contacting the cell further comprises a pharmaceutically acceptable salt or solvate thereof. In a still further aspect, the peptide contacts a mammalian cell. In a yet further aspect, the peptide contacts a human cell.

In various aspects, contacting the cell is via administration of the peptide to a mammal. In a further aspect, contacting the cell is via administration of the peptide to a mammal, and the mammal has been diagnosed with a need for inhibiting Bcr-Abl activity prior to the administering step. In a still further aspect, the method further comprises contacting the cell via administration to a mammal, and further comprising the step of identifying a mammal in need of inhibiting Bcr-Abl activity.

M. CELLS

Also disclosed herein are host cells transformed or transfected with a vector comprising the nucleic acid sequences described elsewhere herein. Also disclosed are host cells comprising the vectors described herein. For example, disclosed is a host cell comprising a vector comprising the nucleic acid sequences described elsewhere herein, operably linked to a control element. Host cells can be eukaryotic or prokaryotic cells. For example, a host cell can be a mammalian cell. Also disclosed are recombinant cells comprising the disclosed nucleic acid sequences or peptides. Further disclosed are recombinant cells producing the disclosed peptides.

Disclosed are recombinant cells comprising one or more of the nucleic acid sequences disclosed herein. In a further aspect, the nucleic acid is capable of producing the peptide of SEQ ID NO:4, SEQ ID NO:5, SEQ ID NO:6, SEQ ID NO:7, or SEQ ID NO:8.

In a further aspect, the recombinant cell is mammalian. In a still further aspect, the recombinant cell is of insect origin. In a yet further aspect, the recombinant cell is a bacterial or yeast cell.

N. TRANSGENICS

Disclosed are transgenic, non-human subjects comprising the nucleic acid sequences disclosed herein which are capable of encoding the peptides disclosed herein. For example, disclosed are transgenic, non-human subjects comprising a nucleic acid sequence, wherein the nucleic acid sequence is capable of encoding a disclosed peptide.

O. ANTIBODIES

Disclosed are antibodies that specifically bind to any of the disclosed peptides herein. In various aspects, the antibodies are polyclonal antibodies. In a further aspect, the antibodies are monoclonal antibodies.

P. KITS

In one aspect, the present invention relates to kits comprising at least one disclosed. The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing vectors, the kit comprising any of the disclosed nucleic acid sequences. The kits also can contain a viral vector.

In a further aspect, the peptide in the kit further comprises a pharmaceutically acceptable salt or solvate thereof. In a still further aspect, the peptide comprises a cell-penetrating peptide.

In various aspects, the kit can further comprises additional components. For example, in a further aspect, the kit can further comprise at least one agent known to increase Bcr-Abl activity. For example, it can be clinically useful when treating a subject with an agent that increases Bcr-Abl activity, e.g. as a side effect of the desired clinical activity of the agent, to package the agent in a kit with a disclosed peptide, which can help to ameliorate the effects of the agent by inhibiting the side effect or unintended effect of increasing Bcr-Abl activity. In a still further aspect, the kit further comprises at least one agent known to decrease Bcr-Abl activity. In a yet further aspect, the kit further comprises at least one agent known to treat a hyperproliferative disorder. In an even further aspect, the kit can comprise at least one Bcr-Abl tyrosine kinase inhibitor. In a still further aspect, the kit can comprise instructions for treating a hyperproliferative disorder. In a yet further aspect, the kit can comprise instructions for treating a disorder associated with a Bcr-Abl dysfunction, a Philadelphia chromosome, or a Bcr-Abl mutation.

In a further aspect, the peptide is co-formulated with the agent known to increase Bcr-Abl activity, agent known to decrease Bcr-Abl activity, agent known to treat a hyperproliferative disorder, and/or Bcr-Abl tyrosine kinase inhibitor.

In a further aspect, the peptide is co-packaged with the agent known to increase Bcr-Abl activity, agent known to decrease Bcr-Abl activity, agent known to treat a hyperproliferative disorder, and/or Bcr-Abl tyrosine kinase inhibitor.

Q. NON-MEDICAL USES

Also provided are the uses of the disclosed compounds and products as pharmacological tools in the development and standardization of in vitro and in vivo test systems for the evaluation of the effects of inhibitors of Bcr-Abl related activity in laboratory animals such as cats, dogs, rabbits, monkeys, rats and mice, as part of the search for new therapeutic agents of targeting Bcr-Abl.

R. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 i. General Methods a. DNA Constructs pmCherry-EV (empty vector), pmCherry-$CC^{mut3}$ and pEGFP-$CC^{mut3}$ have been described previously (Dixon, A. S., et al. (2012) *Mol. Pharm.* 9, 187-195; Dixon, A. S., et al. (2012) *Pharm. Res.* 29, 1098-1109).The lentiviral control vector pCDH-EF-copGFP-EV was adapted from pCDH-CMV-MCS-EF1-copGFP (System Biosciences (SBI), Mountain View, Calif.). The CMV promoter and MCS were excised using SpeI and XbaI with compatible cohesive ends. The CMV fragment was removed using gel purification and the resulting DNA was ligated to form the final construct.

To make pCDH-EF-copGFP-$CC^{mut3}$, sections of the construct were amplified separately by PCR and knit together using overlap extension PCR. First, EF1-copGFP was amplified from the SBI parent plasmid with a 5'SpeI and 3'BamHI site using the following primers: 5'-CAACTAG-TAAGGATCTGCGATCGCTCC-3' and 5'-ccat ctgagtccg-gagcgagatccggtggagc-3.' $CC^{mut3}$ was amplified from pEGFP-$CC^{mut3}$ (see, e.g., Dixon, A. S., et al. (2012) *Mol. Pharm.* 9, 187-195) using the following primers containing a 5'BamHI site, a terminal TAG stop signal and a sequence complimentary to the polyA signal on the 3' overhang: 5'-CTCAGATGGATCCTTATGGTGGACCCGGTGGGCT-TCG-3' and 5'-GTTATCTAGATCTACCGGT-CATAGCTCTTCTTTTCC-3'. Finally, the polyA signal from pEGFP-C1 (Clontech Laboratories, Mountain View, Calif.) was amplified to include a 5' complimentary sequence to $CC^{mut3}$, and a 3' SalI restriction site using primers 5'-GACCCGGTAGATCTAGATAACTGAT-CATAATC-3' and 5'-GCTTACATGCGG CCGCGTC-GACTGTGGGAGGTTTTTTAAAGC-3.' PCR products were combined in two steps, first by combining the $CC^{mut3}$-polyA and then by adding EF-copGFP by overlap extension PCR. The PCR product was digested with SpeI and SalI and ligated to the pCDH-CMV-MCS-EF1-copGFP vector (SBI) also cut with SpeI and SalI. psPAX2 was purchased from Cellecta, Inc. (Mountain View, Calif.), and pVSV-G was purchased from Clontech (Mountainview, Calif.).

b. Ponatinib

Ponatinib HCl salt (AP24534) was obtained from ChemieTek (Indianapolis, Ind., USA) and stored at −20° C. as a 10 mM stock solution. Serial dilutions (100 μM and 10 nM) of stock solution were made prior to cell experiments.

c. Cell Lines, Transfections, Ponatinib Treatment, and Lentivirus Generation

Cells were maintained at 37° C. and 5% $CO_2$ in a humidity-controlled incubator.

K562 Cells Treated with Ponatinib

K562 cells, human leukemia Bcr-Abl$^+$ cells (gifted from Kojo Elenitoba-Johnson, University of Michigan), were grown in RPMI 1640 media supplemented with 10% FBS, 1% penicillin-streptomycin-glutamine, and 0.1% gentamicin (complete medium). The cells were passaged every two to three days, seeded at a density of $5.0 \times 10^4$ cells/mL. Transfections were carried out two days following cell passaging. Then, $2.0 \times 10^6$ cells were collected and transfected with 6 μg pf pEGFP, pEGFP-$CC^{mut3}$, pmCherry, or pmCherry-$CC^{mut3}$ according to the Cell Line Nucleofector Kit V protocol, using the Amaxa Nucleofector II (Lonza Group, Basel, Switzerland). Immediately following transfection, cells were added to 10 mL of RPMI complete medium and treated with ponatinib at 100 pM, 1 nM, or 10 nM doses.

Ba/F3 Cells Treated with Ponatinib

Ba/F3 cells, mouse pro B cells (gifted from Michael Deininger, University of Utah) transduced to express either p210-Bcr-Abl (Ba/F3-p210) or p210-Bcr-Abl containing the T315I mutation (Ba/F3-p210-T315I), were maintained in RPMI complete medium. Parental Ba/F3 cells without Bcr-Abl (also from Deininger), used as control, were grown in RPMI 1640 complete medium supplemented with IL-3 produced in WEHI-3 cells (Lee, J. C., et al. (1982) *J. Immunol.* 128, 2393-2398). All groups of cells were passaged every two to three days, seeded at a density of $1.0 \times 10^5$ cells/mL. Transfection method (Amaxa, Kit V) included program X-001, $3.0 \times 10^6$ cells, and 4 μg of DNA per transfection. In addition, immediately following transfection, transfected cells were incubated in plain RPMI 1640 for 20 min., as per optimized conditions. Cells were then added to 10 mL of RPMI complete medium and treated with respective dose of ponatinib.

Ba/F3 Cells

Stable recombinant Ba/F3 cells transduced with wild type p210 BCR-ABL1 (Daley, G. Q., et al. (1991) *Proc. Natl. Acad. Sci. U.S.A.* 88, 11335-11338), the kinase domain mutants $p210^{T315I}$ $p210^{E255V}$, or the compound mutant $p210^{E255V/T315I}$ were as previously described (La Rosee, P., et al. (2002) *Cancer Res.* 62, 7149-7153; O'Hare, T., et al. (2004) *Blood* 104, 2532-2539). These cells were cultured in RPMI with 10% FBS, 1% penicillin, streptomycin, glutamine, and 0.1% gentamycin (RPMI1640). Additionally 0.1% MycoZap™ (Lonza Bio, Basel, Switzerland) was added to prevent mycoplasma contamination. The non-transduced parental Ba/F3 cell line was grown in RPMI1640 supplemented with 20% WEHI-3B conditioned medium as a source of murine IL-3 (Dexter, T. M., et al. (1980) *J. Exp. Med.* 152, 1036-1047). Ba/F3 cells were transfected with plasmid DNA using the Amaxa nucleofection system (Lonza Bio), following the manufacturer's instructions. Cells were sorted on a BD FACSAria cytometer (BD Biosciences, San Jose, Calif.) for double-positive cells expressing mCherry and GFP then returned to RPMI1640 for subsequent experiments.

Lentivirus Generation

293-FT cells (Life Technologies, Grand Island, N.Y.) were grown in DMEM with 10% FBS (Atlanta Biologicals, Atlanta, Ga.), 1% penicillin, streptomycin, glutamine, MEM-non-essential amino acids, and sodium pyruvate (Life Technologies). Cells were passaged every 2-3 days in T75 flasks, and grown to 65% confluence in T-175 flasks for transfection. For lentivirus generation, cells were transfected with 30 pg of the experimental construct pCDH-EF-copGFP-EV or pCDH-EF-copGFP-$CC^{mut33}$, 5 μg of VSVG and 8 μg of psPAX2 using the Profection® mammalian transfection reagent (Promega, Madison, Wis.) according to manufacturer's instructions. The DNA solution in 3 mL was then added drop-wise to T175 flasks containing 293-FT cells. After 48 h viral particles were complexed with PEG overnight, pelleted, and resuspended in RPMI1640. Lentiviral titers were determined as described (A. S. Corbin, Cancer Res; 73(18); 1-12).

d. Patient Samples and Lentivirus Infection

Mononuclear cells (MNCs) were separated from the peripheral blood of patients with newly diagnosed or therapy-resistant CML with a documented T315I mutation, using Ficoll (Nycomed, Oslo, Norway). Isolation of the CD34$^+$ fraction was done on an autoMACS Pro (Miltenyi Biotech). CD34$^+$ progenitors were maintained at $1 \times 10^6$ cells/mL in RPMI1640 containing 20% FBS and 5 μL/mL StemSpan CC100 (Stem Cell Technologies, Vancouver, BC, Canada). Cells were infected with lentivirus at a multiplicity of infection (MOI) of 5 for each construct at 24 and 48 hours following harvest (fresh cells) or thaw (frozen cells). Cells were sorted on a BD FACSAria cytometer after 72 h, and GFP-positive cells were returned to culture medium for future experiments. All patients gave their informed consent in accordance with the Declaration of Helsinki, and all studies with human specimens were approved by The University of Utah Institutional Review Board (IRB).

e. Kinase Activity (Western Blot)

Western blot was done as previously described (Dixon, A. S., et al. (2012) *Mol. Pharmaceutics* 9, 197-195). Briefly, 48 h following transfection and treatment with ponatinib, $2.0 \times 10^6$ cells were collected from each transfection and treatment group, and subjected to at least one freeze-thaw cycle at −80° C. Next, cells were lysed using RIPA buffer with protease inhibitor (1:200) added and sonicated at 70% amplitude for two pulses of 5 s each. After electrophoresis and transfer, the membrane was probed using a combination of primary antibodies against phospho-c-Abl (Cell Signaling, #2861), phospho-STATS (Abcam, ab32364 phospho-CrkL (Cell Signaling, #3181), and GADPH (Cell Signaling, #5174) as a loading control, followed by incubation with secondary HRP-conjugated antibody (Cell Signaling, #7074). Finally, blots were imaged using a FluorChem FC2 imager (AplhaInnotech) after addition of chemiluminescent substrate (WesternBright Quantum Western blotting detection kit, Advansta). Assay was performed three separate times (n=3).

f. Colony Forming Assay

Both EGFP and EGFP-CC$^{mut3}$ were transfected into separate groups of cells on day 0. One day following transfection, $1.0 \times 10^6$ cells per treatment group were collected and re-suspended in 1.0 mL of PBS. Through serial dilutions, $1.0 \times 10^3$ cells in IMDM (Isocove's modified Dulbecco's media) with 2% FBS were seeded into methylcellulose medium in the absence of cytokines (MethoCult H4230 for K562 cells and MethoCult M3234 for p210 and p210-T315I cells) or in the presence of cytokines (MethoCult GF M3434 for parental Ba/F3 cells). Ponatinib was then added in the correct molar amounts (0, 100 pM, 1 nM, or 10 nM) to the methylcellulose medium. Colonies formed were counted after 7 days of incubation. All reagents were purchased from Stem Cell Technologies, Vancouver, BC, Canada. Assay was run three separate times (n=3) in duplicate.

g. 7AAD and Annexin V Staining

Seventy-two hours following transfection and treatment with ponatinib, 5 mL of cells from each treatment was pelleted and re-suspended in 0.5 mL of 1× Annexin Binding Buffer (Invitrogen). Next, 0.5 µL of 1 mM 7-aminoactinomycin D (Invitrogen) was added to each sample and allowed to incubate for 45 min. Five minutes before flow cytometric analysis, 1.0 µL of Annexin V (APC) (Invitrogen) was added to each sample. Analysis was performed using the FACSCantoII analyzer with BD FACSDiva software. Fluorophores were excited/emitted at the following wavelengths: EGFP, 488/530 nm; mCherry, 587/610 nm; 7AAD, 488/660 nm; and APC, 635/660 nm. Untransfected cells were eliminated from analysis by gating for cells only showing EGFP or mCherry fluorescence. Percentage of apoptosis/necrosis was calculated by combining the transfected cells (EGFP-positive or mCherry-positive) that stained positively for 7AAD and those that stained positively for APC. Assays were run in triplicate (n=3).

h. Caspase-3/7 Assay

Caspase-3/7 assay was performed as previously described (Dixon, A. S., et al. (2012) *Mol. Pharmaceutics* 9, 187-195). Briefly, 48 h following transfection and treatment with ponatinib, $3.0 \times 10^6$ cells were pelleted and frozen at $-80°$ C. After thawing, cells were re-suspended in 50 µL of EnzChek Caspase-3/7 lysis buffer (Invitrogen). Lysates were then mixed with 50 µL of 2×AMC-DEVD substrate in a 96-well plate and allowed to incubate in the dark at room temperature for 30 min. Following incubation, fluorescence was measured on a SpectraMax M2 plate reader (Molecular Devices, Sunnyvale, Calif., USA). Lysates from three separate transfections were analyzed on the same plate for caspase-3/7 activity (n=3).

i. Cell Proliferation Assay

Cell proliferation was assessed using the CellTiter 96® AQueous One Solution Cell Proliferation Assay (MTS assay, Promega) according to manufacturer instructions. Briefly, 5,000 viable cells were added to a single well in 96-well plate in 100 µL RPMI1640. Three independent samples were seeded in duplicate for each time point. Cells were allowed to grow for 3 or 4 days and read at 490 nM on a SpectraMax M2 plate reader (Molecular Devices, Sunnyvale, Calif.) 3 h after incubation with the MTS reagent. In some experiments, cell proliferation was assessed using a Neubauer chamber and trypan blue dye exclusion. TKIs imatinib (at 0 or 2.5 µM for ND CML samples) or ponatinib (at 0, 10, 25, or 50 nM for T315I CML samples) were dosed as appropriate.

Alternatively, seventy-two and 96 h following transfection of either pmCherry or pmCherry-CC$^{mut3}$, trypan blue exclusion was used to determine proliferation/viability of cells (Dixon, A. S., et al. (2012) *Mol. Pharmaceutics* 9, 187-195). Cell counts were performed using a standard light microscope.

j. Apoptosis Assay

For analysis of apoptosis and cell death, cells were pelleted and resuspended in Annexin V-binding buffer (BD Biosciences), stained with anti-Annexin V-APC (BD Biosciences or Life Technologies) and 7-AAD (BD Biosciences or Life Technologies) and analyzed on a BD FACSCanto flow cytometer. In addition to the APC and 7-AAD channels, GFP- and mCherry-positive cells were also recorded.

k. Colony Forming Assay

Following selection of transfected cells by cell sorting, viable cells were enumerated and seeded into methylcellulose as described previously (Dixon, A. S., et al. (2011) *J. Biol. Chem.* 286, 27751-27760). Briefly, mCherry-positive Ba/F3 cells were re-suspended in IMDM with 2% FBS (Stem Cell Technologies) at a concentration of 10,000 cells/mL. Three hundred microliters of this dilution was added to 3 mL of Methocult media (M3434—Ba/F3 p210 wild-type and mutant lines or M3234—Ba/F3 parental, Stem Cell Technologies). Approximately 1100 cells, or 1.2 mL, were seeded per dish in duplicate for each transfection. Colonies were counted 7 days later in an area of 100 µm$^2$ per dish.

Primary cells were seeded in Methocult H4230 (Stem Cell Technologies) as described previously (Fleischman, A. G., et al. (2011). *Blood* 118, 6392-6398). Briefly, lentivirus-infected (GFP$^+$) cells were isolated by FACS and resuspended in RPMI1640. Cells were plated in Methocult H4230 at 1,000 cells/mL supplemented with 1× StemSpan CC100 cytokine mix (StemCell Technologies) with or without TKI as indicated in each experiment. Plates were incubated at 37° C. in a 5% CO$_2$ humidified incubator for 14 days. Colony forming units of granulocyte-macrophage (CFU-GM) were counted on day 14 using an inverted microscope.

l. Statistical Analysis

Figure 7A:
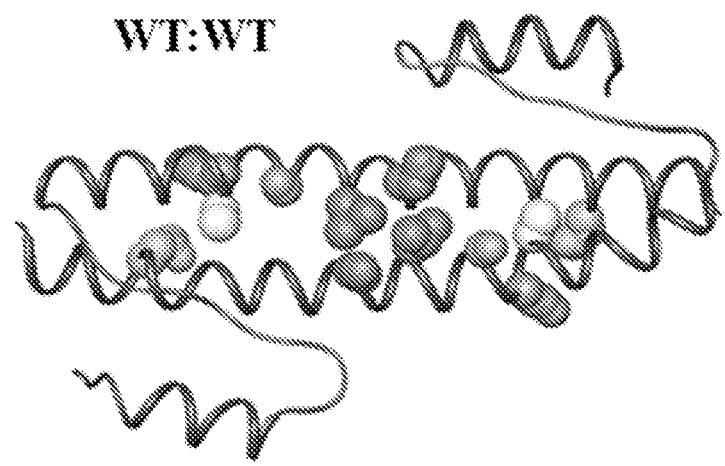
FIGS. 7A, 7B, and 7C show representative data pertaining to the design of a modified coiled-coil (CC) domain. Specifically, 7A shows a ribbon diagram of the wild type (WT) CC homo-dimer. 7B shows a ribbon diagram of the $CC^{mut3}$ homo-dimer. 7C shows a ribbon diagram of the WT-$CC^{mut3}$ heterodimer.
Figure 7B:
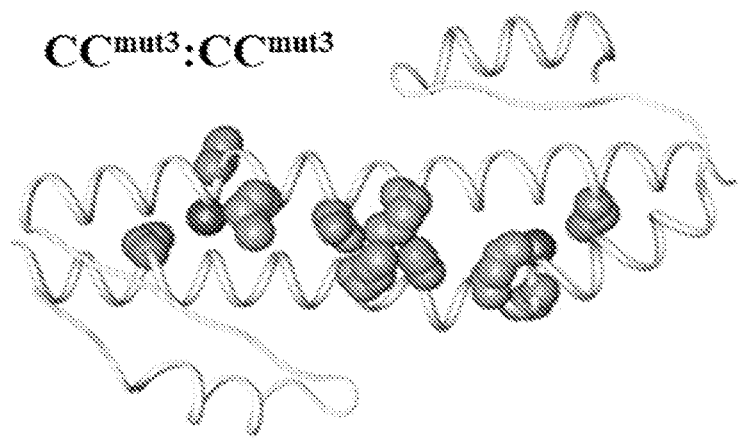
Figure 7C:
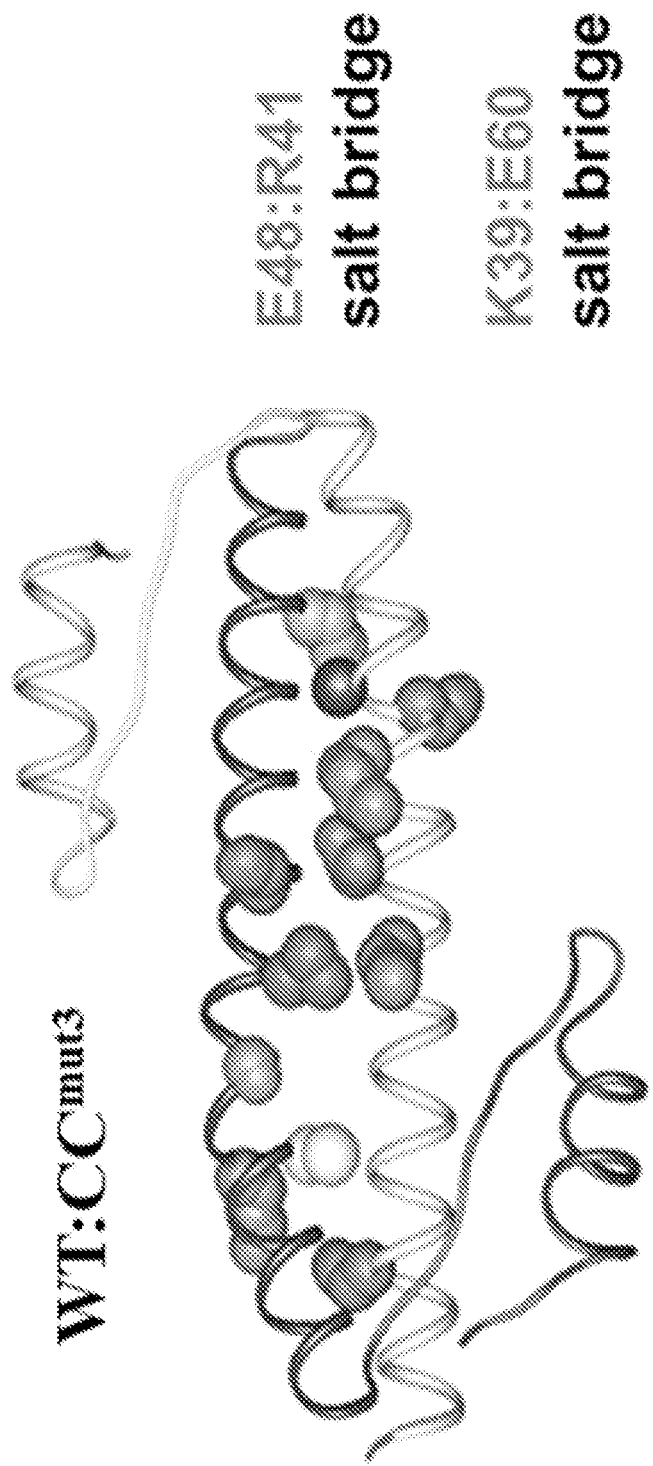

Experiments were analyzed either using one-way ANOVA with Tukey's post-test, or a Student's t test.

ii. Results m. Improved Coiled-Coil Design Enhances Interaction with Bcr-Abl and Induces Apoptosis Design of the modified coiled-coil (CC) domain (FIG. 7) focused on two underlying ideas: 1) disfavor homo-oligomerization between 2 of the mutant coiled-coil molecules (FIG. 7B); and 2) favor hetero-oligomerization between the designed CC and the Bcr-Abl CC (FIG. 7C). This design process allowed for the identification of 6 residues suitable for mutation from the wild-type Bcr-Abl CC to achieve the aforementioned criteria: K39E (disfavor the mutant homo-dimer), S41R (disfavor mutant homo-dimer and salt bridge formation in heterodimer), L45D (disfavor mutant homo-dimer), E48R (disfavor mutant homo-dimer), Q60E (disfavor mutant homo-dimer and salt bridge formation in heterodimer), and C38A (increase helicity, also for crystallization purposes). The end result was termed CC$^{mut3}$.

Figure 8A:
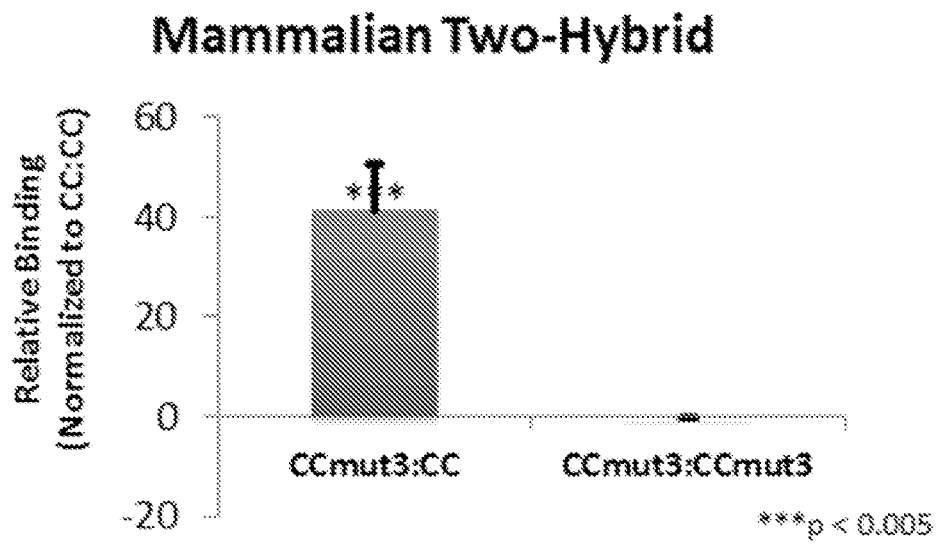
FIGS. 8A and 8B show binding ability of $CC^{mut3}$. A shows representative data demonstrating that $CC^{mut3}$ favors hetero-dimerization. B shows representative data pertaining to the ability of $CC^{mut3}$ to colocalize with WT CC in live cells.

As mentioned above, the design process of $CC^{mut3}$ involved favoring hetero-dimerization with Bcr-Abl while avoiding homo-dimerization with another $CC^{mut3}$ molecule. Thus, a mammalian two-hybrid assay was performed to measure the likelihood of each scenario, using the isolated CC domain from Bcr-Abl instead of the full-length protein (for ease of use). Referring to FIG. 8A, $CC^{mut3}$ strongly favors hetero-dimerization with BCR-ABL (left bar) while at the same time strongly disfavoring homo-oligomerization (right bar).

Figure 8B:
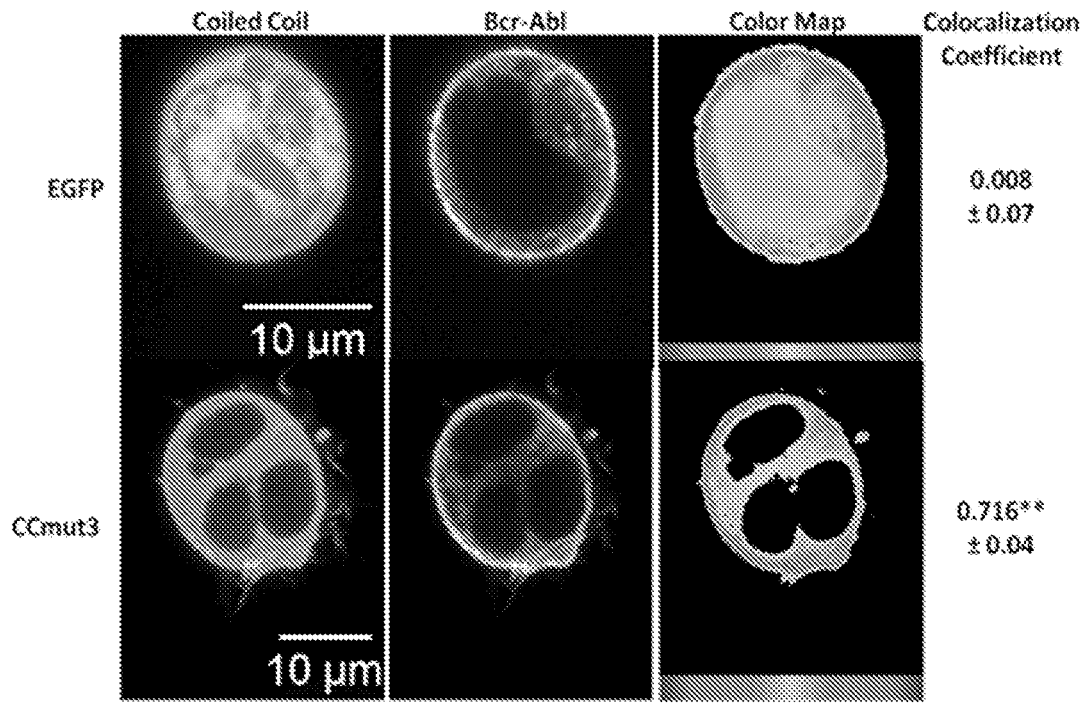

Next, the ability of $CC^{mut3}$ to bind to BCR-ABL in live cells was analyzed (FIG. 8B). Colocalization analysis was performed by co-transfecting mCherry-tagged Bcr-Abl and EGFP-tagged $CC^{mut3}$ into Cos-7 cells. The Costes' coefficient was determined, showing intracellular colocalization of $CC^{mut3}$ and BCR-ABL.

(A) CCmut3 Expression Inhibits Proliferation of Bcr-Abl1-Expressing Cells

Figure 9:
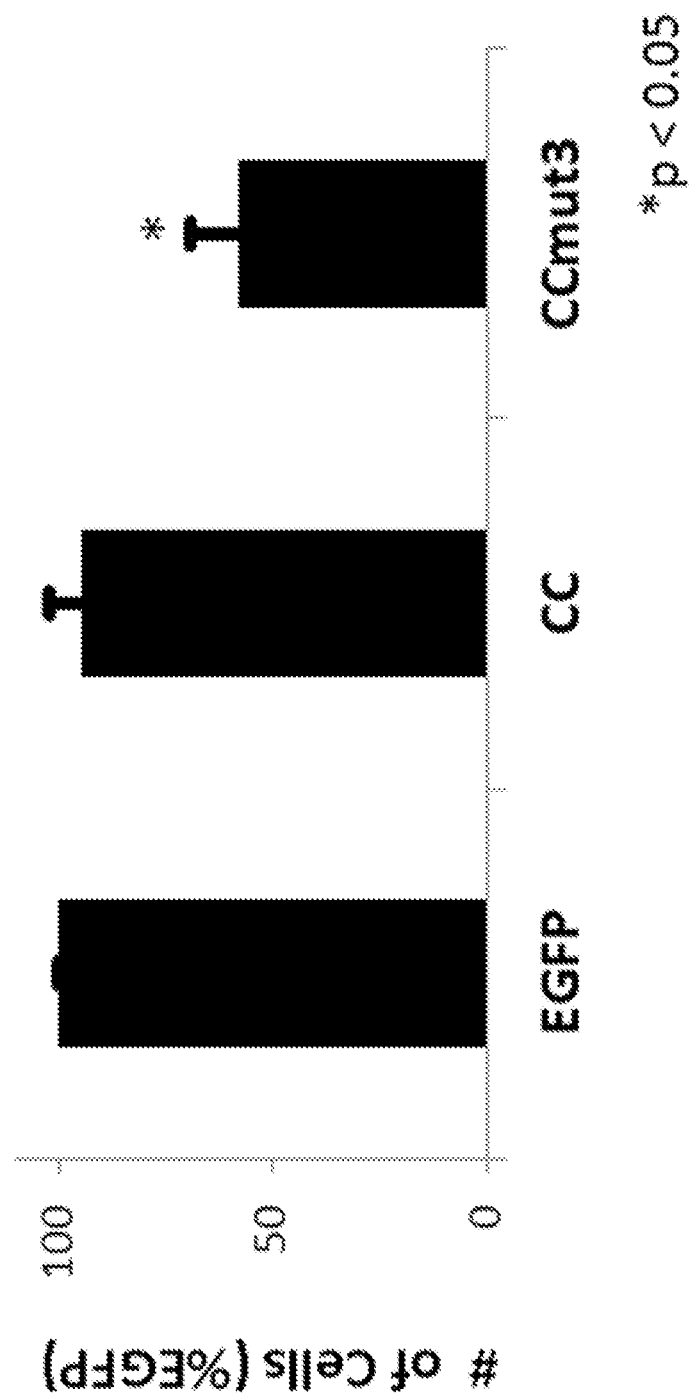
FIG. 9 shows representative data demonstrating that $CC^{mut3}$ inhibits proliferation of Bcr-Abl1-expressing K562 cells.
Figure 10A:
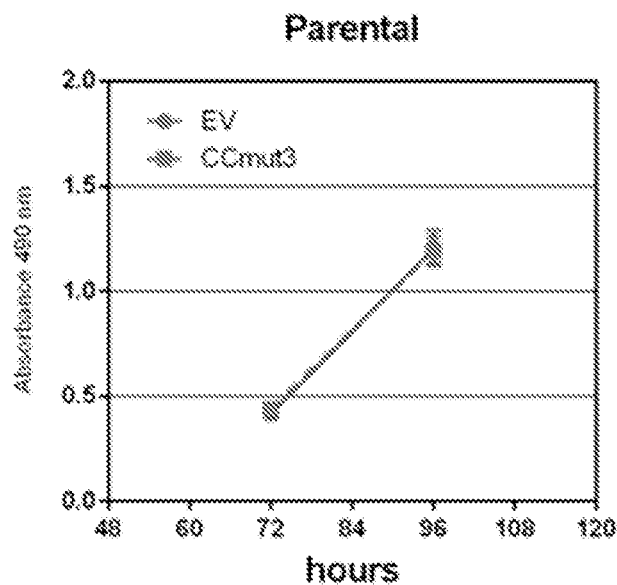
FIGS. 10A-E show representative data demonstrating that $CC^{mut3}$ inhibits proliferation of Bcr-Abl1-expressing Ba/F3 cells. Specifically.
Figure 10B:
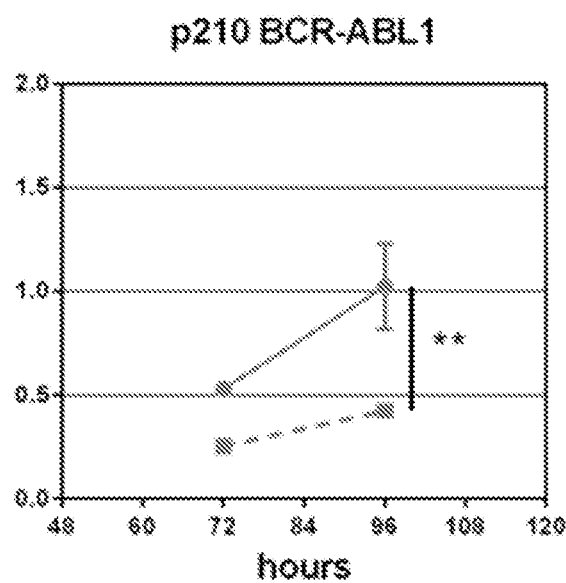
Figure 10C:
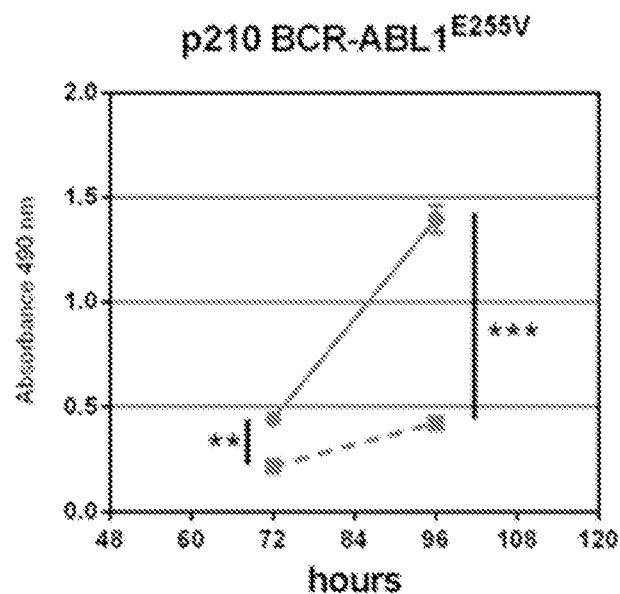
Figure 10D:
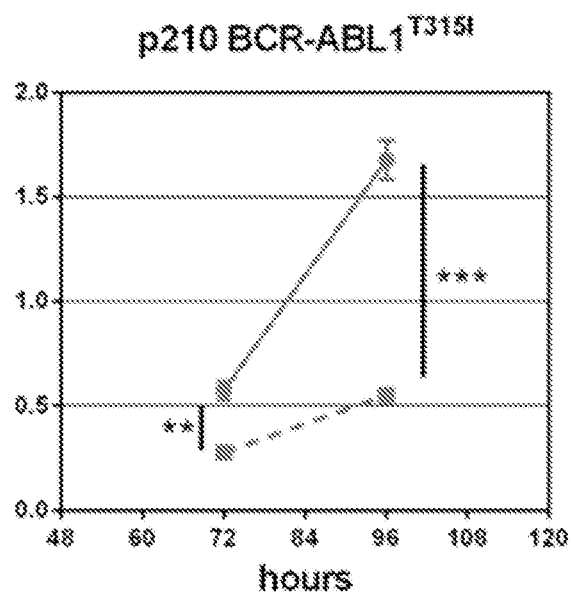
Figure 10E:
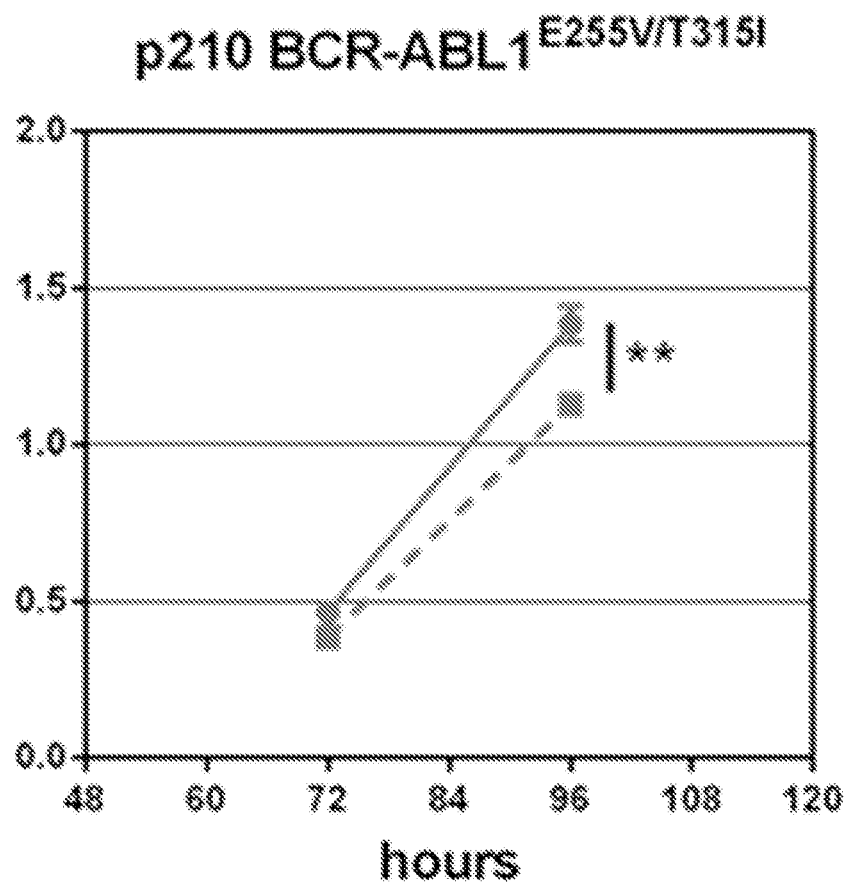

First, the ability of $CC^{mut3}$ to inhibit cell proliferation of K562 cells was studied (FIG. 9). $CC^{mut3}$ showed significantly greater inhibition when compared against EGFP and the WT control. Next, the antiproliferative effects of $CC^{mut3}$ in Ba/F3 cells with p210 BCR-ABL1 (Ba/F3p210$^{BCR-ABL1}$) and in the parental Ba/F3 cells (Ba/F3) were investigated (FIG. 10). Following transfection with empty vector (EV) or $CC^{mut3}$ constructs, proliferation was measured by MTS assay at 72 and 96 h. No difference between EV or $CC^{mut3}$ was observed in Ba/F3 cells (FIG. 10A), while at 96 h proliferation of Ba/F3p210$^{BCR-ABL1}$ was reduced by a more than 2-fold following (FIG. 10B). Next, the effects of $CC^{mut3}$ on cells expressing BCR-ABL1 mutants associated with resistance to imatinib were tested (Bradeen, H. A., et al. (2006) *Blood* 108, 2332-2338). Ba/F3 cells engineered to express either BCR-ABL$^{E255V}$ (Ba/F3p210$^{BCR-ABL1/E255V}$) or BCR-ABL$^{T315I}$ (Ba/F3p210$^{BCR-ABL1/T315I}$) were transfected with EV or $CC^{mut3}$ constructs. At 96 h single mutants showed an approximately 3-fold reduction of proliferation when transfected with $CC^{mut3}$ compared to EV at 72 h (FIGS. 10C and 10D). Ba/F3 cells expressing p210$^{BCR-ABL1/T315I/E255V}$ (Ba/F3p210$^{BCR-ABL1/E255V/T315I}$) showed smaller yet significant reduction in proliferation at 96 h with $CC^{mut3}$ treatment (FIG. 10E).

Figure 11:
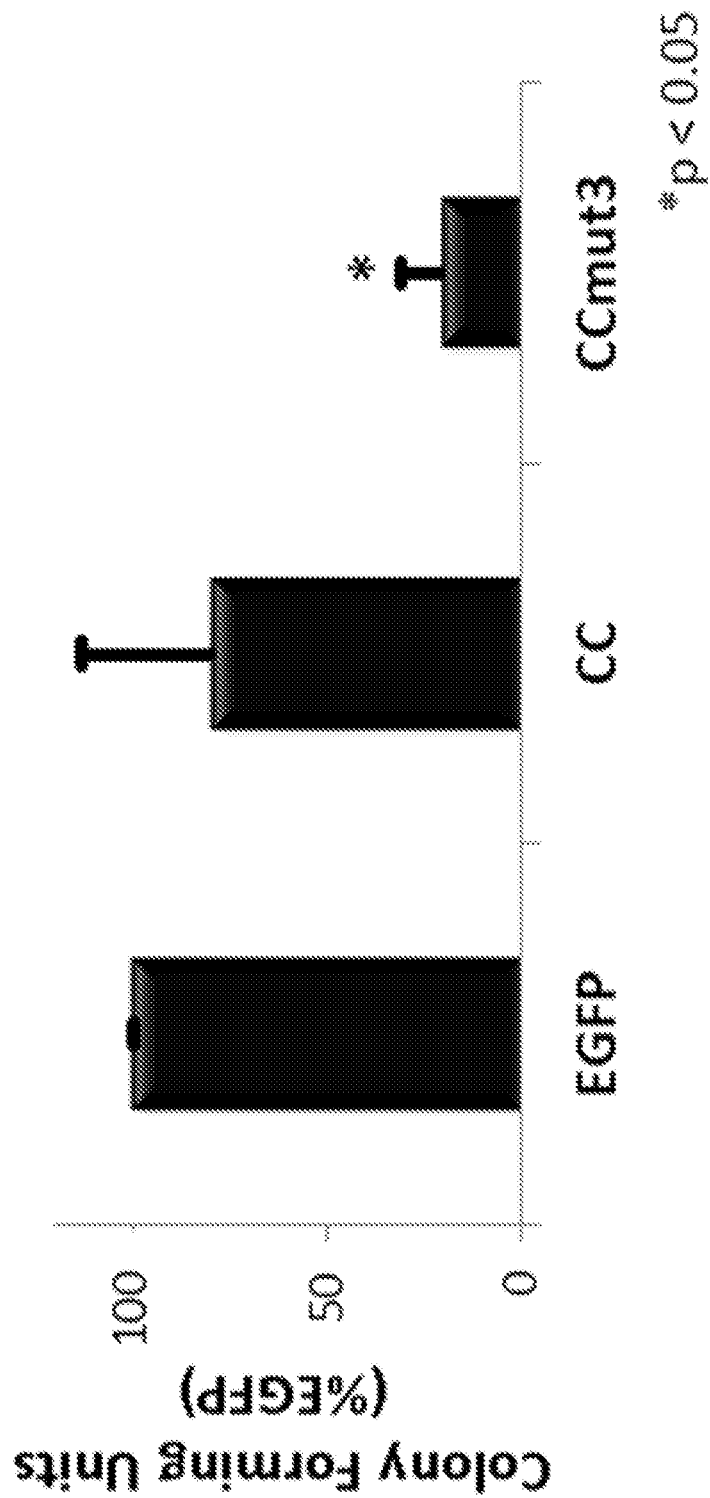
FIG. 11 shows representative data demonstrating that $CC^{mut3}$ inhibits colony formation of Bcr-Abl1-expressing K562 cells.
Figure 12A:
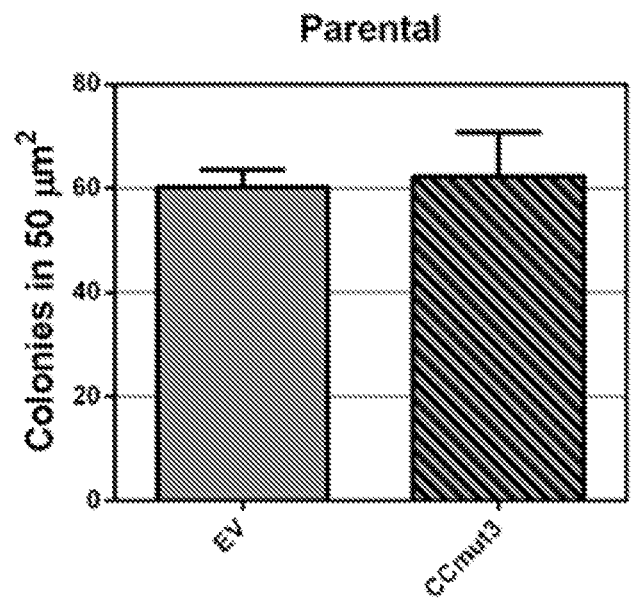
FIGS. 12A-12E shows representative data demonstrating that $CC^{mut3}$ inhibits colony formation of Bcr-Abl1-expressing Ba/F3 cells. Specifically.
Figure 12B:
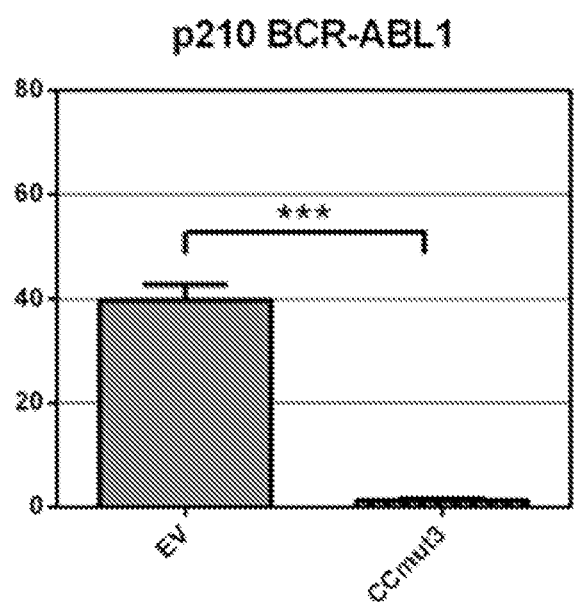
Figure 12C:
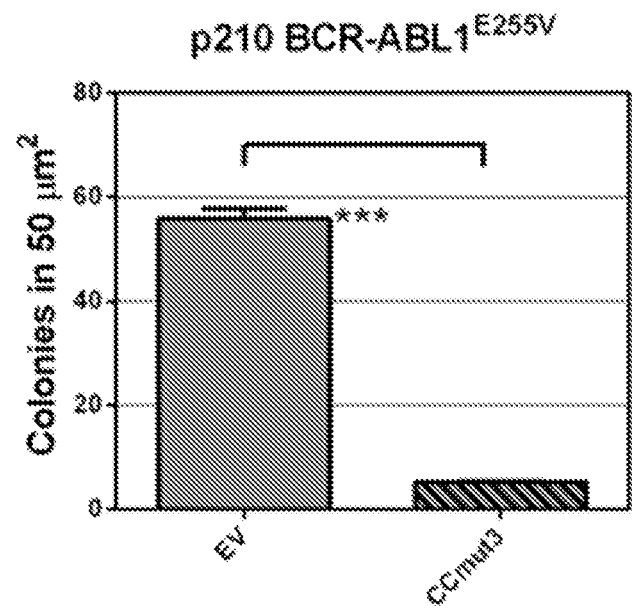
Figure 12D:
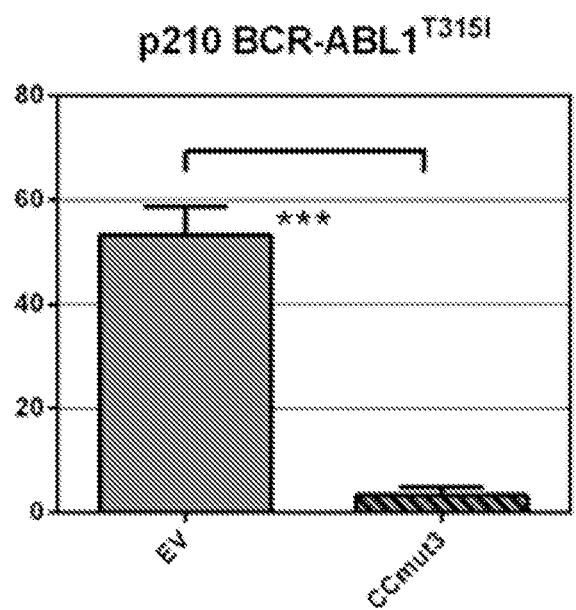
Figure 12E:
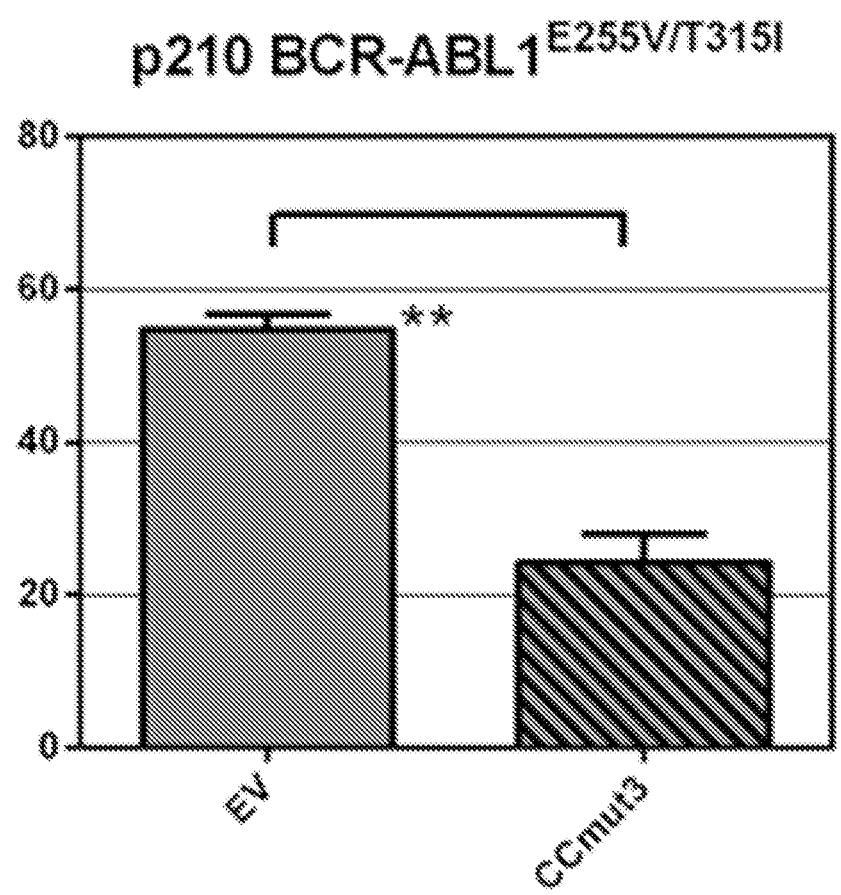

The ability of $CC^{mut3}$ to inhibit transformative ability, or colony formation of K562 cells was then evaluated (FIG. 11). Compared to EGFP and the WT control, $CC^{mut3}$ showed significantly greater inhibition. Next, the effect of $CC^{mut3}$ on colony formation by Ba/F3p210$^{BCR-ABL1}$ cells or the related parental control cell line transfected with either EV or $CC^{mut3}$ was tested (FIG. 12). $CC^{mut3}$ transfection nearly eliminated CFCs when compared to the EV in Ba/F3p210$^{BCR-ABL1}$ cells while normal Ba/F3 cells showed no difference between treatment groups (FIGS. 12A and 12B). Similarly, Ba/F3p210$^{BCR-ABL1/E255V}$ (FIG. 12C) and Ba/F3p210$^{BCR-ABL1/T315I}$ (FIG. 12D) produced a more than 10-fold reduction in CFCs in the $CC^{mut3}$ group compared to EV. Lastly, $CC^{mut3}$ expression in Ba/F3p210$^{BCR-ABL1/E255V/T315I}$ cells reduced CFCs by approximately 50% compared to EV control (FIG. 12E).

Figure 13A:
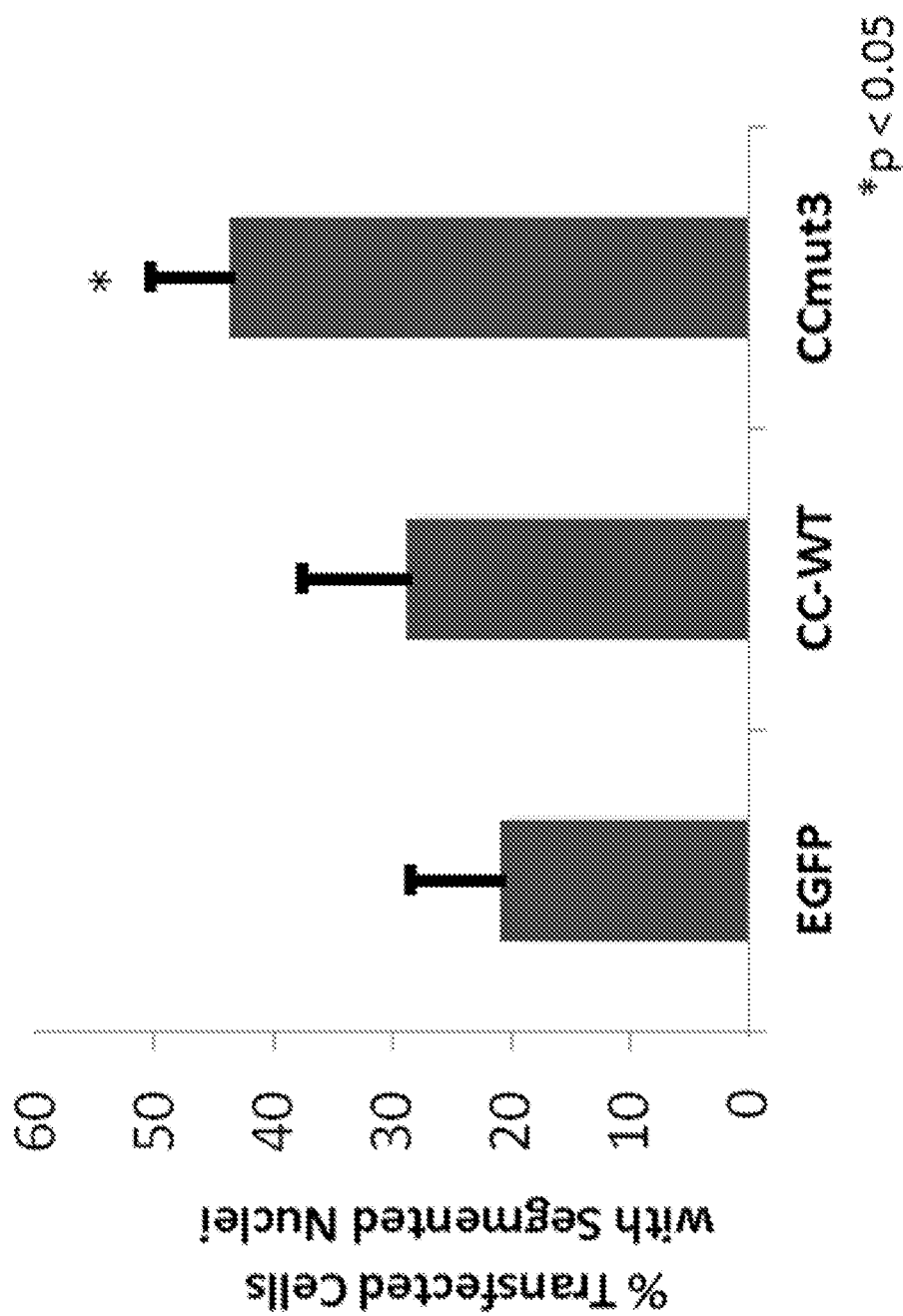
FIGS. 13A and 13B show the apoptosis ability of $CC^{mut3}$.
Figure 13B:
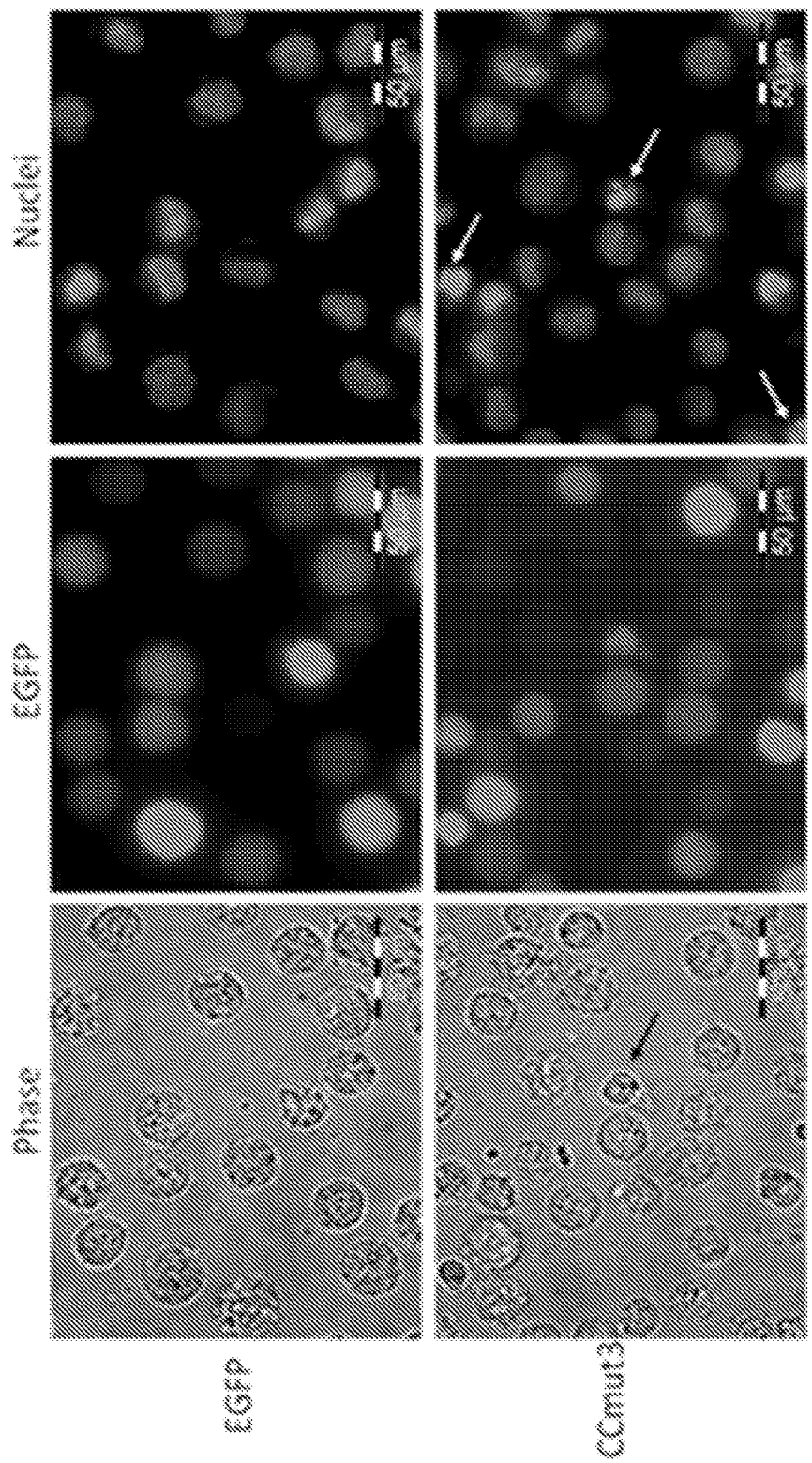
Figure 14A:
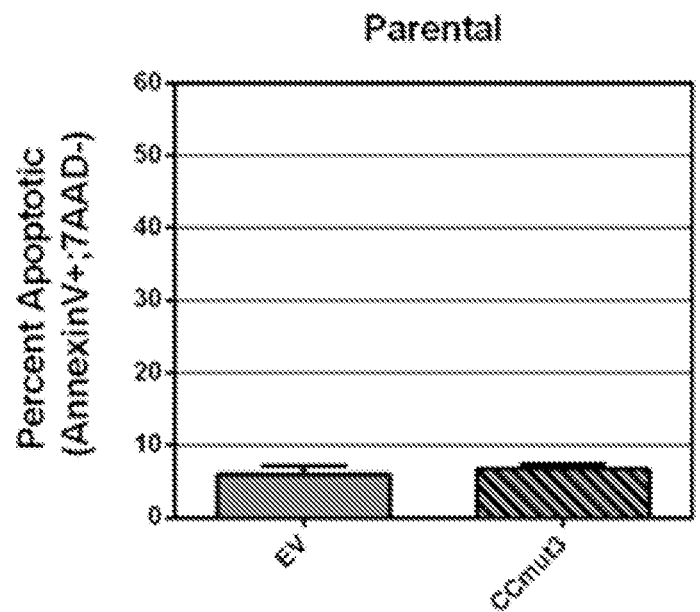
FIGS. 14A-14E show representative data demonstrating that $CC^{mut3}$ induces apoptosis in Bcr-Abl1-expressing Ba/F3 cells. Specifically.
Figure 14B:
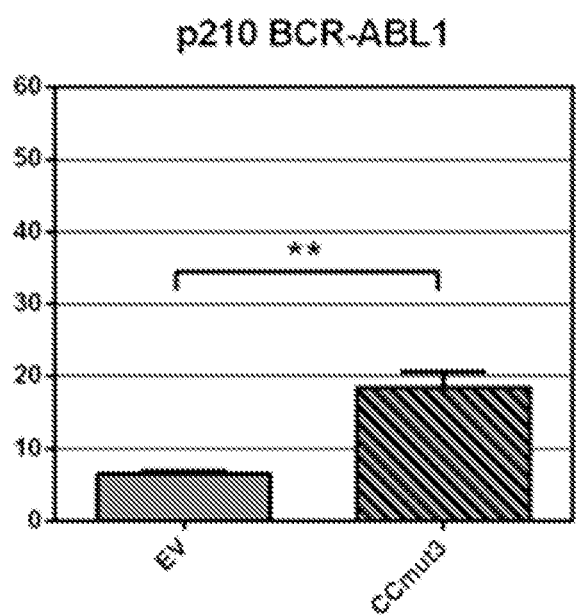
Figure 14C:
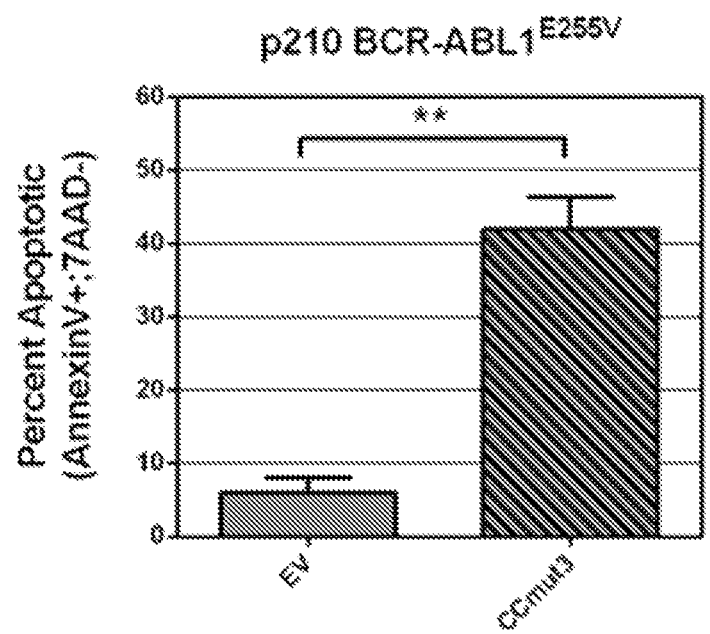
Figure 14D:
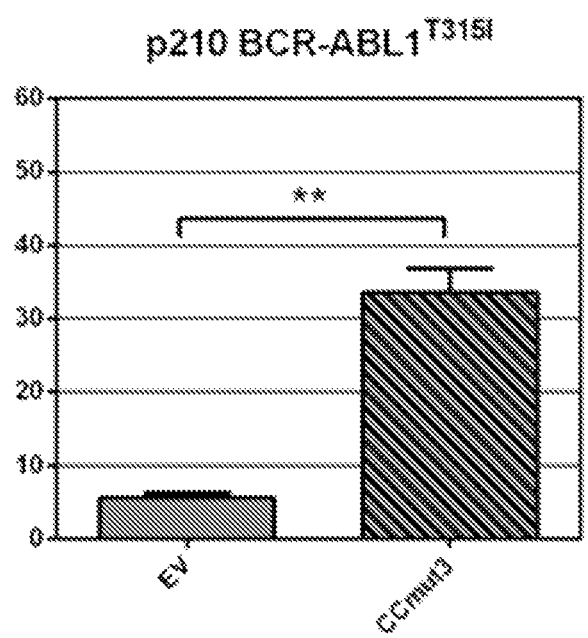
Figure 14E:
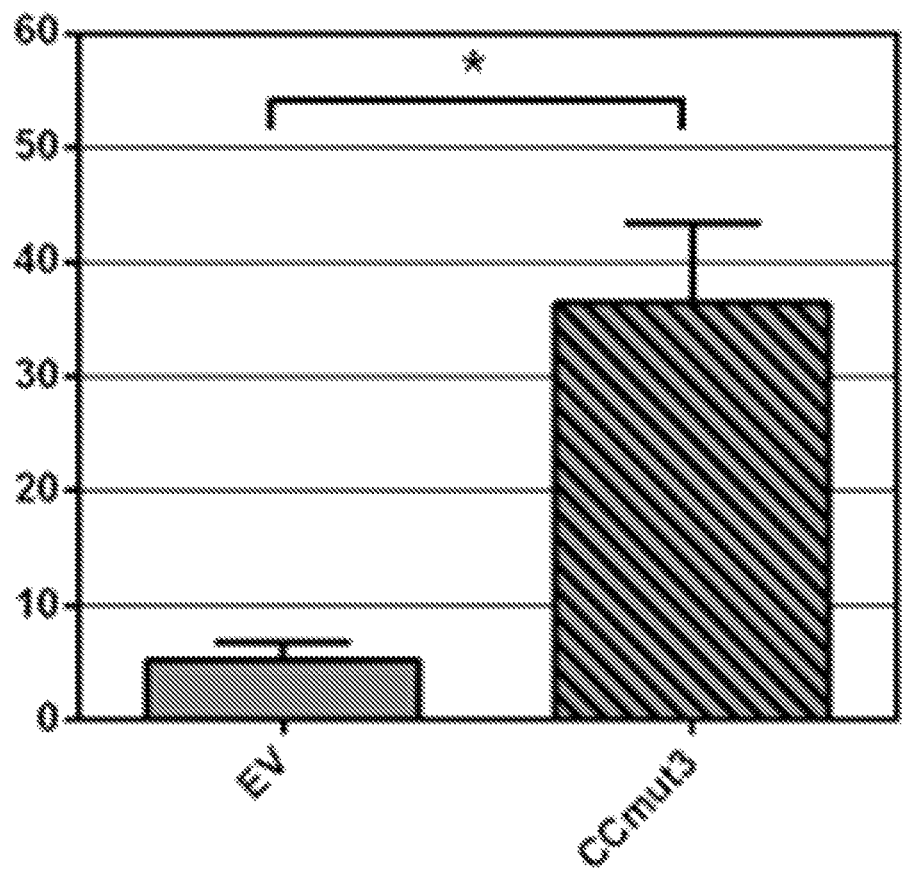

(B) $CC^{mut3}$ Enhances Apoptosis of K562 Cells and Ba/F3-Expressing p210$^{BCR-ABL1}$ $CC^{mut3}$ was then tested for its ability to induce apoptosis in K562 cells. Apoptosis was observed using 3 different methods: 1) nuclear segmentation; 2) induction of the effector Caspase-3/7; and 3) 7AAD/Annexin V staining. A representative image of $CC^{mut3}$ causing apoptosis via nuclear segmentation is depicted in FIG. 13A, with cells containing segmented nuclei indicated by the arrows. FIG. 13B shows the quantitative results of three separate transfections (n=3).

Next, Annexin V and 7-AAD were measured in Ba/F3p210$^{BCR-ABL1}$ cells 72 hours after infection with $CC^{mut3}$ or EV (FIG. 14). Ba/F3p210$^{BCR-ABL1}$ showed an approximately 3-fold increase of apoptotic cells when transfected with $CC^{mut3}$ compared to EV, while there was no effect on the parental cells (FIGS. 14A and 14B). Ba/F3p210$^{BCR-ABL1/E255V}$ and Ba/F3p210$^{BCR-ABL1/T315I}$ cells showed a 6-8-fold increase in apoptosis after infection with $CC^{mut3}$ compared to EV (FIGS. 14C and 14D). Ba/F3 cells expressing the p210BCR-ABL1$^{E255V/T315I}$ were also sensitive to $CC^{mut3}$ (FIG. 14E).

n. Multidomain Targeting of Bcr-Abl

Figure 15:
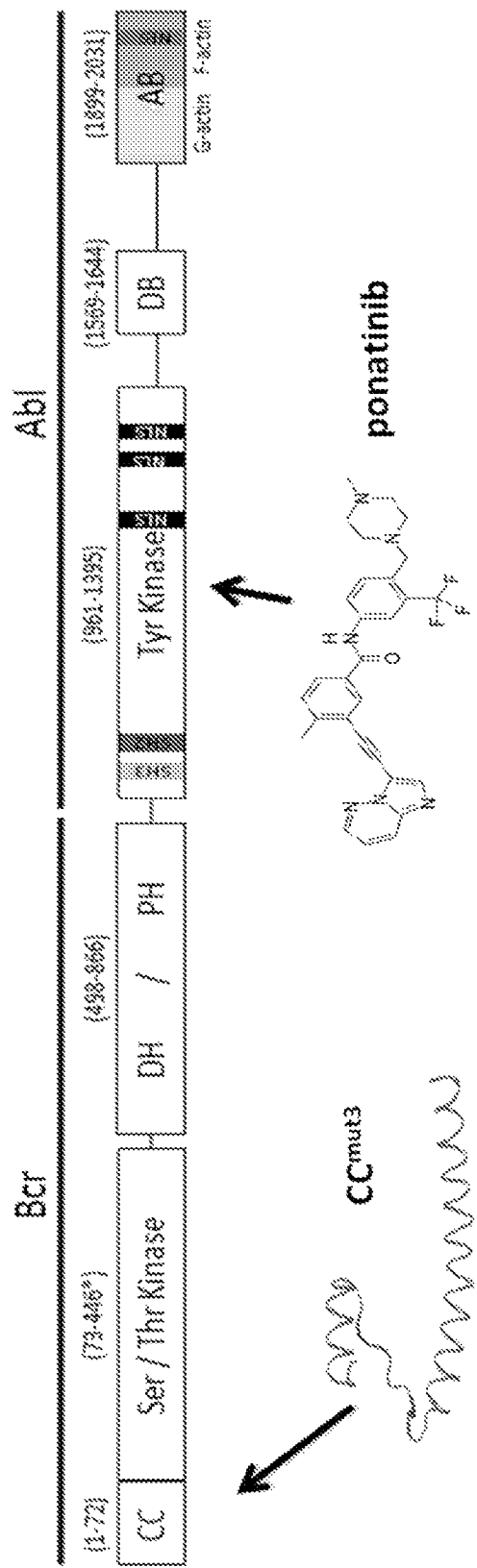
FIG. 15 shows a representative cartoon pertaining to multi-domain targeting of Bcr-Abl.

Using the idea of multidomain targeting, both the oligomerization (CC) domain and the tyrosine kinase (Y-kinase) domain of BCR-ABL were targeted simultaneously to evaluate the possibility of an enhanced therapeutic effect (FIG. 15). This "dual-hit hypothesis" was tested by treating CML cells with both $CC^{mut3}$ and ponatinib (Iclusig™), the most recently approved TKI, (or each agent alone). Experiments were performed in cells containing the wild-type, unmutated form of BCR-ABL (K562; Ba/F3-p210) as well as cells containing the 'gate-keeper' T315I mutation in BCR-ABL (Ba/F3-p210-T315I).

(A) Bcr-Abl Phosphorylation and Downstream Signaling (STATS and CrkL) are Diminished upon Treatment with $CC^{mut3}$ in Combination with Ponatinib Western blots measuring kinase activity were performed using $CC^{mut3}$ and ponatinib to examine the potential oligomeric disruption and signaling inhibition of endogenous Bcr-Abl. A range of ponatinib between 1 and 100 nM was originally tested based on previous in vitro studies (O'Hare, T., et al. (2009) *Cancer Cell* 16, 401-412) in order to determine the lowest dose of ponatinib that could be used in combination with $CC^{mut3}$ (data not shown). The current effective in vivo physiologic therapeutic range of ponatinib is between 60 and 145 nM (Garner, A. P., et al. (2013) *AACR Annual Meeting Abstracts,* 3394).

Figure 16A:
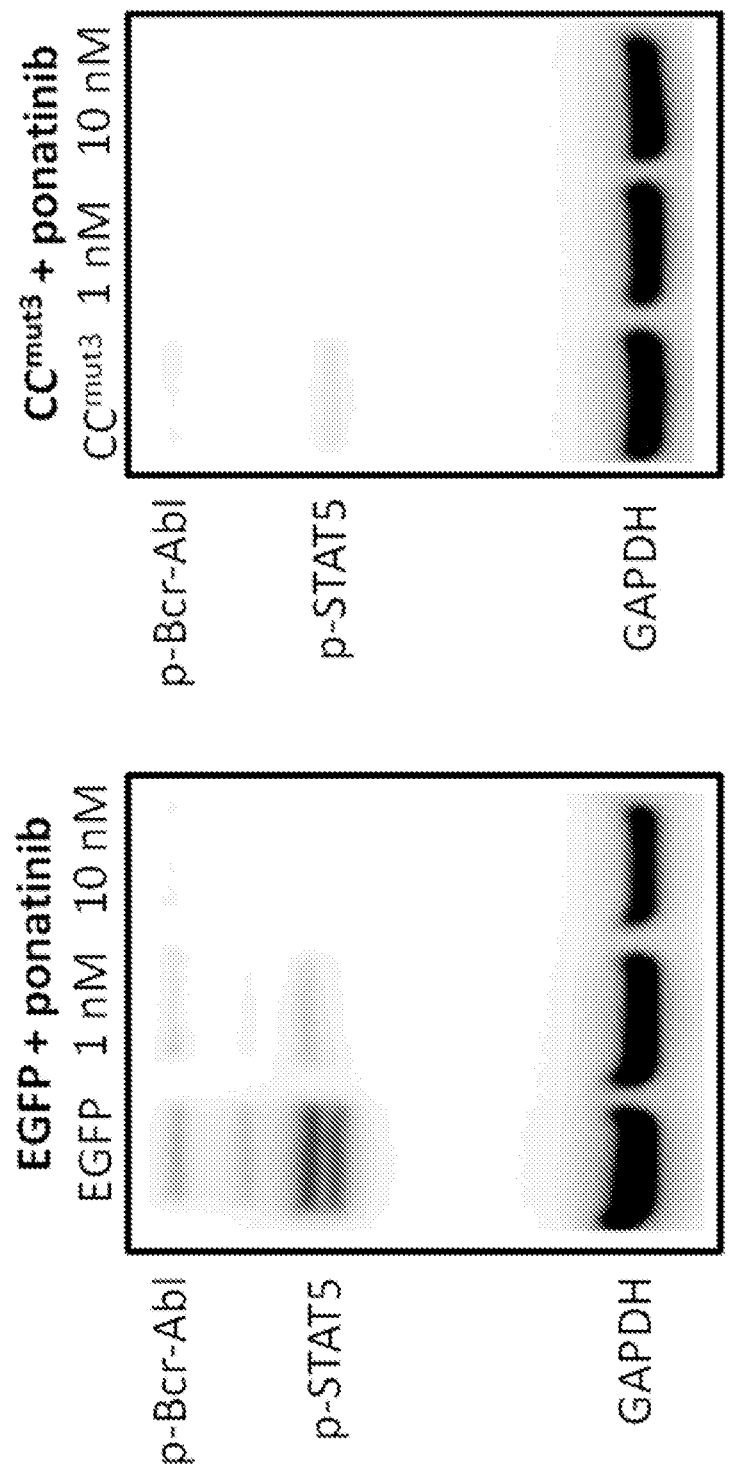
FIGS. 16A and 16B show representative data pertaining to the effect of $CC^{mut3}$ in combination with ponatinib on the kinase activity of Bcr-Abl in K562 cells.
Figure 16B:
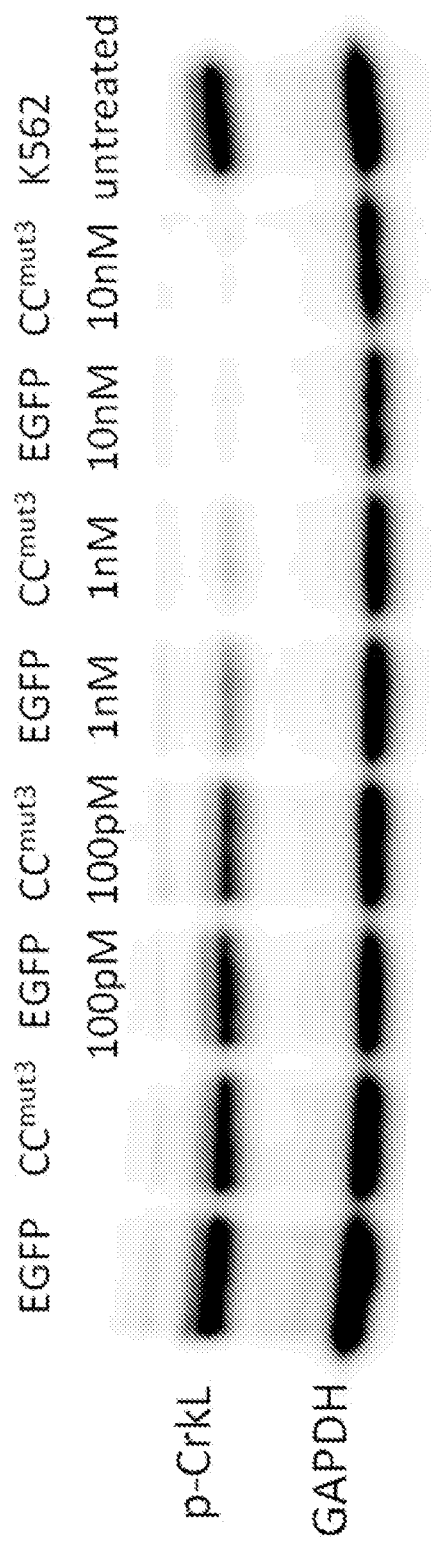

Because Bcr-Abl undergoes trans-autophosphorylation upon dimerization at the coiled-coil domain (McWhirter, J. R., et al. (1993) *Mol. Cell Biol.* 13, 7587-7595), oligomeric disruption in this case was measured according to the phosphorylation state of Br-Abl (FIG. 16A). In addition, inhibition of Bcr-Abl signaling thus inhibition of kinase activity, was measured by examining the phosphorylation states of Bcr-Abl downstream target STATS (FIG. 16A) and direct substrate CrkL (FIG. 16B). When comparing equal doses of ponatinib with or without $CC^{mut3}$ (FIG. 16A, lane 5 vs. lane 2). At this same dose, the phosphorylation of both STATS (FIG. 16A, lane 5) and CrkL (FIG. 16B, lane 6) is greatly diminished. Complete eradication of phosphorylation of STATS and CrkL appears at 10 nM ponatinib (FIG. 16A, lane 3; FIG. 16B, lane 7). One further lower dose of ponatinib, 100 pM, was also tested (FIG. 16B, lanes 3 and 4); no significant difference in CrkL phosphorylation with the combination was observed at this dose. Because p-Bcr-Abl activity is obliterated when 10 nM ponatinib is used in combination with $CC^{mut3}$ (FIG. 16A, lane 6 vs. lane 3), it was determined to reduce ponatinib to a subsaturating dose of 1 nM in subsequent experiments.

(B) $CC^{mut3}$ Plus 1 nM Ponatinib Treatment Activates Caspase-3/7

Figure 17:
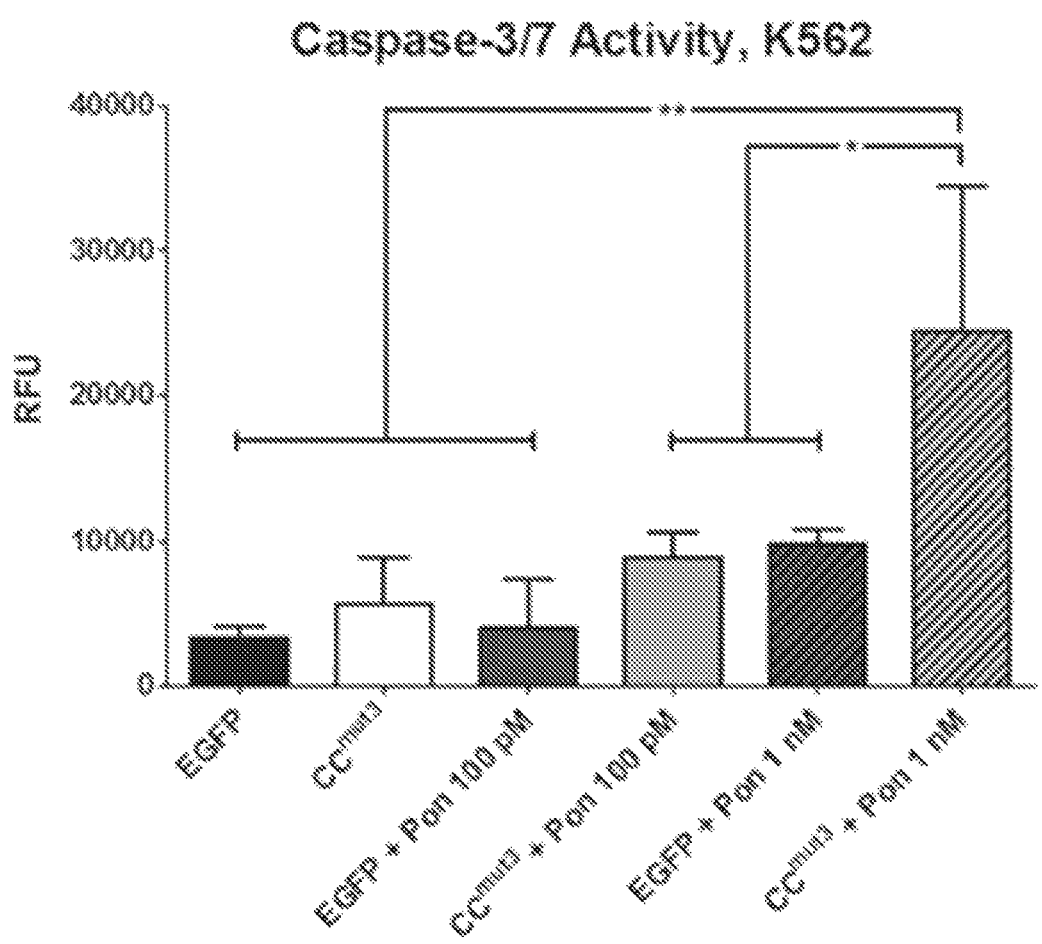
FIG. 17 shows representative data pertaining to effect of $CC^{mut3}$ in combination with ponatinib on apoptosis in Bcr-Abl1-expressing K562 cells.

Following analysis of the phosphorylation state of the signaling pathways, apoptotic induction following treatment was measured. Here, the activity of the effector caspase-3/7 upon treatment was analyzed as a measure of apoptosis. In order to suggest that a combination of $CC^{mut3}$ and ponatinib provides an enhanced effect over each treatment alone, $CC^{mut3}$ plus ponatinib doses were compared against both (i) $CC^{mut3}$ alone and (ii) EGFP with the corresponding ponatinib dose. FIG. 17 shows that the combination consisting of $CC^{mut3}$ and 1 nM ponatinib (last bar) results in significant induction of apoptosis compared to all other groups. Importantly, the enhanced apoptosis seen with this combination (last bar) is significantly greater than both $CC^{mut3}$ alone (second bar) and EGFP with 1 nM ponatinib (fifth bar).

Figure 18A:
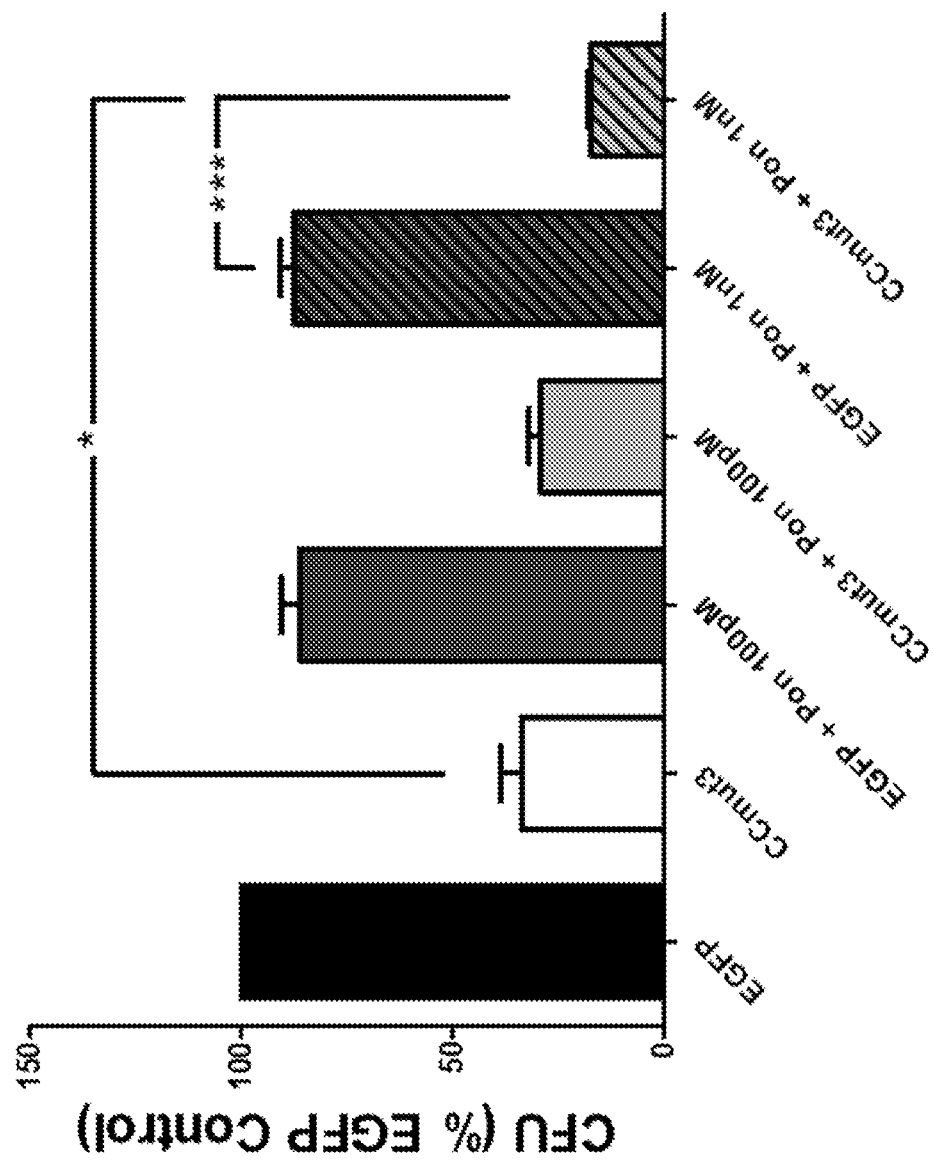
FIGS. 18A and 18B show representative data pertaining to the effect of $CC^{mut3}$ in combination with ponatinib on transformative ability of Bcr-Abl1-expressing K562 (A) and Ba/F3-p210 (B) cells.

(C) Treatment with $CC^{mut3}$ and 1 nM Ponatinib Significantly Decreases the Transformative Ability (Oncogenic Potential) of K562 Cells Transformative ability of K562 cells following treatment with the combination was tested using a colony forming assay, where outgrowth of colonies were a direct measure of oncogenic potential. Results are shown in FIG. 18A. With $CC^{mut3}$ alone, it should be noted that this construct causes a 3-fold decrease in the amount of colonies formed compared to EGFP (FIG. 18A, second bar vs. first bar). With $CC^{mut3}$ plus 1 nM ponatinib (FIG. 18A, last bar) the combination therapy shows a significant effect with a near 6-fold decrease in the amount of colonies formed compared to EGFP (FIG. 18A, last bar vs. first bar), an over 5-fold decrease compared to EGFP plus 1 nM ponatinib (last bar vs. fifth bar), and a 2-fold decrease compared to the number of colonies formed when treated with $CC^{mut3}$ alone (last bar vs. second bar). This highlights specifically the benefit of $CC^{mut3}$+Pon 1 nM compared to $CC^{mut3}$ alone or EGFP+Pon 1 nM, indicated by asterisks in FIG. 18A.

Figure 18B:
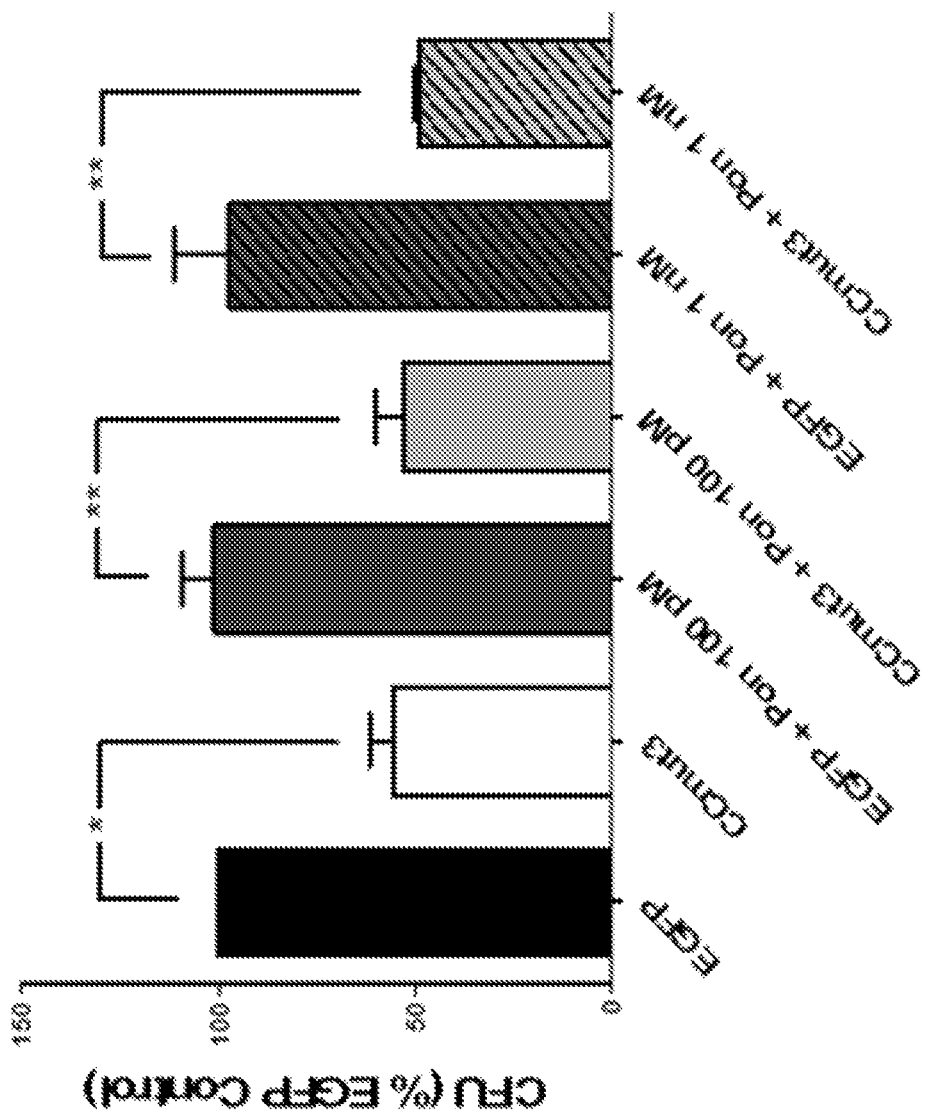

In Ba/F3-p210 cells, however, the reduction in transformative ability seemed to be mainly mediated by treatment with $CC^{mut3}$. In FIG. 18B, $CC^{mut3}$ was significantly lower than the EGFP control (second bar vs. first bar). Likewise, $CC^{mut3}$+Pon 100 pM or $CC^{mut3}$+Pon 1 nM were both significantly lower than ponatinib alone at either dose (fourth bar vs. third bar and sixth bar vs. fifth bar). Importantly, $CC^{mut3}$+Pon 100 pM and $CC^{mut3}$+Pon 1 nM were not significantly lower than $CC^{mut3}$ alone. In other words, the combination did not enhance the reduction in oncogenic potential in this cell line.

Figure 19:
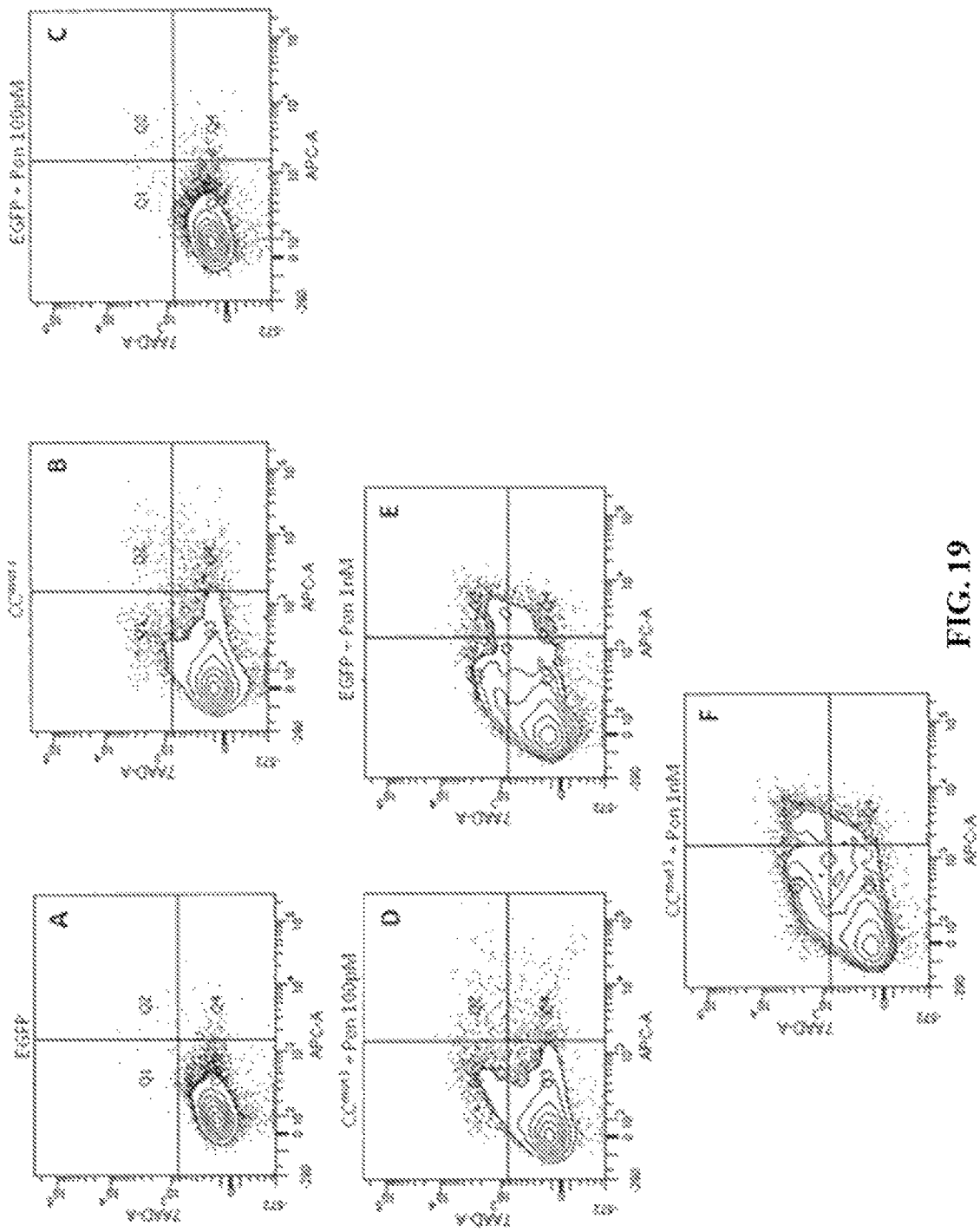
FIGS. 19A-19F show representative contour plots pertaining to the induction of apoptosis and necrosis in K562 cells using $CC^{mut3}$ and/or ponatinib. A) EGFP. B) $CC^{mut3}$. C) EGFP+Pon 100 pM. D) $CC^{mut3}$+Pon 100 pM. E) EGFP+Pon 1 nM. F) $CC^{mut3}$+Pon 1 nM.
Figure 20:
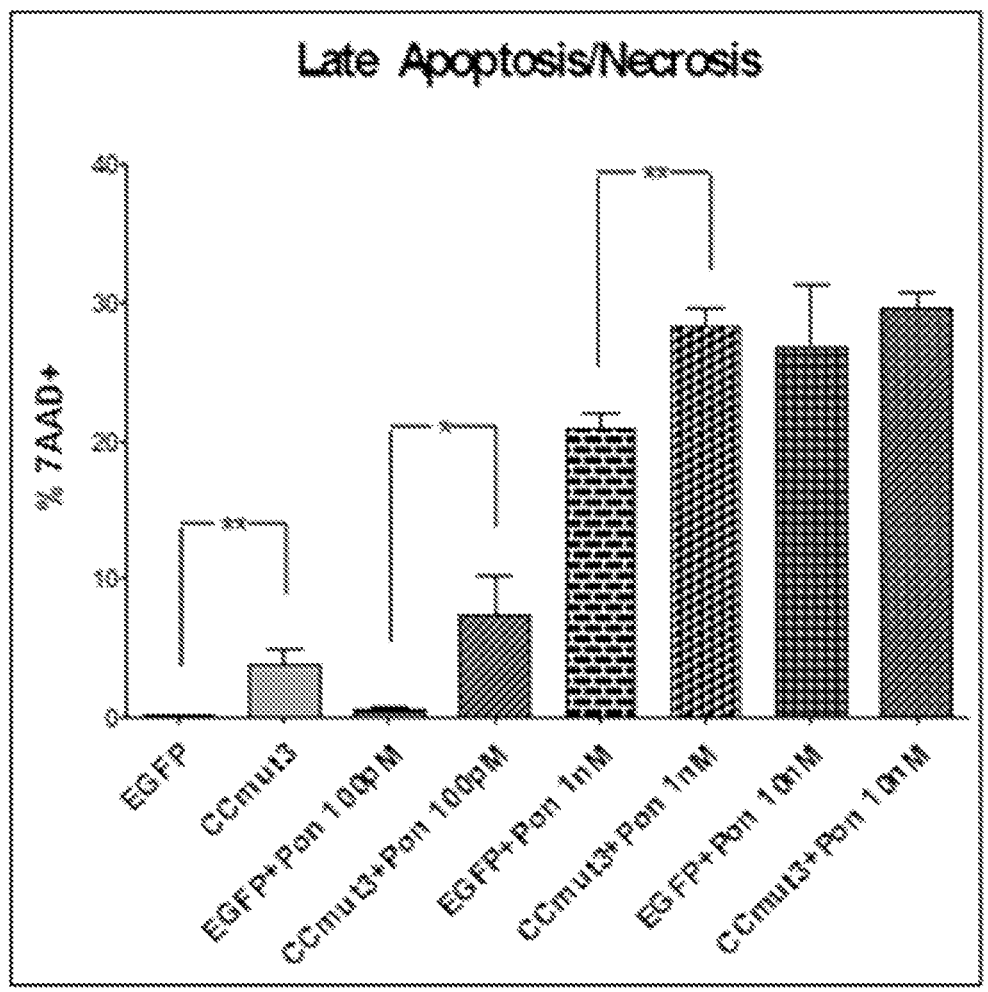
FIG. 20 shows representative data pertaining to the effect of $CC^{mut3}$ in combination with ponatinib on apoptosis and necrosis in K562 cells.

(D) $CC^{mut3}$ Combined with Ponatinib Causes Further Induction of Apoptosis and Necrosis in K562 Cells Flow cytometry was utilized to measure apoptosis and necrosis of cells treated with the combination. 7-Aminoactinomycin D (7AAD), which binds the DNA of dead and dying cells no longer possessing an intact membrane, and Annexin V, which binds to the externalized apoptotic marker, phosphatidylserine, were used to determine apoptosis. To ensure that the effects of the combination treatment were tested, only cells showing EGFP fluorescence (thus, $CC^{mut3}$-positive or positive for control) were selected for and analyzed (ponatinib itself is known to freely enter cells; see O'Hare, T., et al. (2009) Cancer Cell 16, 401-412). As seen in FIG. 19, the combination of $CC^{mut3}$ and 1 nM ponatinib (FIG. 19F) induces the highest percent of apoptosis and necrosis. Notably, this combination is higher than each of its individual components (FIG. 19F vs. 19B, 19E). These results are summarized in FIG. 20.

Figure 21:
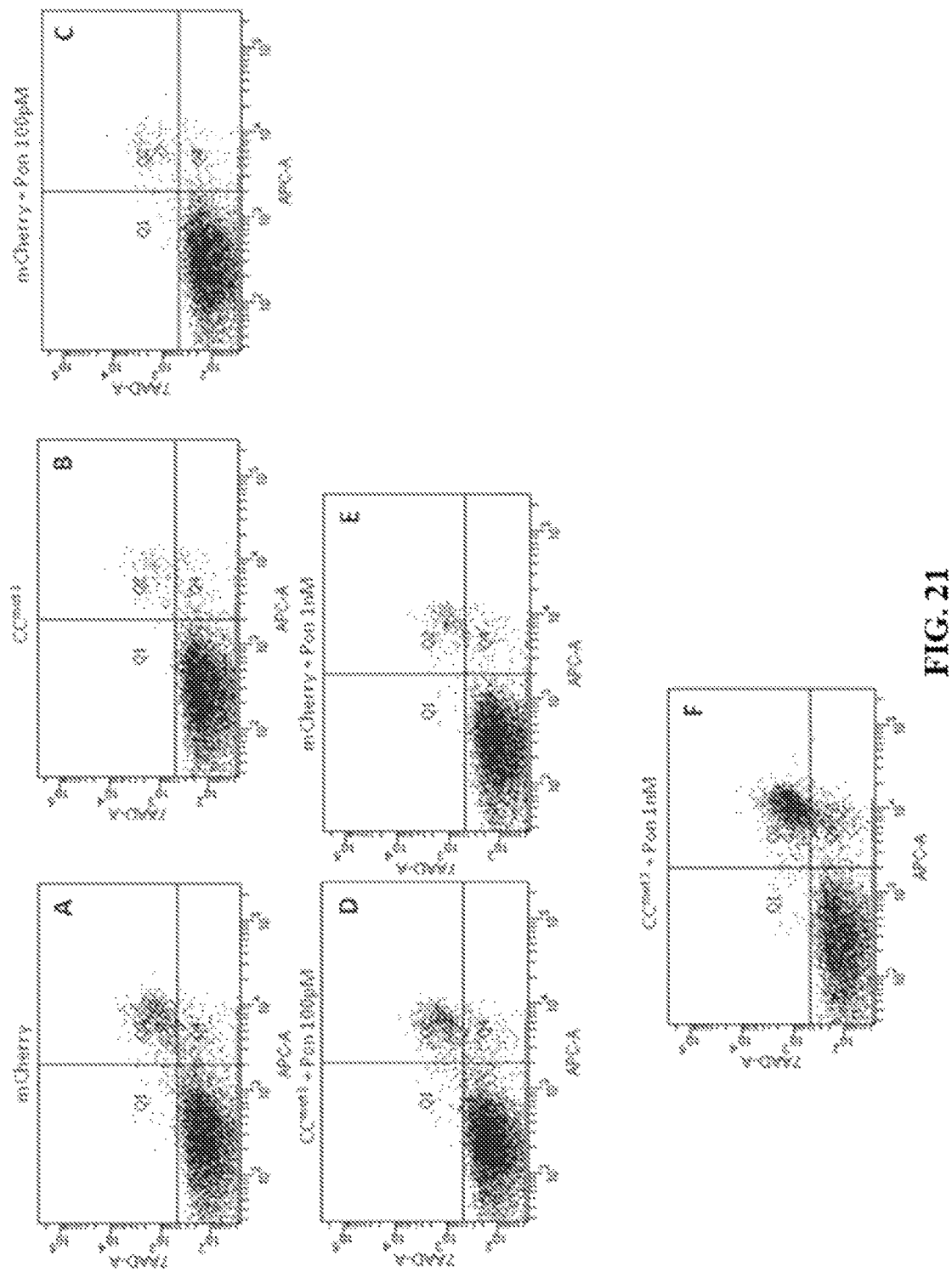
FIGS. 21A-21F show representative contour plots pertaining to the induction of apoptosis and necrosis in Ba/F3-p210 cells using $CC^{mut3}$ and/or ponatinib. A) mCherry. B) $CC^{mut3}$. C) mCherry+Pon 100 pM. D) $CC^{mut3}$+Pon 100 pM. E) mCherry+Pon 1 nM. F) $CC^{mut3}$+Pon 1 nM.
Figure 22:
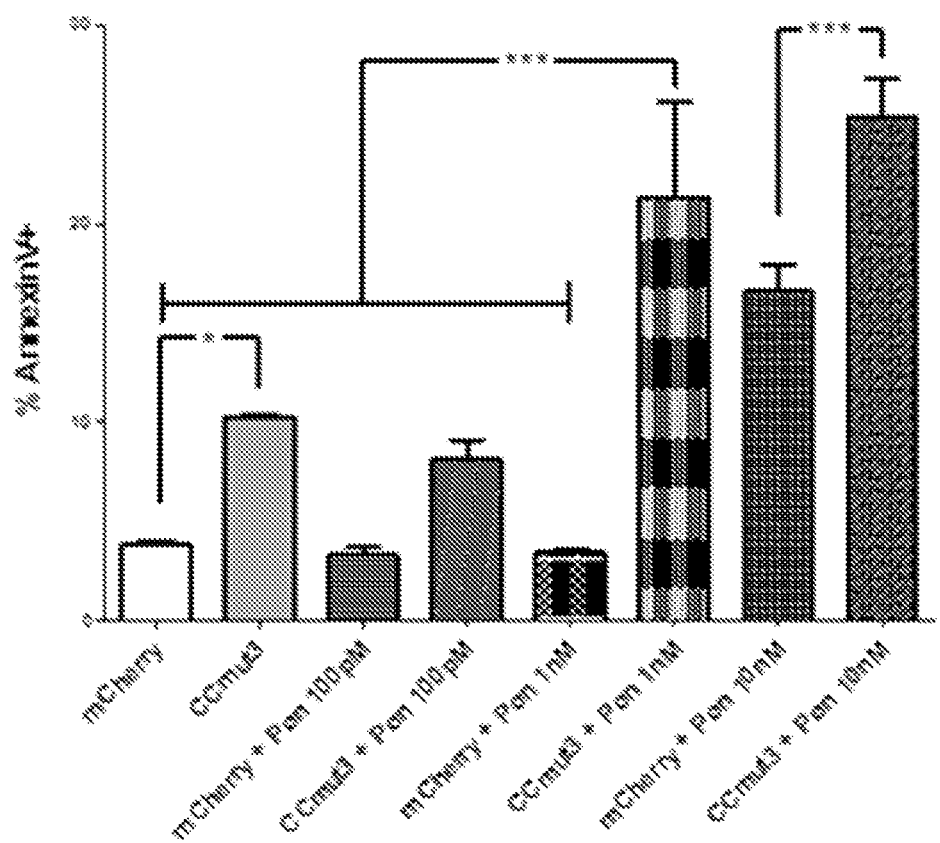
FIG. 22 shows representative data pertaining to the effect of $CC^{mut3}$ in combination with ponatinib on apoptosis and necrosis in Ba/F3-p210 cells.

(E) Increased Apoptotic and Necrotic Effect from $CC^{mut3}$ and Ponatinib is Not K562 Cell Specific To ensure that the combination induces apoptosis and necrosis in other cells harboring Bcr-Abl (besides human K562 cells), experiments were conducted in mouse Ba/F3 cells expressing the 210 kDa Bcr-Abl fusion protein (Ba/F3-p210). The full length p210 form of Bcr-Abl, the product of the Bcr-Abl hybrid gene, causes leukemic cell growth in hematopoetic cell lines and is known to induce leukemia in animal models (Ben-Neriah, Y., et al. (1986) Science 233, 212-214). Ba/F3-p210 cells have been engineered to depend on Bcr-Abl for growth and stably express EGFP along with Bcr-Abl (Sherbenou, D. W., et al. (2008) Leukemia 22, 1184-1190; La Rosee, P., et al. (2002) Cancer Res. 62, 7149-7153). Therefore, in these experiments, mCherry was used as a negative control and as the $CC^{mut3}$ tag (instead of EGFP). Flow cytometry was again utilized to study apoptosis and necrosis, where the cell population that contained both EGFP (Bcr-Abl positive) and mCherry (transfection positive) was analyzed. FIG. 21 shows the induction of apoptosis in Ba/F3-p210 cells, where the data agrees with the results also in K562 cells (FIG. 19). Again, the combination including 1 nM ponatinib (FIG. 21F) shows the highest induction of apoptosis and necrosis, higher than 1 nM ponatinib alone (FIG. 21E) and also higher than $CC^{mut3}$ alone (FIG. 21B). These results are summarized in FIG. 22.

Figure 23:
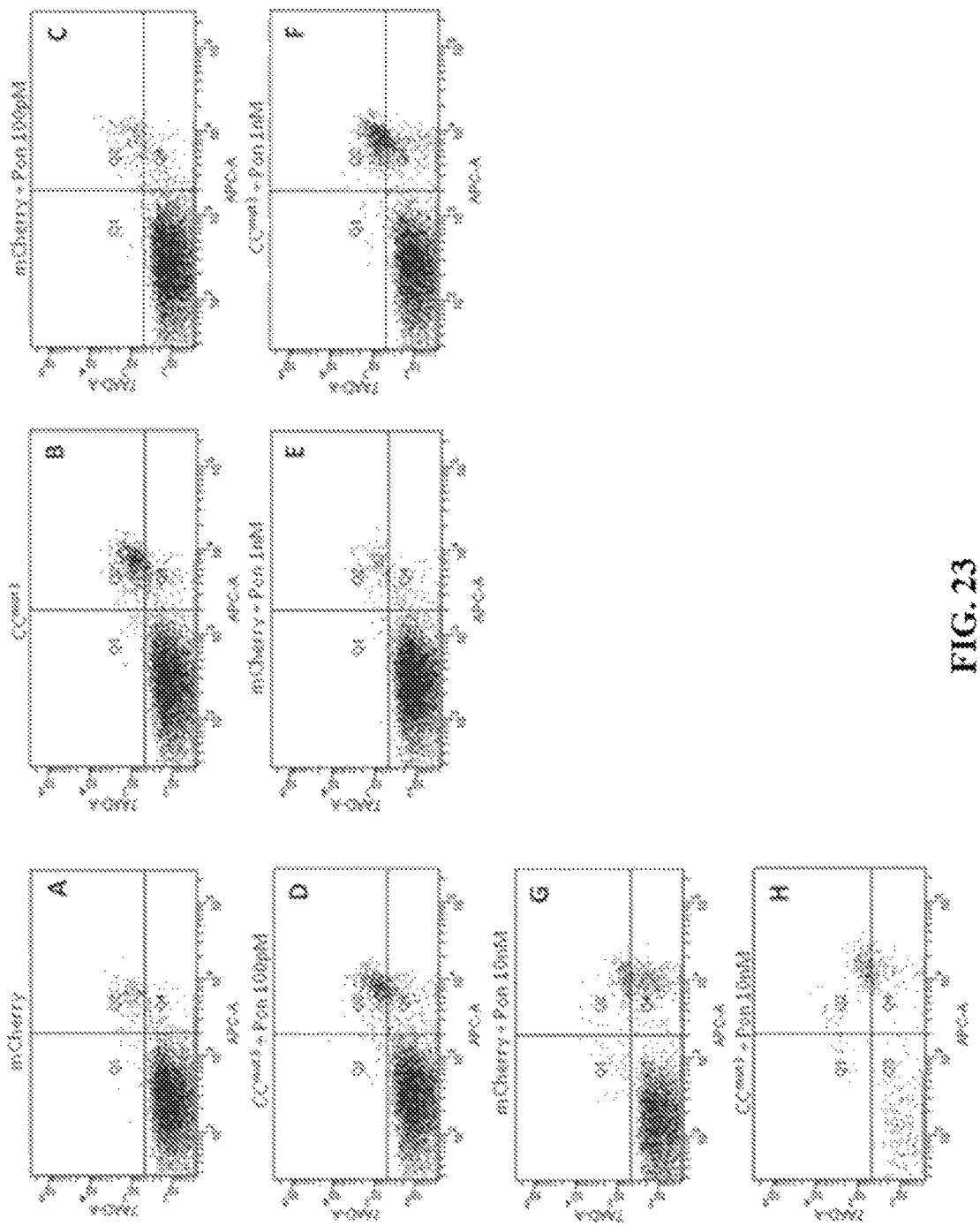
FIGS. 23A-23H show representative contour plots pertaining to the induction of apoptosis and necrosis in Ba/F3-p210-T315I cells using $CC^{mut3}$ and/or ponatinib. A) mCherry. B) $CC^{mut3}$. C) mCherry+Pon 100 pM. D) $CC^{mut3}$+Pon 100 pM. E) mCherry+Pon 1 nM. F) $CC^{mut3}$+Pon 1 nM. G) mCherry+Pon 10 nM. D) $CC^{mut3}$+Pon 10 nM.
Figure 24:
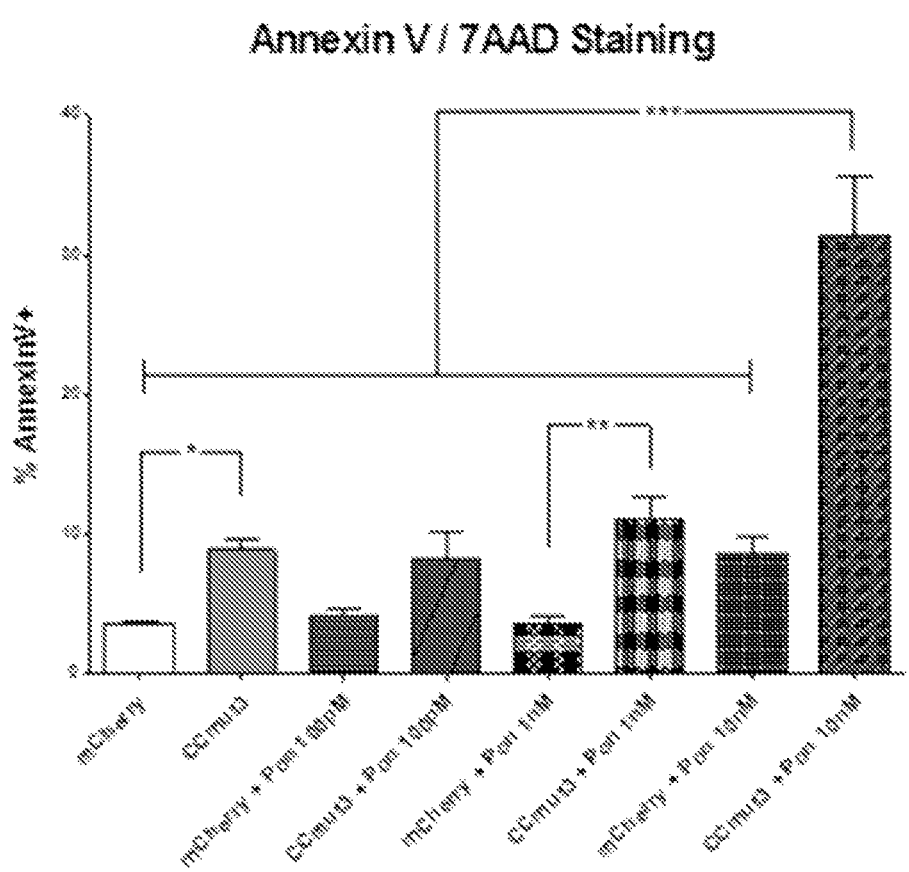
FIG. 24 shows representative data pertaining to the effect of $CC^{mut3}$ in combination with ponatinib on apoptosis and necrosis in Ba/F3-p210-T315I cells.
Figure 25:
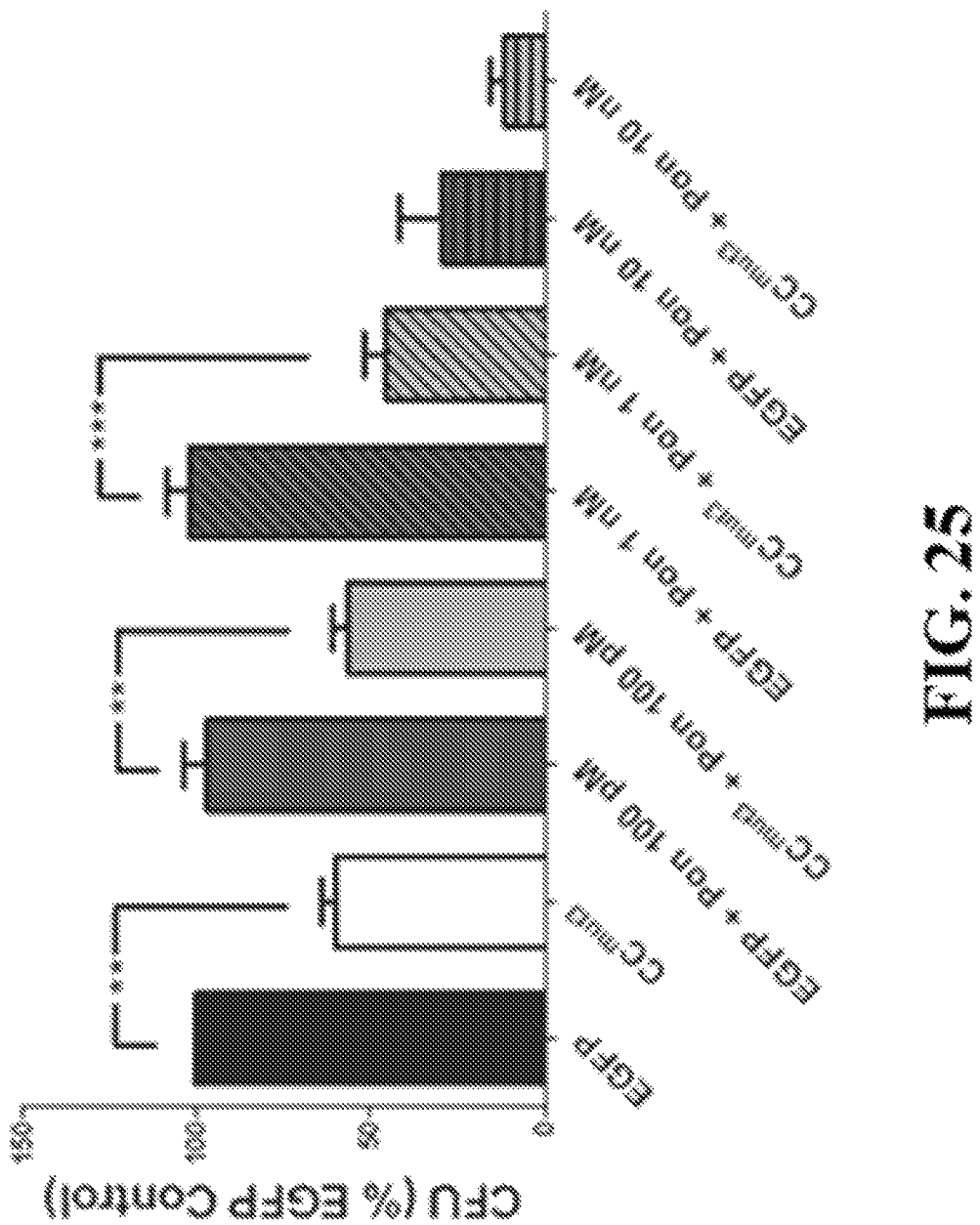
FIG. 25 shows representative data demonstrating the effect of $CC^{mut3}$ and/or ponatinib on Ba/F3-p210-T315I cell transformative ability.
Figures 26A, 26B, 26C:
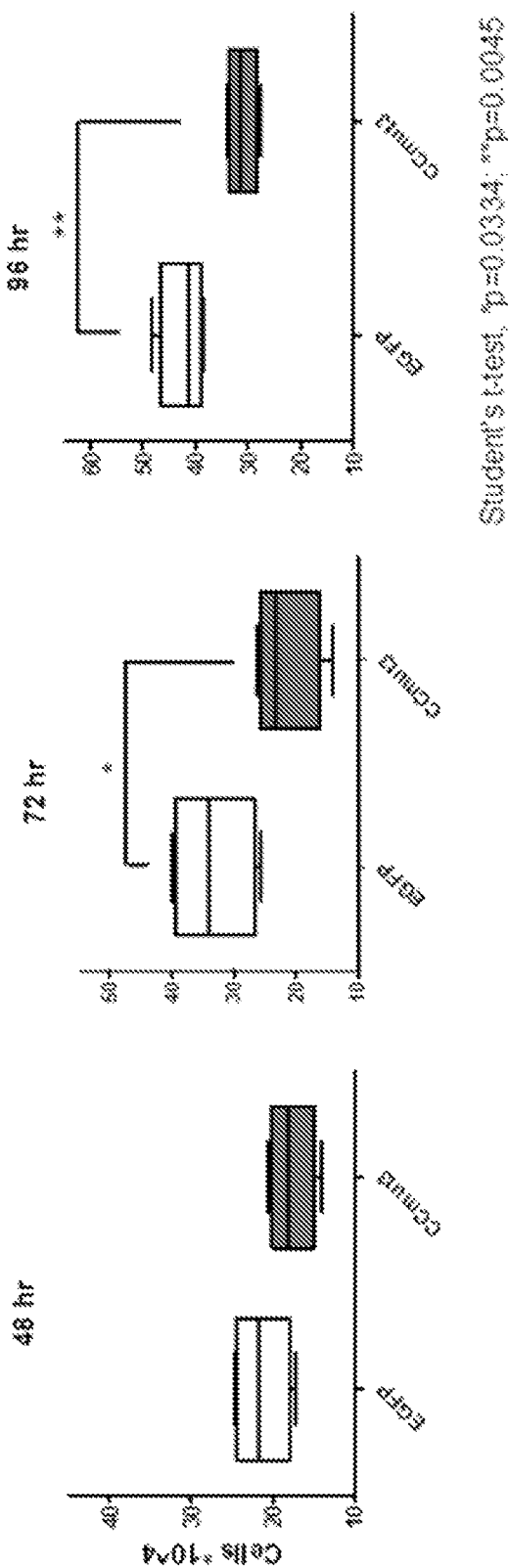
FIGS. 26A, 26B, and 26C show representative data demonstrating the effect of $CC^{mut3}$ alone on Ba/F3-p210-T315I cell proliferation at 48 (A), 72 (B) and 96 (C) h.

(F) Combination Treatment Enhances Induction of Apoptosis in Cells Containing the T315I Mutation Bcr-Abl cells containing the T315I tyrosine kinase domain mutation are known to be resistant to most TKIs. Ponatinib is known to be effective against these cells, albeit with a higher in vitro $IC_{50}$ (O'Hare, T., et al. (2009) Cancer Cell 16, 401-412). Because ponatinib is a pan-inhibitor of Bcr-Abl, higher dosing may lead to unintended inhibition of other receptor tyrosine kinases, potentially leading to increased side effects (in vivo) (Cortes, J. E., et al. (2012) New Engl. J. Med. 367, 2075-2088; Gozgit, J. M., et al. (2011) Mol. Cancer Ther. 10, 1028-1035). Therefore, the combination was tested in Bcr-Abl-containing Ba/F3 cells, which harbor the T315I mutation (Ba/F3-p210-T315I cells) (FIG. 23). Notably, the combinations of $CC^{mut3}$ with both 1 and 10 nM ponatinib showed significantly higher induction of apoptosis/necrosis than corresponding ponatinib doses alone (FIG. 23F vs. 23E and 23H). Overall, $CC^{mut3}$ with 10 nM ponatinib works more effectively than all other treatments (FIG. 23H vs. 23A-G). All results are summarized in FIG. 24.

o. $CC^{mut3}$ Drives the Reduction of Transformative Ability and Decrease in Proliferation of Cells Containing the T315I Mutation Transformative ability of Ba/F3-p210-T315I cells treated with either $CC^{mut3}$ and ponatinib combination was also tested (FIG. 25). Again, $CC^{mut3}$ alone reduced transformative ability, this time by ~40% compared to EGFP control (FIG. 25, second bar vs. first bar). However, as seen in the Ba/F3-p210 experiment, the combination did not provide additional benefit over either agent alone. Therefore, to support the evidence of antiproliferative activity caused by $CC^{mut3}$ alone, a cell proliferation assay was also performed. $CC^{mut3}$ alone was also found to inhibit Ba/F3-p210-T315I cell proliferation (standard trypan blue exclusion assay, FIG. 26), as measured at 72 and 96 h time points.

Figure 27A:
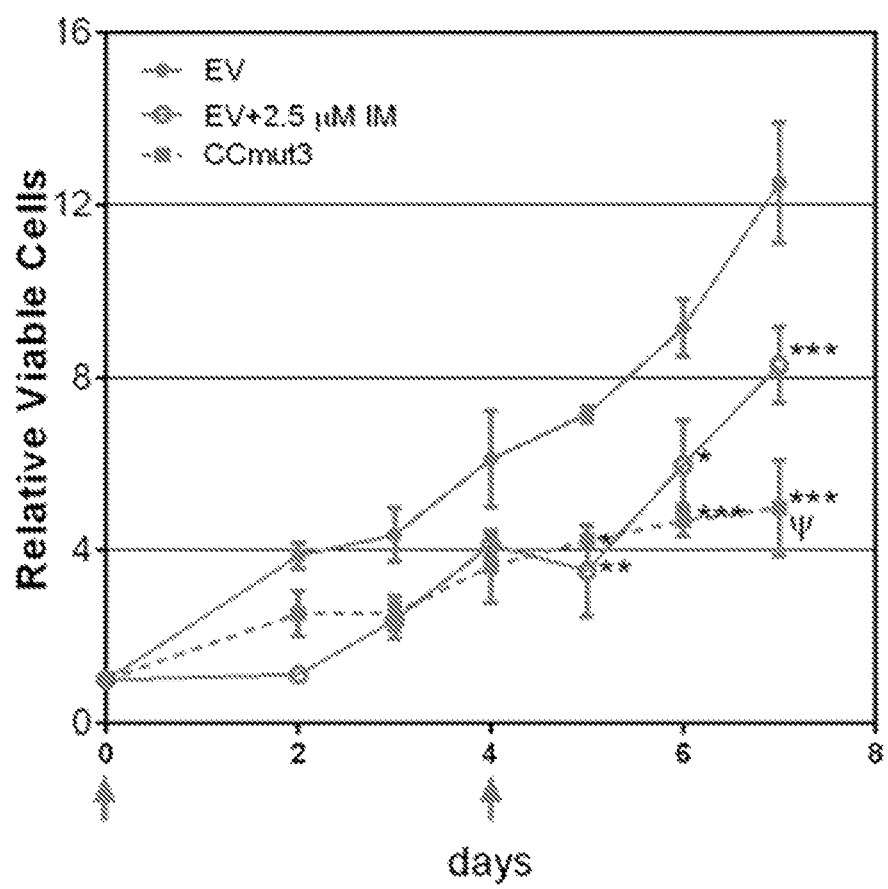
FIGS. 27A, 27B, 27C show representative data pertaining to the effect of ex vivo $CC^{mut3}$ lentiviral therapy on newly diagnosed CML patients. Specifically.
Figure 27B:
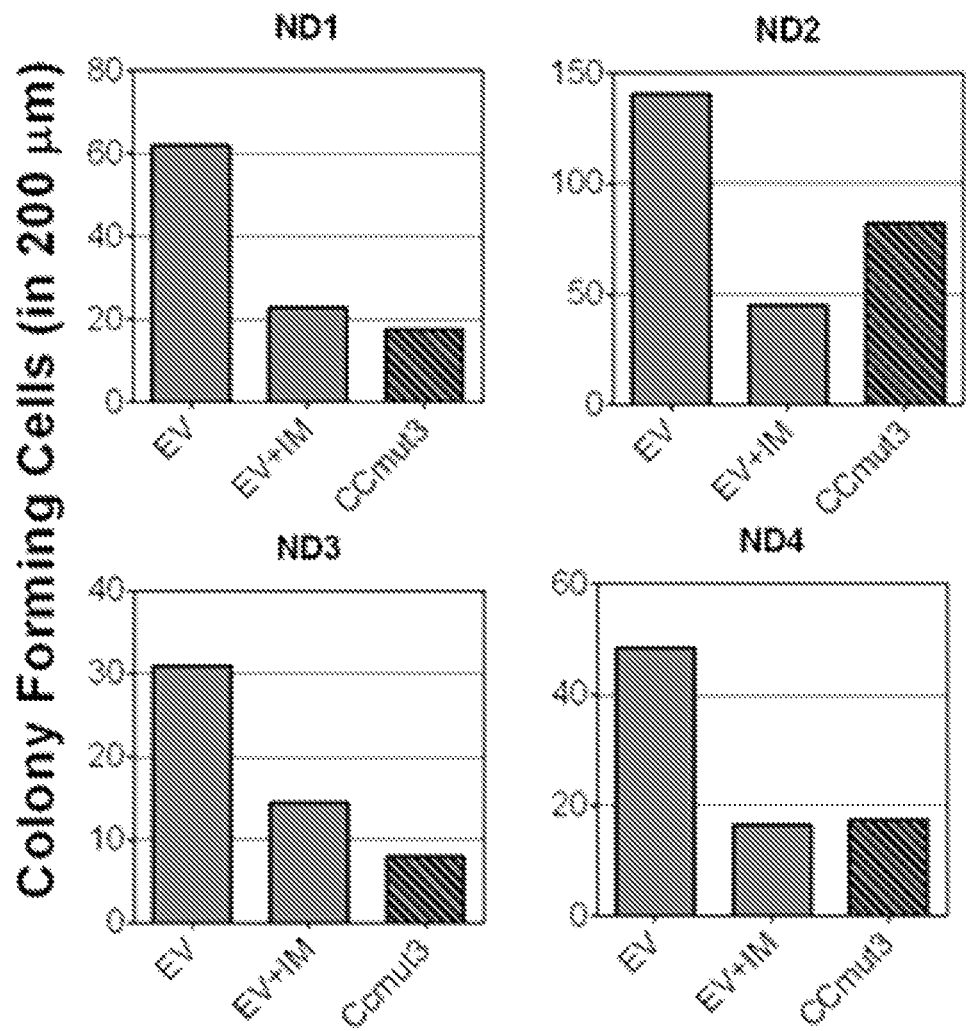
Figure 27C:
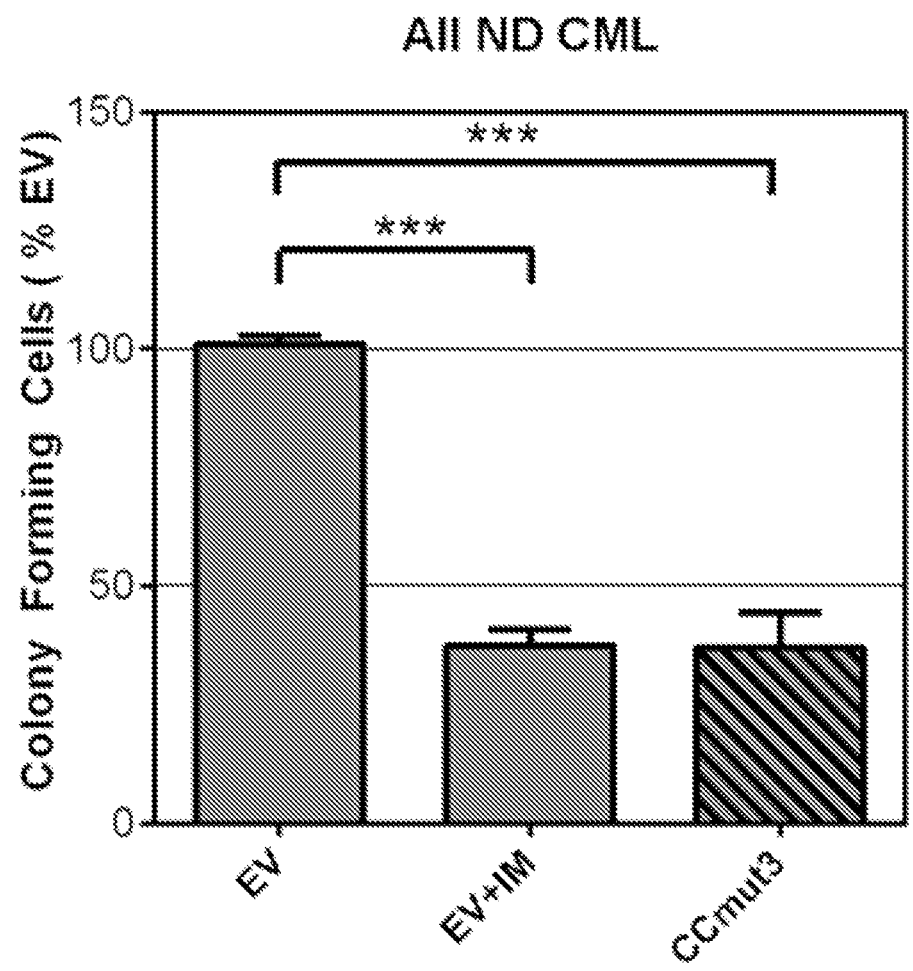
Figure 28A:
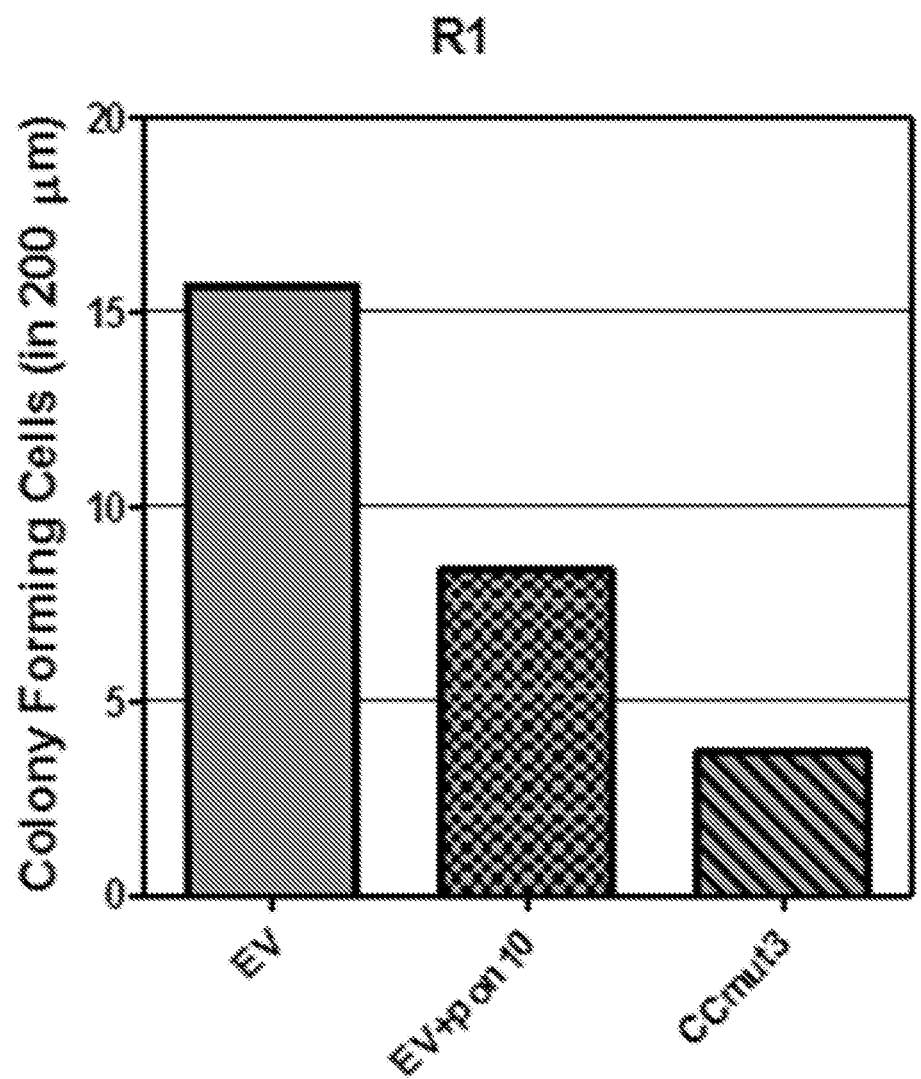
FIGS. 28A, 28B, and 28C show representative data pertaining to the effect of $CC^{mut3}$ on colony formation by T315I mutant primary chronic phase CML cells for one case ex vivo. Specifically.
Figure 28C:
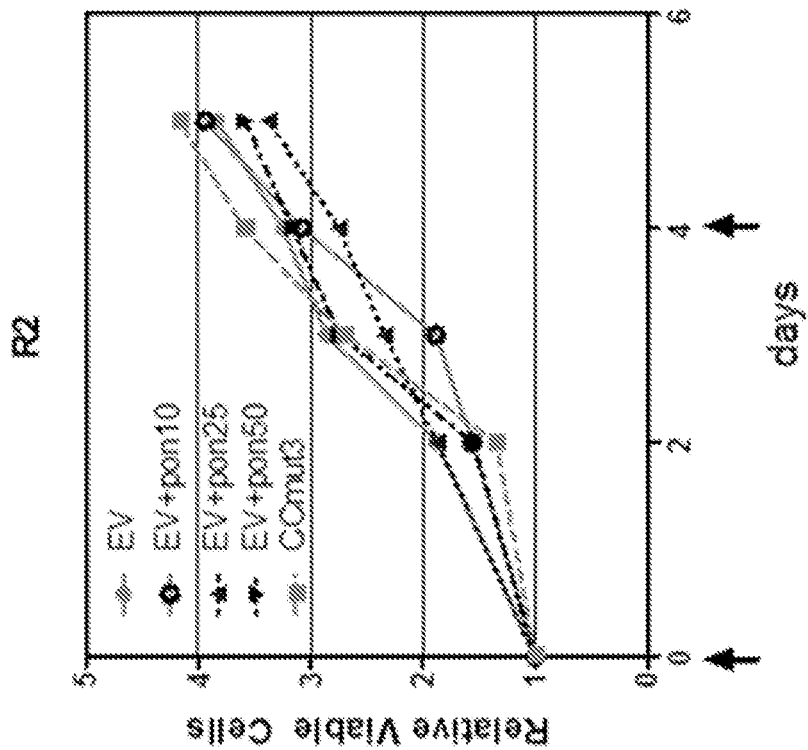
Figure 28B:
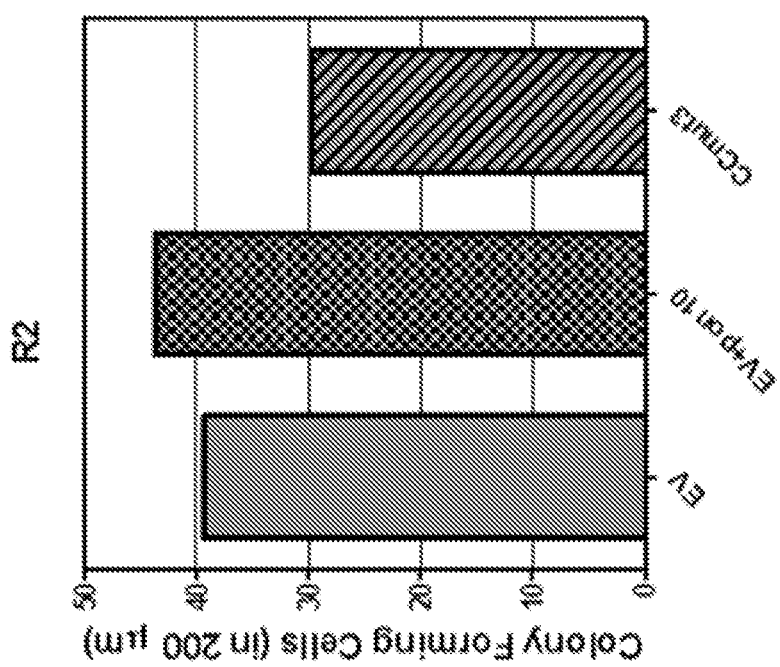

Finally, the $CC^{mut3}$ and ponatinib combination did not have activity in the Ba/F3-parent cells (Bcr-Abl negative and IL-3 dependent cells, data not shown) as expected. Without wishing to be bound by theory, this may suggest that the effects seen were only due to the presence of Bcr-Abl.

p. Cells From Newly Diagnosed CML Patients are Sensitive to $CC^{mut3}$ $CD34^+$ cells were isolated from blood or bone marrow of CML patients, infected with lentivirus expressing EV or $CC^{mut3}$ and cultured in RPMI 1640 with cytokines. For comparison an aliquot of EV-infected cells were treated with 2.5 µM IM. $CC^{mut3}$ reduced cell proliferation by more than 2-fold, a considerably more pronounced reduction of growth than observed with IM (FIG. 27A). Cells were also plated in methylcellulose supplemented with growth factors. Day 14 CFU-GM colony formation was reduced to similar degree, although there was variation across patients (FIGS. 27B and 27C).

q. $CC^{mut3}$ Inhibits Colony Formation by T315I Mutant Primary Chronic Phase CML Cells Finally, the effect of $CC^{mut3}$ expression on CML CD34+ cells expressing BCR-ABL1$^{T315I}$ as determined by Sanger sequencing was investigated. Samples R1 and R2 represent cells from the same individual at two time points approximately 6 months apart (Table 1). Ponatinib was used to assess sensitivity to small molecule inhibition of catalytic activity. In the initial sample (R1) $CC^{mut3}$ and 10 nM ponatinib reduced colony formation to a similar degree (FIG. 28A). In contrast, cells obtained at the time of blastic transformation (R2) were insensitive, although the mutation status had not changed compared to the initial sample (FIG. 28B). Similarly, $CC^{mut3}$ and increasing concentrations of ponatinib had no effect, as seen in liquid culture (FIG. 28C).

Thus, without wishing to be bound by theory, modifying this peptide, including reduction of the size and through the addition of a hydrocarbon staple to the backbone, may serve to overcome the current delivery issues.

Figure 29:
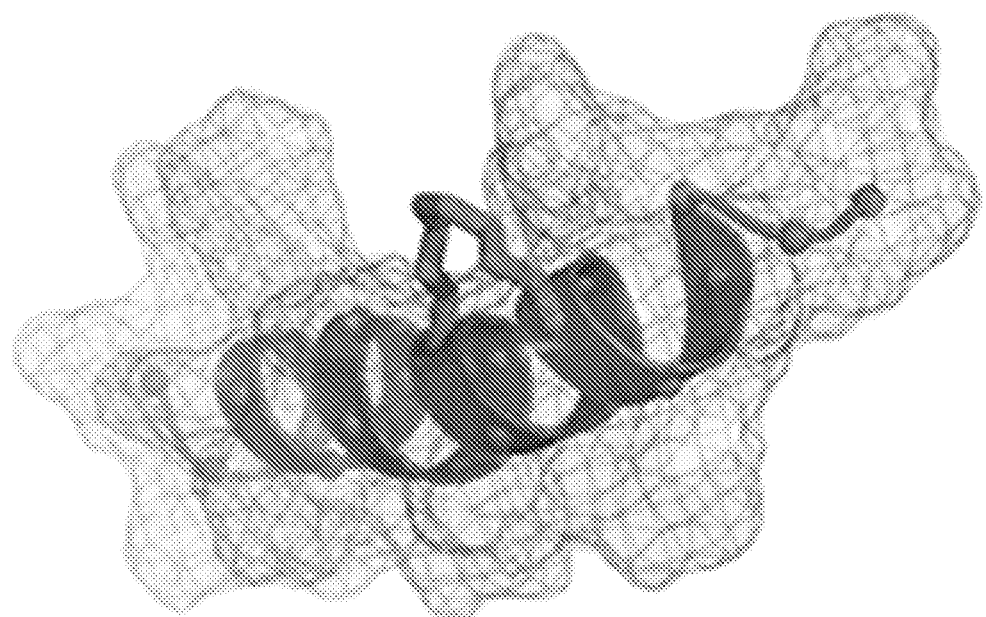
FIG. 29 shows a cartoon representation of a stapled peptide.

Addition of a backbone hydrocarbon staple is a relatively new technique used to stabilize α-helical peptides (FIG. 29) (Schafmeister, C. E., et al. (2000) *J. Am. Chem. Soc.* 122, 5891-5892; Henchey, L. K., et al. (2008) *Curr. Opin. Chem. Biol.* 12, 692-697). Prior to synthesis of the peptide, specific amino acid residues are chosen to undergo modification based on their location in the secondary structure of the peptide. More specifically, these residues must not be involved in interaction with the target, and must exist in the one of the following sequences, representative of approximately 1 or 2 full helical turns in the peptide: i, i+3; i, i+4; or i, i+7 (Schafmeister, C. E., et al. (2000) *J. Am. Chem. Soc.* 122, 5891-5892; Kim, Y. W., et al. (2010) *Org. Lett.* 12, 3046-3049). During synthesis, preferred amino acid residues are replaced with α,α-disubstituted amino acids, which include a stereo-specific alkyl chain of arbitrary length

TABLE 1

| ID | Name | Age | Gender | Disease Status | Disease Phase | Mutation Status | Current/ Previous Therapy |
|---|---|---|---|---|---|---|---|
| 11-310 | ND1 | 8 | F | ND CML | Chronic | — | — |
| 13-105 | ND2 | 29 | M | ND CML | Chronic/Accel. | — | — |
| 12-072 | ND3 | 44 | F | ND CML | — | — | — |
| 12-291 | ND4 | 72 | M | ND CML | Chronic | — | — |
| 12-187 | R1 | 66 | F | IM, DAS Resistant | Accel. | T315I | Hydrea, anagrelide, INF/IM, DAS |
| 13-004 | R2 | 67 | F | PON Resistant | Blast Crisis | T315I | PON/(see R1, FIG. 29B) |

Peripheral blood from CML patients with newly diagnosed (ND) CML or T315I resistant CML was collected and enriched for >90% CD34+ cells. The metrics presented here provide insight into the disease stage and treatment history of the patient samples used in this study. R1 and R2 are from the same patient at two different time points. Abbreviations: INF, peg- interferon; PON, ponatinib; Accel, accelerated; IM, imatinib; DAS, dasatinib.

2. Prophetic Examples a. Design of a Truncated Version of $CC^{mut3}$ Containing a Hydrocarbon Staple in the Peptide Backbone Bcr-Abl requires homo-oligomerization to function as an oncoprotein (McWhirter, J. R., et al. (1993) *Mol. Cell Biol.* 13, 7587-7595). A construct designed to inhibit this oligomerization and prevent Bcr-Abl oncogenic activity has been described (see FIG. 7). This construct, $CC^{mut3}$, was rationally designed based on the Bcr-Abl α-helical coiled-coil (CC) domain to favor specific hetero-oligomerization with Bcr-Abl while at the same time disfavoring homo-oligomerization (Dixon, A. S., et al. (2012) *Mol. Pharm.* 9, 187-195). Because $CC^{mut3}$ is designed based off of the sequence of the native Bcr-Abl CC domain, $CC^{mut3}$ is highly specific for Bcr-Abl. Without wishing to be bound by theory, it is therefore unlikely that it would bind to other proteins containing coiled-coil domain with any noticeable specificity. Importantly, delivering this gene construct via transient transfection is not immediately translatable. In addition, delivering the construct as an unmodified peptide is expected to show a hahlack of stability in circulation and inefficient cell internalization due to its overall −1 charge.

instead of a hydrogen atom at the α position (Scheme 1) (Bird, G. H., et al. (2008) *Methods Enzymol.* 446, 369-386). Once the sequence has been synthesized, the alkyl chains are connected using a ruthenium-catalyzed ring-closing olefin metathesis, thus creating the hydrocarbon staple (Scheme 1) (Kim, Y. W., et al. (2011) *Nat. Protoc.* 6, 761-771).

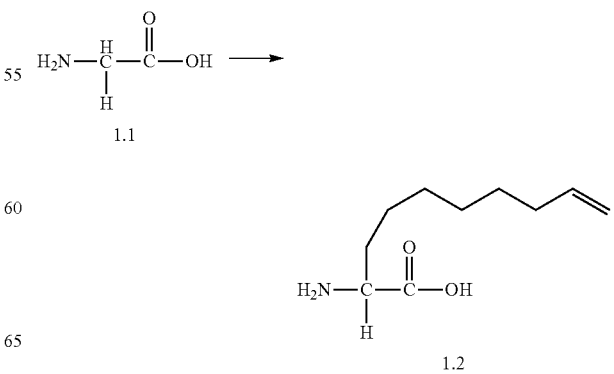

SCHEME 1.

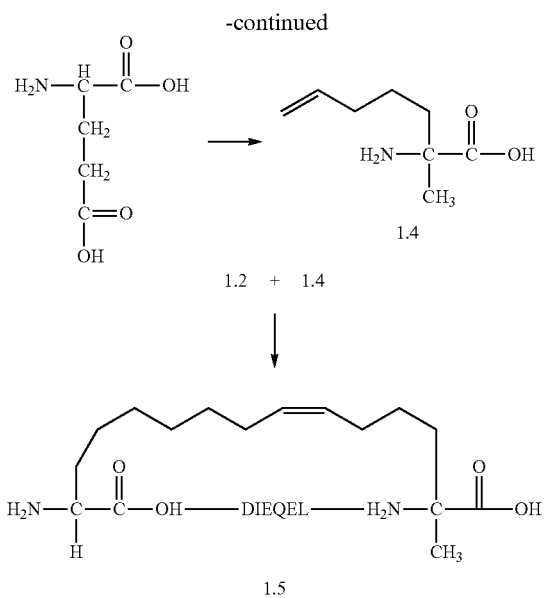

Without wishing to be bound by theory, adding this staple locks the peptide in its α-helical state, thereby limiting the number of attainable conformations in solution. This may result in an increase in percent helicity of the peptide and contribute to a vast improvement in the potency of the therapeutic. Locking the peptide in an α-helical state is primarily responsible for the increase in proteolytic resistance seen with stapled peptides, as proteases are known to bind their substrates in an extended, non-helical conformation (Verdine, G. L. and G. J. Hilinski, (2012) *Methods Enzymol.* 503, 3-33). Thus, by preventing the formation of an extended conformation, stapled peptides show stronger resistance to proteolytic degradation than non-modified peptides. In addition, with a peptide existing in this α-helical state, the polar amide backbone is buried internally due to the intramolecular hydrogen bonding characteristic to helix formation (Verdine, G. L. and G. J. Hilinski, (2012) *Methods Enzymol.* 503, 3-33). Without wishing to be bound by theory, this concealment of hydrophilicity may increase the exposure of hydrophobic residues, adding to an increase in cell membrane permeation. For example, once internalized, a 5-5000-fold increase in target affinity can result due to the vast reduction in the entropic cost of target binding caused by the pre-organized, locked peptide state (Verdine, G. L. and G. J. Hilinski, (2012) *Methods Enzymol.* 503, 3-33; Schafmeister, C. E., et al. (2000) *J. Am. Chem. Soc.* 122, 5891-5892; Bird, G. H., et al. (2010) *Proc. Natl. Acad. Sci. U.S.A.* 107, 14093-14098). Overall, the increases in proteolytic resistance, cell internalization, and enhanced target affinity may result in drastic improvements of the in vitro and in vivo efficacy of the peptide therapeutic. Without wishing to be bound by theory, in various aspects these enhancements could be multiplied even further by adding a second hydrocarbon staple to the backbone of larger peptides (Bird, G. H., et al. (2010) *Proc. Natl. Acad. Sci. U.S.A.* 107, 14093-14098).

(A) Experimental Design

Figure 30A:
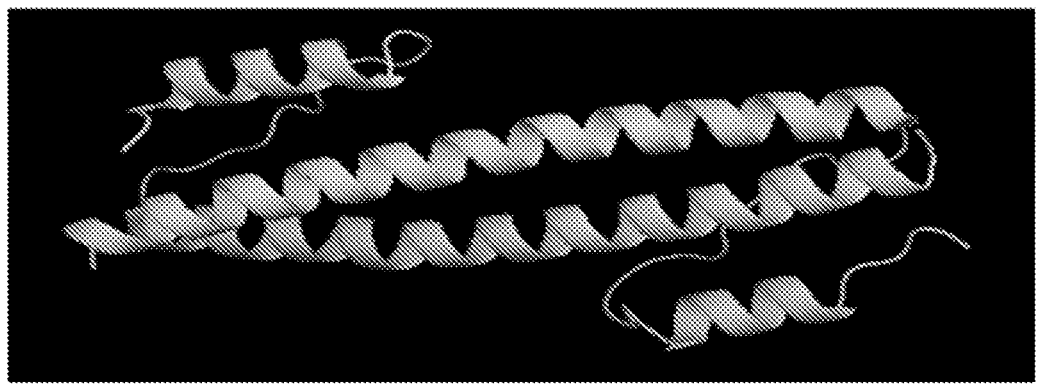
FIGS. 30A, 30B, 30C, 30D, and 30E show representative data pertaining to the design of a stapled peptide. Specifically.
Figure 30B:
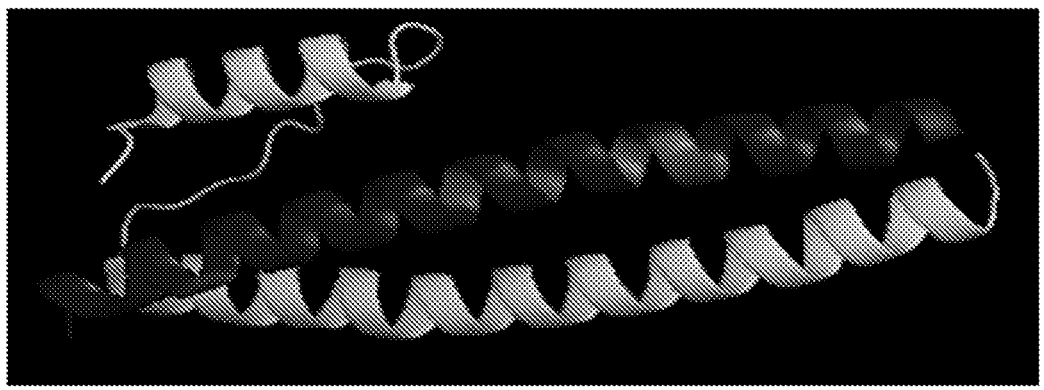
Figure 30C:
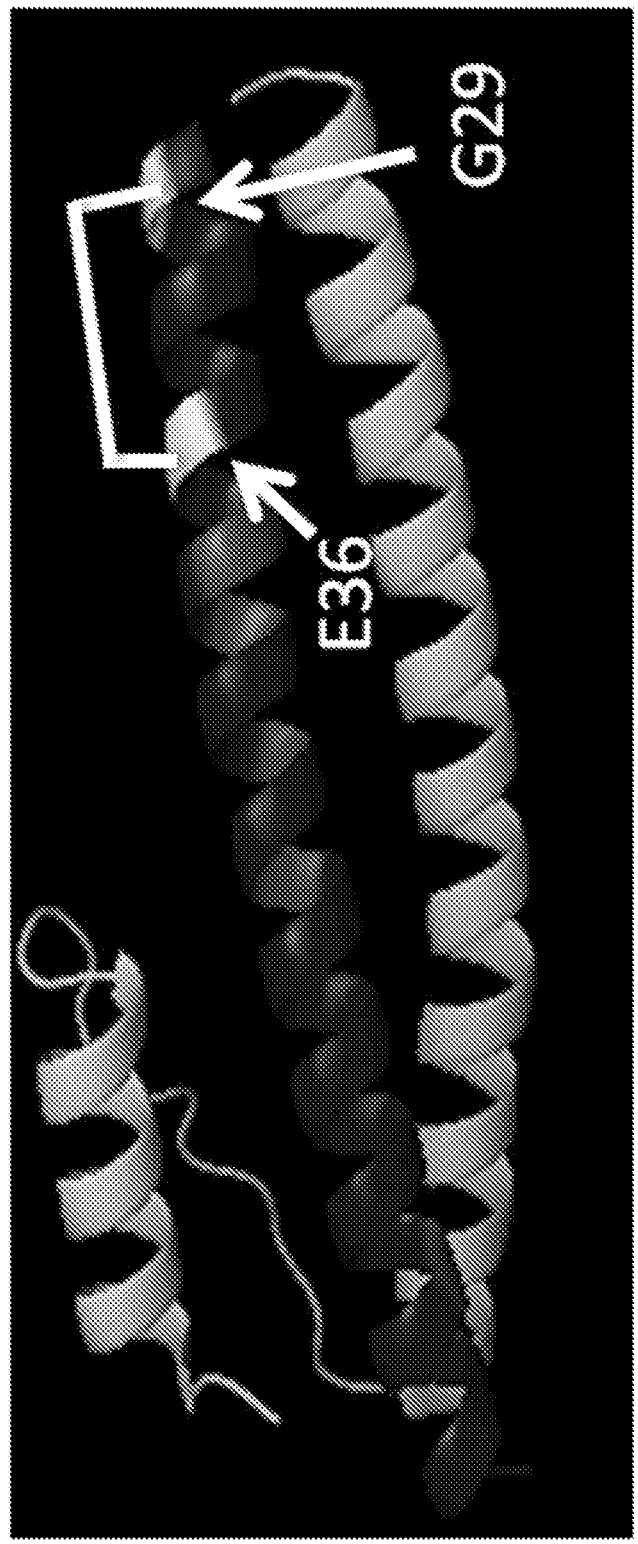
Figure 30D:
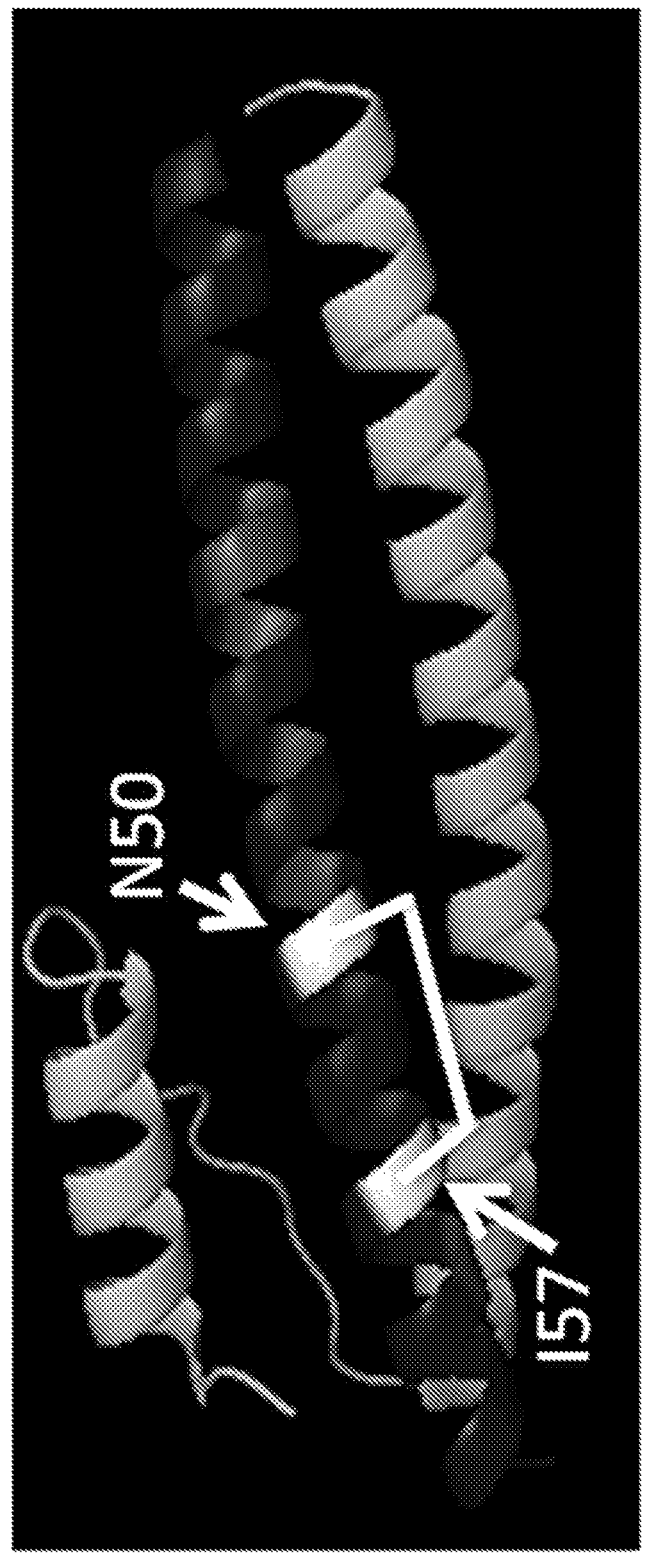
Figure 30E:
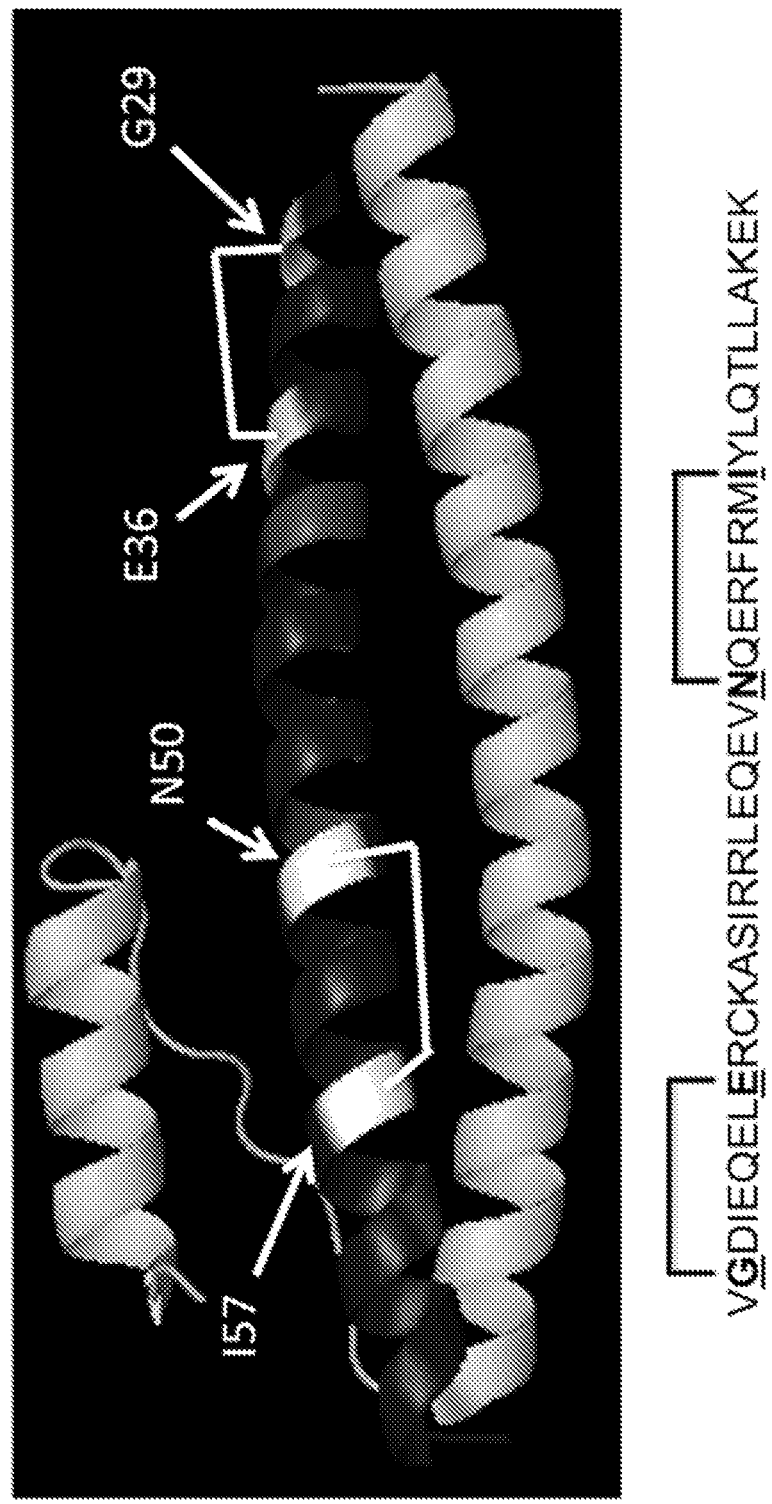
Figure 31:
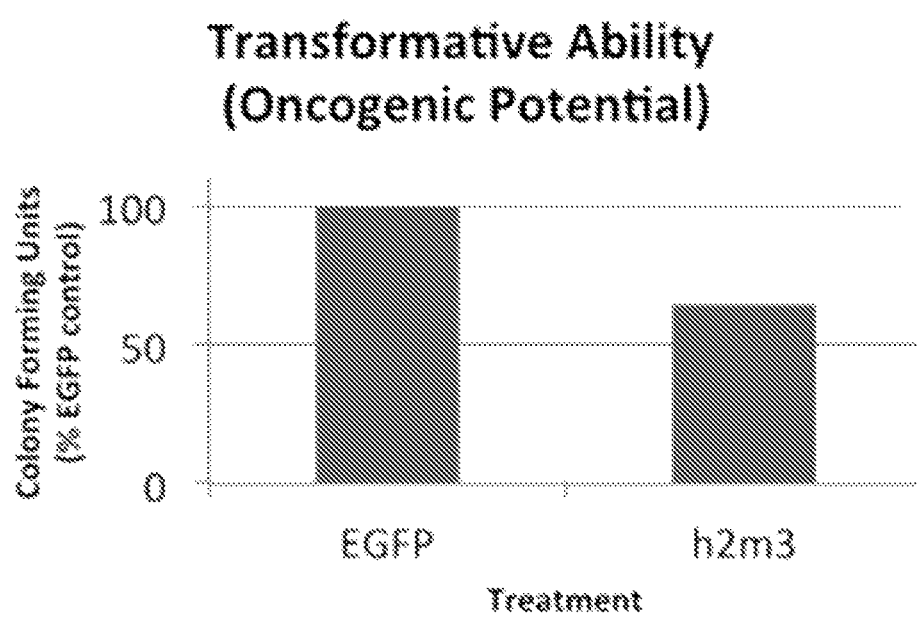
FIG. 31 shows representative preliminary data demonstrating the effect of a truncated version of $CC^{mut3}$ on transformative ability in K562 cells.

The design process of the truncated, stapled-$CC^{mut3}$ peptide is five-fold, as described herein below (FIG. 30). Thus, in various aspects, truncation of the original $CC^{mut3}$ peptide can be based off of the structure of the Bcr-Abl oligomerization domain (Zhao, X., et al. (2002) *Nat. Struct. Biol.* 9, 117-120) (FIG. 30A). The dimer interface of this domain is represented by the α2-helix (also called helix2), comprised of amino acids 28-67. Whereas in the past the full-length of the oligomerization domain has been studied in the $CC^{mut3}$ gene construct, it is herein proposed to use simply the helix2 domain (amino acids 28-67), representing a 40 amino acid peptide. Without wishing to be bound by theory, this truncated, coiled-coil peptide can contain the same amino acid mutations seen in the $CC^{mut3}$ construct (C38A, K39E, S41R, L45D, E48R, Q60E) designed to disfavor Bcr-Abl homo-oligomerization and instead favor hetero-oligomerization between our construct and Bcr-Abl (FIG. 30B) (Dixon, A. S., et al. (2012) *Mol. Pharm.* 9, 187-195). It has been demonstrated that using this helix2 domain, delivered as a gene via nucleofection, is sufficient to inhibit colony formation in K562 cells (FIG. 31).

Briefly, the synthetic hydrocarbon backbone (or backbones) added to the truncated $CC^{mut3}$ peptide must be placed in a location that will not affect the interaction between the two coiled-coil domains. Referring to FIG. 30, two examples of representative, ideal locations for the hydrocarbon staple are illustrated. In both examples, the staple is placed on the backside of the helix2 domain, opposite the dimer interface. Referring to FIG. 30C, the i, i+7 staple is placed on residues G29 and E36. This location, in addition to avoiding the dimerization interface, spans a leucine residue, important in enhancing the resistance to proteolysis from chymotrypsin (Verdine, G. L. and G. J. Hilinski, (2012) *Methods Enzymol.* 503, 3-33). Referring to FIG. 30D, the i, i+7 staple is placed on residues N50 and 157. Here, the staple avoids the dimer interface and also spans two arginine residues (R53, R55), important for protection against trypsin digestion, and a phenylalanine (F54) residue and a methionine residue (M56), important for protection against chymotrypsin digestion (Verdine, G. L. and G. J. Hilinski, (2012) *Methods Enzymol.* 503, 3-33). In both cases, the staple exists in an i, i+7 pattern, leading to nearly two exact turns of the helical structure at 3.6 residues per turn. Without wishing to be bound by theory, this stapled pattern is expected to be more stable than stapling slightly less than one full turn (i, 1+3) or slightly greater than one full turn (i, 1+4). The final constructs, when created, will be termed variants of either DST-$CC^{mut3}$ (Double Stapled, Truncated $CC^{mut3}$, which would represent a $CC^{mut3}$ domain with 2 hydrocarbon staples) or ST-$CC^{m1t3}$ (Stapled, Truncated-$CC^{mut3}$). See Table 2 herein below for more details. In various aspects, all peptides can include a fluorescent tag, attached N-terminally, suitable for imaging in a number of the proposed experiments.

Once the seemingly ideal locations of the staples have been established, the charge of the peptide can be determined at physiological pH based on the amino acid sequence. If it is determined that the peptide has a negative charge and is likely unsuited for cellular internalization, it would be beneficial to mutate un-important negatively charged residues to positively charged residues (Bernal, F., et al. (2007) *J. Am. Chem. Soc.* 129, 2456-2457). In various aspects, these mutations, which would include residues not involved in stabilizing the dimer interface, could include E32Q and/or E46Q.

After identifying residues for staple location and calculations of charge and presumed internalization capability, these designed peptides are computationally modeled prior to synthesis for further study. This computational modeling consists of calculating free energy between our designed peptide and native Bcr-Abl. Biomolecular simulation with "modern protocols (AMBER, explicit solvent, particle mesh Ewald with the new ff12SB protein force field) will be applied (Duan, Y., et al. (2003) *J. Comput. Chem.* 24, 1999-2012; Cerutti, D. S., et al. (2009) *J. Chem. Theory Comput.* 5, 2322). Model structures based on high resolution structures of Bcr-Abl (PDB ID: 1K1F, chains A and B) with the disclosed peptides are relaxed through molecular dynamics (MD) simulation (~50-100 ns), followed by analysis and further free energy simulations to assess the impact of stapling (Grant, B. J., et al. (2010) *Curr. Opin. Struct. Biol.* 20, 142-147; Huo, S., et al. (2002) J Comput. Chem. 23, 15-27; Klepeis, J. L., et al. (2009) *Curr. Opin. Struct. Biol.* 19, 120-127; Kollman, P. A., et al. (2000) *Acc. Chem. Res.* 33, 889-897; Lee, E. H., et al. (2009) *Structure* 17, 1295-1306; Meli, M. and G. Colombo (2009) *Methods Mol. Biol.* 570, 77-153; Steinbrecher, T. and A. Labahn, (2010) *Curr. Med. Chem.* 17, 767-85). Extensive statistical analysis could be done as previously described (Dixon, A. S., et al. (2011) *J. Biol. Chem.* 286, 27751-27760; Dixon, A. S., et al. (2012) *Mol. Pharm.* 9, 187-195). Without wishing to be bound by theory, the information obtained from this computational modeling may indicate the most energetically favorable peptide, which can then be synthesized (for further study), allowing for elimination of the current shotgun approach of synthesizing many stapled peptides prior to any type of analysis.

Once the designs have been computationally modeled and an ideal candidate(s) is/are chosen, the specific peptide(s) is synthesized and ordered in a small quantity from AnaSpec, Inc. (Fremont, Calif.) for testing as described herein below.

Following small quantity synthesis of the lead candidate with a rhodamine fluorescent tag, the design is validated in a high-throughput manner by testing both the internalization and apoptotic activity via FACS methods in K562, Ba/F3-p210, Ba/F3-T315I, and Ba/F3-E255V/T315I cells.

(B) Cell Internalization Via FACS

K562 and each line of Ba/F3 cells (approximately $5.0 \times 10^4$ cells) is treated with micromolar amounts of fluorescently-tagged peptides (see Table 2 below) in serum free media and incubated at 37° C. At pre-determined time points following treatment, cells are pelleted and incubated with 50 µL of trypsin for 5 minutes to cleave any protein adherent to the outside of the cells. After trypsin treatment, the cells undergo a series of washes with FBS-containing media and PBS, followed by another pelleting step, and finally re-suspended in a suitable buffer. Cells are then analyzed by fluorescence-activated cell sorting (FACS) using a FACS Canto instrument (University of Utah Core Facility). Percent of cells displaying fluorescence (thus, positive for peptide internalization) can be calculated for internalization efficiency (Bird, G. H., et al. (2008) *Methods Enzymol.* 446, 369-386).

(C) 7-AAD/Annexin V Staining

Apoptotic activity is assessed using Annexin V/7-AAD staining. 7-Aminoactinomycin D (7-AAD) is a fluorescent dye that can permeate only the membranes of dead and dying cells; thus, a measure of late apoptosis. Annexin V, also a fluorescent dye, measures the presence of externalized phosphatidylserine, a hallmark sign of early apoptosis. Procedurally, treated cells are collected at an optimal time point and re-suspended in 500 µL of Annexin Binding buffer (Invitrogen). 0.5 µL of 7-AAD dye (1 mM) is added to each treatment group 45 minutes prior to analysis, and 1 µL of Annexin V dye is added 10 minutes prior to analysis. Cells are analyzed, using a FACS Canto instrument with BD FACSDiva software (University of Utah Core Facilities). Determination of early and late stage apoptosis has been described previously (Miller, G. D., et al (2013) *Mol. Pharm.*).

(D) Strategy to Improve Peptide Hydrophilicity

Once the peptides are designed and synthesized, they can be reconstituted in solution and analyzed via MS (University of Utah Core Facility) to ensure a high level of purity and to ensure that the sequence is correct. Due to the expected highly hydrophobic nature of the peptides once the staple has been added, solubility in a non-organic solvent may be an issue. More often than not, these peptides are solubilized using DMSO in D5W (Bird, G. H., et al. (2010) *Proc. Natl. Acad. Sci. U.S.A.* 107, 14093-14098; Chang, Y. S., et al. (2013) *Proc. Natl. Acad. Sci. U.S.A.* 110, E3445-3454; Walensky, L. D., et al. (2004) *Science* 305, 1466-1470), which is generally acceptable for in vitro, proof-of-concept studies. However, because it is of high importance to make this work as translatable to a human therapeutic as possible, it may be necessary to formulate these peptides to make them soluble in aqueous solution. Therefore, a design strategy to improve the solubility involves making hydrophobic→hydrophilic amino acid mutations, increasing the exposed hydrophilicity of the peptide (Verdine, G. L. and G. J. Hilinski (2012) *Methods Enzymol.* 503, 3-33). Without wishing to be bound by theory, it is expected that these mutations can be made based on the Pymol structure of the oligomerization domain and analysis of the helical wheel diagram (Dixon, A. S., et al. (2011) *J. Biol. Chem.* 286, 27751-27760). If this strategy does not work, or compromises the cell internalization due to the newly exposed hydrophilic residues, the N-terminus of the peptide can be modified using a water-soluble polymer, such as PEG, to increase its aqueous solubility.

b. Assessment of Biophysical Characteristics, Stability, Internalization Capability, and Therapeutic Activity For the stapled, truncated $CC^{mut3}$ to act as an effective CML therapeutic, it must systemically reach and permeate leukemia cells and interact with Bcr-Abl all while maintaining its α-helical shape. The most favorable aspect in the design of this construct is the idea of locking the peptide in this shape. To ensure the amino acid substitutions made to incorporate the staple did not alter the structure of the peptide, circular dichroism (CD) can be used for validation. Based on CD theory, α-helical peptides absorb differentially polarized light in a characteristic manner, providing two minimum absorption peaks at 208 and 222 nm in the instrument readout (Kelly, S. M. and N. C. Price (2000) *Current Protein and Peptide Science* 1, 349-384). The percentage of the peptide remaining in a helical state can be calculated based on these absorption peaks (see below) and used to determine the efficiency of the added staple. Without wishing to be bound by theory, it is hypothesized that this strategic enhancement in helicity may improve many of the biophysical and biochemical properties of the molecule, including proteolytic resistance, cell permeabilization, and target affinity. Indeed, because the hydrocarbon staple(s) allows maintenance of the helical shape, it is expected to prohibit the peptide from garnering the extended conformation necessary for proteolytic degradation.

Figure 32A:
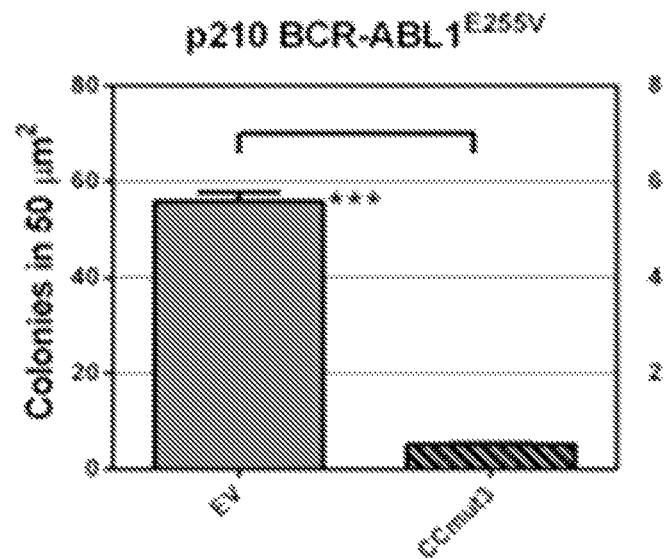
FIGS. 32A, 32B, and 32C show representative data pertaining to the effect of $CC^{mut3}$ on colony formation in Ba/F3 cells harboring the E255V (A), T315I (B) point mutants and the E255V/T315I (C) compound mutant forms of Bcr-Abl.

The expected increase in proteolytic resistance can be measured using both in vitro and ex vivo systems in an attempt to emulate an in vivo system as closely as possible. More specifically, the standard peptide degradation assays, which utilize trypsin, chymotrypsin, and carboxypeptidase A, are completed as these proteases are expected to contribute to more than 20% of protein degradation in vivo (Bruno, B. J., et al. (2013) *Therapeutic Delivery* 4, 1-25). Next, secondary internalization analysis via confocal microscopy is used to determine the subcellular localization of the internalized peptide (Bird, G. H., et al. (2008) *Methods Enzymol.* 446, 369-386). When also staining subcellular organelles or spaces, in this case the cytoplasm, permeation of the peptide into the cell can be confirmed. More specifically, because Bcr-Abl resides in the cytoplasm (Wetzler, M., et al. (1993) *J. Clin. Invest.* 92, 1925-1939), it may be possible to predict the potential effectiveness of DST-CC$^{mut3}$ or ST-CC$^{mut3}$ based on its subcellular location. Thus, in various aspects, measuring reduction of cell proliferation, inhibition of transformative ability, and induction of apoptosis may give actual results of the effectiveness of these peptides in an in vitro system. Cell lines used during in vitro analysis can be representative of both non-mutant, and, more importantly, mutant Bcr-Abl. K562 and Ba/F3-p210 cells contain wild type, non-mutant Bcr-Abl. Additionally, cells containing the "gatekeeper" T315I point mutation (Ba/F3-T315I) and a commonly seen compound mutant E255V/T315I (Ba/F3-E255V/T315I) can be tested, representing a subset of important, highly resistant Bcr-Abl mutations. Inhibition in colony formation of cells containing both the single point mutations E255V (FIG. 32A), T315I (FIG. 32B), and compound E255V/T315I mutations (FIG. 32C) has been demonstrated using CC$^{mut3}$ delivered via lentiviral infection, inhibition. While the extent of inhibition appears to vary between the single and compound mutants in FIG. 32, this may be a byproduct of inconsistent infection rates of the cells. Thus, the cells should be tested using a construct viable for eventual delivery in a human system and treated with a consistent molar amount of peptide for each cell line.

A fluorescent tag is conjugated to the N-terminus of DST-CC$^{mut3}$ or ST-CC$^{mut3}$ following synthesis. It is important to note that this tag, an all cases, requires a fluorescence expression outside of the GFP range (488 nm excitation, 530 nm emission), as the Bcr-Abl stably transduced in the Ba/F3 cells is conjugated with an EGFP tag (La Rosee, P., et al. (2002) *Cancer Res.* 62, 7149-7153; Sherbenou, D. W., et al. (2008) *Leukemia* 22, 1184-1190). In addition, the fluorescent tag needs to avoid the following ranges, depending on the experiment: 7-AAD (488 nm excitation, 647 nm maximum emission), Annexin V (APC, 635 nm excitation, 660 nm emission), and CMAC (cytosol stain, 353 nm excitation, 466 nm emission). Due to these detailed specifications, rhodamine B (575 nm excitation, 595 nm emission) can be used as a fluorescent tag for the peptide.

(A) Experimental Design

Table 2 below provides a description of the constructs to be tested.

TABLE 2

| Construct | Description | Applications |
|---|---|---|
| DST-CC$^{mut3}$ | Double-stapled, truncated CC$^{mut3}$ peptide | All experimental testing |
| A-ST-CC$^{mut3}$ | Version A of stapled, truncated CC$^{mut3}$ peptide (G29-E36 staple, for example) | All experimental testing |
| B-ST-CC$^{mut3}$ | Version B of stapled, truncated CC$^{mut3}$ peptide (N50-I57 staple, for example) | All experimental testing |
| CC$^{mut3}$ | Purified CC$^{mut3}$ peptide | Control for CD, in vitro and ex vivo stability, FACS internalization |
| CPP-CC$^{mut3}$ | Purified CC$^{mut3}$ peptide with cell-penetrating peptide attached | Control for FACS internalization, subcellular distribution, activity assays |

First, it is necessary to assure that the peptide has maintained its helicity in conjunction with assessing the thermal stability of the peptide. Next, the in vitro and ex vivo stability of the peptide are measured. The fraction of peptide that remains intact following the incubation with purified proteases or mouse serum is quantified. Finally, the internalization capability of the peptides, subcellular distribution following internalization, and therapeutic efficacy is studied. The prophetic experiments listed below can be completed, each of them utilizing different time points based off of previously optimized work. It is important to note, as well, that Ba/F3 parent cells can also be used for testing. These cells have not been transduced to express Bcr-Abl, thus are acting as a negative control.

(B) Circular Dichroism

The helicity of the stapled peptide can be analyzed using the Avid 410 CD Spectrometer at the University of Utah. As previously described with a first generation coiled-coil mutant peptide (Dixon, A. S., et al. (2011) *J. Biol. Chem.* 286, 27751-27760), 5-10 μm of our stapled peptide is ideally dissolved in PBS or 5 mM potassium phosphate (pH 7.5). A total of three scans, 190 to 300 nm in 1-nm steps with a 0.5 second averaging time in a 1-mm-path length cuvette, are measured. Percent helicity can be calculated as follows:

$$\% \text{ Helicity} = 100 \times \frac{[\theta_{222}]}{[\theta_{222}^{max}]},$$

$$\text{where } \theta_{222}^{max} = -40,000 \times \left[1 - \frac{2.5}{\#\text{amino acid residues}}\right]$$

(Bird, G. H., et al. (2008) *Methods Enzymol.* 446, 369-86).

Thermal denaturation of the peptide can also be measured. The average of three scans at 222 nm, ranging from 10 to 95° C. in 2° C. increments and back down to 10° C. in 10° C. increments, can be used for data analysis (Walensky, L. D., et al. (2004) *Science* 305, 1466-1470; Walensky, L. D., et al. (2006) *Mol. Cell* 24, 199-210).

(C) In Vitro Stability via Incubation with Purified Proteases 5-10 μg of each peptide is incubated with Trypsin-Agarose (Sigma, ~25 units/mL), α-Chymotrypsin-Agarose (Sigma, ~2700 units/g agarose), or Carboxypeptidase A-Agarose (Sigma, ~300 units/g agarose) for pre-determined times at 37° C. Following incubation, reactions can be quenched by high-speed centrifugation, leaving the remaining peptide in the supernatant of the mixture. The fraction of the starting amount of peptide that has remained intact after the given time points is then analyzed using MS-based detection (University of Utah Core Facilities) (Bird, G. H., et al. (2008) *Methods Enzymol.* 446, 369-386).

(D) Ex Vivo Incubation with Serum

Mouse serum can be obtained by bleeding female nude mice from the tail vein based on the procedure outlined by Argmann & Auwrex (Argmann, C. A. and J. Auwerx (2006) *Curr. Protoc. Mol. Biol.* Chapter 29: p. Unit 29A 3). Whole blood is collected, incubated at room temperature for an hour, and centrifuged to separate the serum. Once an adequate amount has been collected, 5 μg of peptide is incubated with serum at 37° C. for a number of time points. Level of intact peptide remaining at the determined collection points can be quantified using MS-based detection (University of Utah Core Facilities).

(E) Culture and Treatment of Cells

K562, Ba/F3-p210, Ba/F3-T315I, and Ba/F3-E255V/T315I cells are maintained in RPMI 1640 media (Invitrogen) supplemented with 10% FBS (Atlanta Biologicals), 1% Pen-Strep (Invitrogen), 1% L-Glutamine (Invitrogen), and 0.1% Gentamicin (Invitrogen). Ba/F3 parent (Bcr-Abl$^-$)

cells are maintained under the same conditions but also in the presence of IL-3, produced from WEHI-conditioned media (Lee, J. C., et al. (1982) *J. Immunol.* 128, 2393-2398). All initial treatments of cells with the disclosed peptides are in serum-free media.

(F) Subcellular Distribution via Confocal Microscopy

Confocal microscopy images of cells treated with the disclosed stapled peptides can be acquired as previously described (Constance, J. E., et al. (2012) *Pharm. Res.* 29, 2317-2328; Constance, J. E., et al. (2012) *Mol. Pharm.* 9, 3318-3329). Briefly, cells are treated with fluorescently-labeled peptides (see Table 2 herein above) and live cell images are collected in sequential line mode. The cytoplasm of peptide-treated cells is stained using CellTracker™ Blue CMAC (Invitrogen) to allow for co-localization analysis (Dixon, A. S., et al. (2012) *Mol. Pharm.* 9, 187-195). All images can be acquired using the Olympus IX81 FV1000-XY spectral confocal microscope (Imaging Core Facility, University of Utah).

(G) Trypan Blue Exclusion $1.0 \times 10^6$ cells (K562 and each line of Ba/F3 cells) per treatment group are treated with a variety of doses of the disclosed stapled peptides (see Table 2 herein above). Treatment times of cells can be based on the optimal internalization time from the studies described herein above. Following the optimal treatment time, cells are analyzed under a fluorescent microscope. 10 μL aliquots (n=3) of cells are taken from each treatment group and mixed with 10 μL of trypan blue. Cells are then viewed under a fluorescent microscope (those containing the blue dye are viewed as unviable) and analyzed as previously described (Miller, G. D., et al. (2013) *Mol. Pharm.*). Optimal time points and doses for each given cell line can be determined and used for therapeutic efficacy analysis in future experiments.

(H) Colony Forming Assay

The transformative ability (oncogenic potential) of cells treated with peptides from Table 2 can be analyzed via a colony forming assay. K562 and Ba/F3 cells are treated with optimal doses of peptide. 24 h later, $1.0 \times 10^6$ treated cells are collected and re-suspended in PBS. Through serial dilutions in IMDM (Isocove's Modified Dulbecco's Media), $1.0 \times 10^3$ cells are added to 3 mL of methylcellulose media in the absence of cytokines (MethoCult H4230 for K562 and MethoCult M3234 for Bcr-Abl$^+$ Ba/F3 cells (StemCell Technologies)) in 6-well plates (200 mm$^2$ area). 7 days later, colonies formed are counted under a light microscope.

(I) Western Blotting

Bcr-Abl kinase activity can be assessed by looking at the phosphorylation states of Bcr-Abl itself, as well as the downstream signaling molecules STAT5 and CrkL. In short, lysates from an arbitrary number of cells treated with the disclosed constructs can be collected and analyzed via Western blotting. Phosphorylation states are assessed using anti-p-Bcr-Abl, anti-p-STAT5, and anti-p-CrkL antibodies, as previously described (Dixon, A. S., et al. (2012) *Mol. Pharm.* 9, 187-195; Miller, G. D., et al. (2013) *Mol. Pharm.*).

(J) Statistical Analysis

All experiments are run in at least an n=3. FACS cell internalization, protease degradation, cell proliferation analysis (trypan blue exclusion), transformative ability (colony forming assays), and 7-AAD/Annexin V staining can be analyzed via one-way ANOVA with Tukey's post-test to determine statistical significance between groups as previously described (Dixon, A. S., et al. (2012) *Mol. Pharm.* 9, 187-195). Subcellular distribution (colocalization) via confocal microscopy can be analyzed using Pearson's Correlation Coefficient, as previously described (Constance, J. E., et al. (2012) *Pharm. Res.* 29, 2317-2328; Constance, J. E., et al. (2012) *Mol. Pharm.* 9, 3318-3329).

c. Evaluation of DST-CC$^{mut3}$ and/or ST-CC$^{mut3}$ Peptide in CML Patient-Derived Samples Here, the biologic activity of the lead DST-CC$^{mut3}$ or ST-CC$^{mut3}$ construct in leukemia cells derived from CML human patients is evaluated. This method represents a current standard of excellence in CML studies. Patient samples can be obtained, for example, from the Deininger Lab (HCI, University of Utah, see below). Because the mutational status of Bcr-Abl is the largest reason that current therapies would be ineffective, the lead construct will be tested on patient samples with un-mutated Bcr-Abl as well as those containing the T315I point mutation and the E255V/T315I compound mutant. Patient-derived cells treated with the lead construct (DST-CC$^{mut3}$ or ST-CC$^{mut3}$) is compared against treatment with the CPP-CC$^{mut3}$ peptide as well as against ponatinib (as a positive control) and imatinib (as a negative control in cells with the T315I and/or E255V/T315I mutations). (Much of the specifics regarding CML patient samples, including collaborations, was obtained from Dr. Lim re: NIH R01 submission, December 2013. Other portions were obtained from D. Woessner that appeared in an in preparation manuscript using CML patient samples.)

(A) Experimental Design (i) Acquiring CML Patient-Derived Cells

Heparinized bone marrow or leukophoresis products from chronic phase CML can be obtained from patients with Bcr-Abl mRNA-positive chronic-phase CML from HCI Tissue Resource and Applications Core (TRAC), under their umbrella protocol, IRB #10924, after informed consent, using guidelines from, for example, the committee on the Use of Human Subjects for Clinical Research at University of Utah. In addition, M. Deininger, Md., PhD, Chief of Hematology & Hematological Malignancies, HCI, has access to a collaborative leukemia biobank to obtain patient samples. Experiments are not "human subjects" since samples are de-identified prior to use.

(ii) Separation of CML Cells

To specifically obtain CML cells, plasma from collections can be separated, snap frozen and stored at −80° C. After removal of RBCs, white blood cells are fractionated by density gradient centrifugation using Ficoll, allowing separation and collection of mononuclear cells. From there, the CD34$^+$ fraction is isolated using an immunomagnetic column on an autoMACS Pro (Miltenya Biotech). To distinguish those CML cells containing no mutations, point mutations (T315I, specifically) or compound mutations (E255V/T315I), mutational analysis can be routinely carried out.

(iii) Culturing and Treatment of Patient-Derived CML Cells

Cells are maintained at a density of $1 \times 10^6$ cells/mL in RPMI1640 containing 20% FBS and 5 μL/mL StemSpan CC100 (Stem Cell Technologies, Vancouver, BC, Canada). Treatment will consist of adding the lead peptide and controls to the cells in this media. Despite the media containing serum, it will provide a more translatable approach to the proposed therapy at hand.

(iv) Activity Testing

Testing the activity of the lead DST-CC$^{mut3}$ or ST-CC$^{mut3}$ will proceed as described herein above, the only exception occurring with the colony forming assay. The patient-derived samples, after treatment with the disclosed peptide construct (and controls), can be seeded at the same density in MethoCult H4230 media and colony formation analyzed after 14 days, contrary to the 7 days seen with the K562 and Ba/F3 protocols. Analysis of cell proliferation (trypan blue exclusion) and apoptosis induction (7-AAD/Annexin V) is carried out as before.

(B) Statistical Analysis

The number of experiments run is based on the availability of the patient samples, ideally in at least n=3 per Bcr-Abl mutation (or unmutated Bcr-Abl). All assays can be analyzed using a one-way ANOVA with Tukey's post-test, as previously.

d. Additional Prophetic Examples

In various aspects, it is plausible to test the disclosed DST-CC$^{mut3}$ or ST-CC$^{mut3}$ in combination with other agents targeted to Bcr-Abl for an overall enhanced therapeutic effect. For example, the combination of CC$^{mut3}$ and ponatinib has previously shown effectiveness while at the same time lowering the dose of ponatinib used (Miller, G. D., et al. (2013) *Mol. Pharm.*). Other small molecules that could be used in combination with our stapled peptide include, but are not limited to, those that target downstream signaling pathways or secondary leukemia-specific pathways in CML cells (Woessner, D. W. and C. S. Lim (2013) *Mol. Pharm.* 10, 270-277), or therapeutics that may target the CML stem cells specifically (Kinstrie, R. and M. Copland (2013) *Curr. Hematol. Malig. Rep.* 8, 14-21). If for some reason the peptides appear to specifically bind to Bcr-Abl but do not result in inhibition, their later use may be directed toward acting as a targeting motif. Related to this idea, per previous stapled peptide work, using this stapled peptide sequence in a competitive screening manner may help to identify highly affinitive small molecules also capable of Bcr-Abl inhibition at the coiled-coil domain (Cohen, N. A., et al. (2012) *Chem. Biol.* 19, 1175-1186). Because protein-protein interactions (i.e., Bcr-Abl:CC$^{mut3}$) are possibly the most specific type of biochemical interaction, their targeting must be utilized in an attempt to lessen the likelihood of unwanted therapeutic side effects. Most notably, if this method were used, and a small molecule was discovered that was capable of targeting this region of Bcr-Abl, more highly successful delivery in lower molar quantities could exist as a possibility. In addition, it may be beneficial to test the mutational escape capability of Bcr-Abl against the disclosed stapled peptide, which could be completed, for example, by analyzing the CC sequence of Bcr-Abl after culturing Bcr-Abl$^+$ cells in small doses of peptide for an extended period of time. Finally, once the therapeutic efficacy has been tested, it may be beneficial to characterize the pharmacokinetic properties of the finalized construct, whether DST-CC$^{mut3}$ or ST-CC$^{mut3}$.

3. In vitro inhibition of Bcr-Abl with a Coiled-Coil Protein Delivered by a Cell-Penetrating Peptide Chronic myeloid leukemia (CML) is a myeloproliverative disorder characterized by the presence of the Philadelphia chromosome (Ph+). This truncated version of chromosome 22 is formed by a reciprocal translocation between the Abelson (Abl) tyrosine kinase gene of chromosome 9 with the breakpoint cluster (Bcr) gene of chromosome 22, resulting in the formation of the Bcr-Abl fusion gene. The product of this translation, the Bcr-Abl protein, is the causative agent of CML. Bcr-Abl is a constitutively active tyrosine kinase that alters many cellular processes including the JAK-STAT, PI3K/AKT, RAS, and MAPK signaling pathways.

Bcr-Abl is active as a tetramer; the N-terminus of Bcr contains a coiled-coil domain which allows for dimerization and further tetramerization of Bcr-Abl molecules. Once tetramerized, Bcr-Abl trans-autophosphorylates the tyrosine kinase domain present in the Abl portion of the protein, which is responsible for the constitutive kinase activity of Bcr-Abl. Most currently approved therapies target this tyrosine kinase domain, known as tyrosine kinase inhibitors, or TKIs. Treatment with TKIs has transformed CML from a disease with a poor long-term prognosis into a chronic, treatable condition. However, with continued treatment, many patients become resistant to these TKIs due mainly to point mutations in the tyrosine kinase domain that prevent TKI binding. Second and third generation TKIs have been developed specifically to treat those whose disease is resistant to the breakthrough first generation inhibitor, imatinib (Gleevec). Nevertheless, clinical resistance to all second and third generation TKIs, including the most recently approved TKI ponatinib (Iclusig), has already been seen. It is believed that, with continued treatment, patients will inevitably develop point mutations in the tyrosine kinase domain that abrogate TKI effectiveness.

While current agents target the tyrosine kinase domain, another possible target is the coiled-coil domain (CC) at the N-terminus of the protein. A mutant version of the CC present in Bcr (CCmut3) has been created, which preferentially binds to the CC of Bcr-Abl while avoiding autodimerization with itself. CCmut3 prevents dimerization (and therefore tetramerization) of Bcr-Abl, and thereby halts trans-autophosphorylation. Additionally, CCmut3 inhibits both wild-type Bcr-Abl and a clinically-relevant mutant form Bcr-Abl (Bcr-Abl T315I) , while being nontoxic to Bcr-Abl-cells. Additionally, CCmut3 acts additively with ponatinib to further decrease the oncogenicity of Bcr-Abl T315I , the "gatekeeper" mutation.

All of this previous work with CCmut3 was performed via transfection of plasmid DNA or lentiviral infection (patient samples, unpublished data) as proof of concept in vitro and ex vivo. However, transfection or viral delivery is not currently clinically feasible for CML. The aim of this study is to translate these findings by delivering CCmut3 as a protein.

Peptide and protein therapeutics are growing in popularity and commercial use, and cell-penetrating peptides (CPPs) are a promising way to internalize proteins, thus enhancing intracellular activity. CPPs are short, often positively-charged peptides which are able to translocate across cell membranes. These peptides are capable of carrying attached DNA, peptides, and proteins across cell membranes, and some are currently being tested in clinical trials. For this study a leukemia-specific cell-penetrating peptide (CPP) was utilized for delivery of CCmut3 preferentially (if not specifically) to leukemia cells. This CPP has the amino acid sequence CAYHRLRRC, and contains two motifs, a lymph node-homing motif (CAY) and a cell-penetrating motif (RLRR), which gives it a positive charge at physiologic pH. It was discovered by phage display and has shown to be nontoxic to leukemia cells by itself. Further, the CPP entered patient-derived leukemia cells but not non-leukemic patient-derived blood cells.

CCmut3 was tested to determine if it can be an effective treatment for CML when delivered as a protein. CPP-CCmut3 and controls were encoded in plasmids, and corresponding proteins were expressed in *E. coli* and purified. After identity verification, these recombinant proteins were tested for their ability to enter leukemic and non-leukemic cells. 7-AAD/Annexin V staining, colony forming assays, cell proliferation assays, and kinase activity Western blots were then performed to test the anti-oncogenic activity of CPP-CCmut3.

iii. Materials and Methods a. Plasmid Construction

Plasmids encoding wild-type CC (CCwt) and CCmut3 were created as previously described. The DNA encoding the CPP was added with the primers 5'-TAACATTGTACA-CAACTGCGCGTATCATCGCCTGCGCCGCTGCATG-GTGGACCCG GTGGGCTTCGC-3' and 5'-ACT-GAATAAGCTTTTAGCAGCAGCCCGGGCAGCACCGG TCATAGCTCTTCTTTTC CTTGGCCAGCAACG-3', and resulting constructs were subcloned into the ELP-Intein vector (Qiagen, Valencia, Calif., USA) using BsrGI and HindIII restriction sites. An N-terminal 6× histidine tag and HRV-3C (PreScission) protease site (LEVLFQ/GP) were then added with the forward primers 5'-CG-CAAGGGAGCTCCCATCATCATCATCATCATCTT-GAAGTTCTTTTTCAAGGTCCT TGCGCGTAT-CATCGCCTGCG-3' and 5'-CGCAAGGGAGCTCCCATCATCATCATCATCATCT-TGAAGTTCTTTTTCAAGGTCCT ATGGTGGACCCG-GTGGGCTT-3' for the constructs with and without the LS-CPP, respectively. The back primer 5'-TATGCTGGATC-CTTACCGGTCATAGCTCTTC-3' was used for all constructs. The inserts were subcloned into the protein expression vector, pMal-C2x (New England Biolabs) using SacI and BamHI restriction sites. In this way the final constructs encoding maltose binding protein (M)-6× histidine tag (H)-HRV-3C protease site (P)-leukemia-specific cell-penetrating peptide (CPP)-CCmut3 (MHP-CPP-CCmut3), MHP-CPP-CCwt, and MHP-CCmut3 were created.

b. Protein Expression and Purification

BL21(DE3) *E. coli* cells (Invitrogen, Carlsbad, Calif., USA) were transformed with the plasmids described above per the manufacturer's protocol. 5 mL of Rich Medium [10 g tryptone (Sigma Aldrich, St, Louis, Mo., USA), 5 g yeast extract (Sigma Aldrich), 5 g NaCl (ThermoFisher, Waltham, Mass., USA), and 2 g glucose (Sigma Aldrich) per liter] was supplemented with carbenecillin (Invitrogen) to a final concentration of 50 µg/mL. This was seeded with freshly transfected BL21(DE3) cells and grown overnight. 16 hours later, 1 L of rich medium was inoculated with the 5 mL overnight culture and grown at 37° C. until the desired optical density @600 nm (0.4, 0.6, 0.8, 1.0) was reached (Varian Cary 100, Agilent Technologies, Santa Clara, Calif., USA). 0.2 µ filtered (Acrodisc nylon filter, Life Sciences, St. Petersburg, Fla., USA) isopropyl β-D-1-thiogalactopyranoside (IPTG) (GoldBio, St. Louis, Mo., USA) was added to the culture to a final concentration of 0.5 or 1.0 mM to induce protein expression. Cultures were then grown for 4 or 16 hours at 27° C. or 37° C.

After expression, the culture was transferred to 500 mL centrifuge containers and centrifuged at 4000×g for 20 minutes. The supernatant was discarded, and the pellet was resuspended in 45 mL amylose binding buffer (ABB) [20 mL 1.0M Tris-HCl, pH 7.4 (Sigma Aldrich), 11.7 g NaCl (Fisher), 2.0 mL 0.5M EDTA (Fisher), 154 mg DTT (Gold-Bio), with a sufficient quantity of Milli-Q water to make 1 L, filtered with a 0.4 µM nylon vacuum filter (VWR)], transferred to a 50 mL tube, and frozen at −20° C. overnight.

The following morning the sample was thawed on ice and transferred to a 100 mL beaker. Approximately 5 mg of egg white lysozyme (Sigma Aldrich) was added, and the sample was incubated on ice for 1 hour with occasional stirring. After the hour, the sample was sonicated for 6 cycles of 10 seconds on, 15 seconds off at 20% amplitude with the Sonic Dismembrator Model 500 (Fisher Scientific). 50 µL of 10% poly(ethyleneimine) (Sigma Aldrich) was added to the sample to precipitate the DNA. The samples were transferred to centrifuge tubes and spun at 15,000×g for 30 minutes. The supernatant was transferred into a fresh 50 mL tube, and the pellet was saved for analysis. Samples were stored at 4° C. with 0.1% sodium azide (Sigma Aldrich)

The supernatant was then purified on amylose resin (New England Biolabs). After elution with ABB+20% v/v maltose (Sigma Aldrich), the protein was diluted with ABB to a concentration of 0.9 mg/mL, to prevent precipitation during the next step. The proteins were incubated with the HRV-3C (PreScission) protease overnight at 4° C. Next, samples were dialyzed into cobalt binding buffer [7 g sodium phosphate (Sigma Aldrich), 17.5 g NaCl (Fisher) per liter, 0.4 µM filtered] using SnakeSkin dialysis tubing, 3.5 kDa molecular weight cutoff (MWCO) (ThermoFisher). The maltose binding protein and protease site were then removed by running the sample over cobalt resin (GoldBio Technologies). Since the HRV-3C protease also had a His tag it was removed along with the maltose binding protein. Proteins were concentrated to 0.5 mg/mL using a 9 kDa MWCO centrifugal protein concentrator (ThermoFisher), lyophilized, and stored in a desiccant container.

c. Protein Preparation for Experiments

Proteins were resuspended in DPBS (Gibco by Life Technologies, Grand Island, N.Y., USA) at a concentration of 1 mg/mL. Resuspended proteins were then run over a polyacrylamide desalting column (Fisher Scientific, Hanover Park, Ill., USA). CPP-His, which was ordered from LifeTein (South Plainfield, N.J., USA) was run over a column with a MWCO of 1.8 kDa, while the other 3 constructs (CPP-CCmut3, CPP-CCwt, and CCmut3) were run over columns with a 7 kDa MWCO. The samples were then sterile filtered through a 0.22 µM PVDF filter (EMD Millipore, Billerica, Mass., USA) into sterile tubes. The proteins concentrations were found using absorption at 280 nm with extinction coefficients and molecular weight on the Nanodrop 2000 spectrophotometer (Thermo Scientific). These values were corroborated by BCA assays (Thermo Scientific).

d. Cell Lines

Cell lines were maintained at 37° C. and 5% $CO_2$ in a humidity controlled incubator. K562 human leukemia, Bcr-Abl+ cells (a gift from Kojo Elenitoba-Johnson, University of Michigan) were cultured in RPMI 1640 (Invitrogen) with 10% FBS (HyClone Laboratories, Logan, Utah, USA), 1% penicillin/streptomycin (Invitrogen), 1% L-glutamine (Invitrogen) and 0.1% gentamycin (Invitrogen), referred to as complete RPMI. Cells were passaged every 2-3 days and seeded at 50,000 cells/mL.

Ba/F3 murine pro-B cells were transformed to stably express P210 Bcr-Abl, as previously described, 33 and grown in complete RPMI. Non-transformed (parental, Bcr-Abl-) Ba/F3 cells were grown in complete RPMI supplemented with 15% WEHI-3B conditioned media as a source of murine IL-3 required for proliferation. 34 Cells were split every 2-3 days and seeded at 100,000 cells/mL. The parental Ba/F3 cell media always contained 15% WEHI-3B conditioned media, regardless of what other supplements the experiment required to be omitted (FBS, penicillin, streptomycin, gentamicin).

The non-leukemia cell lines HEK-293 (human embryonic kidney cells, a kind gift from Hamid Ghandehari, University of Utah) and MCF7 (human breast cancer cells, ATCC) were grown as monolayers cultured in DMEM (Invitrogen) with 10% FBS, 1% penicillin/streptomycin, 1% 1-glutamine, and 0.1% gentamycin, referred to as complete DMEM. Cells were split 1:5 every 2-3 days when they were 80-90% confluent.

e. Mass Spectrometry

Intact Protein Analysis by ESI/MS:

CPP-CCmut3, CPP-CCwt, and CCmut3 were analyzed via electrospray ionization mass spectrometry (ESI/MS).

For electrospray mass spectrometry (ESI/MS) of intact proteins, samples were purified using the C18 Ziptip (Millipore). ESI/MS analysis of the intact proteins was performed using a Quattro-II mass spectrometer (Micromass, Inc., Milford, Mass., USA). The eluent from Ziptip purification was infused into the instrument at 3 µL/min. Data was acquired with a cone voltage of 50 eV, spray voltage of 2.8 kV, and the instrument was scanned from 800 to 1400 m/z in 4 seconds. Scans were accumulated for about 1 minute. Spectra were combined and multiply-charged molecular ions were deconvoluted into molecular-mass spectrum (i.e. processed into neutral molecular weight) using MaxEnt software (Micromass, Inc.).

f. MALDI/MS Analysis:

CPP-His was analyzed by matrix-assisted laser desorption/ionization mass spectrometry. The mass spectral data shown was collected using delayed ion extraction mode on a Bruker's ultrafleXtrem MALDI-TOF/TOF mass spectrometer (Bruker Corp., Billerica, Mass., USA). Peptide sample was spotted using dried-droplet method. Fresh solution of saturated a-cyano-4-hydroxy cinnamic acid matrix (CHCA) in a solvent system of 50:50 water:acetonitrile 0.1% TFA was prepared by thoroughly mixing the matrix powder with 0.5 mL of solvent in a 1.7 mL Eppendorf tube, and then centrifuged to pellet any un-dissolved matrix. The supernatant of this matrix solution was used for sample preparation for MALDI analysis. Peptide samples (0.5 µL of 1 pmol/µL) were loaded onto a target plate and mixed on the target with 0.5 µL of supernatant of saturated matrix solution. The sample spot was air-dried, followed by co-crystallization of the mixture. The spot was then ablated with a 1 kHz smartbeam-II™ laser technology (Bruker) from the plate while the sample was simultaneously desorbed and ionized, then accelerated into a flight tube. The MALDI spectrum was acquired in reflector mode, which was operated at around 30,000 resolving power over a mass range from 500 to 5000 Da.

g. Peptide Internalization and Kinase Activity Western Blots $1.0 \times 10^6$ cells resuspended in RPMI or DMEM were seeded in a CellStar 6 well plate (Sigma Aldrich). Cells were then treated with the peptides (CPP-CCmut3, CPP-CCwt, CCmut3, and CPP-His) at a final concentration 30 uM. This is a standard concentration used in cell-penetrating peptide studies. For the kinase activity Western blot, cells were treated with peptides for 16 hours.

For the internalization experiment, cells were treated with peptides for 1.5 hours followed by a 15 minute incubation at 37° C. with heparin sulfate, 0.5 mg/mL (a gift from Kuby Balagurunathan, University of Utah). Cells were centrifuged and resuspended in 1 mL plain RPMI. Trypsin was added to a final concentration of 0.1% w/v, and the cells were incubated at 37° C. for 10 minutes. At that time 1 mL FBS was added to neutralize the trypsin. Cells were then centrifuged at 500×g for 10 minutes, followed by 3 rounds of washes with 5 mL cold PBS.

For both kinase activity and internalization Western blots, cells were resuspended in 100 µL of RIPA lysis buffer (Cell Signaling, Danvers, Mass., USA) with 100× protease/phosphatase inhibitor added (Cell Signaling) and transferred into a pre-chilled microcentrifuge tube. Cells were then sonicated, centrifuged at 12,000×g for 15 minutes, and then the supernatant was transferred into a fresh, pre-chilled microcentrifuge tube. A BCA assay (Thermo Scientific) was run per manufacturer's protocol to calculate protein concentrations, and 10 µg of total protein was loaded for each sample.

Following gel electrophoresis on a 10% Bis-Tris gel (Life Technologies) and transfer onto a PVDF membrane (Life Technologies), the membranes were blocked for 1 hour with TBST+5% milk, washed, and probed for the desired proteins. For the kinase activity Western blot, the Cell Signaling PathScan Bcr/Abl activity assay antibody, (CS5300s, Cell Signaling 1:250 dilution) which probes for phospho-Bcr-Abl, phospho-STAT5, phospho-CrkL, and the loading control Rab11 was used.

To analyze internalization, primary antibodies against the N-terminal 20 amino acids of the coiled-coil domain (BCR-N-20 sc-885, Santa Cruz Biotechnology, Santa Cruz, Calif. USA, 1:500 dilution), 6× histidine tag (ab18184, Abcam, Cambridge, Calif., USA, 1:1000 dilution), and actin (ab1801, Abcam, 1:1000 dilution) were used. All primary antibodies were diluted in TBST+5% bovine serum albumin (Sigma Aldrich) and incubated at 4° C. for 16 hours. After 3×5 minute TBST washes secondary antibodies were added and incubated at room temperature for one hour. The anti-rabbit (CS7074s, Cell Signaling, 1:3000), and anti-mouse (ab6814, Abcam, 1:5000) were diluted in TBST+5% milk. Following washes and the addition of the Westernbright chemiluminescent reagent (Bioexpress, Kaysville, Utah, USA) the blots were imaged on a FluorChem FC2 imager (Alphalnnotech, San Leandro, Calif., USA). Western blots were performed three times with samples from three different cell treatments (n=3).

h. Treatment of Cells for Activity Experiments (Colony Forming, Cell Proliferation, 7-AAD/Annexin V, Western Blot Kinase Activity)

$6 \times 10^4$ cells were seeded in a 6-well CellStar plate in RPMI. Proteins (30 µM) or imatinib (standard dosing of 1.0 or 2.5 µM) were added, and PBS was added to a final volume of 1 mL. 16 hours after the treatment, 1 mL of complete RPMI was added to the wells.

i. 7-AAD and Annexin V Staining 48 or 72 hours after treatment with the proteins (30 µM) or imatinib (2.5 µM), 1.0 mL of cells from each treatment was pelleted and resuspended in 0.5 mL of 1× Annexin Binding Buffer (Invitrogen). 0.5 µL of 1 mM 7-AAD (Invitrogen) was added to each sample, followed by a 45 minute incubation on ice. Five minutes before analysis via flow cytometry, 1.0 µL of Annexin V (APC) (Invitrogen) was added to each sample. Analysis was performed using the FACS Canto-II (BD BioSciences, University of Utah Core Facility) with FACS Diva software. 7-AAD and APC were excited at 488 and 635 nm wavelengths, and emissions were detected at 660 nm. Percentage of apoptosis/necrosis was calculated by the percentage of cells that stained positive for 7-AAD and/or APC. Independent treatments were tested three times (n=3).

j. Colony Forming Assay

This experiment was carried out as before with the modifications noted below. 16 hours after treatment with proteins (30 µM) or imatinib (1.0 µM), 1.0×104 cells were transferred to 1 mL IMDM (Iscove's modified Dulbecco's media) with 2% FBS, and from this $3.0 \times 10^3$ cells were taken and seeded in 3 mL Methocult media in the absence of cytokines (H4230 media for K562, M3234 media for Ba/F3-P210) or in the presence of cytokines (GF M3434 media for parental Ba/F3 cells). Imatinib, but not proteins, was added again to the Methocult media for the imatinib-treated cells to a final concentration of 1.0 µM. $1 \times 10^3$ cells (in 1.1 mL) were seeded in a 6-well plate (CellStar), in duplicate for each treatment. 7 days after seeding cells, colonies were counted in a 100 µm2 area per well. Independent treatments were tested 3 times in duplicate (n=3). All reagents for the CFA were purchased from Stem Cell Technologies, Vancouver, BC, Canada.

k. Cell Proliferation 16 hours following treatment cells were transferred to a 25 cm2 flask, where 4 mL of complete RPMI was added. At 48, 72, and 96 hours post-treatment, trypan blue (Life Technologies) was used to determine cell viability. Cell counts were performed using both a standard light microscope and Countess automated cell counter (Invitrogen). Independent treatments were tested three times (n=3).

iv. Results a. Protein Constructs were Expressed and Purified

Figures 33A, 33B, 33C, 33D, 33E, 33F:
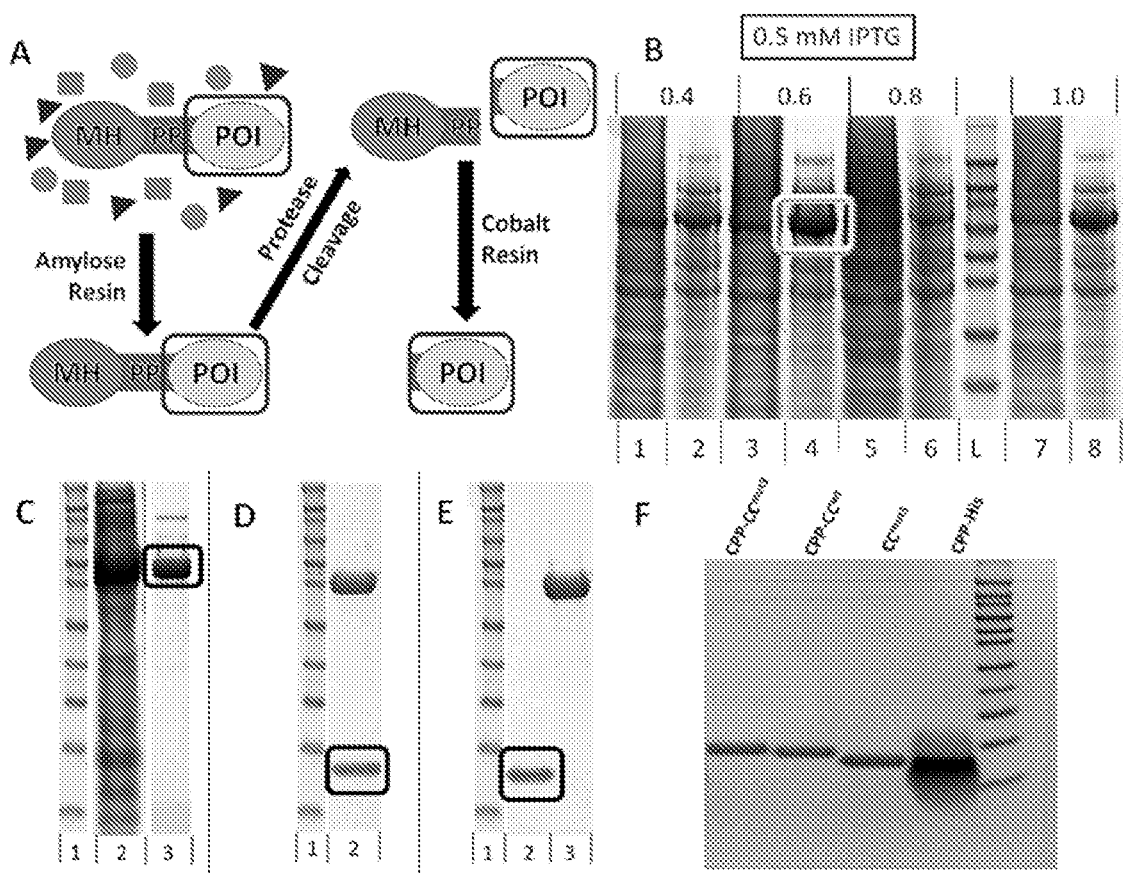
FIGS. 33A, 33B, 33C, 33D, 33E, and 33F show the expression and purification of proteins. Protein of interest (POI) is boxed in all figures. (A) Overview of the purification scheme. MH-PP-POI is purified from the crude extract on an amylose column. The POI is then cleaved away from the affinity tags. Finally, the affinity tags are separated from the POI on a cobalt column (representative gel shown). (B) Expression of fusion proteins was found to be optimal when induced at OD=0.6 at 600 nm with 0.5 mM IPTG, and then grown for 4 hours at 37° C. Lanes alternate between pellets (odd) and supernatants (even), taken after lysis and centrifugation. Samples were then (C) purified on amylose resin, (D) cleaved with the HRV-3C protease, (E) and the affinity/solubility tags were separated from proteins of interest on a cobalt column. (F) Purity was tested via SDS-PAGE gel. MH=Maltose Binding Protein and 6× Histidine tag. PP=PreScission Protease site; POI=Protein of interest; IPTG=isopropyl β-D-1-thiogalactopyranoside.

A graphical overview of the protein purification scheme can be found in FIG. 33A. Constructs were successfully cloned and then transformed into BL21(DE3) *E. coli* cells, and this was followed by optimization of fusion protein expression. After lysis, DNA precipitation, and centrifugation, the supernatant containing the protein of interest (POI) was collected and run on a SDS-PAGE gel and stained with Simply Blue SafeStain (Invitrogen). Optimal expression was achieved when the cultures were induced at a 0.6 OD at 600 nm with 0.5 mM IPTG and then grown for 4 hours at 37° C. (FIG. 33B, lane 4, boxed).

The supernatants (containing the POI) collected after lysis were then loaded onto an amylose resin column and washed with amylose binding buffer (ABB) until <0.1 mg/mL of protein was flowing off the column. At this point, the POI was eluted with ABB+20% v/v maltose (FIG. 33C, lane 3). In order to remove the maltose binding protein, the recombinant protein was cleaved with HRV-3C protease (FIG. 33D, lane 2). The proteins were diluted to 0.9 mg/mL prior to cleavage in order prevent precipitation upon cleavage. After dialysis into cobalt binding buffer the POIs were loaded onto a cobalt resin. The POIs flow through the column (FIG. 33E, lane 2), while the histidine tags of the maltose binding protein and HRV-3C protease adhere to the column (FIG. 33E, lane 3). Samples were tested for purity by SDS-PAGE gel and all found to be >95% purity (FIG. 33F). Proteins were then lyophilized and stored desiccated at −20° C.

Figures 34A, 34B, 34C, 34D:
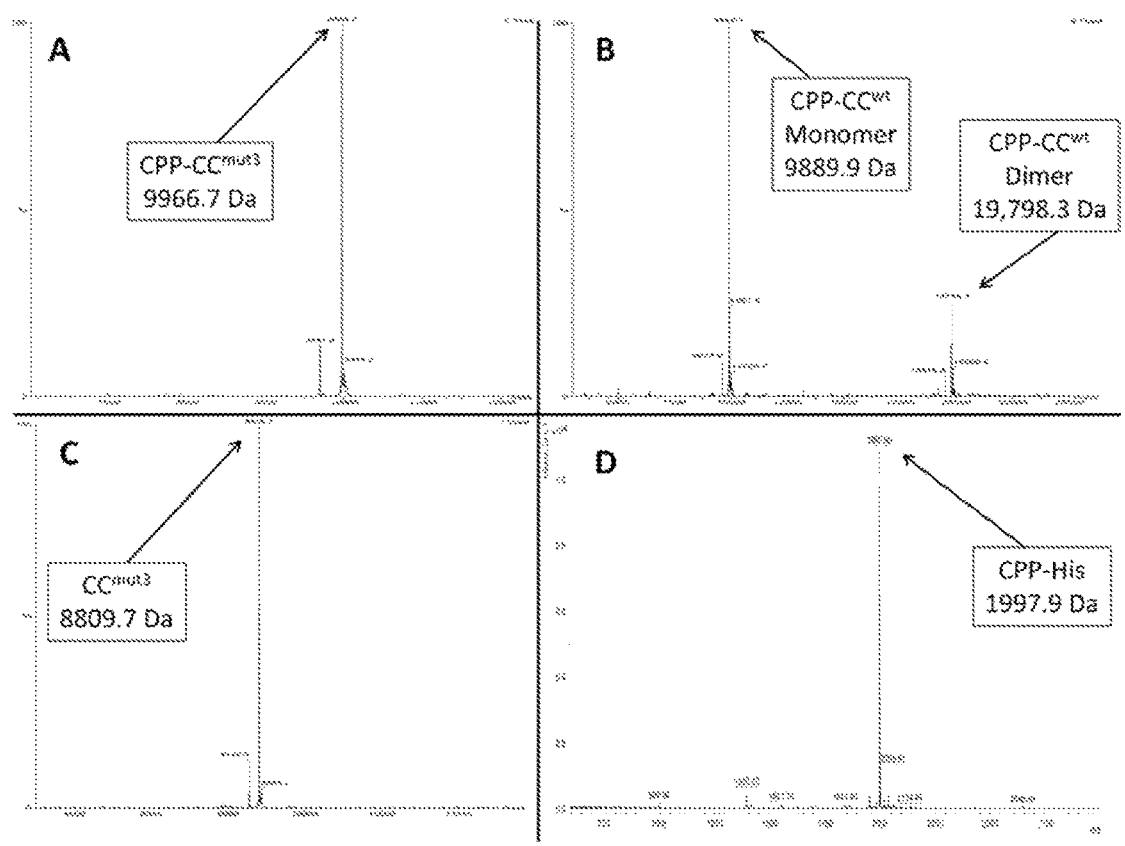
FIGS. 34A, 34B, 34C, and 34D show that mass spectroscopy supports the identity and purity of the constructs. (A) The sole major peak for CPP-CCmut3 agrees with theory (theoretical MW 9969.6 Da, experimental MW 9966.7 Da) and supports the presence of a disulfide bond leading to cyclization of the CPP. (B) CPP-CCwt has two major peaks, the first representative of a monomer and the second of a covalent CC:CC dimer (theoretical MW 9901.7 Da, experimental MW 9889.9 Da, 19,798.3 Da). (C) The major peak from CCmut3 agrees with theory (theoretical 8810.2 Da, experimental 8809.7 Da). (D) CPP-His's only major peak agrees with the theoretical MW and belies the presence of a cyclizing disulfide bridge in the CPP (theoretical 2000.3 Da, experimental 1997.9 Da).

To verify the identity of the purified proteins, their sequences were analyzed using mass spectrometry (FIG. 34). A 2 Da difference between predicted and experimental masses of CPP-CCmut3 indicates an intramolecular disulfide bond (FIG. 34A, theoretical MW 9969.6 Da, experimental MW 9966.7 Da). As there are only 2 cysteine residues in the protein, the disulfide bridge must be formed within the CPP, thus cyclizing it. This is known to be required for internalization for this leukemia-specific CPP. A portion of CPP-CCwt appeared to be present as a dimer (FIG. 34B, theoretical MW 9901.7 Da, experimental MW 9889.9 Da, 19,798.3 Da). CPP-CCmut3 did not exhibit this dimerization which implies that mutations introduced into the CC inhibited homo-oligemerization of CCmut3. Results for CCmut3 without the cell-penetrating peptide as well as CPP-His matched theoretical molecular weights and support cyclization of the CPP in CPP-His (FIG. 34C, theoretical 8810.2 Da, experimental 8809.7 Da; FIG. 34D, theoretical 2000.3 Da, experimental 1997.9 Da). Minor peaks were seen for CPP-CCmut3, CPP-CCwt, and CCmut3 with a mass shift of approximately 279.7. The major peak in each of the mass spectrometry combined with the SDS-PAGE gel showed construct purity of >95%.

b. LS-CPP Delivers Proteins Specifically to Blood Cells

Figure 3:
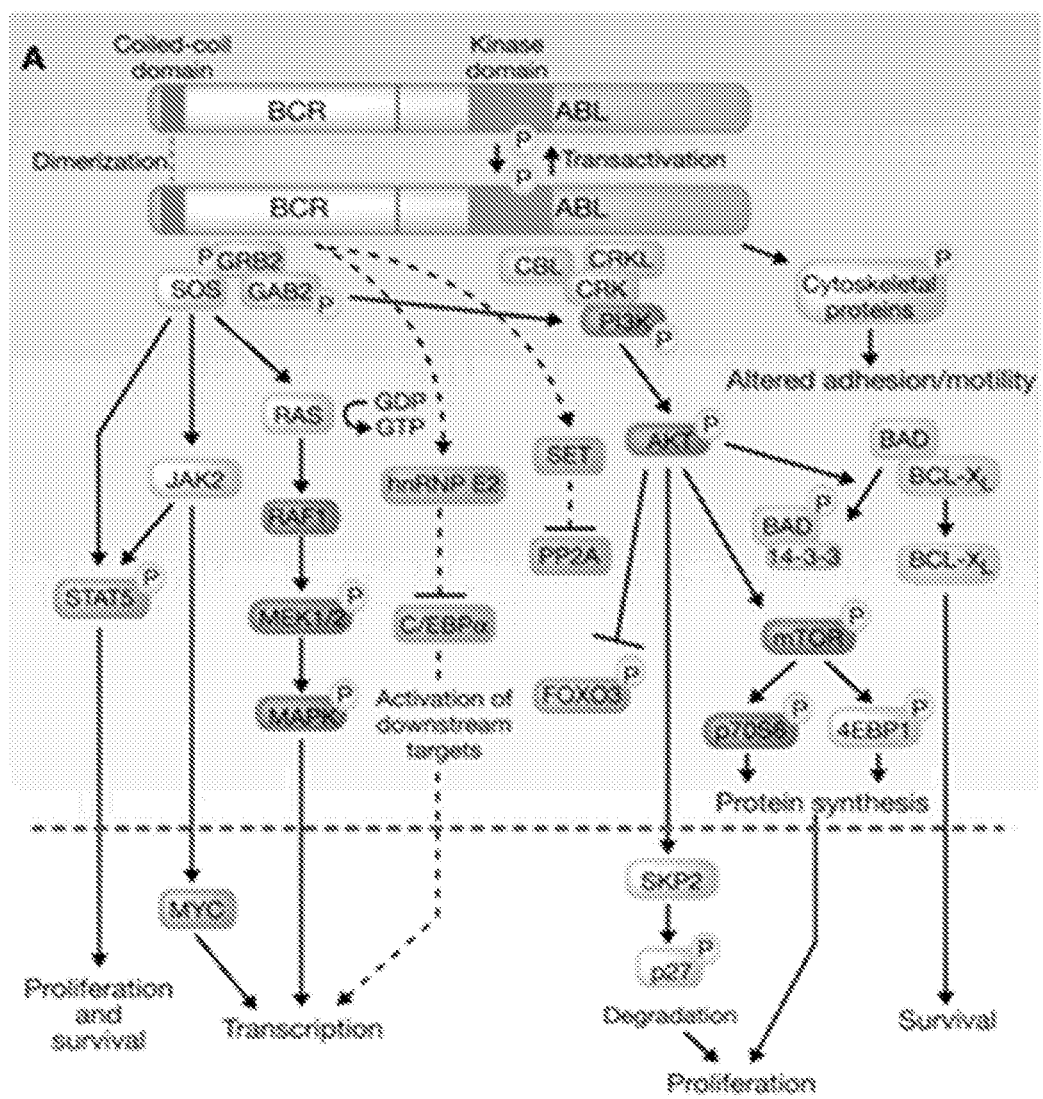
FIG. 3 shows a representative cartoon illustrating the signaling cascade of the Bcr-Abl fusion protein.
Figures 35A, 35B, 35C, 35D, 35E:
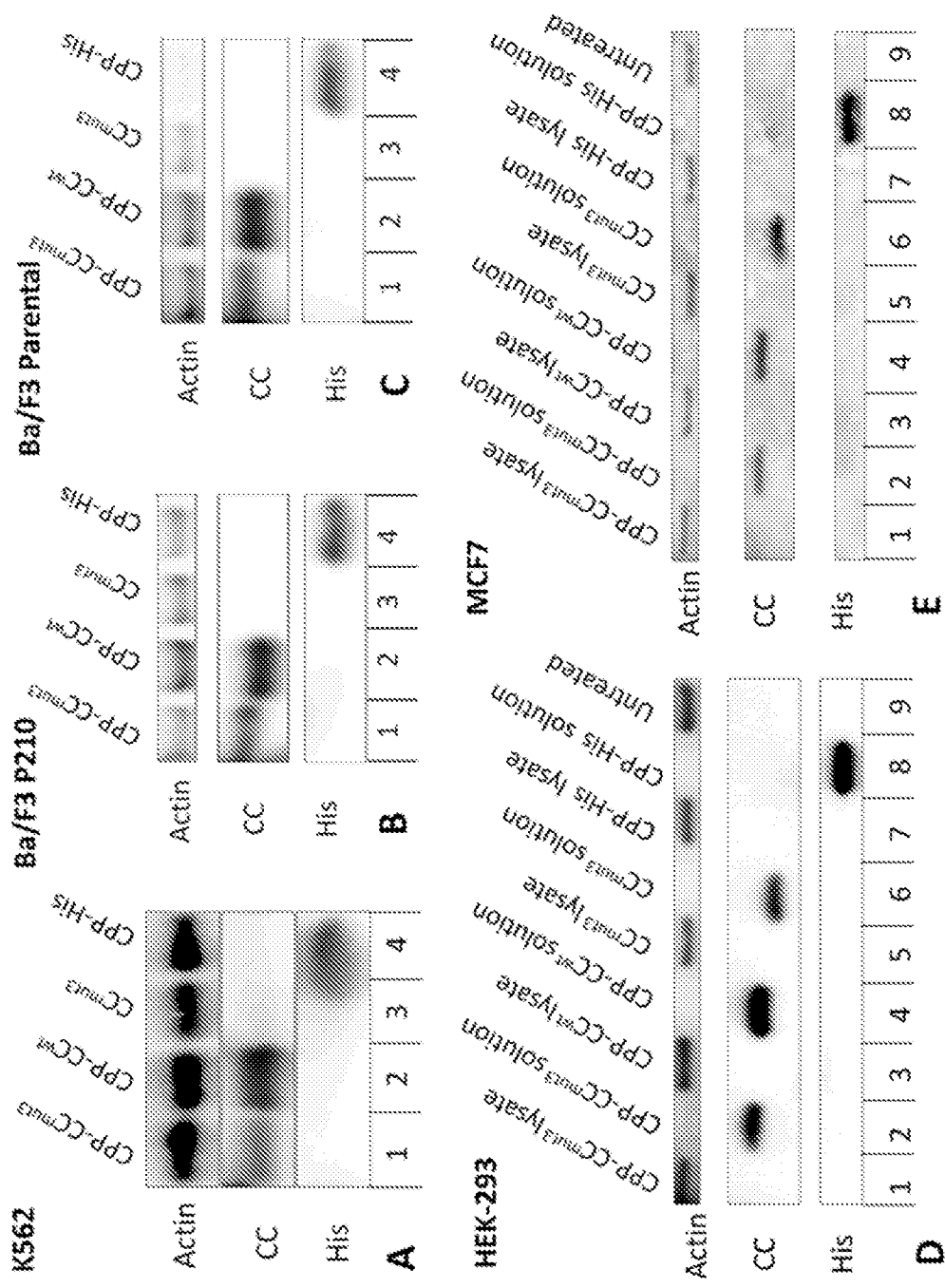
FIGS. 35A, 35B, 35C, 35D, and 35E show internalization Western Blots. (A) In leukemic K562 cells, constructs with the cell-penetrating peptide were able to enter, while CCmut3 without the CPP was unable to enter the cells. (B, C) In Ba/F3-P210 and parental Ba/F3 cells, only those proteins with the CPP were internalized. (D, E) In non-leukemic HEK-293 and MCF7 cells, none of the proteins were able to enter the cells. For D and E, lanes alternate between cell lysates (odd lanes) and purified protein solutions (even lanes, run as a control for the antibody). n=3 for all, representative images shown.

Proteins were added to $1 \times 10^6$ K562 cells at a final concentration of 30 μM, a dose that was chosen based on the original doses used by Nishimura et al. as well as a pilot dosing 7-AAD performed with CPP-CCmut3. Western blots with antibodies against the CC and His tag were used (FIG. 35). The Western blot in FIG. 3 shows that all constructs with the CPP were internalized by K562 cells (FIG. 35A, lanes 1, 2, and 4), while CCmut3 without the CPP was not internalized (FIG. 35A, lane 3).

The same internalization study was carried out with Ba/F3 pro-B mouse cells in both unmodified Ba/F3 cells and Ba/F3 cells engineered to stably express the 210 kDa variant of Bcr-Abl (Ba/F3-P210), thus giving it a CML phenotype. All of the constructs with the CPP were internalized into both cell lines (FIG. 35B, 3C, lanes 1, 2, and 4). As the only modification between these cells is the presence of Bcr-Abl, differences between these cell lines in activity assays allows for understanding if the activity of CPP-CCmut3 is Bcr-Abl dependent.

Two non-leukemic cell lines previously shown by Nishimura et al. to not internalize this CPP were tested to determine if the CPP is indeed leukemia-specific. HEK-293 human embryonic kidney cells and MCF7 human breast cancer cells were treated with the proteins and peptide, and cell lysates were probed for the presence of the CC and His motifs. FIG. 35D (Hek-293) and FIG. 35E (MCF7) are representative Western blots showing that none of the constructs entered these non-leukemic cells. The odd lanes are the cell lysates of the treated cells, while the even lanes are a solution of the purified proteins, as a positive control for the antibodies. The absence of bands in the cell lysate lanes (odd numbered lanes) indicates the lack of entry of these proteins into the cells (FIGS. 35D, 35E).

c. Activity in K562 Cells

Figures 36A, 36B, 36C, 36D, 36E:
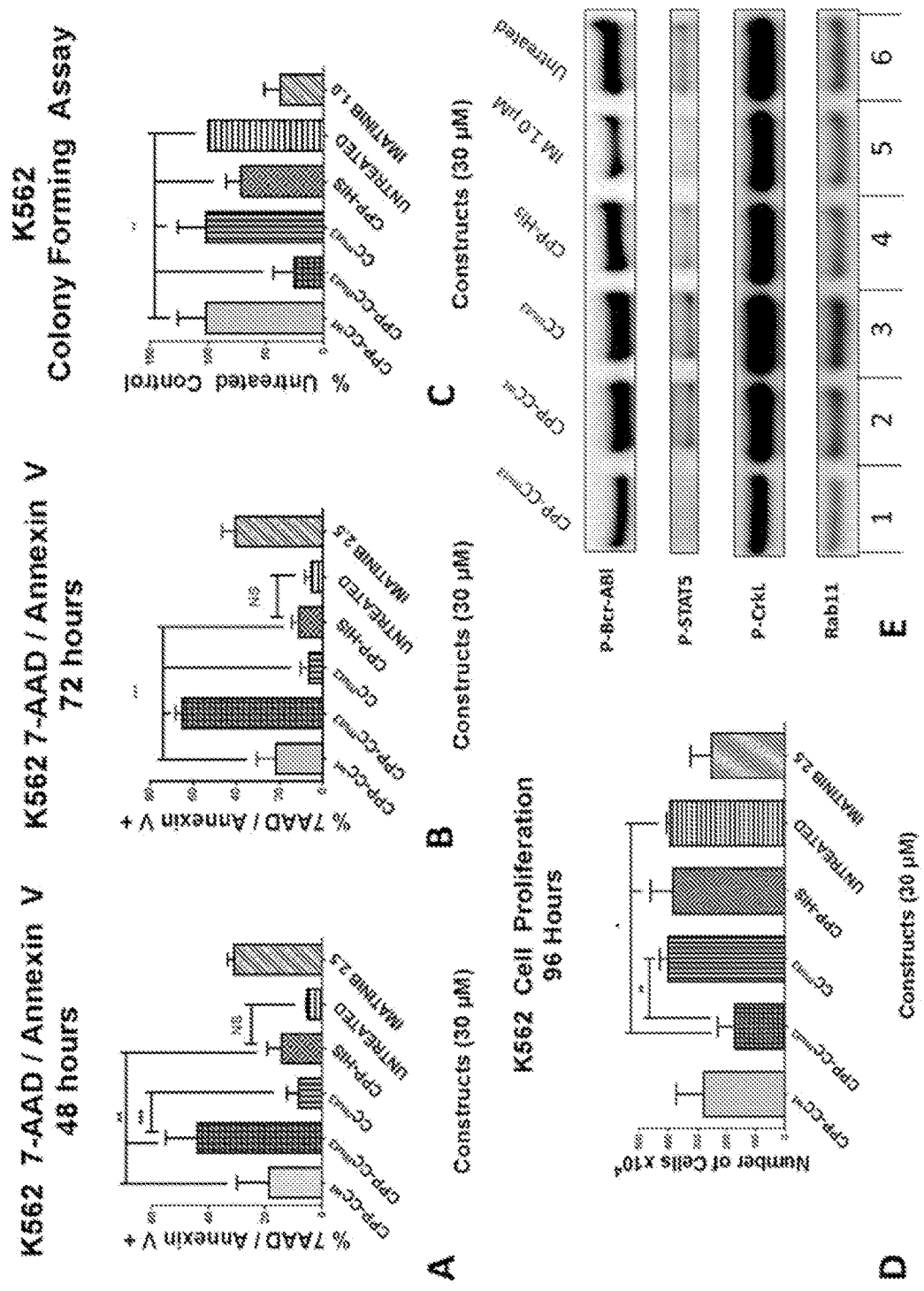
FIGS. 36A, 36B, 36C, 36D, and 36E show that internalized CPP-CCmut3 induces apoptosis/necrosis, reduces proliferation, inhibits colony forming, and reduces phosphorylation of Bcr-Abl in K562 cells. (A, B) In the 7-AAD/Annexin V assay, CPP-CCmut3 was superior at inducing apoptosis and necrosis compared to all treatments except imatinib at both 48 and 72 hours post-treatment. (C) In a test of transformative ability, CPP-CCmut3 reduced colony forming. (D) In this cell proliferation assays, CPP-CCmut3 decreased the proliferation of K562 cells. (E) In kinase activity Western blots, CPP-CCmut3 qualitatively deceased phosphorylation of Bcr-Abl as well as its downstream targets CrkL and STATS (representative blot shown). n=3 for all experiments. Values reported as overall means±SD; one-way ANOVA with Tukey's post test, $*p<0.05$, $p<0.01$, $*p<0.001$.

After these studies showed protein delivery to leukemic cells, experiments were performed to investigate if CPP-CCmut3 is active in Bcr-Abl+K562 leukemia cells. To this end, the first experiment carried out utilized 7-AAD and Annexin V staining, a flow cytometry assay testing for induction of necrosis and apoptosis, respectively. Cells were prepared for flow cytometry and percentages of 7-AAD and/or Annexin V positive cells were calculated at 48 hours (FIG. 36A) and 72 hours (FIG. 36B) after treatment. CPP-CCmut3 was superior in inducing apoptosis compared to CPP-CCwt, as well as the negative controls CCmut3 and CPP-His (FIGS. 36A and 36B, bar 2 vs. bars 1, 3, and 4). While CPP-His was internalized into K562 cells (FIG. 36A, lane 4), it did not induce apoptosis/necrosis compared to untreated cells (FIGS. 36A and 36B, bar 4 vs. bar 5). CCmut3 without the cell-penetrating peptide did not induce apoptosis (FIGS. 36A and 36B, bar 3), presumably because it did not enter K562 cells (FIG. 35A, lane 3).

CPP-CCmut3 was then tested for its ability to inhibit transformative ability and oncogenic potential in K562 cells via the colony forming assay (FIG. 36C) and cell proliferation (trypan blue cell proliferation assay, FIG. 36D). Both of these experiments concur with the apoptosis/necrosis assays; CPP-CCmut3 was more effective at reducing cell proliferation and transformative ability of K562 cells than CPP-His and CCmut3 (FIGS. 36C, 36D, bar 2 vs. bar 3 and 4), but was not statistically different from imatinib (FIGS. 36C, 36D, bar 2 vs. bar 6). CPP-CCmut3 was superior to CPP-CCwt in the colony forming assay, but not in the cell proliferation assay (FIGS. 36C, 36D, bar 2 vs. bar 1). CPP-His and CCmut3 were ineffective at reducing cell proliferation and colony forming compared to untreated cells, indicating that the effect is specific to internalized CCmut3.

Figure 4A:
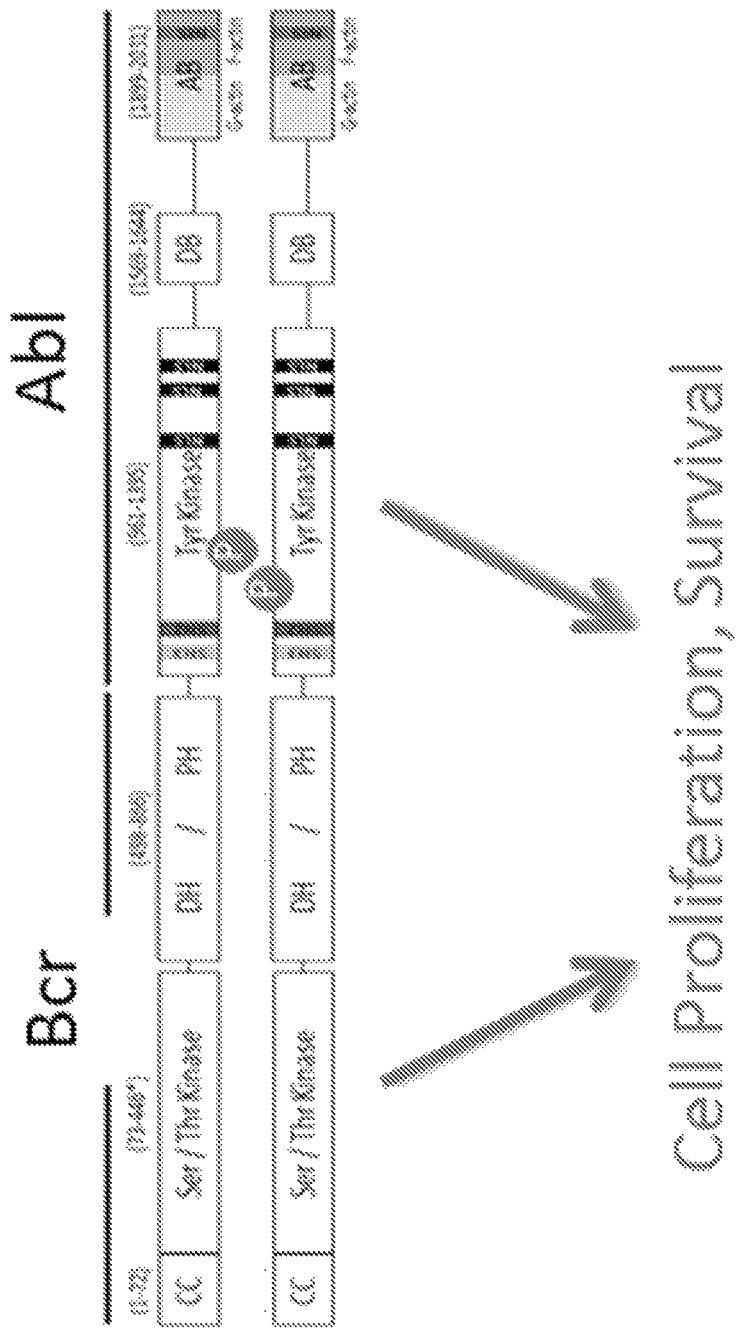
FIGS. 4A and 4B are cartoons pertaining to CML therapies based on targeting the tyrosine kinase domain.
Figure 4B:
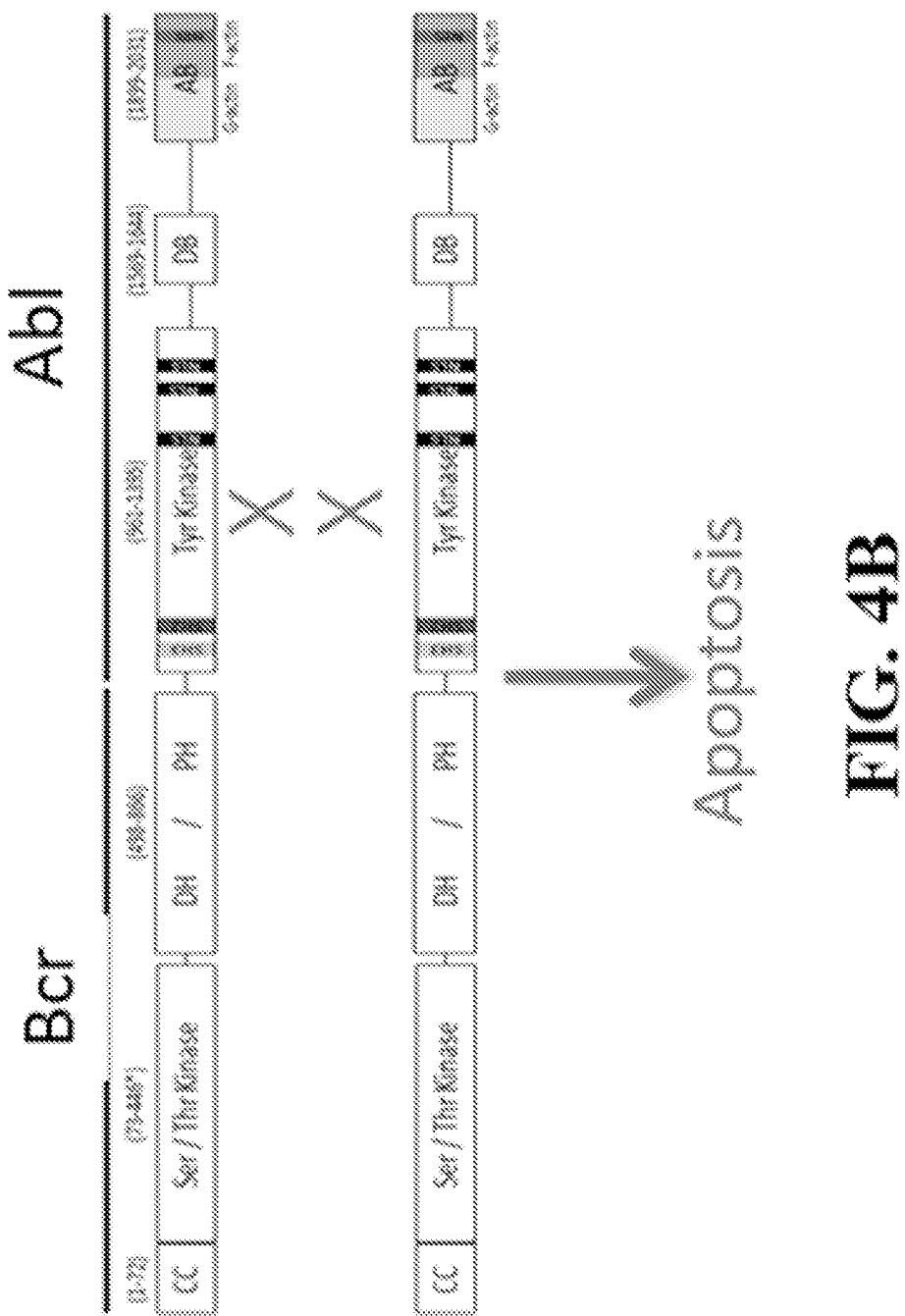
Figure 5:
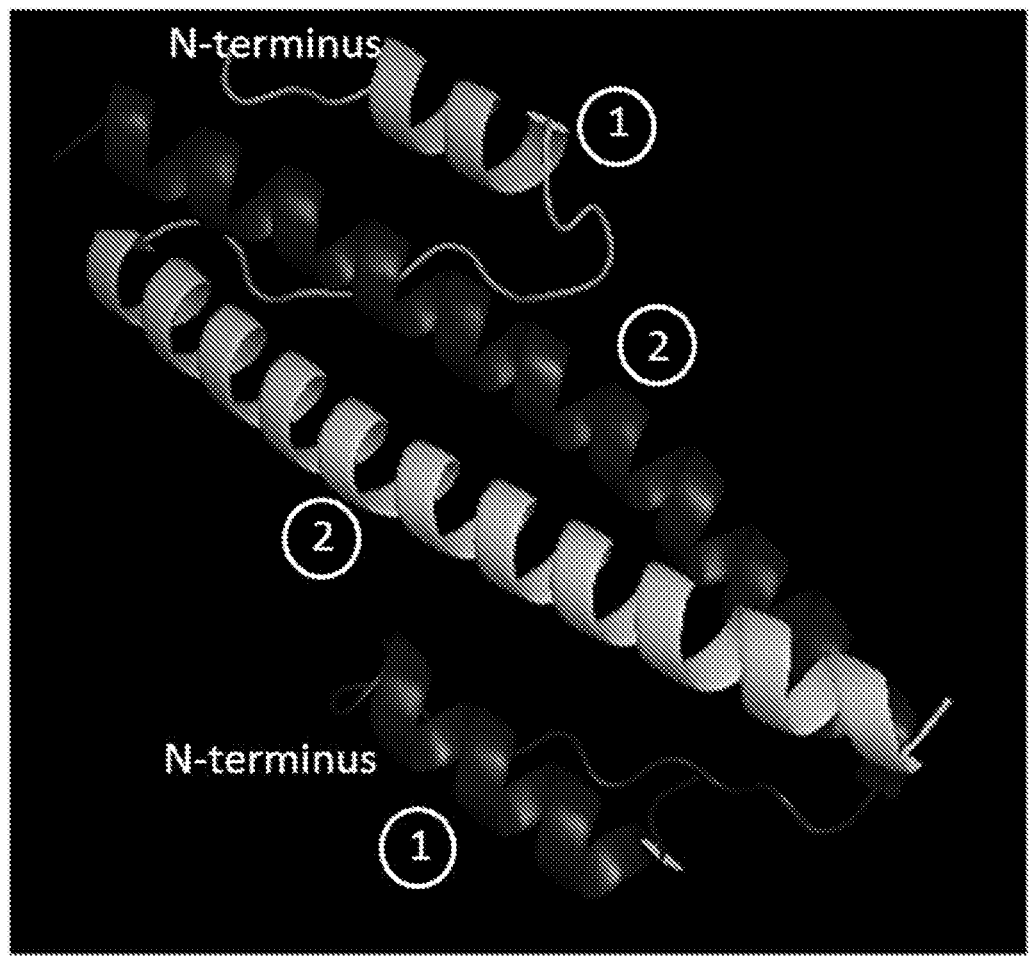
FIG. 5 shows a representative cartoon pertaining to dimerization of Bcr-Abl.
Figure 6:
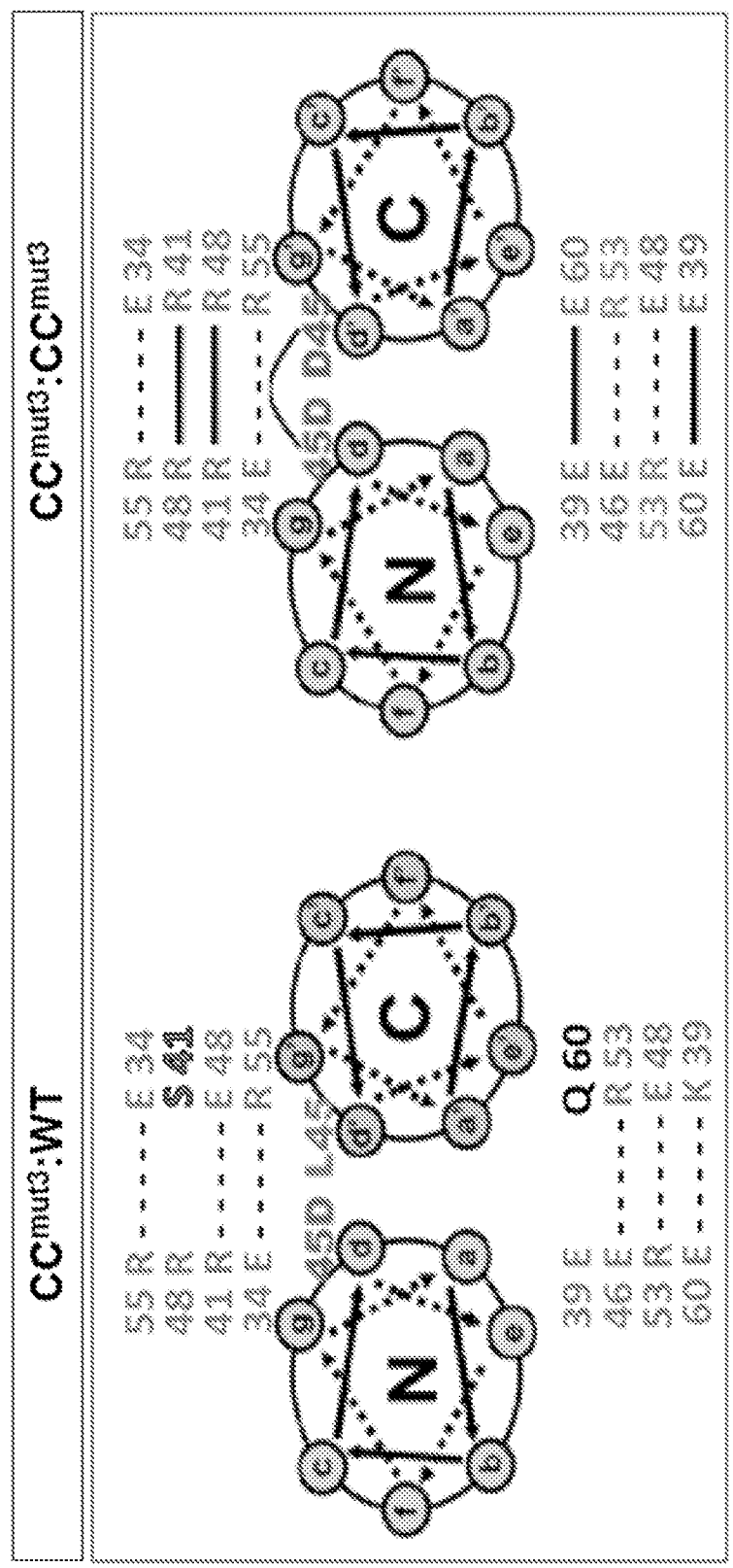
FIG. 6 shows a representative cartoon pertaining to the design of a mutant construct to favor hetero-dimerization, while disfavoring homo-dimerization.

Finally, a kinase activity Western blot was performed using antibodies probing for phospho-Bcr-Abl as well as its known downstream phosphorylation targets STATS (phospho-STATS) and CrkL (phospho-CrkL) (FIG. 4E).23 CPP-CCmut3 (FIG. 36E, lane 1) and imatinib (FIG. 36E, lane 5) both qualitatively decreased phosphorylation of Bcr-Abl (row A) as well as its downstream targets STATS (row B) and CrkL (row C) (FIG. 36E, compare CPP-CCmut3, lane 1, rows A, B, and C to untreated, lane 6, rows A, B, and C).

d. Activity in Ba/F3 Cells

Figures 37A, 37B, 37C, 37D:
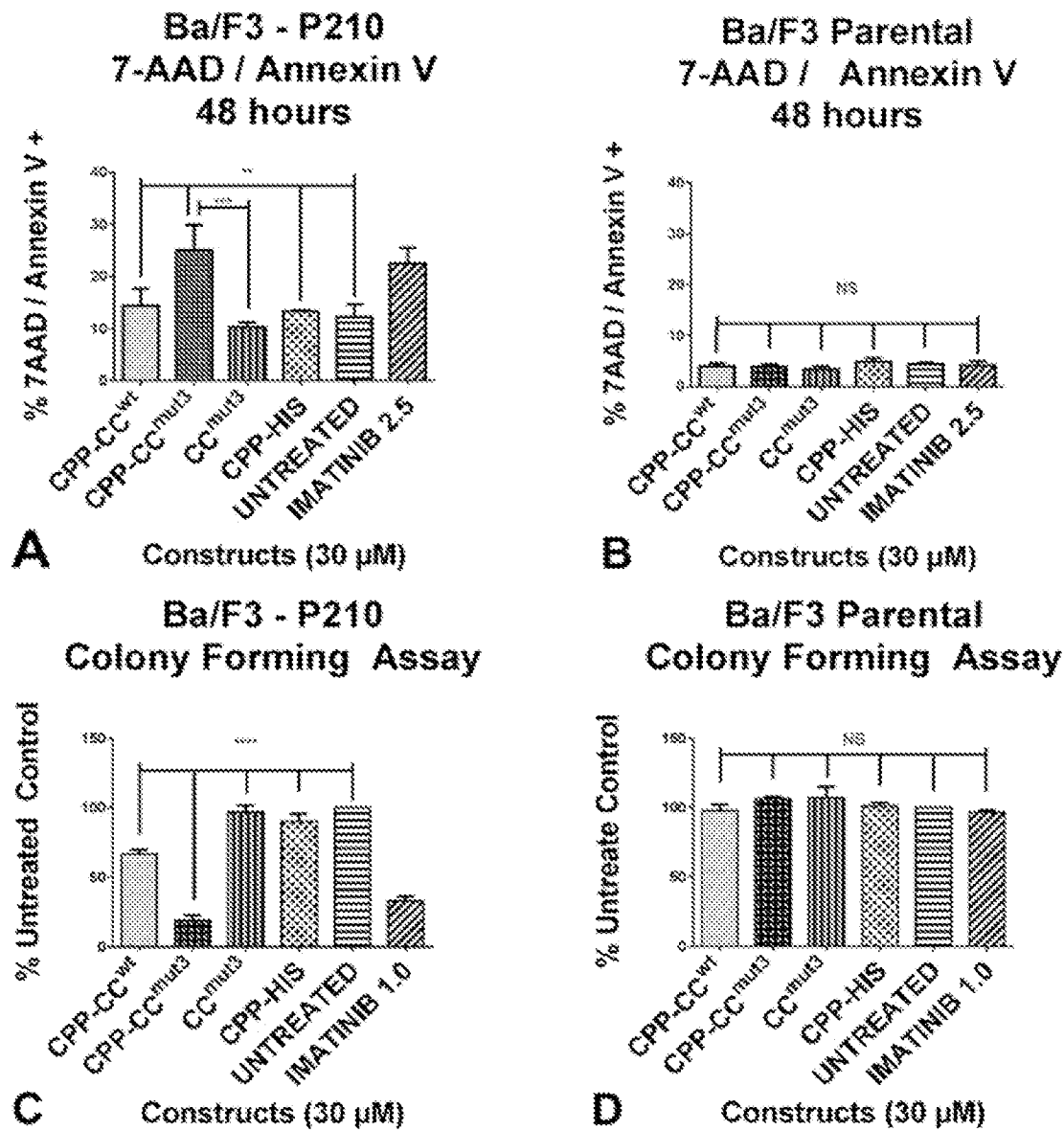
FIGS. 37A, 37B, 37C, 37D, 37E, and 37F show CPP-CCmut3 is active in Bcr-Abl+Ba/F3-P210 cells but not parental, Bcr-Abl-Ba/F3 Parental cells. (A, B) CPP-CCmut3 induced apoptosis and necrosis in Bcr-Abl+Ba/F3-P210 cells (A), while it caused no effect on parental, Bcr-Abl-Ba/F3 cells (B). (C, D) CPP-CCmut3 decrease colony formation in Ba/F3-P210 cells (C) while having no effect on parental Ba/F3 cells (D). (E,F) Similarly, in the cell proliferation assay, CPP-CCmut3 inhibited cell proliferation in Ba/F3-P210 cells (E) while none of the treatments had an effect on the proliferation of parental Ba/F3 cells (F). n=3 for all experiments, values reported as overall means±SD; one-way ANOVA with Tukey's post test, $*p<0.05$, $p<0.01$, $*p<0.001$, $****p<0.0001$.

To further study the effects of CPP-CCmut3, apoptosis/necrosis, colony forming, and cell proliferation assays were carried out in both Bcr-Abl+ and Bcr-Abl-Ba/F3 lineages. As previous experiments demonstrated CPP-CCmut3 entered both cell types, these assays were performed to determine if CPP-CCmut3 was active only in the Bcr-Abl+ Ba/F3-P210 cells and not the Bcr-Abl-Ba/F3 parental cells. 7-AAD/Annexin V experiments were carried out in these two cell lines at 48 hours post treatment (FIGS. 37A, 37B). In Ba/F3-P210 cells, CPP-CCmut3 was again superior to CPP-CCwt, CCmut3, and CPP-His in inducing apoptosis/necrosis (FIG. 37A, bar 2 vs. bars 1, 3, and 4) but was not statistically different from imatinib (FIG. 37A, bar 2 vs. bar 6). Further, CPP-His and CCmut3 lacking the CPP were not statistically different from the untreated control (FIG. 37A, bars 3, 4, and 5). In the parental, Bcr-Abl– cells, no treatment (protein or imatinib) induced apoptosis/necrosis over the control (FIG. 37B). These results therefore indicate that the activity of CPP-CCmut3 requires the presence of Bcr-Abl to induce apoptosis/necrosis.

Figures 37E, 37F:
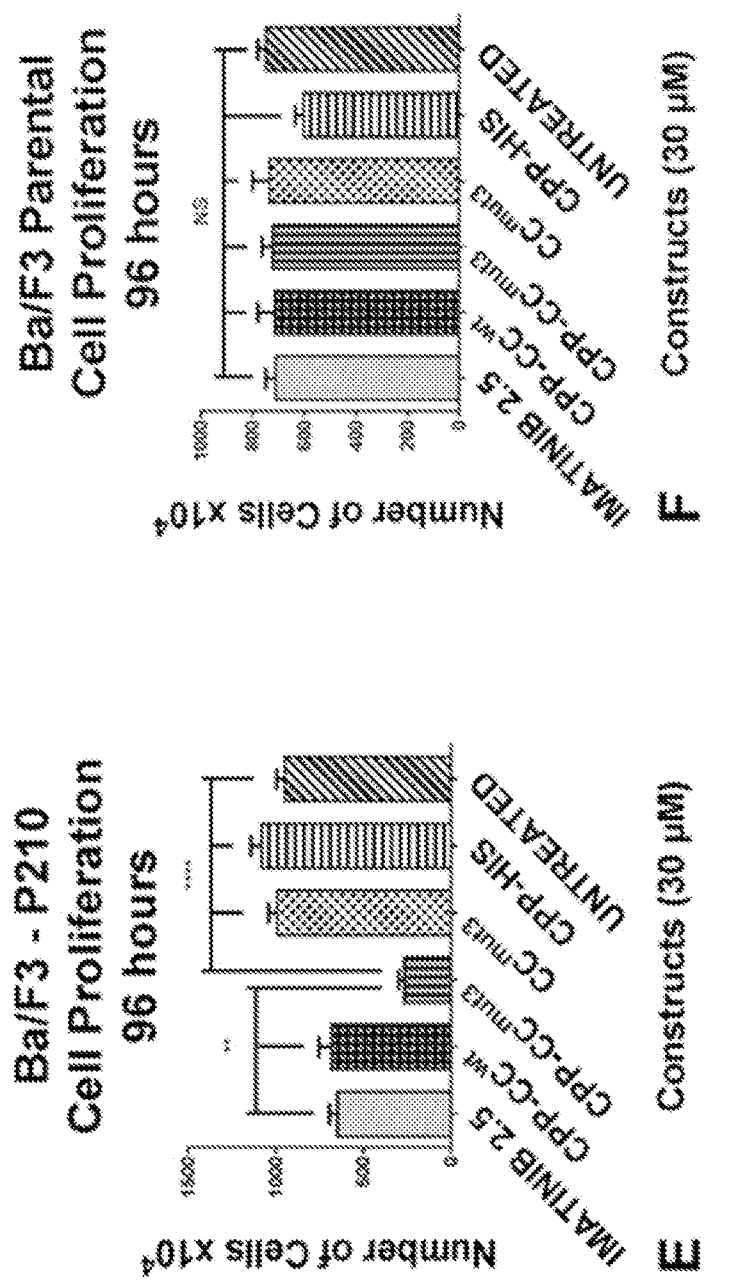

The results of the colony forming (FIGS. 37C, 37D) and cell proliferation assays (FIGS. 37E, 37F) agree with the flow cytometry results (FIGS. 37A, 37B). In Ba/F3-P210 cells CPP-CCmut3 was superior at inhibiting colony formation than all other treatments except imatinib 1.0 µM (FIG. 37C, bar 2 vs. bars 1, 3, and 4), whereas none of the treatments caused a difference in colony formation in the parental Ba/F3 cells (FIG. 37D), as expected. The same trend was seen in the cell proliferation assay; at 96 hours, CPP-CCmut3 inhibited cell proliferation to a greater extent that all other treatments in Ba/F3-P210 cells (FIG. 37E, bar 3), and no treatment effects were seen from either imatinib or proteins in parental Ba/F3 cells (FIG. 37F).

v. Discussion

CCmut3 inhibits Bcr-Abl phosphorylation, induces apoptosis, and inhibits proliferation and transformative ability of CML cells. Gene delivery methods were used where cells were either transfected or virally infected. As these transfection methods are currently not clinically achievable for blood cancers, the purpose of this study was to deliver CCmut3 as a protein. A leukemia-specific cell-penetrating peptide previously discovered by phage display was fused to CCmut3. CPP-CCmut3, as well as controls CPP-CCwt and CCmut3 (lacking the CPP) were cloned, expressed, and purified while the 15 amino acid peptide control CPP-His was purchased.

CPP-CCmut3 entered K562 human leukemia cells (FIG. 35A, lane 1) as well as two variants of Ba/F3 pro-B mouse cells, one of which expresses Bcr-Abl (Ba/F3-P210) (FIGS. 35B, 3C, lane 1). In addition to penetrating the cells, CPP-CCmut3 caused apoptosis/necrosis, reduced cell proliferation, and reduced transformative ability in K562 and Ba/F3-P210 cells while having no toxic effects on parental, BCR-Abl-Ba/F3 cells (FIGS. 36A-D, bar 2, 37A-D, bar 2, and FIGS. 37E-F, bar 3). Further, a Western blot of K562 cells demonstrated that CPP-CCmut3 decreases phosphorylation of Bcr-Abl as well as its downstream targets CrkL and STATS (FIG. 36E, lane 1).

Since constructs containing the CPP did not internalize into MCF7 or HEK-293 cells, activity assays were not conducted for these non-blood cell lines. The activity experiments in the leukemia cells demonstrated that only internalized proteins were active (see CPP-CCmut3 vs CCmut3), and as none of the proteins were taken up by MCF7 or HEK-293 cells, none should be active against the non-leukemic cells. This is supported by experiments from Nishimura et al., where a mitochondrial-toxic peptide was conjugated to the LS-CPP, and was only toxic to the cells that internalized the construct.

CPP-CCmut3 has two built-in safeguards against non-specific toxicity. The first safeguard is the leukemia-specific CPP which preferentially delivers the construct to leukemia cells. The second is the Bcr-Abl specificity of CCmut3. It has previously been shown that, not only does CCmut3 induce apoptosis in Bcr-Abl+ cells, but is also nontoxic to Bcr-Abl-cells. 22-24 It is shown in this study that CPP-CCmut3 enters but is nontoxic to the parental, Bcr-Abl-Ba/F3 cells (FIGS. 35C and 37B, D, F), further supporting this claim. To verify the leukemic-specificity of the CPP, internalization experiments testing if CPP-CCmut3 enters two non-leukemic cell lines (MCF7 and HEK-293) were carried out. In agreement with the original paper that discovered the LS-CPP, no internalization of proteins was observed in these cell lines (FIGS. 35D, 35E). Further, Nishmura et al. showed lack of internalization correlated with the lack of induction of apoptosis of a mitochondrial-toxic peptide in 6 other cell lines including U251MG, A549, PC-9, PC-3, HepG2, and WM115 as well as patient-derived normal blood cells including T-lymphocytes, monocytes, and macrophages, demonstrating leukemia cell specificity. Therefore, no activity experiments were carried out in these non-leukemic cells.

Others have attempted to use CCwt to inhibit Bcr-Abl, however with limited efficacy compared to CCmut3. Further, only non-specific CPPs have been used to deliver CCwt. 38-41 Therefore, CPP-CCmut3 has added specificity and potency against Bcr-Abl+ cells via the optimized CCmut3 and the leukemia-specific CPP.

While TKIs have revolutionized CML treatment, patients often become resistant, which led to the development of second and third generation TKIs. It is thought that resistance to any (even future) generation of TKI is inevitable, as Bcr-Abl can mutate to avoid TKI binding, known as mutational escape. Indeed, compound mutants (two point mutations in one molecule of Bcr-Abl) that confer resistance to ponatinib, a third generation agent, are already therapeutically problematic. CCmut3 has many contact points with the CC of Bcr-Abl; therefore, it is unlikely that any single point mutation would be sufficient to prevent binding of CCmut3. Further, any combination of mutations that disrupts CC:CCmut3 binding would likely also prevent two CC motifs from Bcr-Abl molecules from forming a dimer. To clarify, any mutation or mutations that allowed the native CC of Bcr-Abl to avoid binding by CCmut3 would also inhibit Bcr-Abl dimerization, thereby resulting in auto-inactivation. Thus CCmut3 avoids "mutational escape" by Bcr-Abl.20

Whereas CCmut3 can be resistant to mutational escape, it is important that CCmut3 be effective in patients who are already resistant to TKIs. Derivatives of the Ba/F3 cells which express Bcr-Abl with clinically relevant point mutations in the tyrosine kinase domain have been developed. CCmut3, when delivered as a plasmid, is effective against Bcr-Abl point mutations T315I,24 E255V, and compound mutant E255V/T315I. Further, CCmut3 is effective against primary patient samples with mutant Bcr-Abl (including Bcr-Abl T315I) when delivered lentivirally.

CCmut3 and TKIs target different domains of Bcr-Abl, and combination therapy with CCmut3 and ponatinib resulted in additive effects. Further, the combination allows for a dose reduction of ponatinib, which can be clinically relevant as ponatinib has severe toxic effects which are thought to be dose-dependent.

This work indicates the feasibility of delivering CCmut3 as a protein. However, CCmut3 can be further modified to improve translation potential. To that end, stability-enhancing modifications such as PEGylation, hyperglycosylation, or hydrocarbon stapling can be implemented. Stapling peptides has been shown to increase helicity, enhance serum stability, improve cell penetration, and possibly allow for oral delivery. A truncated, hydrocarbon stapled version of CCmut3 is currently being modeled and developed in our lab. Combining the CPP and a truncated, stapled CCmut3 will maximize stability, specificity, and membrane permeability. This stapled peptide can then be tested in animal models of CML. With the effectiveness of CCmut3 against compound mutants and additive effects with TKIs, CCmut3 can play an important role in the future of CML treatment.

4. A Coiled-Coil Mimetic Intercepts BCR-ABL1 Dimerization in Native and Kinase-Mutant Chronic Myeloid Leukemia Chronic myeloid leukemia (CML) is caused by BCR-ABL1, the product of a reciprocal translocation t(9;22)(q34;q11), resulting in a shortened chromosome 22, also known as the Philadelphia chromosome. BCR-ABL1 is a constitutively active tyrosine kinase and the target of small-molecule inhibitors, including the first clinical tyrosine kinase inhibitor (TKI), imatinib. Overall, imatinib has demonstrated considerable efficacy in CML, with high rates of complete hematologic and cytogenetic responses that have translated into improved progression-free and overall survival compared to non-TKI therapies such as interferon-γ. Although many imatinib responses are durable, some patients develop kinase domain mutations that confer resistance to imatinib and are associated with clinical relapse. These mutations impair imatinib binding and restore BCR-ABL1 kinase activity. To overcome this type of resistance, the second-generation TKIs, dasatinib, nilotinib, and bosutinib, and most recently the third-generation TKI, ponatinib, were developed. Second generation TKIs are active against most imatinib-resistant BCR-ABL1 mutants, with the exception of T315I (BCR-ABL1T315I). In contrast to imatinib and second generation TKIs, ponatinib is effective against the T315I mutant, representing a major therapeutic breakthrough. Thus far, no single mutation (except for I315M, which emanates from T315I) has been shown to confer resistance to ponatinib; however, multiple mutations in the same BCR-ABL1 molecule, referred to as compound mutations, can confer resistance to ponatinib both in vitro and in patients with clinical resistance to approved TKIs.

Rational therapy of CML has generally focused on targeting the BCR-ABL1 catalytic site, but kinase domain mutations that impair or block drug binding limit the scope of this approach. The N-terminal coiled-coil (CC) dimerization domain of BCR-ABL1 has been shown to be critically important for BCR-ABL1 kinase activity and could thus represent an alternative therapeutic target. A peptidomimetic to block dimerization has been explored by several groups. Ruthardt et al. reported that introduction of a peptidomimetic of helix α2 of the CC dimerization region reduced BCR-ABL1 phosphorylation and inhibited the proliferation of cells expressing native and mutant BCR-ABL1. However, the isolated native helix α2 alone was inactive in cells expressing the T315I mutant.

We recently described two iterations of a mutant CC (called CCmut2 and CCmut3) with preferential specificity toward hetero-oligomerization with the CC region of BCR-ABL1 over homo-oligomerization with itself. This construct is similar to the Ruthardt helix α2 mimetic, but contains the full-length CC domain. Additionally, CCmut3 incorporates engineered mutations to enhance binding specificity within helix α2 and demonstrates inhibitory activity against cells expressing native BCR-ABL1 or the T315I mutant. Here, we have studied the effects of CCmut3 against kinase domain mutant variants of BCR-ABL1 in both cell lines and primary CD34+ cells from newly diagnosed and TKI-resistant CML patients.

vi. Materials and Methods a. DNA Constructs pmCherry-EV (empty vector) and pmCherry-CCmut3 have been described. The lentiviral control vector pCDH-EF1-copGFP-EV was adapted from pCDH-CMV-MCS-EF1-copGFP (System Biosciences (SBI), Mountain View, Calif., USA). The CMV promoter and multiple cloning sites were excised using SpeI and XbaI with compatible cohesive ends. The CMV fragment was removed using gel purification and the resulting DNA was ligated to form the final construct.

To make pCDH-EF1-copGFP-CCmut3, sections of the construct were amplified separately by PCR and joined using overlap extension PCR. First, EF1-copGFP was amplified from the SBI parent plasmid with a 5'-SpeI and 3'-BamHI site using the following primers: 5'-CAACTAG-TAAGGATCTGCGATCGCTCC-3' and 5'-CCATCTGAGTCCGGAGCGAGATCCGGTGGAGC-3.' CCmut3 was amplified from pEGFP-CCmut3 as described 26 using primers containing a 5'-BamHI site, a terminal TAG stop signal and a sequence complementary to the polyA signal on the 3' overhang: 5'-CTCAGATGGATCCT-TATGGTGGACCCGGTGGGCTTCG-3' and 5'-GT-TATCTAGATCTACCGGTCATAGCTCTTCTTTTCC-3'.
Finally, the polyA signal from pEGFP-C1 (Clontech Laboratories, Mountain View, Calif., USA) was amplified to include a 5' complementary sequence to CCmut3, and a 3'-SalI restriction site: 5'-GACCCGGTAGATCTAGA-TAACTGATCATAATC-3' and 5'-GCTTACATGCGG CCGCGTCGACTGTGGGAGGTTTTTTAAAGC-3.' PCR products were combined in two steps, first by combining the CCmut3-polyA and then by adding EF1-copGFP by overlap extension PCR. The PCR product was digested with SpeI and SalI and ligated to the SpeI and SalI-digested pCDH-CMV-MCS-EF1-copGFP vector (SBI). The lentiviral packaging plasmid psPAX2 was purchased from Cellecta, Inc. (Mountain View, Calif., USA), and the viral envelope plasmid pVSV-G was purchased from Clontech Laboratories.

b. Cell Lines and Patient Samples

Stable Ba/F3 cells transduced with native (p210) BCR-ABL1, the kinase domain mutants BCR-ABL1T315I, BCR-ABL1E255V, or the compound mutant BCR-ABL1E255V/T315I were cultured. Briefly, cells were cultured in RPMI 1640 with 10% FBS, 100 U/ml penicillin-streptomycin, 2 mM L-glutamine, and 0.1% gentamycin (complete RMPI medium). Additionally, 0.1% MycoZap™ (Lonza Bio, Basel, Switzerland) was added to prevent mycoplasma contamination. The non-transduced parental Ba/F3 cell line was grown in RPMI 1640 supplemented with 20% WEHI-3B conditioned medium as a source of murine IL-331. To introduce CCmut3 or empty vector (EV), Ba/F3 cells were transfected with plasmid DNA using the Amaxa nucleofection system (Lonza, Basel, Switzerland) using program X-001 following the manufacturer's instructions. Cells were sorted on a BD FACSAria cytometer (BD Biosciences, San Jose, Calif., USA) for double-positive cells expressing mCherry and GFP prior to use in experiments.

Mononuclear cells (MNCs) from peripheral blood of patients with newly diagnosed or TKI-resistant CML were separated by Ficoll (Nycomed, Oslo, Norway), and the CD34+ fraction was isolated using an autoMACS Pro Separator (Miltenyi Biotech, San Diego, Calif., USA). Purity was determined to be >90% by flow cytometric analysis using a Guava 6HT flow cytometer (Millipore, Billerica, Mass., USA). CD34+ progenitors were maintained at $1 \times 10^6$ cells/mL in RPMI 1640 containing 20% FBS and 5 µL/mL StemSpan CC100 (Stem Cell Technologies, Vancouver, BC, Canada). Sanger sequencing was used to confirm BCR-ABL1 genotype.

c. Lentivirus Generation and Infection

293FT cells (Life Technologies, Grand Island, N.Y., USA) were grown in DMEM with 10% FBS, 100 U/ml penicillin-streptomycin, 2 mM L-glutamine, 0.1 mM MEM-non-essential amino acids, and 1 mM sodium pyruvate (Life Technologies, Grand Island, N.Y., USA). Cells were passaged every 2-3 days in T75 flasks, and grown to 65% confluence in T175 flasks for transfection. For lentivirus generation, cells were co-transfected with the experimental construct pCDH-EF1-copGFP-EV or pCDH-EF1-copGFP-CCmut3, pVSV-G and psPAX2 using the Profection® mammalian transfection system (Promega, Madison, Wis., USA) according to manufacturer's instructions. After 48 h, viral particles were complexed with polyethylene glycol overnight, pelleted, and concentrated to 100× in RPMI 1640. Lentiviral titers were determined. Primary CML cells were infected with lentivirus at a multiplicity of infection of 5 for each construct at 24 and again at 48 h following harvest (fresh cells) or thaw (frozen cells), respectively. Cells were sorted on a BD FACSAria cytometer for GFP-positive cells after 72 h prior to use in experiments.

d. Cell Proliferation Assays

Cell proliferation was assessed using a methanethiosulfonate-based viability assay (MTS assay) utilizing CellTiter 96® AQueous One Solution Cell Proliferation Assay (Promega) according to manufacturer instructions. Briefly, $5 \times 10^3$ viable cells were suspended in 100 µL complete RPMI medium per well in 96-well plates. Three independent samples were seeded in duplicate for each time point. Cell growth was assessed by MTS assay at 72 and 96 h. Readings at 490 nM were taken on a SpectraMax M2 plate reader (Molecular Devices, Sunnyvale, Calif., USA) after a 3 h incubation with MTS reagent. In patient sample experiments, cell proliferation was assessed by trypan blue exclusion. TLI treatments in cells were at the following concentrations for the listed patient-samples: imatinib (0 or 2.5 µM) for newly diagnosed (ND) CML samples; ponatinib (0, 10 nM) for CML samples harboring BCR-ABL1T315I.

e. Apoptosis Assays

For analysis of apoptosis and necrotic cell death, cells were pelleted and resuspended in Annexin V-binding buffer (BD Biosciences), stained with anti-Annexin V-APC and 7-AAD (BD Biosciences or Life Technologies) and analyzed on a BD FACSCanto flow cytometer. In addition to the APC and 7-AAD channels, GFP- and mCherry-positive cells were also recorded.

f. Colony Forming Assays

Following selection of transfected cells by cell sorting, methylcellulose colony assays were performed by plating in 0.9% methylcellulose (Stem Cell Technologies; M3234 for Ba/F3 BCR-ABL1 native and mutant lines; M3434 for Ba/F3 parental cells; H4230 for CML patient samples). mCherry-positive Ba/F3 cells ($1.1 \times 10^3$ cells/plate) or GFP-positive primary CML CD34+ cells ($1 \times 103$ cells/plate) were seeded per dish in duplicate. In the case of CML patient samples, cells were plated in the presence of 1× StemSpan CC100 cytokine cocktail (StemCell Technologies). All cells were plated with or without the indicated TKI in three or more independent experiments. Plates were incubated at 37° C. in a 5% CO2 humidified incubator. Colonies were counted 7-14 days later in an area of 50 µm2 per dish using an inverted microscope.

g. Statistics

Data are expressed as the means±SEM from at least 3 independent experiments unless otherwise stated. Briefly, significant differences between groups in Ba/F3 cell proliferation experiments (n=3 in technical duplicates) were assessed in GraphPad Prism 5 (GraphPad Software, La Jolla, Calif., USA) using a two-way ANOVA with Bonferroni's multiple comparisons test. A two-tailed student's t-test was used to determine significant differences in Ba/F3 colony forming experiments (n=3 in technical duplicates) and flow cytometric analysis of apoptosis (n=3). One-way ANOVA and Tukey's multiple comparision's test was used for primary ND CML cell colony forming assays (n=4 in technical duplicates). A p-value of <0.05 was considered significant for all experiments.

h. Immunoblot Analysis

Western blots were completed using primary antibodies against BCR (anti-BCR-N20, #sc-885, Santa Cruz Biotechnology, Dallas, Tex.); Tubulin (anti-β-Tubulin, #2128, Cell Signaling Technologies, Danvers, Mass.); Actin (anti-β-Actin, #4967, Cell Signaling Technologies). An HRP-linked secondary anti-rabbit IgG antibody (#7074, Cell Signaling Technologies) and developed using WesternBright Quantum HRP substrate (Advansta, Menlo Park, Calif.). Blots were visualized and digitally captured on a FluorChem FC2 (ProteinSimple, San Jose, Calif.). CCmut3 peptide (8 kDa) was expressed in bacteria and column purified. Bright field and GFP+ images were collected using an EVOS FL cell imaging station (Life Technologies).

vii. Results a. CCmut3 Expression Inhibits Proliferation, Increases Apoptosis, and Impairs Survival of Cell Lines Expressing Native BCR-ABL1.

Figure 38:
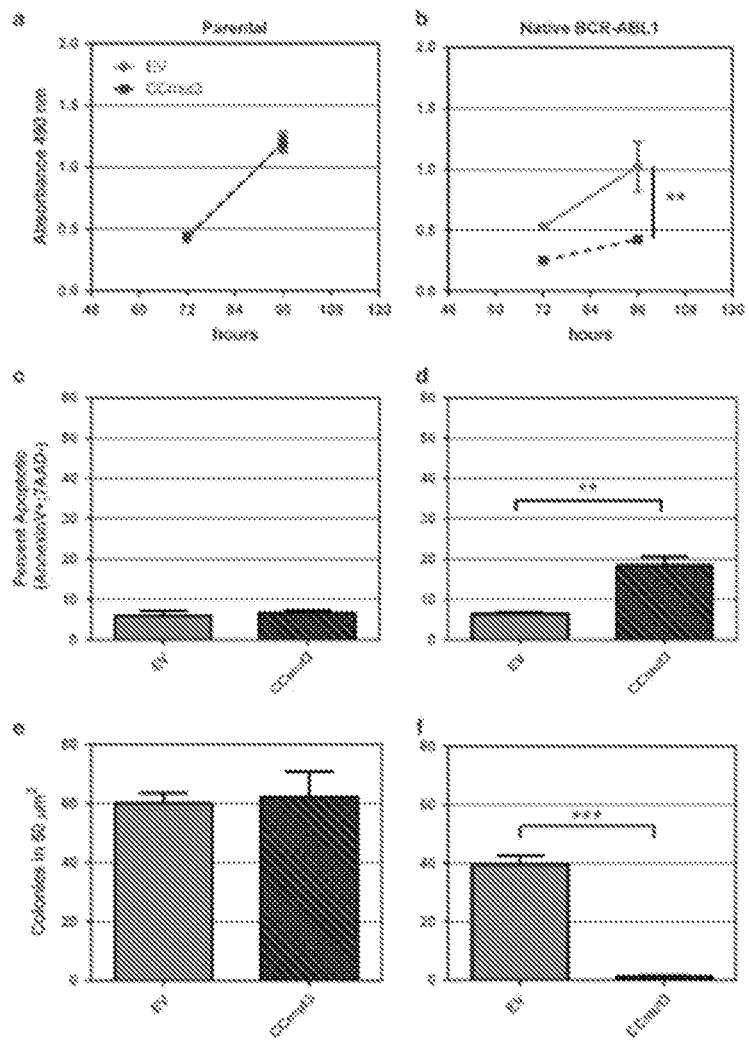
FIGS. 38A-38F show that CCmut3 reduces proliferation, increases apoptosis, and impairs survival of Ba/F3 cells expressing native BCR-ABL1, with no effect on parental Ba/F3 cells. (a, b) Proliferation of Ba/F3 parental cells were not affected by expression of the CCmut3 (blue boxes) compared to EV controls (red circles) (a), whereas CCmut3 treatment of Ba/F3 cells expressing native BCR-ABL1 significantly reduced proliferation at 96 h compared to controls (b). (c, d) Apoptotic cell populations at 72 h were quantified following flow cytometric analyses of transfected (GFP+) cells. Panels indicate apoptotic populations (Annexin V-positive/7-AAD-negative) of Ba/F3 parental cells (c), and Ba/F3 cells expressing native BCR-ABL1 (d). (e, f) Colony forming ability of Ba/F3 parental cells were not affected by expression of the EV control or CCmut3 (e), while colony formation by Ba/F3 cells expressing native BCR-ABL1 was greatly reduced in the CCmut3 treatment group compared with EV (f) (n=3). All graphs display mean±S.E.M. $p<0.01$, $*p<0.001$.
Figure 44:
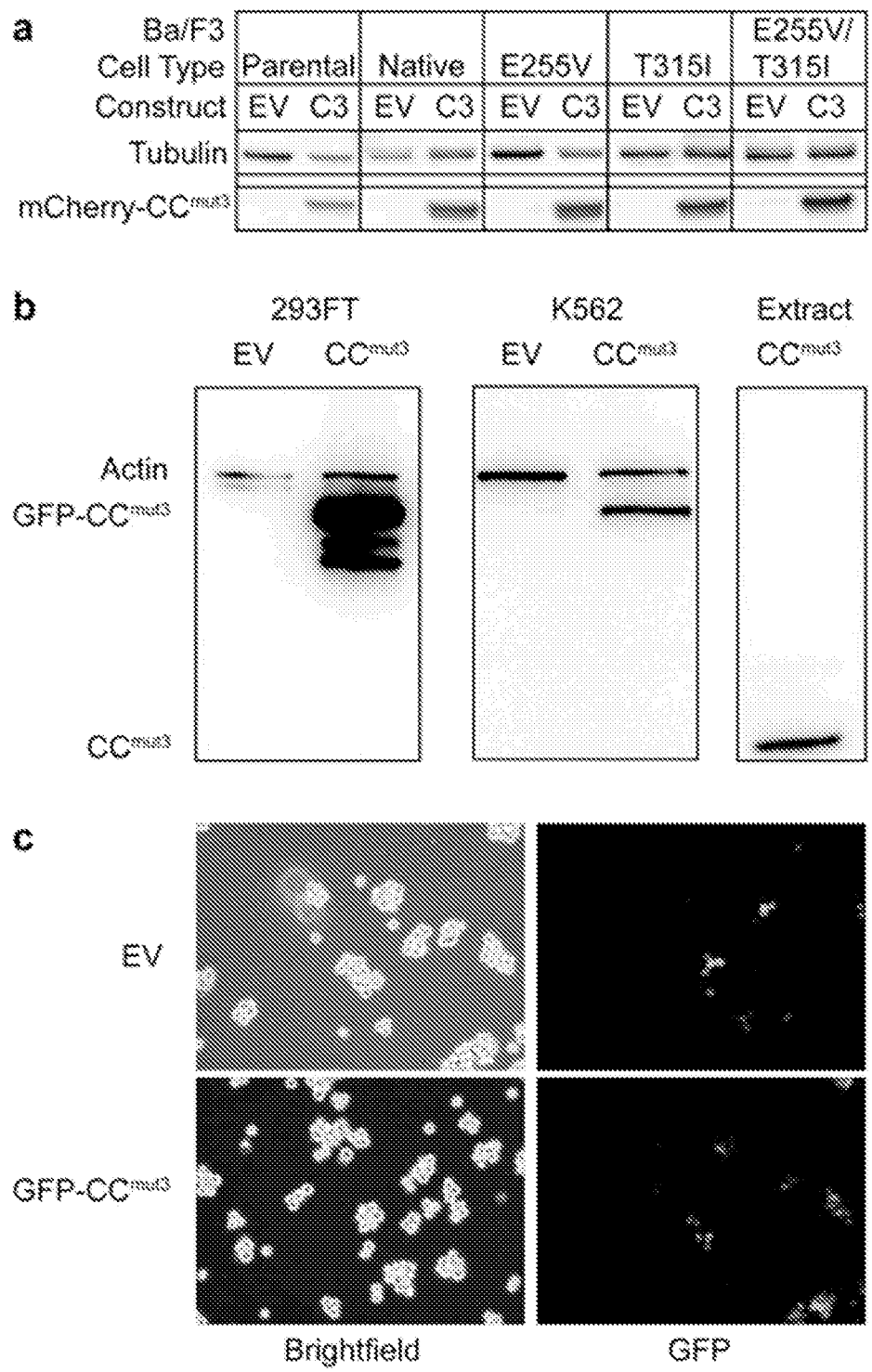
FIGS. 44A, 44B, and 44C show confirmation of CCmut3 expression in cells following transfection or transduction. a) Western blot of Ba/F3 cells transfected with EV or mCherry-CCmut3(C3). EV-transfected cells have no CCmut3, whereas CCmut3-transfected cells display the mCherry-CCmut3 fusion at an expected 35 kDa as detected by an N-terminal anti-BCR antibody. b) Western blots for CCmut3 in 293FT virus production cells following transfection; K562 CML cells 48 h after infection; and purified CCmut3 peptide (8 kDa) extract from bacterial cells without the GFP fusion. c) Images of K562 cells following viral transduction with either EV or CCmut3 in brightfield (left) or GFP (right).

The antiproliferative effects of CCmut3 were investigated in Ba/F3 cells expressing native BCR-ABL1 and in unmanipulated parental Ba/F3 cells. Expression of the CCmut3 construct was confirmed by immunoblot analyses (FIG. 44a). Following transfection with EV or the CCmut3 construct, proliferation was measured by MTS assay at 72 and 96 h. No difference between EV or CCmut3 was observed in parental Ba/F3 cells at either time point (FIG. 38a), whereas proliferation of Ba/F3 cells expressing native BCR-ABL1 was reduced by >2-fold at 96 h (FIG. 38b). To determine whether CCmut3 promoted apoptosis, Annexin V and 7-AAD were measured at 72 h in BCR-ABL1 cells with CCmut3 or EV. While there was no effect on the parental cell line (FIG. 38), BCR-ABL1-expressing cells showed an approximately 3-fold increase of apoptotic cells when transfected with CCmut3 compared to the EV control (FIG. 38d). Finally, the effect of CCmut3 on survival of parental and native BCR-ABL1-expressing Ba/F3 cells was tested by colony formation assays. Similar to its effects on cell proliferation, CCmut3 nearly eliminated colony forming ability compared to the EV in BCR-ABL1-expressing cells, with no effect on parental Ba/F3 controls (FIGS. 38e and 38f). These data confirm that the CCmut3 mimetic is effective in the Ba/F3 cell line system expressing the BCR-ABL1 oncoprotein.

b. CCmut3 Inhibits Proliferation, Increases Apoptosis, and Impairs Survival of Cell Lines Harboring BCR-ABL1 Single Kinase Domain Mutants.

Next the effects of CCmut3 on Ba/F3 cells expressing BCR-ABL1 mutants associated with clinical imatinib failure were tested. Ba/F3 cells engineered to express either BCR-ABLE255V or BCR-ABLT315I were transfected with EV or CCmut3 constructs. Expression of the CCmut3 construct was again confirmed by immunoblot analyses (FIG. 44a). At 96 h, single mutants showed an approximately 3-fold reduction of proliferation when transfected with CCmut3 compared to EV, whereas a lesser, yet significant difference was noted at the 72 h time point (FIGS. 39a and 39b). Both BCR-ABLE255V and BCR-ABLT315I cells demonstrated a 6-8-fold increase in apoptosis (AnnexinV+/7AAD−) after transfection with CCmut3 when compared to the EV after 72 h (FIGS. 39c and 39d). Lastly, the effects of CCmut3 on survival of Ba/F3 cells harboring single BCR-ABL1 mutants were assessed by plating in colony formation assays. CCmut3 expression produced a >10-fold reduction of colony forming ability in both BCR-ABLE255V (FIG. 39e) and BCR-ABLT315I cells (FIG. 39f) compared to the EV controls. Altogether, these data demonstrate that CCmut3 not only inhibits growth of cells harboring non-mutated BCR-ABL1, but also inhibits growth of cells harboring clinically relevant BCR-ABL1 kinase domain single mutants.

c. CCmut3 Exerts Anti-Apoptotic and Survival Inhibitory Effects on Cell Lines Harboring a Ponatinib-Resistant BCR-ABL1 Compound Mutant.

Figure 39:
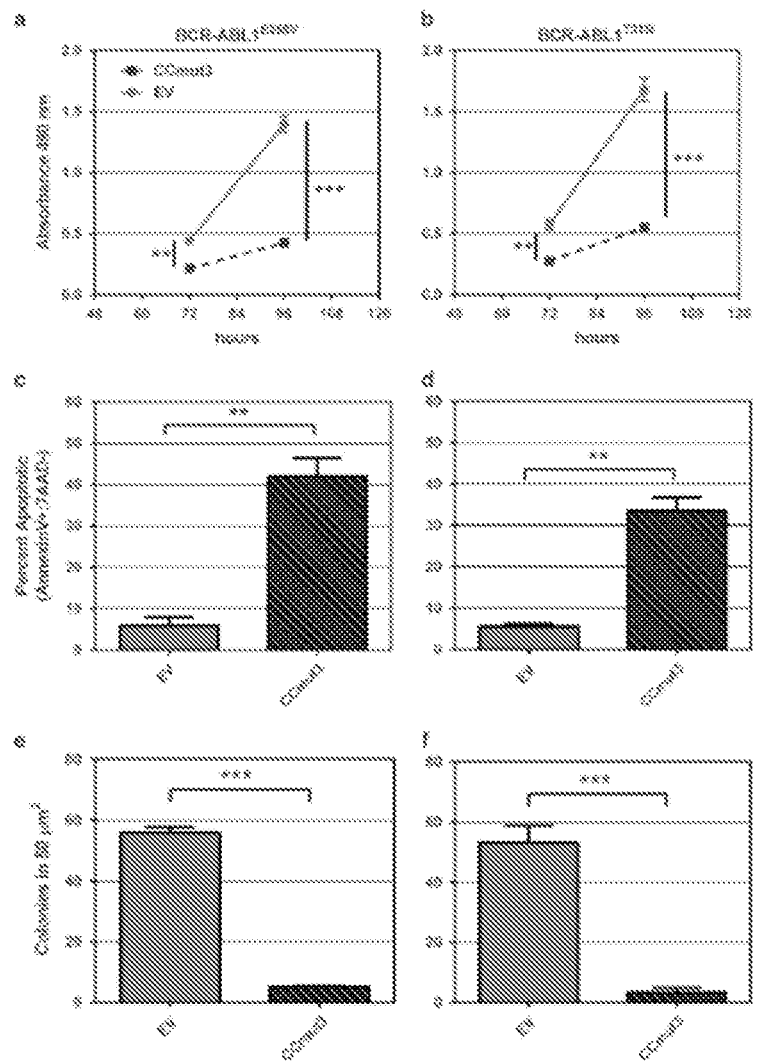
FIGS. 39A-39F. CCmut3 inhibits BCR-ABL1-driven proliferation and increases apoptosis in single-mutant BCR-ABL1. (a, b) A significant reduction of proliferative capacity was observed following CCmut3 (blue boxes) but not EV expression (red circles) of Ba/F3 cells expressing the single BCR-ABL1 mutants E255V (a) or T315I (b) at both 72 and 96 h (n=3). (c, d) An increase of apoptosis was observed in Ba/F3 BCR-ABL1E255V (c) and Ba/F3 BCR-ABL1T315I (d) cells at 72 h. (e, 0 Colony formation of Ba/F3 mutants E255V (e) and T315I (f) represented significantly fewer colonies per unit area CCmut3 compared to EV groups (n=3). Graphs display mean±S.E.M. $p<0.01$, $*p<0.001$.
Figure 40:
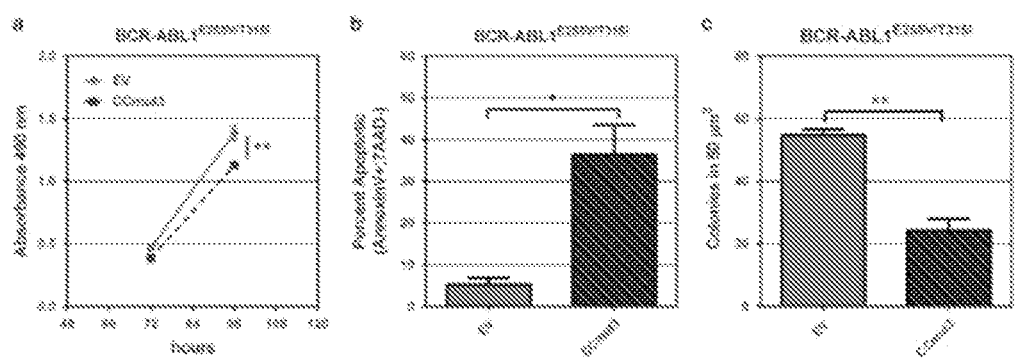
FIGS. 40A, 40B, and 40C show that CCmut3 enhances apoptosis, and reduces colony forming ability of compound-mutant BCR-ABL1 cells. (a) Ba/F3 cells expressing the BCR-ABL1E255V/T315I compound mutant demonstrate a small yet significant growth reduction at 96 h but not 72 h with CCmut3 treatment compared to EV controls (n=3). (b) Enhanced apoptosis was evident in Ba/F3 BCR-ABL1E255V/T315I cells when expressing CCmut3 compared to EV controls (n=3). (c) Colonies per unit area were again reduced in the compound mutant cell line (Ba/F3 BCR-ABL1E255V/T315I) by CCmut3 compared to EV controls (n=3). Graphs display mean±S.E.M. $*p<0.05$, $**p<0.01$.

Compound mutations are arising as a clinical problem in patients undergoing sequential TKI therapy. To determine whether CCmut3 also has growth inhibitory effects on cells harboring BCR-ABL1 compound mutants, we introduced CCmut3 or the EV into Ba/F3 cells expressing the highly TKI-resistant BCR-ABLE255V/T315I compound mutant. Expression of the CCmut3 construct was again confirmed by immunoblot analyses (FIG. 44a). Importantly, CCmut3 significantly reduced proliferation of compound mutant cells at 96 h (FIG. 40a), although the effects were far less pronounced than that observed in the single kinase domain mutant cells (FIGS. 39a and 39b). However, CCmut3 effectively induced apoptosis of Ba/F3 cells expressing BCR-ABLE255V/T315I (FIG. 40b) to a similar degree seen in single kinase mutants 72 h following transfection (FIGS. 39c and 39d). Importantly, CCmut3 expression in cells harboring the BCR-ABLE255V/T315I compound mutant reduced colony forming ability by approximately 50% compared to EV controls (FIG. 40c). Thus, these data extend the effects of CCmut3 to include not only native and single kinase domain mutant BCR-ABL1, but also cells harboring highly TKI-resistant compound mutant clones.

d. CD34+ cells from CML patients harboring native or T315I mutant BCR-ABL1 are sensitive to CCmut3.

Figure 41:
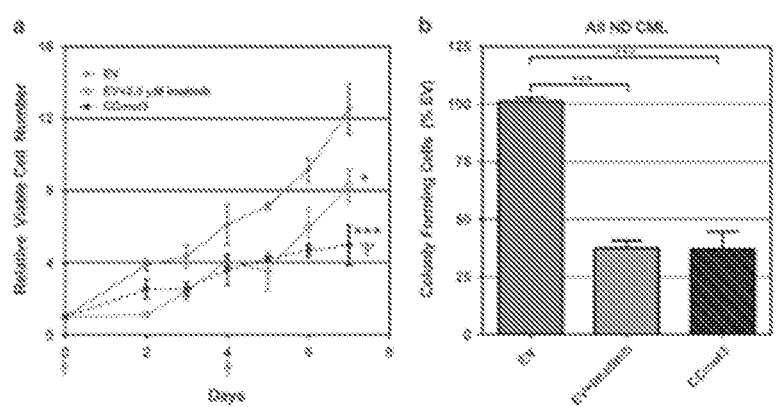
FIGS. 41A and 41B show that cells from newly diagnosed CML patients are sensitive to CCmut3 lentiviral therapy ex vivo. (a) Equal number of cells were seeded on day 0 for each group and plotted as fold-change of starting cell number compared to controls on days 2-7. Imatinib was added on days 0 and 4 (indicated by orange arrows) to the EV+2.5 µM imatinib group only (n=3). $*p<0.05$ compared to EV, $*p<0.001$ compared to EV, $\psi p<0.05$ compared to EV+2.5 µM imatinib group. (b) Colony forming cells were assessed 14 days following seeding in methylcellulose. Individual patient samples were counted in duplicate and normalized to the EV control. 2.5 µM imatinib and CCmut3 are equally effective in reducing colony number (n=4). Graphs display mean±S.E.M. $*p<0.001$.

Lentivirus expressing CCmut3 or EV (FIG. 44b-c) was used to infect CD34+ cells isolated from blood or bone marrow of ND CML patients, and cultured in complete RPMI 1640 with cytokines. For comparison, EV-expressing cells were also treated with 2.5 imatinib. CCmut3 reduced cell growth by more than 2-fold as determined by trypan blue exclusion, a significant reduction compared to inhibition by imatinib (FIG. 41a). Cells were also assessed for colony formation by plating in methylcellulose supplemented with growth factors. The effects of CCmut3 on colony formation were similar to that of imatinib, inhibiting CML CD34+ cells from four independent newly diagnosed patient samples by ~60% (FIG. 41b).

Figure 42:
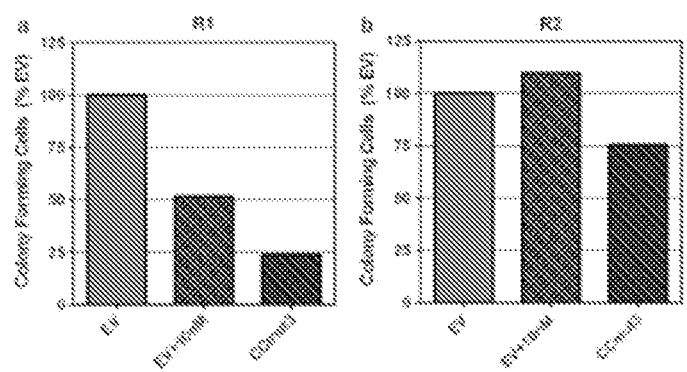
FIGS. 42A and 42B show CCmut3 is effective in a patient sample from a CML patient in accelerated phase harboring BCR-ABL1T315I, with a less pronounced effect upon blastic transformation. Colony forming assays were set up with two longitudinal samples from the same patient, R1 and R2, separated by a 6-month interval. Each sample was thawed and lentivirally transduced with CCmut3 or the EV control. Following cell sorting for transduction, each sample was plated in triplicate. (a) R1 displays sensitivity to 10 nM ponatinib (gray checked bars), but even greater sensitivity to transduction with CCmut3 (blue checked bars) compared to untreated EV-transduced controls (red solid bar). (b) R2 is a sample from the same individual after ponatinib failure and transformation to blast crisis (see Supplemental Table 1). While ponatinib treatment minimally increases colony forming ability, CCmut3 treatment resulted in a ~25% reduction in colony formation.

Additionally, the effect of CCmut3 expression on primary human CD34+ CML cells expressing BCR-ABL1T315I as determined by Sanger sequencing of two samples (R1 and R2) obtained from the same individual at two time points approximately 6 months apart, during which the patient was treated with ponatinib was investigated (Table 3). Ponatinib was used to assess sensitivity to inhibition of BCR-ABL1 catalytic activity. In the initial sample (R1) obtained when the patient was in accelerated phase CML, 10 nM ponatinib and CCmut3 reduced colony formation by 47% and 76%, respectively (FIG. 42a). In contrast, while cells obtained at the time of blastic transformation (R2) were insensitive to treatment with ponatinib, CCmut3 was still able to reduce colony formation by 25% (FIG. 42b). Importantly, Sanger sequencing confirmed that the mutation status had not changed compared to the initial sample. Altogether, these data indicate that like ponatinib, CCmut3 has activity in CML patients harboring the T315I mutant.

TABLE 3

Patient metrics for ex vivo experiments with lentiviral transduction.
Peripheral blood from CML patients with newly diagnosed (ND)
CML or resistant CML ® was collected and enriched for
>90% CD34+ cells. The metrics presented here provide
insight into the disease stage and treatment history of the patient
samples used in this study. R1 and R2 represent two different
samples from the same patient about six months apart.
Supplementary Table 1. Patient metrics for ex vivo
experiments with lentiviral transduction.

| Sample Name | Age | Sex | Disease Phase | BCR-ABL1 Kinase Domain Mutations | Therapy |
|---|---|---|---|---|---|
| ND1 | 8 | F | Chronic | none | none |
| ND2 | 29 | M | Chronic/Accelerated | none | none |
| ND3 | 44 | F | not determined | none | none |
| ND4 | 72 | M | Chronic | none | none |
| R1 | 66 | F | Accelerated | T315I | hydroxyurea, anagrelide, peg-interferon, imatinib, dasatinib |
| R2 | 67 | F | Blast Crisis | T315I | ponatinib | viii. Discussion

Figure 43:
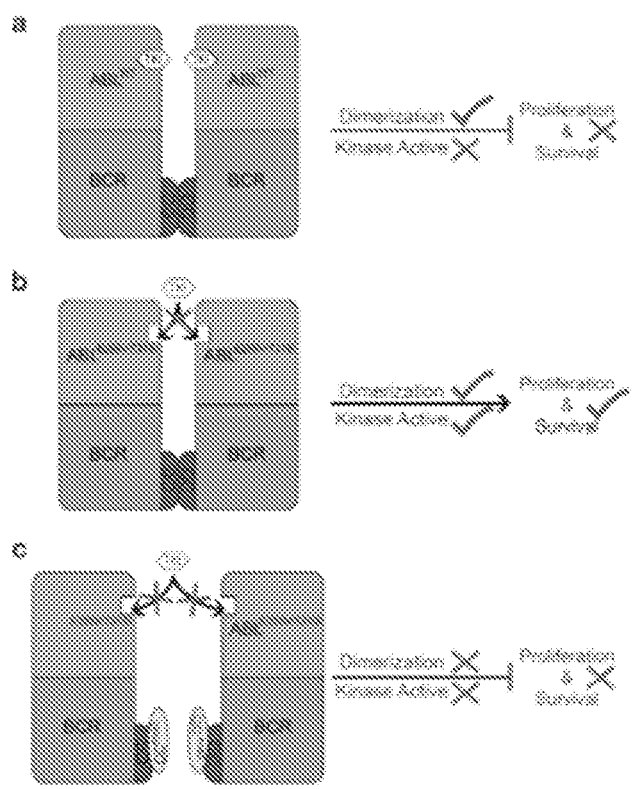
FIGS. 43A, 43B, and 43C show BCR-ABL1 inhibition state in native and mutant forms by TKI or by CCmut3. (a) TKIs bind to the catalytic site of the BCR-ABL1 fusion protein. Proliferation and survival are blocked through kinase inhibition, irrespective of dimerization. (b) In compound mutant BCR-ABLE255V/T315I, TKIs are unable bind to the catalytic site. Dimerization and kinase activity remain intact. (c) CCmut3 expression leads to competitive disruption of dimerization, preventing transphosphorylation, autophosphorylation and kinase activation of native, single and compound mutant BCR-ABL1.

TKIs are an effective and generally well-tolerated therapy for CML. However, a subset of patients fail TKIs due to drug resistance or intolerance. BCR-ABL1 kinase-dependent resistance is often the product of BCR-ABL1 kinase domain mutations that impair or prevent TKI binding to the catalytic site, which has led to the development of second and third generation inhibitors. Because kinase domain-targeted inhibitors are subject to resistance arising from mutations in this domain, the ability of CCmut3, a coiled-coil dimerization domain inhibitor, was examined to impair growth and viability of CML cells by disrupting oligomerization, the key event necessary for autophosphorylation and activation of BCR-ABL1 kinase (FIG. 43). CCmut3 was computationally designed to include mutations that not only enhance interactions with BCR-ABL1, but also to incorporate charge-charge repulsions that destabilize CCmut3 homodimer formation. The net result is the preferential heterodimerization between CCmut3 and BCR-ABL1.

Previous studies demonstrated that CCmut3 inhibits proliferation and induces apoptosis in K562 CML cells. This study shows the effects of CCmut3 against native and mutant BCR-ABL1, using murine pro-B cells (Ba/F3) engineered to express native and kinase domain mutant BCR-ABL1, as well as primary CML CD34+ cells obtained from newly diagnosed or therapy-resistant patients. CCmut3 was found to reduce proliferation and colony formation and increased apoptosis of CML cell lines and patient samples expressing native BCR-ABL1 (FIGS. 38b, 38d, 38f, and 41); CCmut3 had no measurable toxicity in BCR-ABL1-negative cells (FIGS. 38a, c, e). Importantly, this is the first evidence of CCmut3 efficacy in primary CML patient samples.

Figure 32B:
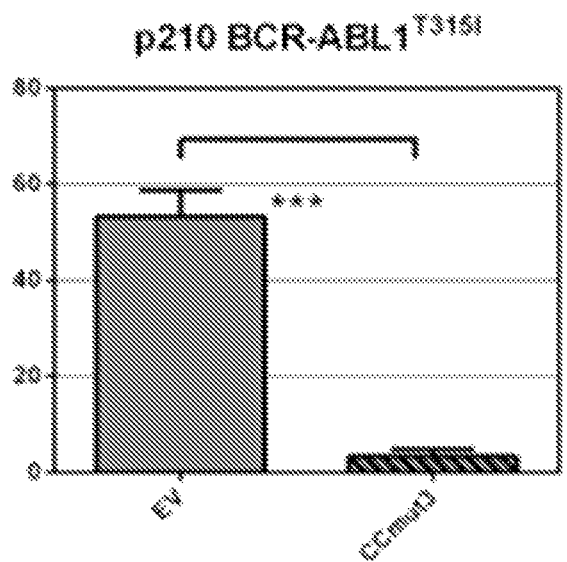
Figure 32C:
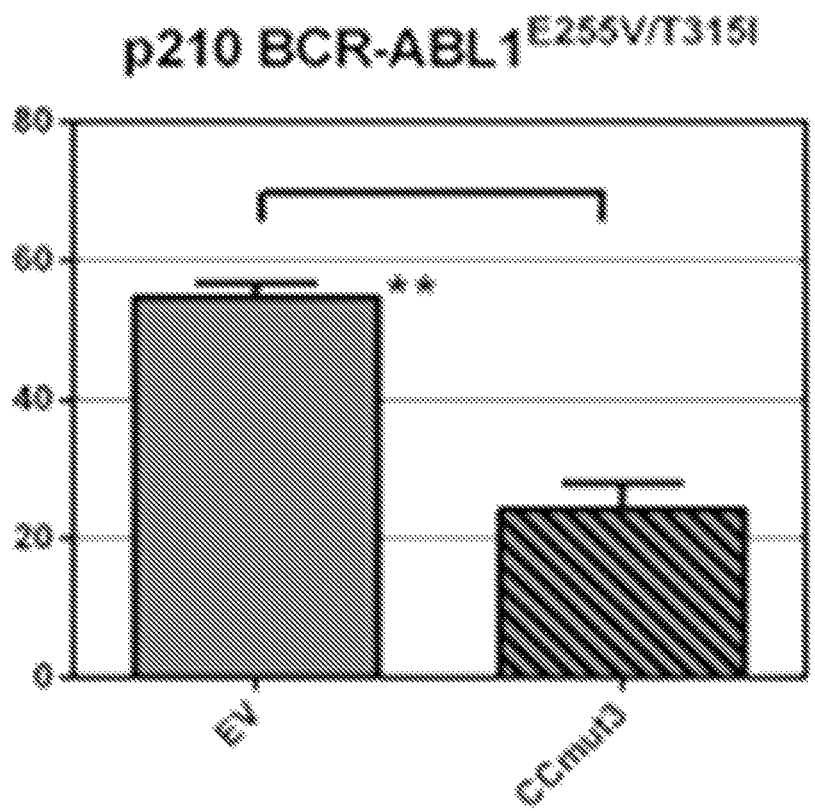

While all TKIs currently act directly on the kinase domain, alternative mechanisms of BCR-ABL1 inhibition can circumvent mutation-driven TKI resistance. Consistent with native BCR-ABL1 inhibition by CCmut3, the CC mimetic is effective in single BCR-ABL1 kinase domain mutants. A significant inhibition of growth and viability introduced by CCmut3 in BCR-ABL1E255V and BCR-ABL1T315I (FIGS. 39 and 39b), as well as a >5-fold increase in apoptosis (FIGS. 39c and 39d). Moreover, a marked reduction of colony forming potential was observed in both Ba/F3 cells expressing BCR-ABL1E255V and BCR-ABL1T315I (FIGS. 39e and 39f) and in a sample from a BCR-ABL1T315I CML patient following CCmut3 expression (FIG. 42a). However, CCmut3 showed only minimal activity in a longitudinal sample obtained after the patient had developed resistance to ponatinib and progressed to the blastic phase of disease (FIG. 32b). These data indicate that this patient may have developed a BCR-ABL1 kinase-independent mechanism of resistance.

The emergence of compound mutations in the kinase domain that confer resistance to multiple TKIs is of increasing clinical importance. To this end, we examined CCmut3 in compound-mutant BCR-ABL1E255V/T315I cells, which are resistant to ponatinib, the most advanced tyrosine kinase inhibitor in clinical use. Importantly, CCmut3 significantly increased apoptosis and reduced colony formation of BCR-ABL1E255V/T315I-expressing cells (FIG. 40b, 40c), with a lesser effect on cell proliferation (FIG. 40a). The cause of the comparably weaker activity of CCmut3 in cell proliferation assays is unknown and remains to be determined in structural studies. Taken together, this shows that CCmut3 expression is not only effective against CML cells expressing native and single kinase domain mutant BCR-ABL1, but also against cells harboring compound-mutant BCR-ABL1 that are resistant to multiple TKIs, providing proof of principle that targeting the dimerization domain of BCR-ABL1 can overcome kinase domain mutation-based TKI resistance (FIG. 43). Furthermore, we speculate that CCmut3 will not be prone to mutational escape routes seen with traditional kinase inhibitors (the selection or genesis of mutant BCR-ABL1 molecules which are TKI-resistant), because any mutations in BCR-ABL1 that would reduce binding to the CCmut3 would also reduce the ability of BCR-ABL1 to dimerize, thereby precluding autophosphorylation and resulting in a monomeric, auto-inhibited kinase. This may translate into a lower likelihood of clinical resistance due to point mutations. Another as yet hypothetical advantage of blocking dimerization may be the inhibition of BCR-ABL1 functions that are kinase-independent, yet require formation of BCR-ABL1 dimers or multimers. These functions persist upon TKI-mediated inhibition of BCR-ABL1 and may contribute to the innate TKI resistance of primitive CML cells.

In contrast to small molecule drugs, peptides present considerably greater drug delivery challenges. In the present study, CCmut3 was transcribed in cells following lentiviral infection with an expression construct. Direct application of this therapy could include intramedullary injection of lentivirus encoding CCmut3 as explored in hemophilia therapy. However, a challenge with this approach in cancer is to achieve 100% transduction efficiency. Therefore, we are currently formulating CCmut3 as a stapled peptide for therapeutic use in future in vivo studies. Stapled peptides improve drug delivery by their resistance to degradation, improved cell permeation, and increased in vivo half-life compared to conventional peptide therapeutics. Addition of a leukemia-specific cell-penetrating peptide motif might allow targeting of this peptide to CML stem cells. For instance, recent reports have identified antigens specifically or preferentially expressed on primitive CML cells, such as CD25, CD26 and the interleukin-1 receptor associated protein (IL1RAP). Therefore, an antibody-CCmut3 peptide conjugate could be formulated for leukemic stem cell targeting. Combination of BCR-ABL1 inhibition by CCmut3 along with inhibition of stem cell survival or self-renewal pathways may result in robust eradication of the CML stem cell.

5. Truncating and Capping the CCmut3 α-Helix for Improved Delivery and Stability Oncogenicity in chronic myeloid leukemia (CML) is driven by the fusion protein tyrosine kinase BCR-ABL. In order to aberrantly activate the downstream signaling characteristic of this disease, BCR-ABL must homo-oligomerize via a coiled-coil domain located at its N-terminus. Removing this domain, or simply disrupting oligomerization, eliminates the oncogenic activity of BCR-ABL. Previously, a modified version of this coiled-coil domain was created, designed to enhance the binding affinity to native BCR-ABL while decreasing the likelihood of homo-oligomerization. This α-helical construct, termed CCmut3, delivered as a gene, has shown the ability to inhibit oligomerization and thus eradicate the oncogenic function of BCR-ABL. To improve the deliverability of the CCmut3 construct truncation and helical capping techniques were carried out. Because the interactions between CCmut3 and the BCR-ABL coiled-coil domain can exist at the α-helix2 interface, CCmut3 was truncated to include the α-helix2 domain (with flanking residues), termed Helix2mut3. Next, to further truncate Helix2mut3 and include α-helix-stabilizing capping residues (serine on the N-terminus and glycine on the C-terminus), a construct called cappedHelix2mut3 was developed. While Helix2mut3 outperformed negative control EGFP in cell proliferation, colony forming, and apoptosis, it did not provide an advantage over the full-length CCmut3 construct. Additionally, cappedHelix2mut3 failed to out-perform the negative control in preliminary cell proliferation and colony forming assays. These results have led to experiments to identify alternative methods to increase deliverability of CCmut3.

A potential target for CML therapy is the N-terminal oligomerization domain. This 72-amino acid coiled-coil (CC) region is the location responsible for the homo-oligomerization of BCR-ABL. Previously, a construct was designed targeting this domain, termed CCmut3, which was shown to inhibit proliferation and transformative ability and to induce apoptosis in CML cells (16).

Figure 45:
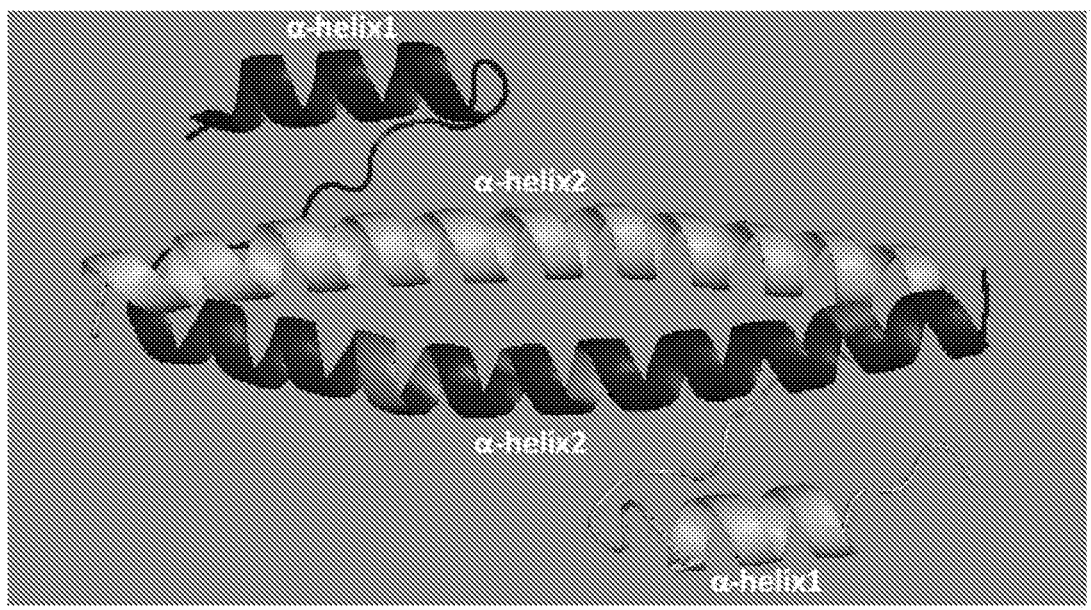
FIG. 45 is a structural representation of hetero-oligomerization between BCR-ABL CC domain (top α-helix2 and bottom α-helix1) and CCmut3 (top α-helix1 and bottom α-helix2). The lighter shaded residues on CCmut3 (bottom α-helix2) are representative of the C38A, K39E, S41R, L45D, E48R, and Q60E mutations, characteristic of CCmut3.
Figure 46:
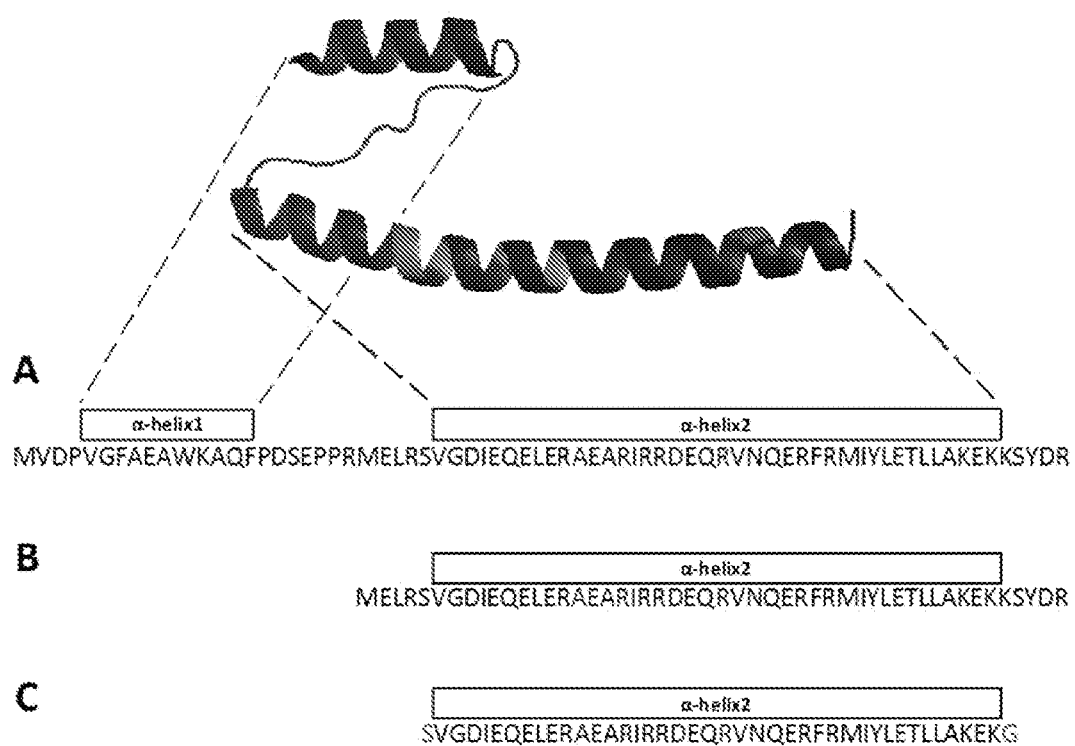
FIGS. 46A, 46B, and 46C show the sequences of coiled-coil constructs used for BCR-ABL inhibition. Mutations characteristic to CCmut3 appear in blue, both in the above coiled-coil image and in all three of the sequences. A) CCmut3: Full length CCmut3 construct contains both α-Helix1 and α-Helix2. B) Helix2mut3: Truncated version of CCmut3 to include only the α-Helix2 and flanking residues. C) cappedHelix2mut3: Capped and further truncated version of CCmut3; includes only α-Helix2 with N-terminal serine cap at residue 27 (S27) and C-terminal glycine cap at residue 68 (G68).

Further modifications to the CCmut3 construct were carried out to improve its deliverability as a peptide. The notion that CCmut3 deliverability can be enhanced through helical truncation thereby, resulting in a smaller peptide leading to a more simplified delivery. Structurally, the BCR-ABL oligomerization domain consists of two α-helices, termed α-helix1 and α-helix2. Because CCmut3 design was based on this structure, it, too, consists of α-helix1 and α-helix2 domains. FIG. 45 shows CCmut3 interacting with the BCR-ABL CC domain. Interactions in the CCmut3:BCR-ABL heterodimer can occur between the α-helix2 regions of each respective molecule. Therefore, and based on results from previous studies, it is believed that the α-helix2 region of CCmut3 can be useful for efficient BCR-ABL inhibition. In the experiments carried out, the mutations incorporated into CCmut3 are contained within the α-helix2 domain. Thus by removing α-helix1, it is thought that the engineered specificity or affinity for the BCR-ABL CC will be lost. The construct created was called Helix2mut3 (FIG. 46B). More specifically, it contains amino acids 23-72 from the original CCmut3 domain (FIG. 46A).

Next, to simplify delivery and enhance efficacy, further truncation of CCmut3 along with the addition of helix-stabilizing capping residues to each end of the α-helix2 domain were completed. Previous work has shown that capping helices with specific residues is known to thermodynamically stabilize the α-helices in peptides. In an α-helix, the first four N—H groups (from the N-terminal end) and the last four C═O groups lack intrahelical hydrogen bonds. Therefore, adding residues adjacent to these N- and C-terminal ends can compensate for these missing hydrogen bonds and stabilize the helical shape. The following nomenclature for capping α-helices appears as follows: Ncap-N1-N2-N3- . . . -C3-C2-C1-Ccap; where N1 is the first residue of the helix, and Ncap is the residue immediately preceding the last residue of the helix (and the same is true for the C-terminus as well). Because the α-helix2 in CCmut3 begins at residue 28 and ends at residue 67, we used those residues as our N1 and C1 residues, respectively. Further, two commonly used capping residues were incorporated: serine (a hydrogen bond donor) as Ncap and glycine (a hydrogen bond acceptor) as Ccap. The final construct, comprising amino acids 28-67 of CCmut3, serine at the Ncap position, and glycine at the Ccap position, was termed cappedHelix2mut3 (FIG. 46C).

The next set of studies was carried out to identify whether or not truncating and/or capping the helix results in a construct capable of BCR-ABL inhibition.

ix. Materials and Methods a. Construction of Plasmids and Mutagenesis; Construction of Helix2WT and Helix2mut3

The plasmids pEGFP-CC, pEGFP-CCmut3, and pmCherry-CCmut3 were constructed. pEGFP-Helix2mut3 was created through site-directed mutagenesis using pEGFP-CCmut3 as a template. The mutagenesis primers for construction of pEGFP-Helix2mut3 were as follows: 5'-AGTTCCCGGACTCAGAGCCCAGATCTATG-GAGCTGCGCTCAGTGGG-3' and 5'-CCCACT-GAGCGCAGCTCCATAGATCTGGGCTCTGAGTC-CGGGAACT-3'. Here, the mutagenic primers were designed to include a BglII restriction site before residue 23 in the CCmut3 domain. Following insertion, the BglII restriction enzyme (New England BioLabs, Ipswich, Mass., USA) was used to digest out the region between the vector MCS and residue 23, eliminating residues 1-22 in the CC construct.

b. Construction of CappedHelix2mut3

The plasmid pmCherry-CappedHelix2mut3 was constructed using pmCherry-CCmut3 as a template, using the following method, the method comprising: 1) insertion of BglII restriction site prior to residue 27, to create Ser27 as the N-terminal cap; 2) insertion of Gly residue and stop codon as C-terminal cap after residue 67; and 3) removal of residues 1-26 using BglII digestion, leaving final CappedHelix2mut3 product comprising residues 27-68 with Ser27 as N-terminal cap and Gly68 as C-terminal cap. The mutagenesis primers for step 1 were as follows: 5'-CA-GAGCCCCGCGCATGGAGAGATCTTCAGTGGGC-GACATCGAGCA-3' and 5'-TGCTCGATGTCGCCCACT-GAAGATCTCTCCATGCGCGGGGGCTCTG-3'. For step 2, the mutagenesis primers were as follows: 5'GCTGGC-CAAGGAAAAGGGGTAG TATGACCGGTCTCG-3' and 5'-CGAGACCGGTCATACTACCCCTTTTCCTTG GCCAGC-3'.

c. Cell Lines and Transient Transfection

K562 and Ba/F3-p210 cells were maintained and passaged.

Transfection of K562 Cells

Two days following cell passaging, 2.0×106 cells were collected by centrifugation at 500×g for 10 min for each transfection group. Following cell collection, 6 lig DNA (pEGFP, pEGFP-CC, pEGFP-CCmut3, pEGFP-Helix2WT, pEGFP-Helix2mut3, pmCherry, pmCherry-CCmut3, or pmCherry-CappedHelix2mut3) was transfected into cells according to the Cell Line Nucleofector® Kit V protocol (program T-013) using the Amaxa Nucleofector II (Lonza Group, Basel, Switzerland). Following transfection, the DNA/cell mixture was added to 10 mL Complete RPMI 1640 media and allowed to incubate at 37° C. for 24, 48, or 72 h until analysis, depending on the assay.

Transfection of Ba/F3-p210 Cells

Two days following cell passaging, 3.0×106 cells were collected by centrifugation at 750×g for 10 min for each transfection group. Following collection, 4 µg DNA was transfected into cells according to the Cell Line Nucleofector® Kit V protocol (program X-001) using the Amaxa Nuelcofector II. Following nucleofection, the DNA/cell mixture was added to 500 µL plain RPMI and incubated for 20 min. After incubation, the 500 µL cell/DNA/RPMI mixture was added to complete RPMI 1640 media and allowed to incubate at 37° C. for 72 h until analysis.

d. Fluorescence Microscopy and DNA Segmentation

Nuclear segmentation analysis was performed as previously described (16). Briefly, immediately prior to cellular analysis, 2-well live cell chambers were treated for 1.5 min with poly-L-lysine (Sigma-Aldrich, St. Louis, Mo., USA), to allow cell adhesion in the wells. Forty-eight h following transfection, the transfected K562 cells were transferred to the pretreated 2-well live cell chambers. Cells were incubated for 15 min at 37° C. following the addition of 0.3 µL Hoechst H33342 nuclear stain (Life Technologies, Carlsbad, Calif., USA). Cells were then imaged using an inverted fluorescence microscope (Olympus IX701F, Scientific Instrument Co., Sunnyvale, Calif., USA) equipped with an F-view Monochrome CCD camera. Fields of view were selected based on EGFP fluorescence when viewing using a 40× oil immersion objective. Nuclei from cells that were positively transfected (positive for EGFP fluorescence) were categorized as either healthy (round or kidney-shaped nuclei) or segmented (punctate staining of nuclei), and the percentage of cells with segmented DNA was calculated (n=3 in replicate).

e. Cell Proliferation

Forty-eight or 72 h following transfection, 100 µL of treated K562 or Ba/F3-p210 cells was mixed with 100 µL trypan blue solution (Life Technologies). The numbers of viable cells (those impermeable to the trypan blue dye) from four different quadrants in an INCYTO™ C-CHIP™ Neubauer hemacytometer (VWR International, Radnor, Pa., USA) were counted using a standard light microscope. Quadrant counts were then averaged to obtain the number of viable cells per mL. For experiments using the Helix2mut3 construct, counts were performed on one aliquot per transfection (n=3 in replicate). In experiments involving the CappedHelix2mut3 construct, counts were performed three times using separate 100 pt aliquots from one transfection (n=1 in triplicate).

f. Colony Forming Assays

Briefly, K562 or Ba/F3-p210 cells were transfected according to the protocol above. One day following transfection, 1.0×106 cells per transfection group were collected and re-suspended in sterile PBS. One hundred μL of this resuspension was then serially diluted in Isocove's Modified Dulbecco's media (IMDM) to obtain a concentration of 1.0×104 cells/mL. From this dilution, 300 μL was added into 3.0 mL of methylcellulose medium (H4230 medium for K562 cells, M3234 medium for Ba/F3-p210 cells) in the absence of cytokines, to obtain a final concentration of 1.0×103 cells/mL. Finally, 1.1 mL of cell/methylcellulose mixture was seeded in duplicate and allowed to grow at 37° C. and 5% CO2 for 7 days. Colony formation was assessed by counting colonies in two 200 μm2 areas on the plate. Experiments were performed once in duplicate (n=1 in duplicate). All kit reagents and media were purchased from Stem Cell Technologies (Vancouver, BC, Canada).

g. Statistical Analysis

In instances where three separate transfections were used as replicates for a single assay, all data were analyzed using a one-way ANOVA with Tukey's posttest.

x. Results

The goal of these studies was to determine whether truncating and/or capping CCmut3 can eliminate or interfere with its BCR-ABL inhibitory ability. Therefore, the designed constructs were compared side-by-side to CCmut3 in cell proliferation, transformative ability, and apoptosis assays. Detailed descriptions of the constructs that were tested in the following studies appear in Table 4.

a. CCmut3 Inhibits Transformative Ability to a Greater Degree than Helix2mut3

Figure 47:
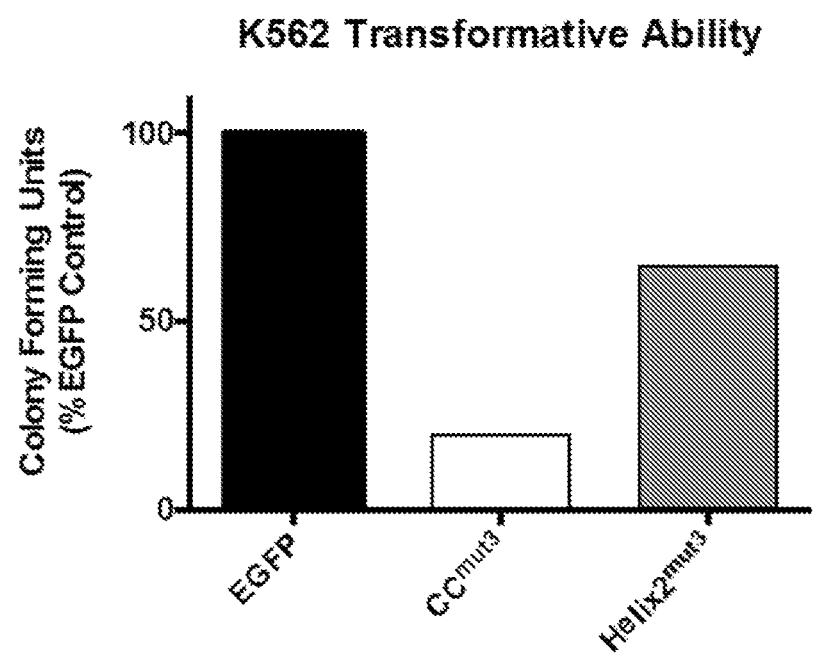
FIG. 47 is a bar graph showing colony forming assay: transformative ability of K562 cells. Colony forming units were counted 7 days following seeding into methylcellulose media. Assay was performed one time in duplicate (n=1 in duplicate); data are normalized to EGFP control and presented as the mean of the two colony counts for each construct.

First, the ability of Helix2mut3 to inhibit transformative ability of K562 cells was assessed. Following transfection of these cells with Helix2mut3, CCmut3, or EGFP control, a colony forming assay was conducted, where outgrowth of colonies were a measure of transformative ability of K562 cells. Results from this study, in duplicate (n=1 in duplicate), are shown in FIG. 47. All data were normalized to the EGFP negative control. Results show that CCmut3 reduced colony formation to approximately 20% of control (FIG. 47, middle bar), whereas Helix2mut3 (FIG. 47 last bar from left) reduced colony formation to approximately 67% of EGFP control. Both CCmut3 and Helix2mut3 showed inhibitory activity.

TABLE 4

Descriptions of the mutant CC constructs.

| Construct | Residues* | Description |
|---|---|---|
| $CC^{mut3}$ | 1-72 | BCR-ABL CC domain with the following mutations: C38A, K39E, S41R, L45D, E48R, Q60E |
| Helix2$^{mut3}$ | 23-72 | α-helix2 of wild-type BCR-ABL CC domain plus five flanking residues on each end with the following mutations: C38A, K39E, S41R, L45D, E48R, Q60E |

TABLE 4-continued

Descriptions of the mutant CC constructs.

| Construct | Residues* | Description |
|---|---|---|
| cappedHelix2$^{mut3}$ | 27-68 | α-helix2 of wild-type BCR-ABL CC domain with helical capping residues S27 and G68 and the following mutations: C38A, K39E, S41R, L45D, E48R, Q60E |

*Signifies the amino acid residue numbering of the full-length BCR-ABL CC (for example, to create Helix2mut3, the first 22 amino acids of the BCR-ABL CC domain were removed).

b. Helix2mut3 Inhibits Proliferation and Induces Apoptosis to a Similar Extent as CCmut3

Figure 48:
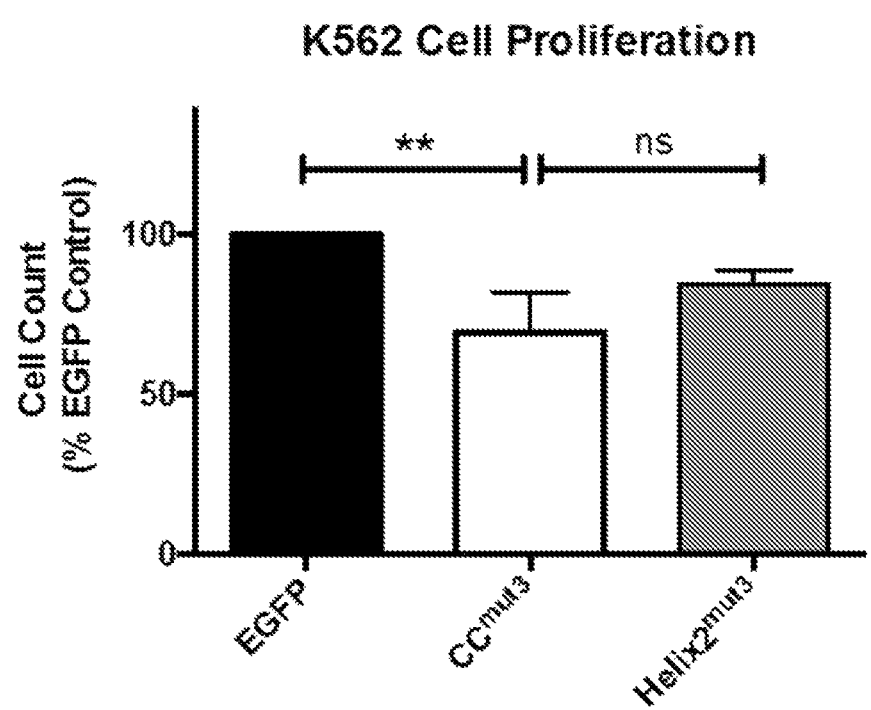
FIG. 48 is a bar graph showing a cell proliferation assay: viability of K562 cells. Viability was assessed 48 h following transfection using trypan blue exclusion; cells not permeated by trypan blue dye were considered viable. Assay was performed using three separate transfections (n=3). Data are normalized to EGFP control and presented as overall mean±SEM; one-way ANOVA with Tukey's post-test, **$p<0.005$.

Next, proliferation of cells treated with Helix2mut3 was studied. K562 cells were transfected with EGFP control, CCmut3, or Helix2mut3, and the viability of cells was then analyzed 48 h following treatment via trypan blue exclusion; results are presented in FIG. 48. Treatment with CCmut3 (FIG. 48, middle bar) resulted in a statistically significant decrease in the proliferation of K562 cells.

A significant decrease was not seen in the proliferation of cells treated with Helix2mut3 (FIG. 48, far right bar) when compared to EGFP control. Further a significant difference was not observed between the growth of cells treated with CCmut3 and those treated with Helix2mut3 (FIG. 48, middle bar and far right bar, respectively). The outcome of these studies show a similar therapeutic profile between CCmut3 and Helix2mut3.

Finally, induction of apoptosis was studied in K562 cells treated with EGFP negative control, CCmut3, and Helix2mut3. The apoptosis assay used was DNA segmentation, which involved analyzing the morphology of the nucleus of cells treated with the constructs described herein. Healthy K562 cells contain round or kidney-shaped nuclei, while the nuclei apoptotic cells can display a punctate pattern. Percentage of apoptotic cells can be determined by calculating the amount of cells with segmented nuclei compared to the number of total cells transfected (all three constructs were tagged with EGFP, thus EGFP-positive cells were considered positively transfected). Therefore, 48 h following transfection, the nuclei of treated cells were analyzed using fluorescence microscopy. Results appear in FIG. 49.

Figure 49:
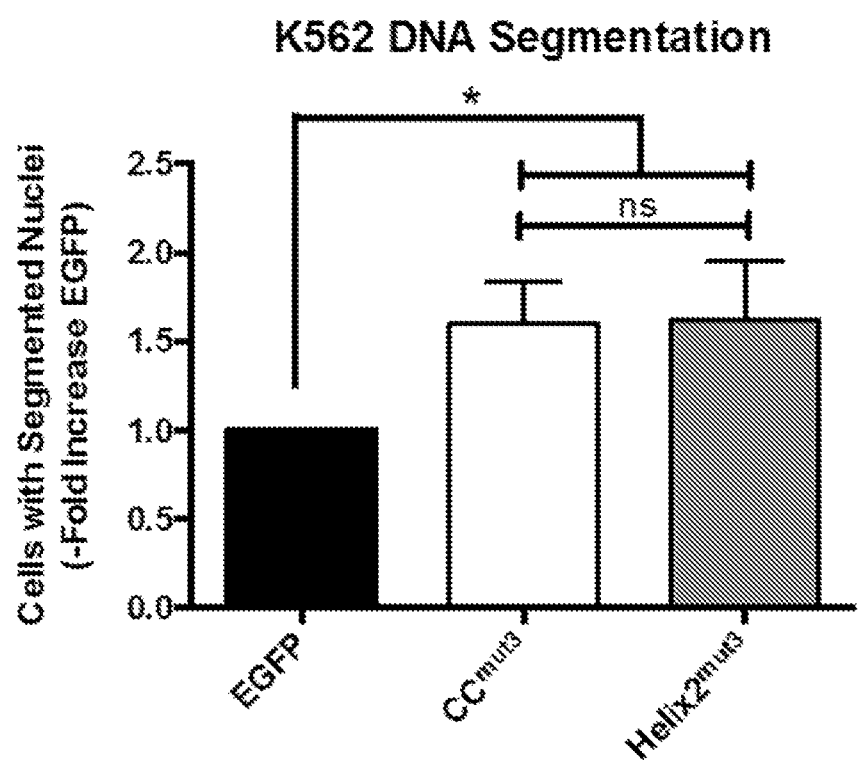
FIG. 49 is a bar graph showing a nuclear (DNA) segmentation assay: induction of apoptosis in K562 cells. Quantitation of apoptosis 48 h following transfection based on the shape of the nucleus of K562 cells. Cells were characterized as healthy if they displayed round or kidney-shaped nuclei; apoptotic cells were characterized by punctate staining of the nucleus. Percentage of apoptosis was calculated by analyzing four or five fields of view; each containing between 20 and 50 cells each. Only cells positively transfected (EGFP-positive) were analyzed. Data were normalized to EGFP control and are presented as overall mean±SEM; one-way ANOVA with Tukey's posttest; *$p<0.05$.

An increase in apoptosis was seen in cells treated with CCmut3 (FIG. 49, middle bar) compared to the EGFP control (FIG. 49, leftmost bar). Different from the cell proliferation results, a statistically significant increase in apoptosis was seen in cells treated with Helix2mut3 (FIG. 49, rightmost bar) when compared to EGFP. However, as similar to the cell proliferation assay, apoptosis was induced to a similar extent between both CCmut3 and Helix2mut3, as no significant difference was apparent. Both the cell proliferation and DNA segmentation assays were performed three times using three separate transfections (n=3).

An increase in apoptosis was seen in cells treated with CCmut3 (FIG. 49, middle bar) compared to the EGFP control (FIG. 49, leftmost bar). Different from the cell proliferation results, a statistically significant increase in apoptosis was seen in cells treated with Helix2mut3 (FIG. 49, rightmost bar) when compared to EGFP. However, as similar to the cell proliferation assay, apoptosis was induced to a similar extent between both CCmut3 and Helix2mut3, as no significant difference was apparent. Both the cell proliferation and DNA segmentation assays were performed three times using three separate transfections (n=3).

c. Further Helical Truncation and Capping Do Not Provide a Therapeutic Benefit to CCmut3

Figure 50:
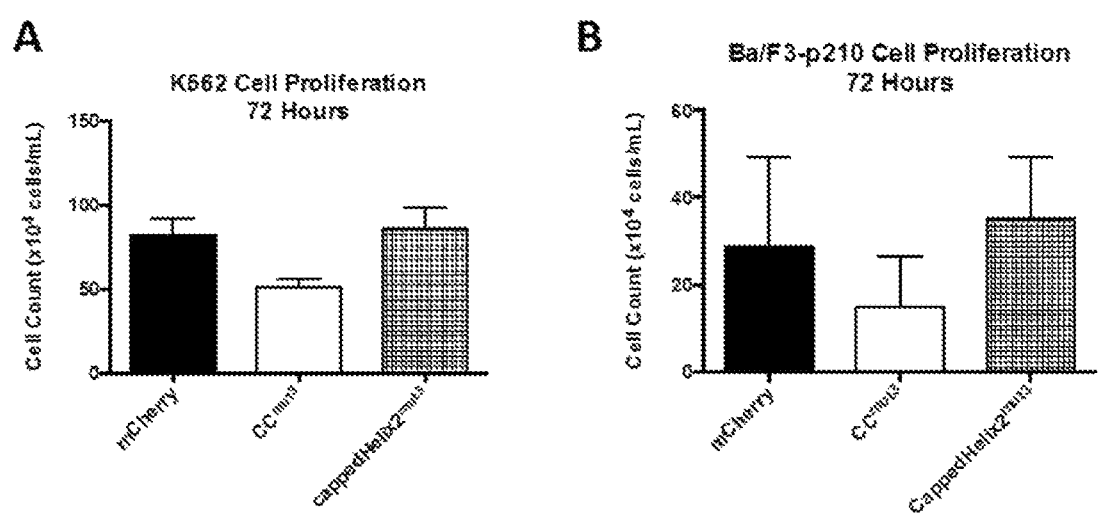
FIGS. 50A and 50B are bar graphs showing cell proliferation assays: viability of K562 cells (A) and Ba/F3-p210 cells (B). Viability was assessed 72 h following transfection using trypan blue exclusion; cells not permeated by trypan blue dye were considered viable. Assay was performed using three separate cell counts, but only from one individual transfection (n=1). Data are presented as overall mean±SEM of the three counts.

The next set of experiments was carried out to further improve the Helix2mut3 construct by additional truncation and through the addition of helical capping residues for stabilization. These efforts resulted in the creation of cappedHelix2mut3, described in Table 4. the proliferation of both K562 and Ba/F3-p210 treated with cappedHelix2mut3 was analyzed. Seventy-two h following transfection, viability of cells was determined via trypan blue exclusion. The effects of cappedHelix2mut3 to CCmut3 and an mCherry as a negative control were compared. Results are presented in FIG. 50. In K562 cells, CCmut3 (FIG. 50A, middle bar) again showed potent inhibition of cell proliferation compared to mCherry control (FIG. 50A, leftmost bar). The cappedHelix2mut3 construct (FIG. 50A, rightmost bar), however, did not display inhibition of cell proliferation. These results were replicated to a similar extent in Ba/F3-p210 cells, shown in FIG. 50B. Therefore, this effect does not appear to be cell line specific.

Lastly, a colony forming assay, in both K562 and Ba/F3-p210 cells testing the activity of the cappedHelix2mut3 construct was also performed (n=1). Results showed the same pattern as in the cell proliferation studies; thus, data are not shown. Therefore, these studies show that further truncation of CCmut3 and the addition of the chosen capping residues (N-terminal serine and C-terminal glycine) do not provide an additional therapeutic benefit to CCmut3.

xi. Discussion

It was previously demonstrated that coiled-coil mutants can inhibit BCR-ABL activity . Additionally, we showed that CCmut3 was the first N-terminally targeted agent to be active alone against T315I mutant BCR-ABL. While the 50-amino acid (aa 23-72) truncated CCmut3 construct, Helix2mut3, still showed activity, truncating the construct even further (aa 27-68) and capping the helix, creating cappedHelix2mut3, eradicated BCR-ABL inhibitory activity.

The activity of Helix2mut3 compared to both the negative control and to CCmut3 can be assay-dependent. In a measure of transformative ability, Helix2mut3 prevented outgrowth of colonies to a greater extent than the EGFP control, however, not as well as the full length CCmut3. In the cell proliferation assay, the inhibitory effect provided by Helix2mut3 was not statistically different than the EGFP control, but at the same time was not less potent than the CCmut3 effect (no significant difference between the two). Finally, in the DNA segmentation apoptosis assay, both Helix2mut3 and CCmut3 significantly induced apoptosis in K562 cells to a similar extent, with no statistical difference in this induction. Thus, Helix2mut3 can act with similar potency as the full length CCmut3. Truncating CCmut3 does not provide an added effect in terms of inhibiting BCR-ABL. Added effects by truncation may be apparent, however, when a CCmut3-based peptide is administered in vivo.

The slight decreases in potency seen with truncation can perhaps be attributed to the removal of the α-helix1 from CCmut3. While contacts between CCmut3 and BCR-ABL can occur at the α-helix2 dimerization interface, the presence of α-helix1 can provide a stabilizing effect as it wraps on the backside of α-helix2 of the opposite monomer (FIG. 45). And removal of the α-helix1 can result in a less stabilizing effect. α-helices can be stabilized by including helical capping residues on both the N- and C-terminal ends of the helix. To compensate for the stability and potency lost by removing α-helix1, serine was chosen as an N-terminal cap and glycine as a C-terminal cap, creating a construct, called cappedHelix2mut3.

The results using cappedHelix2mut3 showed no evidence of BCR-ABL inhibition in two different CML cell lines, even when compared to negative control. It is likely that the favorable energy gained by adding the helix caps did not overcome the interactions lost by removing the α-helix1. This lack of inhibition can be explained, however, by the identity of the stabilizing residues chosen as the N and C caps. Though N-terminal serine and C-terminal glycine provide stabilizing benefits for some α-helices, not all helices behave the same based on their immediate surrounding residues. Additionally, certain residues are better suited for positions directly proximal to the helix cap on both sides. Different combinations of N and C caps and different combinations of N1, N2, etc. residues can be tested; however, changing too many residues for stabilization purposes can in fact negatively impact the specificity and binding capacity of our construct.

6. Improved Design of a BCR-ABL Coiled-Coil Domain Inhibitor

In a therapeutic termed CCmut2, five mutations (C38A, S41R, L45D, E48R, and Q60E) were made to the BCR-ABL CC domain to improve hetero-oligomerization between BCR-ABL and CCmut2 while at the same time disfavoring homo-oligomerization between two CCmut2 molecules. To improve upon that concept, an additional mutation that could be made was identified, K39E. Incorporating this mutation along with the other five mutations previously mentioned is the basis for CCmut3. Specifically, by mutating the lysine at position 39 to a glutamate, an additional charge-charge repulsion was introduced into the CCmut3 dimer. Although this extra repulsion was expected to further disfavor homo-oligomerization between two CCmut3 molecules, the biologic activity of CCmut2 and CCmut3 (both delivered as plasmid DNA) was found to be similar. The K39E mutation resulted in improved oligomerization and colocalization with BCR-ABL. Therefore, CCmut3 was used as the starting point to which further improvements would be made.

xii. Targeting the CC and Tyrosine Kinase Domain Leads to Increased Therapeutic Efficacy and Dose-Lowering Effect of Ponatinib In this study, the results show that combining CCmut3 (as plasmid DNA) and ponatinib led to a dose-lowering effect of ponatinib and provided increased therapeutic efficacy in vitro. Analyzing kinase activity, oncogenic potential, and induction of apoptosis, the results show that the combination had a greater impact than treatment with either agent alone. Additionally, the effectiveness of an N-terminally targeted agent (CCmut3) against cells containing T315I mutant BCR-ABL was reported. This combination approach can be used to lower the dose of ponatinib in an attempt to avoid serious off-target effects.

xiii. Design of a CCmut3 Stapled Peptide

To improve delivery, a CCmut3 peptide containing an all-hydrocarbon staple was designed. Residues suitable for addition of the hydrocarbon staple have been identified. Following design validation by molecular simulation dynamics, peptides can be synthesized and further characterized and analyzed for activity in CML cells.

Biologic protein-protein interactions can be highly specific, and in some cases requiring multiple contact points for selectivity (22). Due to this type of specificity, these interactions represent a target for designing therapeutics. Thus, using a peptide to target this interaction provides an opportunity to maintain the interaction specificity, which can limit off-target effects. In the case of chronic myeloid leukemia, or CML, the constitutively active protein BCR-ABL requires homo-oligomerization to fulfill its function as an oncogenic driver. This homo-oligomerization occurs via a coiled-coil domain located on the N-terminal portion of the BCR-ABL protein. Disrupting this oligomerization, in turn, has been shown to inhibit BCR-ABL activity and thus prevent CML activation.

Figure 51:
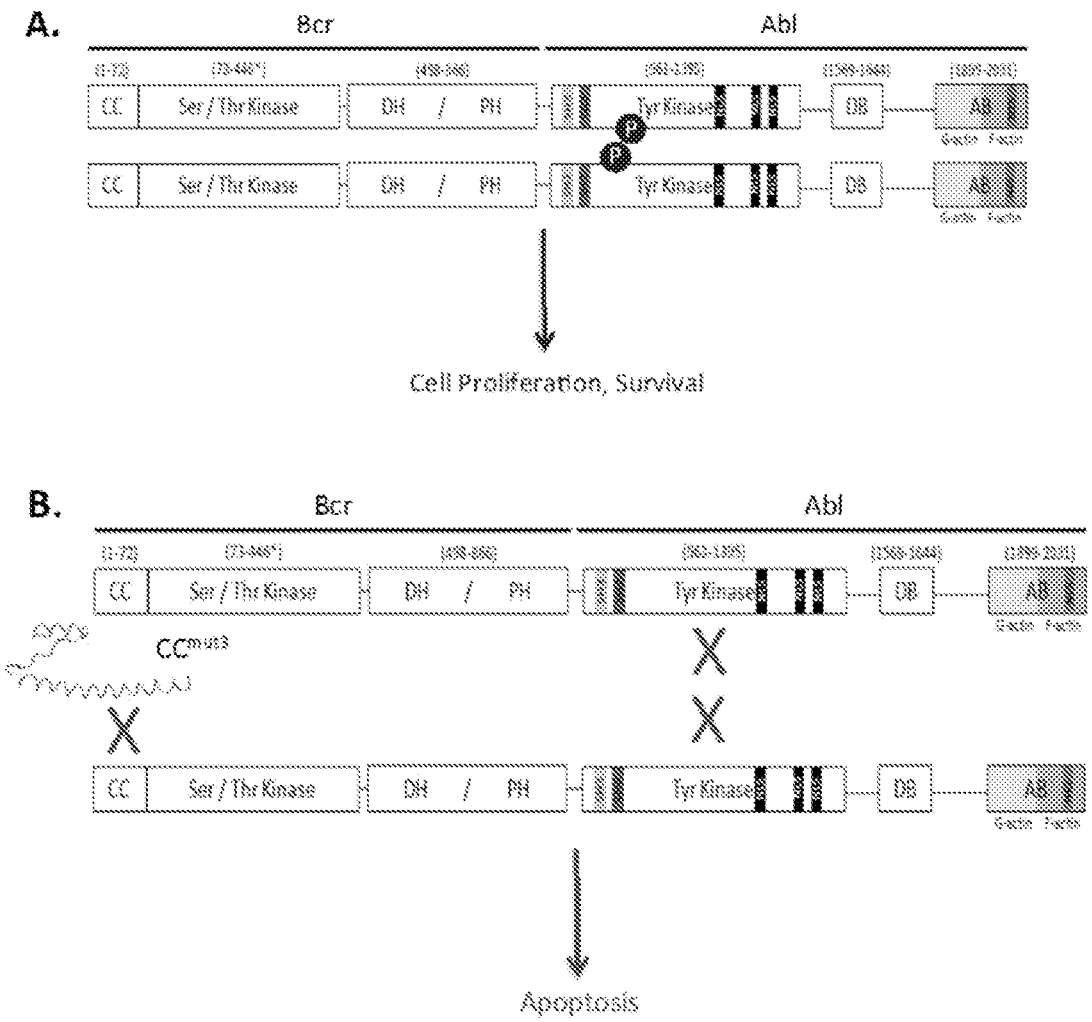
FIGS. 51A and 51B show the disruption of BCR-ABL oligomerization inhibits oncogenic function. A) Through homo-oligomerization via the coiled-coil (CC) domain on the N-terminus, BCR-ABL undergoes trans-autophosphorylation at the tyrosine kinase domain to elicit the oncogenic signals for cell proliferation and survival. B) Blocking oligomerization of BCR-ABL using CCmut3 inhibits the trans-autophorylation capability and induces apoptosis in CML cells.

Previously, a construct capable of interfering with BCR-ABL oligomerization that further inhibits its function as an oncoprotein was designed (FIG. 51). This construct, termed CCmut3, mimics the BCR-ABL coiled-coil domain but is comprised of amino acid mutations designed to disfavor homo-oligomerization of CCmut3 and instead favor hetero-oligomerization between CCmut3 and BCR-ABL. Previous results indicate that this construct can be clinically significant. Thus, the next set of experiments were carried out to fine-tune and formulate this construct into a practical, deliverable peptide that can inhibit BCR-ABL in vivo. Delivering the α-helical CCmut3 as an unmodified peptide can likely show a lack of stability in circulation and inefficient cell internalization due to its overall −3 charge. Thus, to overcome current delivery limitations, modifications to this peptide, including reducing the size and adding a hydrocarbon staple to the backbone (and to some peptides with the hydrocarbon staple, adding the LS-CPP as well) were carried out.

Using peptides to target protein-protein interactions can provide an advantage over small molecules in that specificity for the target can be fine-tuned (32). However, delivery issues of peptides, including decreased serum stability, susceptibility to
proteolysis (leading to shortened serum half-life), and lack of cell permeability when targeting intracellular molecules, often limit peptide therapy. One current approach in overcoming barriers of peptide delivery involves stabilizing α-helical peptides through the addition of a hydrocarbon staple on the peptide backbone. The hydrocarbon staple can lock the α-helical shape of the peptide, thereby increasing its stability, cell permeability, and target affinity while lowering its susceptibility to proteolysis.

Figure 52:
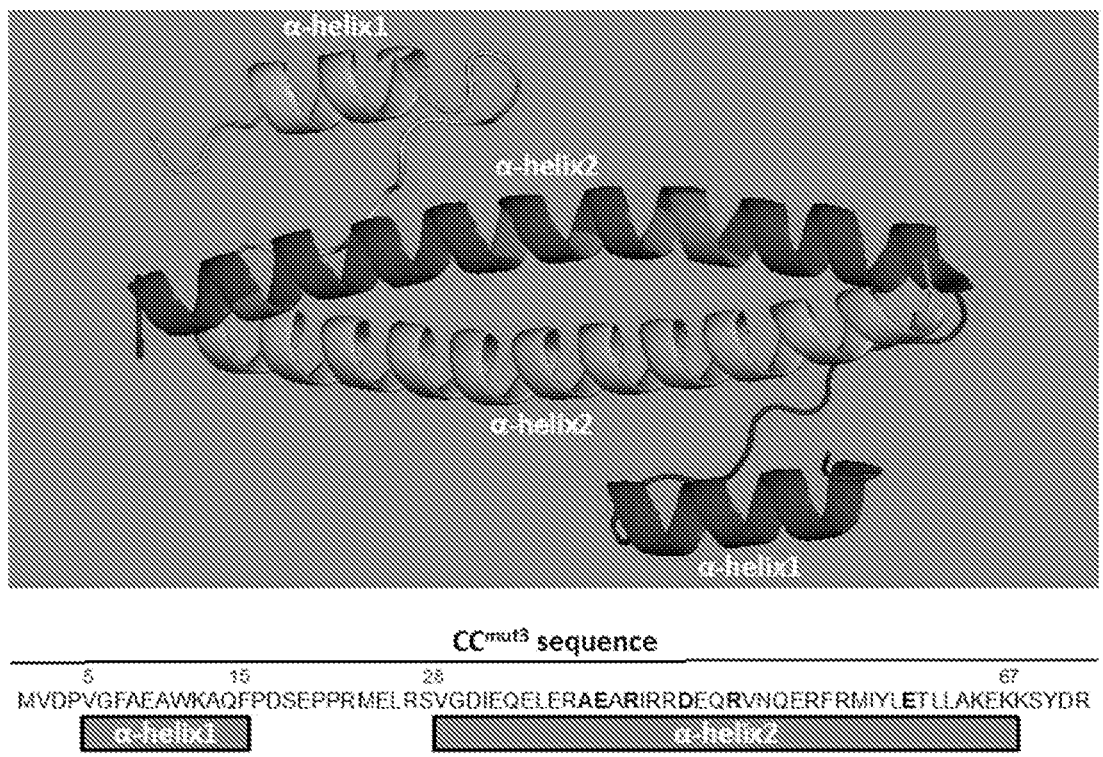
FIG. 52 shows CCmut3 dimerization with BCR-ABL CC. Representative image of CCmut3 (top α helix 2 and bottom α helix 1) interacting with the BCR-ABL coiled-coil (CC) oligomerization domain (top α helix 1 and bottom α helix 2). The lighter shaded residues are those characteristic of the CCmut3 mutations (C38A, K39E, S41R, L45D, E48R, Q60E). Below the image is the CCmut3 amino acid sequence, with bolded residues representing CCmut3 mutations. Regions represented by α-helix1 (amino acid residues 5-15, labeled) and α-helix2 (residues 28-67, labeled) are highlighted in both the dimerization image (above) and the amino acid sequence (below).

To this end, a deliverable, truncated CCmut3 stapled peptides (further termed ST-CCmut3 for Stapled, Truncated-CCmut3) with and without the previously mentioned LS-CPP for improved delivery and an enhanced therapeutic effect have been designed. The design was first completed by thorough analysis of the three-dimensional structure of CCmut3 bound with the BCR-ABL oligomerization domain (FIG. 52). Because interactions can occur within α-helix2, this domain (comprising amino acids 28-67 with respect to the full length CCmut3) was selected and thought to be important for effective inhibition of BCR-ABL.

Thus, this 40-amino acid domain, still incorporating the same mutations that define CCmut3, was used for further analysis. Within α-helix2, locations thought to be unimportant for ST-CCmut3:BCR-ABL interhelical interaction were identified for incorporation of the residues needed to create the hydrocarbon staple. Following identification of the staple locations, designs were submitted for computational modeling using molecular dynamics simulations to calculate the relative free energy of binding between ST-CCmut3 and BCR-ABL. Three ST-CCmut3 candidates were identified and selected for synthesis and further analysis. These candidates were stable and showed binding to BCR-ABL in computational modeling experiments.

xiv. Use of the Coiled-Coil Helical Wheel Diagram

Figure 53:
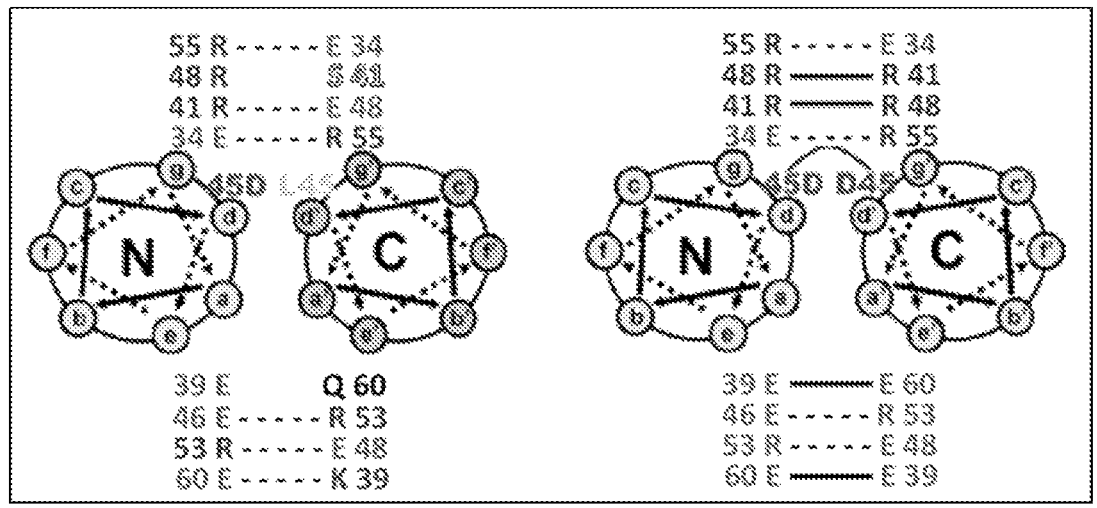
FIG. 53 shows helical wheels of CCmut3:BCR-ABL (left) and CCmut3:CCmut3 oligomerization (right). CCmut3 represented with the cyan color; BCR-ABL represented with the gray color. Above and below the helical wheels are individual residues from each domain. Side chains of those residues are color-coded, as follows: blue=basic, red=acidic, yellow=serine. Potential ionic interactions are shown with the dotted lines, whereas potential charge-charge repulsions are shown with a solid line. This figure was adapted from Dixon et al. (2011).

To create a deliverable form of CCmut3, residues suitable for attachment of a hydrocarbon staple were identified. α,α-disubstituted amino acids are inserted in the peptide sequence for the hydrocarbon staple attachment. These α,α-disubstituted amino acids should not hinder the structure of the helix nor the target interface. To avoid these regions, both the Pymol (PDB) structure of ST-CCmut3:BCR-ABL interaction (FIG. 52) and a coiled-coil helical wheel diagram were examined. FIG. 53 shows the helical wheel diagrams of (A) CCmut3:BCR-ABL dimerization and (B) CCmut3:CCmut3 dimerization. Coiled-coils are comprised of 3.5 residues per helical turn, and thus have two full turns that encompass seven amino acids, assigned positions a, b, c, d, e, f and g. For the purpose of designing locations to incorporate the α-methyl, α-alkenyl amino acids, we wanted to avoid the interface at which the two coiled-coil domains interact. Specifically, this would include any residues at positions a, d (both often involved in protein-protein hydrophobic interaction), e, and g (often involved in interhelical electrostatic interactions). Thus, this leaves positions b, c, and f available for modification. Residues and their residue number corresponding to the full-length CCmut3 that exist in these positions can be seen in Table 5.

Additionally, hydrocarbon staples exist in one of the following sequences, representative of approximately one or two full helical turns in the peptide: i, i+3; i, i+4; or i, i+7 further limiting the identification of residues suitable to replace with α-methyl, α-alkenyl amino acids. The proposed sequences include residues spaced with the i, i+7 pattern. The rationale is for the staple to cover a larger portion of the peptide, and that by spacing seven residues apart, two full turns of the helix cam be encompassed, thus providing greater stability than either of the i, i+3 or i, i+4 options.

TABLE 5

Amino acid residue identification and corresponding coiled-coil helical wheel position in the α-helix2 of CCmut3. Highlighted bars (positions b, c, and f) exist on the backside of the helix and are not involved in interhelical interaction between CCmut3 and BCR-ABL. These highlighted residues represent possible locations for incorporation of α,α-disubstituted amino acids for synthesis of hydrocarbon staples.

| Position | Residue and number | | | | | |
|---|---|---|---|---|---|---|
| a | V28 | L35 | I42 | V49 | M56 | L63 |
| b | G29 | E36 | R43 | N50 | I57 | A64 |
| c | D30 | R37 | R44 | Q51 | Y58 | K65 |
| d | I31 | A38 | D45 | E52 | L59 | E66 |
| e | E32 | E39 | E46 | R53 | E60 | K67 |
| f | Q33 | A40 | Q47 | F54 | T61 | — |
| g | E34 | R41 | R48 | R55 | L62 | — | a. Use of Molecular Dynamics Simulations to Validate Stapled Peptide Design

Previous research using stapled peptides has shown that experimental results do not always corroborate the intellectual design of peptides. In other words, incorporating the staple onto the peptide, despite following the design criteria, can actually disrupt the three-dimensional structure and distort the binding. This distortion can in turn affect the biophysical characteristics of the peptides, especially interaction affinity with the target. Due to the high cost of synthesis of stapled peptides (between $1500 and $5000 per peptide, depending on the source), it is important to determine whether or not a staple connecting certain residues can alter the stability of the monomer or dimer prior to synthesis.

It is expected that molecular dynamics simulations can be performed to determine dimerization stability of stapled peptides. In brief, free energy of binding between the disclosed stapled peptides and the CC of BCR-ABL can be determined. Biomolecular simulation with modern protocols (AMBER, explicit solvent, particle mesh Ewald with the new ff12SB protein force field) can be applied. Model structures based on high resolution structures of Bcr-Abl (PDB ID: 1K1F, chains A and B) with our designed peptides will be relaxed through molecular dynamics (MD) simulation (~50-100 ns), followed by analysis and further free energy simulations to assess the impact of stapling. The information obtained from this computational modeling can give the most energetically favorable peptides, the top three of which will be synthesized.

xv. Results

Thirty-two combinations of amino acid residues have been identified for inclusions of single i, i+7 staples and i, i+7 double staple variants into the ST-CCmut3 peptide. Fourteen single i, i+7 staples and 18 combinations of i, i+7 double staples were designed. Table 6 shows the staple locations that were identified.

These staple locations and designs (e.g., the structures and sequences) will be analyzed using molecular dynamics simulations. Using the helical wheel and the Pymol structure, a candidate was identified and comprises double i, i+7 staples at residues 29/36 and 50/57 (Table 6).

TABLE 6

Residue numbers of the designed locations for single and double i, i + 7 staples.
Bold represents our original top design candidate.
Single and Double i, i + 7 Staples for CC$^{mut3}$

| Single i, i + 7 Staples | Double i, i + 7 Staples |
| --- | --- |
| 29/36 | 29/36-43/50 |
| 30/37 | 29/36-44/51 |
| 33/40 | 29/36-50/57 |
| 36/43 | 29/36-51/58 |
| 37/44 | 30/37-43/50 |
| 40/47 | 30/37-44/51 |
| 43/50 | 30/37-50/57 |
| 44/51 | 30/37-51/58 |
| 47/54 | 33/40-43/50 |
| 50/57 | 33/40-44/51 |
| 51/58 | 33/40-50/57 |
| 54/61 | 33/40-51/58 |
| 57/64 | 36/43-44/51 |
| 58/65 | 36/43-50/57 |
|  | 36/43-51/58 |
|  | 37/44-50/57 |
|  | 37/44-51/58 |
|  | 43/50-51/58 | xvi. Discussion

Maintaining the heterodimeric stability following the addition of the hydrocarbon staple is important. When it comes to binding endogenous BCR-ABL, it is important that the coiled-coil (helical) structure be sustained. As mentioned above, the coiled-coil described herein is specific for BCR-ABL (binding in an antiparallel fashion), which means both the sequence and the structure are important. In order to interact, aligning the salt bridges in the e to e' and g to g' fashion is also important. "Locking" the peptide in a shape that permits the aforementioned interactions to take place is important due to the binding energetics. It is estimated that because the peptide has now preformed a helix, the entropic cost will be reduced, allowing an overall free energy gain and favorable binding. As also mentioned, the addition of a staple is also important for resistance against proteolytic degradation, as it prevents the peptide from adopting an extended conformation. Preformation of an α-helix in this case is also expected to lead to increased cell permeabilization due to the masking of the polar backbone within the helix. Finally, it is expected that a loss in binding enthalpy due to the truncation of the helix will occur. However, this loss can be overcome by the reduced entropic cost of binding due to hydrocarbon stapling, similar to the design of a stapled peptide to disrupt the cJun-cFos coiled-coil interaction.

Both single and double staple variants of the truncated CCmut3 were designed. Double staples, were chosen to increase the amount of peptide encompassed by the hydrocarbon staples. Greater coverage can provide greater proteolytic stability by forming an "umbrella" over more sites of potential proteolysis. Additionally, more efficient cell internalization is likely due to a larger amount of exposed hydrophobicity, which can aid in crossing the cell membrane. Further, staples incorporated toward the N-terminus to can lead to greater α-helical induction. Locking the N-terminus in a helical state before introduction into physiological milieu, can lead to improved therapeutic efficacy as maintaining the α-helical structure is the basis of improvements provided by stapled peptides.

a. Characterize the Stapled and Truncated CCmut3 Proteins

The stapled peptides described herein can be tested for their ability to inhibit BCR-ABL in CML cells. The effects of these stapled peptides can be tested on four different Bcr-Abl+ cell lines: K562 (human, nonmutant), Ba/F3-p210 (murine, nonmutant), Ba/F3-T315I (murine, T315I kinase domain mutation), and Ba/F3-E255V/T315I (murine, E255V/T315I kinase domain compound mutations). It is hypothesized that the ST-CCmut3 peptide will inhibit all forms of mutant BCR-ABL.

Figure 54:
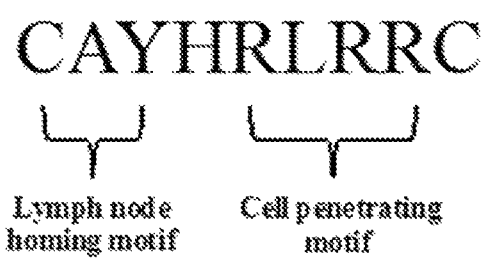
FIG. 54 show a leukemia-specific cell-penetrating peptide sequence. The above sequence corresponds to a leukemia-specific cell-penetration peptide, discovered via phage display by Nishimura et al. (56). The beginning portion, cysteine-alanine-tyrosine (CAY), represents a lymph node homing motif. The poly-arginine portion toward the end, arginine-leucine-arginine-arginine (RLRR), represents the cell penetrating motif.

Next, the activity the stapled peptide or peptides will be tested in primary cells obtained from patients. This method is currently a standard of excellence for CML studies. As with the in vitro testing in BCR-ABL+Ba/F3 cells, patient samples containing various BCR-ABL mutational statuses will be obtained. Patient samples comprising the T315I mutant and the E255V/T315I mutant, will be studied. These experiments can provide translatable data for use of our stapled peptide therapeutic in humans.

b. Addition of a Leukemia-Specific Cell-Penetrating Peptide to the ST-CCmut3 Peptide The stapled peptide described herein can also be fused to a cell-penetrating peptide to increase the ability of the peptide to internalize efficiently into cells. Recent studies show the delivery of the full-length CCmut3 as a recombinant peptide fused to a leukemia-specific cell-penetrating peptide (LS-CPP). This LS-CPP, discovered by Nishimura et al. is a short, 9-amino acid peptide with both a lymph node homing motif and a poly-arginine protein transduction domain (FIG. 54).

The use of LS-CPP has been validated as a CPP when fused to full-length CCmut3, showing successful leukemia cell-specific delivery and therapeutic activity of the peptide in multiple CML cell lines. The CPP can be fused to the N-terminus of the ST-CCmut3 peptide. The staples can remain on the CPP-T-CCmut3 peptide for the other characteristic improvements that these hydrocarbon backbones provide.

Next, an N-ethyl-N-nitrosurea (ENU)-based mutagenesis screen can be carried out to analyze self-inactionvation of BCR-ABL oligomerization. Briefly, BCR-ABL+Ba/F3 cells can be subjected to treatment with the ENU mutagen, which randomly inserts mutations into cellular DNA. Following ENU-treatment overnight, cells can be treated with ST- CCmut3. ST-CCmut3 exposure can be validated through the use of a fluorescent tag (rhodamine or FITC, for example), using fluorescence activated cell sorting (FACS) analysis. Any cells that continued to grow after positive exposure to both ENU and ST-CCmut3 can be isolated for their DNA to be amplified and analyzed. DNA analysis, in this sense, permits the identification of any mutations that can lead to ST-CCmut3 inactivation.

c. Targeting the BCR-ABL Tetramerization Domain

Inhibiting BCR-ABL tetramerization is an alternative strategy in CML therapy. Immediately following BCR-ABL translation, the protein exists in the cell in a monomeric state. The next step toward activation includes dimer formation by two monomers. Following this process, two dimers can interact and form a tetramer. Since tetramerization is the final step before BCR-ABL becomes active, it has been hypothesized that creating a therapeutic against the tetramerization domain can be a viable option.

Interactions involved in the BCR-ABL dimerization domain have been extensively studied and this has been used as the basis for the design of our BCR-ABL dimerization inhibitor, CCmut3. However, interactions involved in BCR-ABL tetramerization have not yet been described. Although the tetrameric structure is available (Pymol PDB ID: 1K1F), specific interactions between two BCR-ABL dimers have not been extensively studied. Comprehensive analysis these specific dimer-dimer interactions can be carried out to design a tetramerization inhibitor.

S. REFERENCES

Argmann, C. A. and J. Auwerx (2006) Collection of blood and plasma from the mouse. *Curr. Protoc. Mol. Biol.* Chapter 29, p. Unit 29A 3.

Bartram, C. R., et al. (1983) Translocation of c-abl oncogene correlates with the presence of a Philadelphia chromosome in chronic myelocytic leukemia. *Nature* 306, 277-280.

Baskiewicz-Masiuk, M. and Machalinski, B. (2004) The role of the STATS proteins in the proliferation and apoptosis of the CML and AML cells. *Eur. J. Haematol.* 72, 420-429.

Beissert, T., et al. (2008) Targeting of the N-terminal coiled coil oligomerization interface by a helix-2 peptide inhibits unmutated and imatinib-resistant BCR/ABL. *Int. J. Cancer* 122, 2744-2752.

Ben-Neriah, Y., et al. (1986) The chronic myelogenous leukemia-specific P210 protein is the product of the bcr/abl hybrid gene. *Science* 233, 212-214.

Bernal, F., et al. (2007) Reactivation of the p53 tumor suppressor pathway by a stapled p53 peptide. *J. Am. Chem. Soc.* 129, 2456-2457.

Bird, G. H., et al. (2008) Synthesis and biophysical characterization of stabilized alpha-helices of BCL-2 domains. *Methods Enzymol.* 446, 369-386.

Bird, G. H., et al. (2010) Hydrocarbon double-stapling remedies the proteolytic instability of a lengthy peptide therapeutic. *Proc. Natl. Acad. Sci. U S A.* 107, 14093-14098.

Bradeen, H. A., et al. (2006) Comparison of imatinib mesylate, dasatinib (BMS-354825), and nilotinib (AMN107) in an N-ethyl-N-nitrosourea (ENU)-based mutagenesis screen: high efficacy of drug combinations. *Blood* 108, 2332-2338.

Branford, S., et al. (2003) Detection of BCR-ABL mutations in patients with CML treated with imatinib is virtually always accompanied by clinical resistance, and mutations in the ATP phosphate-binding loop (P-loop) are associated with a poor prognosis. *Blood* 102, 276-283.

Bruno, B. J., et al. (2013) Basics and recent advances in peptide and protein drug delivery. *Therapeutic Delivery* 4, 1-25.

Burke, A. C., et al. (2011) Current status of agents active against the T315I chronic myeloid leukemia phenotype. *Expert Opin. Emerg. Drugs* 16, 85-103.

Calabretta, B., and Perrotti, D. (2004) The biology of CML blast crisis. *Blood* 103, 4010-4022.

Cancer.org. (2013) What are the key statistics about chronic myeloid leukemia? Available from: http://www.cancer.org/cancer/leukemia-chronicmyeloidcml/detailedguide/leukemia-chronic-myeloid-myelogenous-key-statistics.

Capdeville, R., et al. (2002) Glivec (STI571, imatinib), a rationally developed, targeted anticancer drug. *Nat. Rev. Drug Discov.* 1, 493-502.

Carella, A. M., et al. (2010) Kinase domain mutations of BCR-ABL identified at diagnosis before imatinib-based therapy are associated with progression in patients with high Sokal risk chronic phase chronic myeloid leukemia. *Leuk. Lymphoma* 51, 275-278.

Cassuto, O., et al. (2012) All tyrosine kinase inhibitor-resistant chronic myelogenous cells are highly sensitive to ponatinib. *Oncotarget.* 3, 1557-1565.

Cerutti, D. S., et al. (2009) Staggered Mesh Ewald: An extension of the Smooth Particle-Mesh Ewald method adding great versatility. *J. Chem. Theory Comput.* 5, 2322.

Chang, Y. S., et al. (2013) Stapled alpha-helical peptide drug development: a potent dual inhibitor of MDM2 and MDMX for p53-dependent cancer therapy. *Proc. Natl. Acad. Sci. U.S.A.* 110, E3445-3454.

Cohen, N. A., et al. (2012) A competitive stapled peptide screen identifies a selective small molecule that overcomes MCL-1-dependent leukemia cell survival. *Chem. Biol.* 19, 1175-1186.

Constance, J. E., et al. (2012) Selective targeting of c-Abl via a cryptic mitochondrial targeting signal activated by cellular redox status in leukemic and breast cancer cells. *Pharm. Res.* 29, 2317-2328.

Constance, J. E., et al. (2012) Enhanced and selective killing of chronic myelogenous leukemia cells with an engineered BCR-ABL binding protein and imatinib. *Mol. Pharm.* 9, 3318-3329.

Cortes, J. E., et al. (2012) Ponatinib in refractory Philadelphia chromosome-positive leukemias. *N. Engl. J. Med.* 367, 2075-88.

Daley, G. Q., et al. (1991) Blast crisis in a murine model of chronic myelogenous leukemia. *Proc. Natl. Acad. Sci. U.S.A.* 88, 11335-11338.

Demehri, S., et al. (2010) The function of the pleckstrin homology domain in BCR-ABL-mediated leukemogenesis. *Leukemia* 24, 226-229.

Dexter, T. M., et al. (1980) Growth of factor-dependent hemopoietic precursor cell lines. *J. Exp. Med.* 152, 1036-1047.

Dixon, A. S., et al. (2011) Disruption of Bcr-Abl coiled coil oligomerization by design. *J. Biol. Chem.* 286, 27751-27760.

Dixon, A. S., et al. (2012) Improved coiled-coil design enhances interaction with Bcr-Abl and induces apoptosis. *Mol. Pharm.* 9, 187-195.

Dixon, A. S., et al. (2012) Changing the subcellular location of the oncoprotein Bcr-Abl using rationally designed capture motifs. *Pharm. Res.* 29, 1098-1109.

Druker, B. J., et al. (1996) Effects of a selective inhibitor of the Abl tyrosine kinase on the growth of Bcr-Abl positive cells. *Nat. Med.* 2, 561-566.

Duan, Y., et al. (2003) A point-charge force field for molecular mechanics simulations of proteins based on condensed-phase quantum mechanical calculations. *J. Comput. Chem.* 24, 1999-2012.

Eide, C. A., et al. (2011) Resistance profiling of BCR-ABL compound mutations linked to tyrosine kinase inhibitor therapy failure in chronic myeloid leukemia [abstract]. *Blood (ASH Annual Meeting Abstracts)* 118, 1416.

Evans, J. P., et al. (1987) Tyrosine protein kinase substrates in Philadelphia-positive human chronic granulocytic leukemia derived cell lines (K562 and BV173): detection by using an immunoblotting technique. *Leukemia* 1, 524-525.

Fleischman, A. G., et al. (2011) TNFalpha facilitates clonal expansion of JAK2V617F positive cells in myeloproliferative neoplasms. *Blood* 118, 6392-6398.

Garner, A. P., et al. (2013) Ponatinib, a pan-BCR-ABL inhibitor, potently inhibits key activating and drug-resistant KIT mutants found in GIST [Abstract 3394]. *AACR Annual Meeting Abstracts.*

Gentilucci, L., et al. (2010) Chemical modifications designed to improve peptide stability: incorporation of non-natural amino acids, pseudo-peptide bonds, and cyclization. *Curr. Pharm. Des.* 16, 3185-3203.

Gozgit, J. M., et al. (2011) Potent activity of ponatinib (AP24534) in models of FLT3-driven acute myeloid leukemia and other hematologic malignancies. *Mol. Cancer Ther.* 10, 1028-1035.

Grant, B. J., et al. (2010) Large conformational changes in proteins: signaling and other functions. *Curr. Opin. Struct. Biol.* 20, 142-147.

Grimley, P. M., et al. (1999) Stat5a and Stat5b: fraternal twins of signal transduction and transcriptional activation. *Cytokine Growth Factor Rev.* 10, 131-157.

Hanfstein, B., et al. (2012) Early molecular and cytogenetic response is predictive for long-term progression-free and overall survival in chronic myeloid leukemia (CML). *Leukemia* 26, 2096-2102.

Hantschel, O. and Superti-Furga, G. (2004) Regulation of the c-Abl and Bcr-Abl tyrosine kinases. *Nat. Rev. Mol. Cell Biol.* 5, 33-44.

Hantschel, O., et al. (2005) Structural basis for the cytoskeletal association of Bcr-Abl/c-Abl. *Mol Cell* 19, 461-473.

Hazlehurst, L. A., et al. (2009) Signaling networks associated with BCR-ABL-dependent transformation. *Cancer Control* 16, 100-107.

Hehlmann, R., et al. (1993) Randomized comparison of busulfan and hydroxyurea in chronic myelogenous leukemia: prolongation of survival by hydroxyurea. The German CML Study Group. *Blood* 82, 398-407.

Hehlmann, R., et al. (2011) Tolerability-adapted imatinib 800 mg/d versus 400 mg/d versus 400 mg/d plus interferon-alpha in newly diagnosed chronic myeloid leukemia. *J. Clin. Oncol.* 29, 1634-1642.

Henchey, L. K., et al. (2008) Contemporary strategies for the stabilization of peptides in the alpha-helical conformation. *Curr. Opin. Chem. Biol.* 12, 692-697.

Hochhaus, A., et al. (2007) Dasatinib induces notable hematologic and cytogenetic responses in chronic-phase chronic myeloid leukemia after failure of imatinib therapy. *Blood* 109, 2303-2309.

Huang, W. S. et al. (2010) Discovery of 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a potent, orally active pan-inhibitor of breakpoint cluster region-abelson (BCR-ABL) kinase including the T315I gatekeeper mutant. *J. Med. Chem.* 53, 4701-4719.

Huo, S., I. et al. (2002) Computational alanine scanning of the 1:1 human growth hormone-receptor complex. *J. Comput. Chem.* 23, 15-27.

Inman, S. Late-stage ponatinib study discontinued. 2013; available from: http://www.onclive.com/web-exclusives/Frontline-Late-Stage-Ponatinib-Study-Discontinued.

Jabbour, E., et al. (2010) Choosing the best treatment strategy for chronic myeloid leukemia patients resistant to imatinib: weighing the efficacy and safety of individual drugs with BCR-ABL mutations and patient history. *Leukemia* 24, 6-12.

Jabbour, E., and Kantarjian, H. (2012) Chronic myeloid leukemia: 2012 update on diagnosis, monitoring, and management. *Am. J. Hematol.* 87, 1037-1045.

Kelly, S. M. and N. C. Price (2000) The use of circular dichroism in the investigation of protein structure and function. *Current Protein and Peptide Science* 1, 349-384.

Khorashad, J. S., et al. (2013) BCR-ABL1 compound mutations in tyrosine kinase inhibitor-resistant CML: frequency and clonal relationships. *Blood* 121, 489-498.

Kim, Y. W., et al. (2010) Introduction of all-hydrocarbon i,i+3 staples into alpha-helices via ring-closing olefin metathesis. *Org. Lett.* 12, 3046-3049.

Kim, Y. W., et al. (2011) Synthesis of all-hydrocarbon stapled alpha-helical peptides by ring-closing olefin metathesis. *Nat. Protoc.* 6, 761-771.

Kin, Y., et al. (2001) The Dbl homology domain of BCR is not a simple spacer in P210BCR-ABL of the Philadelphia chromosome. *J. Biol. Chem.* 276, 39462-39468.

Kinstrie, R. and M. Copland (2013) Targeting chronic myeloid leukemia stem cells. *Curr. Hematol. Malig. Rep.* 8, 14-21.

Klamova, H., et al. (2010) Dasatinib in imatinib-resistant or -intolerant CML patients: data from the clinical practice of 6 hematological centers in the Czech Republic. *Neoplasma* 57, 355-359.

Klepeis, J. L., et al. (2009) Long-timescale molecular dynamics simulations of protein structure and function. *Curr. Opin. Struct. Biol.* 19, 120-127.

Kollman, P. A., et al. (2000) Calculating structures and free energies of complex molecules: combining molecular mechanics and continuum models. *Acc. Chem. Res.* 33, 889-897.

Koren-Michowitz, M., et al. (2010) Activity and tolerability of nilotinib: a retrospective multicenter analysis of chronic myeloid leukemia patients who are imatinib resistant or intolerant. *Cancer* 116, 4564-4572.

La Rosee, P., et al. (2002) Activity of the Bcr-Abl kinase inhibitor PD180970 against clinically relevant Bcr-Abl isoforms that cause resistance to imatinib mesylate (Gleevec, STI571). *Cancer Res.* 62, 7149-7153.

Le Coutre, P., et al. (2008) Nilotinib (formerly AMN107), a highly selective BCR-ABL tyrosine kinase inhibitor, is active in patients with imatinib-resistant or -intolerant accelerated-phase chronic myelogenous leukemia. *Blood* 111, 1834-1839.

Lee, E. H., et al. (2009) Discovery through the computational microscope. *Structure* 17, 1295-1306.

Lee, J. C., et al. (1982) Constitutive production of a unique lymphokine (IL 3) by the WEHI-3 cell line. *J. Immunol.* 128, 2393-2398.

Liu, J.; et al. (1993) BCR-ABL tyrosine kinase is autophosphorylated or transphosphorylates P160 BCR on tyrosine predominantly within the first BCR exon. *Oncogene* 8, 101-109.

Maru, Y.; Witte, O. N. (1991) The BCR gene encodes a novel serine/threonine kinase activity within a single exon. *Cell* 67, 459-468.

Mauro, M. J. and B. J. Druker (2001) STI571: targeting BCR-ABL as therapy for CML. *Oncologist* 6, 233-238.

McWhirter, J. R., et al. (1993) A coiled-coil oligomerization domain of Bcr is essential for the transforming function of Bcr-Abl oncoproteins. *Mol. Cell Biol.* 13, 7587-7595.

Meli, M. and G. Colombo (2009) Molecular simulations of peptides: a useful tool for the development of new drugs and for the study of molecular recognition. *Methods Mol. Biol.* 570, 77-153.

Mian, A. A., et al. (2009) The gatekeeper mutation T315I confers resistance against small molecules by increasing or restoring the ABL-kinase activity accompanied by aberrant transphosphorylation of endogenous BCR, even in loss-of-function mutants of BCR/ABL. *Leukemia* 23, 1614-1621.

Mian, A. A., et al. (2009) Oligomerization inhibition, combined with allosteric inhibition, abrogates the transformation potential of T315I-positive BCR/ABL. *Leukemia* 23, 2242-2247.

Miao, Y. J. and Wang, J. Y. (1996) Binding of A/T-rich DNA by three high mobility group-like domains in c-Abl tyrosine kinase. *J. Biol. Chem.* 271, 22823-22830.

Miller, G. D., et al. (2013) Multidomain Targeting of Bcr-Abl by Disruption of Oligomerization and Tyrosine Kinase Inhibition: Toward Eradication of CML. *Mol. Pharm.* 10, 3475-3483.

Mulcahy, N. (2013) Leukemia drug ponatinib (Iclusig) pulled from market. Available from: http://www.medscape.com/viewarticle/813531.

Naldini, L., et al. (1986) Phosphotyrosine antibodies identify the p210c-abl tyrosine kinase and proteins phosphorylated on tyrosine in human chronic myelogenous leukemia cells. *Mol. Cell Biol.* 6, 1803-1811.

Natalello, A., et al. (2012) Biophysical characterization of Met-G-CSF: effects of different site-specific mono-pegylations on protein stability and aggregation. *PLoS One* 7, e42511.

Neelakantan, P., et al. (2012) Platelet dysfunction associated with ponatinib, a new pan BCR-ABL inhibitor with efficacy for chronic myeloid leukemia resistant to multiple tyrosine kinase inhibitor therapy. *Haematologica* 97, 1444.

Nowell, P. C. (1962) The minute chromosome (Ph1) in chronic granulocytic leukemia. *Blut.* 8, 65-66.

O'Brien, S., et al. (2011) NCCN Task Force report: tyrosine kinase inhibitor therapy selection in the management of patients with chronic myelogenous leukemia. *J. Natl. Compr. Canc. Netw.* 9 Suppl 2, S1-25.

O'Hare, T., et al. (2004) Inhibition of wild-type and mutant Bcr-Abl by AP23464, a potent ATP-based oncogenic protein kinase inhibitor: implications for CML. *Blood* 104, 2532-2539.

O'Hare, T., et al. (2007) Bcr-Abl kinase domain mutations, drug resistance, and the road to a cure for chronic myeloid leukemia. *Blood* 110, 2242-2249.

O'Hare, T., et al. (2009) AP24534, a pan-BCR-ABL inhibitor for chronic myeloid leukemia, potently inhibits the T315I mutant and overcomes mutation-based resistance. *Cancer Cell* 16, 401-412.

O'Hare, T., et al. (2012) Pushing the limits of targeted therapy in chronic myeloid leukemia. *Nat. Rev. Cancer* 12, 513-526.

Ohnishi, K., et al. (1995) A randomized trial comparing interferon-alpha with busulfan for newly diagnosed chronic myelogenous leukemia in chronic phase. *Blood* 86, 906-916.

Preyer, M., et al. (2011) Interplay between kinase domain autophosphorylation and F-actin binding domain in regulating imatinib sensitivity and nuclear import of BCR-ABL. *PloS One* 6, e17020.

Razzak, M. (2013) Haematology: Ponatinib: the next TKI challenge. *Nat. Rev. Clin. Oncol.* 10, 65.

Ren, R. (2002) The molecular mechanism of chronic myelogenous leukemia and its therapeutic implications: studies in a murine model. *Oncogene* 21, 8629-8642.

Rowley, J. D. (1973) Letter: A new consistent chromosomal abnormality in chronic myelogenous leukemia identified by quinacrine fluorescence and Giemsa staining. *Nature* 243, 290-293.

Sawyers, C. L., et al. (2002) Imatinib induces hematologic and cytogenetic responses in patients with chronic myelogenous leukemia in myeloid blast crisis: results of a phase II study. *Blood* 99, 3530-3539.

Schafmeister, C. E., et al. (2000) An all-hydrocarbon cross-linking system for enhancing the helicity and metabolic stability of peptides. *J. Am. Chem. Soc.* 122, 5891-5892.

Schaller-Schoenitz, M., et al. (2011) Function of STAT5 Isoforms in Bcr-Abl Positive Cells. *ASH Annual Meeting Abstracts*.

Shami, P. J. and M. Deininger (2012) Evolving treatment strategies for patients newly diagnosed with chronic myeloid leukemia: the role of second-generation BCR-ABL inhibitors as first-line therapy. *Leukemia* 26, 214-224.

Sherbenou, D. W., et al. (2008) Characterization of BCR-ABL deletion mutants from patients with chronic myeloid leukemia. *Leukemia* 22, 1184-1190.

Sierra, J. R., et al. (2010) Molecular mechanisms of acquired resistance to tyrosine kinase targeted therapy. *Mol. Cancer* 9, 75.

Steinbrecher, T. and A. Labahn (2010) Towards accurate free energy calculations in ligand protein-binding studies. *Curr. Med. Chem.* 17, 767-785.

Van Etten, R. A., et al. (1994) The COOH terminus of the c-Abl tyrosine kinase contains distinct F- and G-actin binding domains with bundling activity. *J. Cell Biol.* 124, 325-340.

Verdine, G. L. and G. J. Hilinski (2012) Stapled peptides for intracellular drug targets. *Methods Enzymol.* 503, 3-33.

Walensky, L. D., et al. (2004) Activation of apoptosis in vivo by a hydrocarbon-stapled BH3 helix. *Science* 305, 1466-1470.

Walensky, L. D., et al. (2006) A stapled BID BH3 helix directly binds and activates BAX. *Mol. Cell* 24, 199-210.

Wetzler, M., et al. (1993) Subcellular localization of Bcr, Abl, and Bcr-Abl proteins in normal and leukemic cells and correlation of expression with myeloid differentiation. *J. Clin. Invest.* 92, 1925-1939.

Woessner, D. W., et al. (2011) Development of an effective therapy for chronic myelogenous leukemia. *Cancer J.* 17, 477-486.

Woessner, D. W. and C. S. Lim (2013) Disrupting BCR-ABL in combination with secondary leukemia-specific pathways in CML cells leads to enhanced apoptosis and decreased proliferation. *Mol. Pharm.* 10, 270-277.

Zhang, J., et al. (2009) Targeting cancer with small molecule kinase inhibitors. *Nat. Rev. Cancer* 9, 28-39.

Zhao, X., et al. (2002) Structure of the Bcr-Abl oncoprotein oligomerization domain. *Nat. Struct. Biol.* 9, 117-20.

Bartram, C. R.; et al. Translocation of c-abl oncogene correlates with the presence of a Philadelphia chromosome in chronic myelocytic leukaemia. Nature 1983, 306, (5940), 277-80.

Woessner, D. W.; Lim, C. S.; Deininger, M. W. Development of an effective therapy for chronic myelogenous leukemia. Cancer J 2011, 17, (6), 477-86.

Cilloni, D.; Saglio, G. Molecular pathways: BCR-ABL. Clinical cancer research: an official journal of the American Association for Cancer Research 2012, 18, (4), 930-7.

McWhirter, J. R et al. A coiled-coil oligomerization domain of Bcr is essential for the transforming function of Bcr-Abl oncoproteins. Mol Cell Biol 1993, 13, (12), 7587-95.

Zhao, X.; et al. Structure of the Bcr-Abl oncoprotein oligomerization domain. Nat Struct Biol 2002, 9, (2), 117-20.

Liu, J.; et al. BCR-ABL tyrosine kinase is autophosphorylated or transphosphorylates P160 BCR on tyrosine predominantly within the first BCR exon. Oncogene 1993, 8, (1), 101-9.

Hochhaus, A.; et al. Favorable long-term follow-up results over 6 years for response, survival, and safety with imatinib mesylate therapy in chronic-phase chronic myeloid leukemia after failure of interferon-alpha treatment. Blood 2008, 111, (3), 1039-43.

Hunter, T. Treatment for chronic myelogenous leukemia: the long road to imatinib. J Clin Invest 2007, 117, (8), 2036-43.

Branford, S.; et al. Detection of BCR-ABL mutations in patients with CML treated with imatinib is virtually always accompanied by clinical resistance, and mutations in the ATP phosphate-binding loop (P-loop) are associated with a poor prognosis. Blood 2003, 102, (1), 276-83.

Sierra, J. R.; Cepero, V.; Giordano, S. Molecular mechanisms of acquired resistance to tyrosine kinase targeted therapy. Mol Cancer 2010, 9, 75.

Radich, J. Structure, function, and resistance in chronic myeloid leukemia. Cancer Cell 2014, 26, (3), 305-6.

Cortes, J.; et al. Clinical roundtable monograph: Emerging treatment options for TKI-resistant chronic myelogenous leukemia. Clin Adv Hematol Oncol 2012, 10, (10 Suppl 19), 1-16.

Kimura, S., Ando, T, Kojima, K. BCR-ABL Point Mutations and TKI Treatment in CML Patients. J. Hematol Transfus 2014, 2, (3), 1022-1034.

Zabriskie, M. S.; et al. BCR-ABL1 Compound Mutations Combining Key Kinase Domain Positions Confer Clinical Resistance to Ponatinib in Ph Chromosome-Positive Leukemia. Cancer Cell 2014, 26, (3), 428-442.

Bauer, R. C.; et al. Sequential inhibitor therapy in CML: in vitro simulation elucidates the pattern of resistance mutations after second- and third-line treatment. Clin Cancer Res 2013, 19, (11), 2962-72.

Gorbunova, A.; Porozov, Y., Structural modeling of BCR-ABL drug resistance mutations. In Moscow Conference on Computational Molecular Biology, Moscow, Russia, 2011; pp 291-292.

Storey, S. Chronic myelogenous leukaemia market. Nat Rev Drug Discov 2009, 8, (6), 447.

Lovly, C. M.; Shaw, A. T. Molecular pathways: resistance to kinase inhibitors and implications for therapeutic strategies. Clin Cancer Res 2014, 20, (9), 2249-56.

Zhang, J.; Yang, P. L.; Gray, N. S. Targeting cancer with small molecule kinase inhibitors. Nat Rev Cancer 2009, 9, (1), 28-39.

O'Hare, T.; Zabriskie, M. S.; Eiring, A. M.; Deininger, M. W. Pushing the limits of targeted therapy in chronic myeloid leukaemia. Nat Rev Cancer 2012, 12, (8), 513-26.

Woessner, D. W.; Lim, C. S. Disrupting BCR-ABL in combination with secondary leukemia-specific pathways in CML cells leads to enhanced apoptosis and decreased proliferation. Mol Pharm 2013, 10, (1), 270-7.

Dixon, A. S.; et al. Improved coiled-coil design enhances interaction with Bcr-Abl and induces apoptosis. Mol Pharm 2012, 9, (1), 187-95.

Dixon, A. S.; et al. Disruption of Bcr-Abl coiled coil oligomerization by design. J Biol Chem 2011, 286, (31), 27751-60.

Miller, G. D.; et al. Multidomain targeting of Bcr-Abl by disruption of oligomerization and tyrosine kinase inhibition: toward eradication of CML. Mol Pharm 2013, 10, (9), 3475-83.

Dixon, A. S.; et al. Changing the subcellular location of the oncoprotein Bcr-Abl using rationally designed capture motifs. Pharm Res 2012, 29, (4), 1098-109.

Bruno, B. J.; Miller, G. D.; Lim, C. S. Basics and recent advances in peptide and protein drug delivery. Ther Deliv 2013, 4, (11), 1443-67.

Carter, P. J. Introduction to current and future protein therapeutics: a protein engineering perspective. Exp Cell Res 2011, 317, (9), 1261-9.

Koren, E.; Torchilin, V. P. Cell-penetrating peptides: breaking through to the other side. Trends Mol Med 2012, 18, (7), 385-93.

Copolovici, D. M.; Langel, K.; Eriste, E.; Langel, U. Cell-penetrating peptides: design, synthesis, and applications. ACS Nano 2014, 8, (3), 1972-94.

Madani, F.; et al. Mechanisms of cellular uptake of cell-penetrating peptides. J Biophys 2011, 2011, 414729.

Vasconcelos, L.; Parn, K.; Langel, U. Therapeutic potential of cell-penetrating peptides. Ther Deliv 2013, 4, (5), 573-91.

Nishimura, S.; et al. Combinatorial targeting of the macropinocytotic pathway in leukemia and lymphoma cells. J Biol Chem 2008, 283, (17), 11752-62.

Deng, M.; Daley, G. Q. Expression of interferon consensus sequence binding protein induces potent immunity against BCR/ABL-induced leukemia. Blood 2001, 97, (11), 3491-7.

Bunce, C. M.; et al. Comparison of the levels of inositol metabolites in transformed haemopoietic cells and their normal counterparts. Biochem J 1993, 289 (Pt 3), 667-73.

Mian, A. A.; et al. Oligomerization inhibition, combined with allosteric inhibition, abrogates the transformation potential of T315I-positive BCR/ABL. Leukemia 2009, 23, (12), 2242-7.

Beissert, T.; et al. Targeting of the N-terminal coiled coil oligomerization interface of BCR interferes with the transformation potential of BCR-ABL and increases sensitivity to STI571. Blood 2003, 102, (8), 2985-93.

Guo, X. Y.; et al. Peptide containing the BCR oligomerization domain (AA 1-160) reverses the transformed phenotype of p210bcr-abl positive 32D myeloid leukemia cells. Oncogene 1998, 17, (7), 825-33.

Huang, Z. L.; et al. TAT-CC fusion protein depresses the oncogenicity of BCR-ABL in vitro and in vivo through interrupting its oligomerization. Amino Acids 2013, 44, (2), 461-72.

Wang, H. X.; et al. Cell-penetrating fusion peptides OD1 and OD2 interact with Bcr-Abl and influence the growth and apoptosis of K562 cells. Mol Cell Biochem 2014, 385, (1-2), 311-8.

Huang, Z.; et al. Purification of TAT-CC-HA protein under native condition, and its transduction analysis and biological effects on BCR-ABL positive cells. Biomed Pharmacother 2011, 65, (3), 183-92.

Beissert, T.; Hundertmark, A.; Kaburova, V.; Travaglini, L.; Mian, A. A.; Nervi, C.; Ruthardt, M. Targeting of the N-terminal coiled coil oligomerization interface by a helix-2 peptide inhibits unmutated and imatinib-resistant BCR/ABL. Int J Cancer 2008, 122, (12), 2744-52.

La Rosee, P.; et al. Activity of the Bcr-Abl kinase inhibitor PD180970 against clinically relevant Bcr-Abl isoforms that cause resistance to imatinib mesylate (Gleevec, STI571). Cancer Res 2002, 62, (24), 7149-53.

O'Hare, T.; et al. Inhibition of wild-type and mutant Bcr-Abl by AP23464, a potent ATP-based oncogenic protein kinase inhibitor: implications for CML. Blood 2004, 104, (8), 2532-9.

Cortes, J. E.; et al. Ponatinib in refractory Philadelphia chromosome-positive leukemias. N Engl J Med 2012, 367, (22), 2075-88.

Razzak, M. Haematology: Ponatinib—the next TKI challenge. Nat Rev Clin Oncol 2013, 10, (2), 65.

Verdine, G. L.; Hilinski, G. J. Stapled peptides for intracellular drug targets. Methods Enzymol 2012, 503, 3-33.

Nowell P C. The minute chromosome (Ph1) in chronic granulocytic leukemia. Blut 1962 April; 8: 65-66.

Bartram C R, de Klein A, Hagemeijer A, van Agthoven T, Geurts van Kessel A, Bootsma D, et al. Translocation of c-abl oncogene correlates with the presence of a Philadelphia chromosome in chronic myelocytic leukaemia. Nature 1983 Nov. 17-23; 306(5940): 277-280.

Druker B J, Tamura S, Buchdunger E, Ohno S, Segal G M, Fanning S, et al. Effects of a selective inhibitor of the Abl tyrosine kinase on the growth of Bcr-Abl positive cells. Nat Med 1996 May; 2(5): 561-566.

Naldini L, Stacchini A, Cirillo D M, Aglietta M, Gavosto F, Comoglio P M. Phosphotyrosine antibodies identify the p210c-abl tyrosine kinase and proteins phosphorylated on tyrosine in human chronic myelogenous leukemia cells. Molecular and cellular biology 1986 May; 6(5): 1803-1811.

Evans J P, Wickremasinghe R G, Hoffbrand A V. Tyrosine protein kinase substrates in Philadelphia-positive human chronic granulocytic leukemia derived cell lines (K562 and BV173): detection by using an immunoblotting technique. Leukemia 1987 June; 1(6): 524-525.

Hanfstein B, Muller M C, Hehlmann R, Erben P, Lauseker M, Fabarius A, et al. Early molecular and cytogenetic response is predictive for long-term progression-free and overall survival in chronic myeloid leukemia (CML). Leukemia 2012 September; 26(9): 2096-2102.

Sawyers C L, Hochhaus A, Feldman E, Goldman J M, Miller C B, Ottmann O G, et al. Imatinib induces hematologic and cytogenetic responses in patients with chronic myelogenous leukemia in myeloid blast crisis: results of a phase II study. Blood 2002 May 15; 99(10): 3530-3539.

Hochhaus A, Kantarjian H M, Baccarani M, Lipton J H, Apperley J F, Druker B J, et al. Dasatinib induces notable hematologic and cytogenetic responses in chronic-phase chronic myeloid leukemia after failure of imatinib therapy. Blood 2007 Mar. 15; 109(6): 2303-2309.

le Coutre P, Ottmann O G, Giles F, Kim D W, Cortes J, Gattermann N, et al. Nilotinib (formerly AMN107), a highly selective BCR-ABL tyrosine kinase inhibitor, is active in patients with imatinib-resistant or -intolerant accelerated-phase chronic myelogenous leukemia. Blood 2008 Feb. 15; 111(4): 1834-1839.

Hehlmann R, Heimpel H, Hasford J, Kolb H J, Pralle H, Hossfeld D K, et al. Randomized comparison of busulfan and hydroxyurea in chronic myelogenous leukemia: prolongation of survival by hydroxyurea. The German CML Study Group. Blood 1993 Jul. 15; 82(2): 398-407.

Ohnishi K, Ohno R, Tomonaga M, Kamada N, Onozawa K, Kuramoto A, et al. A randomized trial comparing interferon-alpha with busulfan for newly diagnosed chronic myelogenous leukemia in chronic phase. Blood 1995 Aug. 1; 86(3): 906-916.

Branford S, Rudzki Z, Walsh S, Parkinson I, Grigg A, Szer J, et al. Detection of BCR-ABL mutations in patients with CML treated with imatinib is virtually always accompanied by clinical resistance, and mutations in the ATP phosphate-binding loop (P-loop) are associated with a poor prognosis. Blood 2003 Jul. 1; 102(1): 276-283.

Azam M, Latek R R, Daley G Q. Mechanisms of autoinhibition and STI-571/imatinib resistance revealed by mutagenesis of BCR-ABL. Cell 2003 Mar. 21; 112(6): 831-843.

Woessner D W, Lim C S, Deininger M W. Development of an effective therapy for chronic myelogenous leukemia. Cancer J 2011 November-December; 17(6): 477-486.

Weisberg E, Manley P W, Cowan-Jacob S W, Hochhaus A, Griffin J D. Second generation inhibitors of BCR-ABL for the treatment of imatinib-resistant chronic myeloid leukaemia. Nature reviews Cancer 2007 May; 7(5): 345-356.

Cortes J E, Kantarjian H, Shah N P, Bixby D, Mauro M J, Flinn I, et al. Ponatinib in refractory Philadelphia chromosome-positive leukemias. The New England journal of medicine 2012 Nov. 29; 367(22): 2075-2088.

Cortes J E, Kim D W, Pinilla-Ibarz J, le Coutre P, Paquette R, Chuah C, et al. A phase 2 trial of ponatinib in Philadelphia chromosome-positive leukemias. The New England journal of medicine 2013 Nov. 7; 369(19): 1783-1796.

Zabriskie M S, Eide C A, Tantravahi S K, Vellore N A, Estrada J, Nicolini F E, et al. BCR-ABL1 Compound Mutations Combining Key Kinase Domain Positions Confer Clinical Resistance to Ponatinib in Ph Chromosome-Positive Leukemia. Cancer Cell 2014 Sep. 8; 26(3): 428-442.

O'Hare T, Shakespeare W C, Zhu X, Eide C A, Rivera V M, Wang F, et al. AP24534, a pan-BCR-ABL inhibitor for chronic myeloid leukemia, potently inhibits the T315I mutant and overcomes mutation-based resistance. Cancer Cell 2009 Nov. 6; 16(5): 401-412.

Zhang J, Yang P L, Gray N S. Targeting cancer with small molecule kinase inhibitors. Nature reviews Cancer 2009 January; 9(1): 28-39.

Zhao X, Ghaffari S, Lodish H, Malashkevich V N, Kim P S. Structure of the Bcr-Abl oncoprotein oligomerization domain. Nat Struct Biol 2002 February; 9(2): 117-120.

McWhirter J R, Galasso D L, Wang J Y. A coiled-coil oligomerization domain of Bcr is essential for the transforming function of Bcr-Abl oncoproteins. Molecular and cellular biology 1993 December; 13(12): 7587-7595.

Beissert T, Hundertmark A, Kaburova V, Travaglini L, Mian A A, Nervi C, et al. Targeting of the N-terminal coiled coil oligomerization interface by a helix-2 peptide inhibits unmutated and imatinib-resistant BCR/ABL. International journal of cancer Journal international du cancer 2008 Jun. 15; 122(12): 2744-2752.

ian A A, Oancea C, Zhao Z, Ottmann O G, Ruthardt M. Oligomerization inhibition, combined with allosteric inhibition, abrogates the transformation potential of T315I-positive BCR/ABL. Leukemia 2009 December; 23(12): 2242-2247.

Dixon A S, Pendley S S, Bruno B J, Woessner D W, Shimpi A A, Cheatham T E, 3rd, et al. Disruption of Bcr-Abl coiled coil oligomerization by design. The Journal of biological chemistry 2011 Aug. 5; 286(31): 27751-27760.

Dixon A S, Miller G D, Bruno B J, Constance J E, Woessner D W, Fidler T P, et al. Improved coiled-coil design enhances interaction with Bcr-Abl and induces apoptosis. Molecular pharmaceutics 2012 Jan. 1; 9(1): 187-195.

Miller G D, Woessner D W, Sirch M J, Lim C S. Multidomain targeting of Bcr-Abl by disruption of oligomerization and tyrosine kinase inhibition: toward eradication of CML. Molecular pharmaceutics 2013 Sep. 3; 10(9): 3475-3483.

Daley G Q, Van Etten R A, Baltimore D. Blast crisis in a murine model of chronic myelogenous leukemia. Proceedings of the National Academy of Sciences of the United States of America 1991 Dec. 15; 88(24): 11335-11338.

La Rosee P, Corbin A S, Stoffregen E P, Deininger M W, Druker B J. Activity of the Bcr-Abl kinase inhibitor PD180970 against clinically relevant Bcr-Abl isoforms that cause resistance to imatinib mesylate (Gleevec, STI571). Cancer research 2002 Dec. 15; 62(24): 7149-7153.

O'Hare T, Pollock R, Stoffregen E P, Keats J A, Abdullah O M, Moseson E M, et al. Inhibition of wild-type and mutant Bcr-Abl by AP23464, a potent ATP-based oncogenic protein kinase inhibitor: implications for CML. Blood 2004 Oct. 15; 104(8): 2532-2539.

Dexter T M, Garland J, Scott D, Scolnick E, Metcalf D. Growth of factor-dependent hemopoietic precursor cell lines. The Journal of experimental medicine 1980 Oct. 1; 152(4): 1036-1047.

Corbin A S, O'Hare T, Gu Z, Kraft I L, Eiring A M, Khorashad J S, et al. KIT signaling governs differential sensitivity of mature and primitive CML progenitors to tyrosine kinase inhibitors. Cancer Res 2013 Sep. 15; 73(18): 5775-5786.

Fleischman A G, Aichberger K J, Luty S B, Bumm T G, Petersen C L, Doratotaj S, et al. TNFalpha facilitates clonal expansion of JAK2V617F positive cells in myeloproliferative neoplasms. Blood 2011 Dec. 8; 118(24): 6392-6398.

Eide C A, Zabriskie M S, Adrian L T, Lange T, Deininger M W, Druker B J, et al. Resistance Profiling of BCR-ABL Compound Mutations Linked to Tyrosine Kinase Inhibitor Therapy Failure in Chronic Myeloid Leukemia. Blood 2011 Nov. 18; 118(21): 616-616.

Redaelli S, Piazza R, Rostagno R, Magistroni V, Perini P, Marega M, et al. Activity of bosutinib, dasatinib, and nilotinib against 18 imatinib-resistant BCR/ABL mutants. J Clin Oncol 2009 Jan. 20; 27(3): 469-471.

Khorashad J S, Kelley T W, Szankasi P, Mason C C, Soverini S, Adrian L T, et al. BCR-ABL1 compound mutations in tyrosine kinase inhibitor-resistant CML: frequency and clonal relationships. Blood 2013 Jan. 17; 121(3): 489-498.

Shah N P, Skaggs B J, Branford S, Hughes T P, Nicoll J M, Paquette R L, et al. Sequential ABL kinase inhibitor therapy selects for compound drug-resistant BCR-ABL mutations with altered oncogenic potency. The Journal of clinical investigation 2007 September; 117(9): 2562-2569.

Jabbour E, Kantarjian H. Chronic myeloid leukemia: 2012 update on diagnosis, monitoring, and management. American journal of hematology 2012 November; 87(11): 1037-1045.

Koren-Michowitz M, le Coutre P, Duyster J, Scheid C, Panayiotidis P, Prejzner W, et al. Activity and tolerability of nilotinib: a retrospective multicenter analysis of chronic myeloid leukemia patients who are imatinib resistant or intolerant. Cancer 2010 Oct. 1; 116(19): 4564-4572.

Jabbour E, Hochhaus A, Cortes J, La Rosee P, Kantarjian H M. Choosing the best treatment strategy for chronic myeloid leukemia patients resistant to imatinib: weighing the efficacy and safety of individual drugs with BCR-ABL mutations and patient history. Leukemia 2010 January; 24(1): 6-12.

Hehlmann R, Lauseker M, Jung-Munkwitz S, Leitner A, Muller M C, Pletsch N, et al. Tolerability-adapted imatinib 800 mg/d versus 400 mg/d versus 400 mg/d plus interferon-alpha in newly diagnosed chronic myeloid leukemia. J Clin Oncol 2011 Apr. 20; 29(12): 1634-1642.

O'Hare T, Eide C A, Deininger M W. Bcr-Abl kinase domain mutations, drug resistance, and the road to a cure for chronic myeloid leukemia. Blood 2007 Oct. 1; 110(7): 2242-2249.

Carella A M, Garuti A, Cirmena G, Catania G, Rocco I, Palermo C, et al. Kinase domain mutations of BCR-ABL identified at diagnosis before imatinib-based therapy are associated with progression in patients with high Sokal risk chronic phase chronic myeloid leukemia. Leukemia & lymphoma 2010 February; 51(2): 275-278.

Klamova H, Faber E, Zackova D, Markova M, Voglova J, Cmunt E, et al. Dasatinib in imatinib-resistant or -intolerant CML patients: data from the clinical practice of 6 hematological centers in the Czech Republic. Neoplasma 2010; 57(4): 355-359.

Smith K M, Yacobi R, Van Etten R A. Autoinhibition of Bcr-Abl through its SH3 domain. Molecular cell 2003 July; 12(1): 27-37.

Eiring A M, Page B D, Kraft I L, Mason C C, Vellore N A, Resetca D, et al. Combined STAT3 and BCR-ABL1 inhibition induces synthetic lethality in therapy-resistant chronic myeloid leukemia. Leukemia 2014 Aug. 19.

Torchilin V P, Lukyanov A N. Peptide and protein drug delivery to and into tumors: challenges and solutions. Drug discovery today 2003 Mar. 15; 8(6): 259-266.

Wang X, Chen L, Ye P, Chiang A, Miao C H. Development of Direct Intra-Bone Marrow Gene Transfer of Lentiviral Vectors Containing a B-Domain Variant of Human Factor VIII for Hemophilia A Treatment. ASH Annual Meeting Abstracts 2011 Nov. 18, 2011; 118(21): 4710-.

Walensky L D, Bird G H. Hydrocarbon-stapled peptides: principles, practice, and progress. Journal of medicinal chemistry 2014 Aug. 14; 57(15): 6275-6288.

Bruno B J, Miller G D, Lim C S. Basics and recent advances in peptide and protein drug delivery. Therapeutic delivery 2013 November; 4(11): 1443-1467.

Nishimura S, Takahashi S, Kamikatahira H, Kuroki Y, Jaalouk D E, O'Brien S, et al. Combinatorial targeting of the macropinocytotic pathway in leukemia and lymphoma cells. The Journal of biological chemistry 2008 Apr. 25; 283(17): 11752-11762.

Jaras M, Johnels P, Hansen N, Agerstam H, Tsapogas P, Rissler M, et al. Isolation and killing of candidate chronic myeloid leukemia stem cells by antibody targeting of IL-1 receptor accessory protein. Proceedings of the National Academy of Sciences of the United States of America 2010 Sep. 14; 107(37): 16280-16285.

Herrmann H, Sadovnik I, Cerny-Reiterer S, Rulicke T, Stefanzl G, Willmann M, et al. Dipeptidylpeptidase IV (CD26) defines leukemic stem cells (LSC) in chronic myeloid leukemia. Blood 2014 Jun. 19; 123(25): 3951-3962.

Jamieson C H. Chronic myeloid leukemia stem cells. Hematology/the Education Program of the American Society of Hematology American Society of Hematology Education Program 2008: 436-442.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A peptide comprising,
a Bcr-Abl coiled-coil oligomerization domain comprising the sequence of SEQ ID NO:1, SEQ ID NO:2, SEQ ID NO:3, SEQ ID NO:4, SEQ ID NO:5, or SEQ ID NO:6;
wherein a pair of amino acids are modified to be α,α-disubstituted amino acids, wherein at least one of the amino acids in the pair is at position 29, 30, 33, 36, 37, 40, 43, 44, 47, 50, 51, 54, 57, 58, 61, 64 or 65 of the sequence of SEQ ID NO:1, SEQ ID NO:2, or SEQ ID NO:3 or at position 2, 3, 6, 9, 10, 13, 16, 17, 20, 23, 24, 27, 30, 31, 34, 37, 38 of the sequence of SEQ ID NO:4, SEQ ID NO:5, or SEQ ID NO:6, wherein the pair of amino acids are in the i, i+3; i, i+4; or i, i+7 configuration;
wherein the Bcr-Abl coiled-coil oligomerization domain comprises at least one alpha helix stabilizing moiety.

2. A peptide comprising,
a Bcr-Abl coiled-coil oligomerization domain, wherein the Bcr-Abl coiled-coil oligomerization domain comprises the sequence of VGDIEQELERAEARIRRDEQRVNQERFRMIYLETLLAKEK (amino acids 28-67 of SEQ ID NO:7);
wherein a pair of amino acids are modified to be α,α-disubstituted amino acids, wherein at least one of the amino acids in the pair is at position 2, 3, 6, 9, 10, 13, 16, 17, 20, 23, 24, 27, 30, 31, 34, 37, 38 of the sequence VGDIEQELERAEARIRRDEQRVNQERFRMIYLETLLAKEK, wherein the pair of amino acids are in the i+3; i, i+4; or i, i+7 configuration;
wherein the Bcr-Abl inhibitory activity of the Bcr-Abl coiled-coil oligomerization domain comprising the sequence of VGDIEQELERAEARIRRDEQRVNQERFRMIYLETLLAKEK (amino acids 28-67 of SEQ ID NO:7) is greater than that of SEQ ID NO:1; and
wherein the Bcr-Abl coiled-coil oligomerization domain comprises at least one alpha helix stabilizing moiety.

3. A peptide comprising,
a Bcr-Abl coiled-coil oligomerization domain, wherein the Bcr-Abl coiled-coil oligomerization domain comprises the sequence of SEQ ID NO:8;
wherein a pair of amino acids are modified to be α,α-disubstituted amino acids, wherein at least one of the amino acids in the pair is at position 2, 3, 7, 10, 11, 14, 17, 18, 21, 24, 25, 28, 31, 32, 35, 38, 39 of the sequence SEQ ID NO:8, wherein the pair of amino acids are in the i, i+i, i+4; or i, i+7 configuration;
wherein one or more amino acid(s) of the Bcr-Abl coiled-coil oligomerization domain designated by X in SEQ ID NO:8 is an amino acid different from the corresponding amino acid of SEQ ID NO:4;
wherein the Bcr-Abl inhibitory activity of the Bcr-Abl coiled-coil oligomerization domain comprising the sequence of SEQ ID NO:8 is greater than that of SEQ ID NO:4; and
wherein the Bcr-Abl coiled-coil oligomerization domain comprises at least one alpha helix stabilizing moiety.

4. A method of treating a Bcr-Abl inhibitor responsive hyperproliferative disorder in a mammal, comprising the step of administering to the mammal an effective amount of at least one peptide of claim 1.

5. A method of inhibiting Bcr-Abl activity in a mammal, comprising the step of administering to the mammal an effective amount of at least one peptide of claim 1.

6. The method of claim 5, further comprising a pharmaceutically acceptable salt or solvate of the peptide.

7. The method of claim 5, wherein the peptide comprises a cell-penetrating peptide.

8. The method of claim 5, wherein the mammal is human.

9. The method of claim 5, wherein the mammal has been diagnosed with a need for inhibiting Bcr-Abl activity prior to the administering step.

10. The method of claim 5, further comprising the step of identifying a mammal in need of inhibiting Bcr-Abl activity.

11. A method of inhibiting Bcr-Abl activity in at least one cell, comprising the step of contacting the cell with an effective amount of at least one peptide of claim 1.

12. A method of treating Bcr-Abl inhibitor responsive hyperproliferative disorder in a mammal, comprising the step of administering to the mammal an effective amount of at least one peptide of claim 2.

13. A method of treating a Bcr-Abl inhibitor responsive hyperproliferative disorder in a mammal, comprising the step of administering to the mammal an effective amount of at least one peptide of claim 3.

14. A method of inhibiting Bcr-Abl activity in a mammal, comprising the step of administering to the mammal an effective amount of at least one peptide of claim 2.

15. A method of inhibiting Bcr-Abl activity in a mammal, comprising the step of administering to the mammal an effective amount of at least one peptide of claim 3.

16. A method of inhibiting Bcr-Abl activity in at least one cell, comprising the step of contacting the cell with an effective amount of at least one peptide of claim 2.

17. A method of inhibiting Bcr-Abl activity in at least one cell, comprising the step of contacting the cell with an effective amount of at least one peptide of claim 3.

18. The peptide of any one of claims 1, 2, and 3, wherein the at least one alpha helix stabilizing moiety is a hydrocarbon staple, an acetylenic crosslink, a lactam bridge, or a combination thereof.

19. The peptide of claim 1, wherein each α,α-disubstituted amino acid is a α-methyl,α-alkenylglycine or α-hydro, α-alkenylglycine residue having the structure:

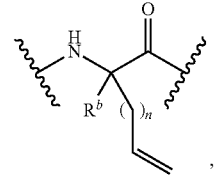

wherein n is an integer between 1 and 10, inclusive; and wherein $R^b$ is H or methyl.

20. The peptide of claim 2, wherein each α,α-disubstituted amino acid is a α-methyl,α-alkenylglycine or α-hydro, α-alkenylglycine residue having the structure:

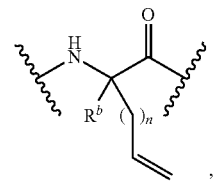

wherein n is an integer between 1 and 10, inclusive; and wherein $R^b$ is H or methyl.

21. The peptide of claim 3, wherein each α,α-disubstituted amino acid is a α-methyl,α-alkenylglycine or α-hydro,α-alkenylglycine residue having the structure:
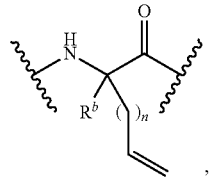
wherein n is an integer between 1 and 10, inclusive; and wherein $R^b$ is H or methyl.
* * * * *

SEQUENCE LISTING

```
<160> NUMBER OF SEQ ID NOS: 23

<210> SEQ ID NO 1
<211> LENGTH: 72
<212> TYPE: PRT
<213> ORGANISM: Artificial Sequence
<220> FEATURE:
<223> OTHER INFORMATION: synthetic construct; wt Bcr coiled coil domain

<400> SEQUENCE: 1

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg
65                  70

<210> SEQ ID NO 2
<211> LENGTH: 72
<212> TYPE: PRT
<213> ORGANISM: Artificial Sequence
<220> FEATURE:
<223> OTHER INFORMATION: synthetic construct; mutant Bcr coiled coil
      domain

<400> SEQUENCE: 2

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Ala Lys Ala Arg Ile Arg Arg Asp Glu Gln Arg
        35                  40                  45

Val Asn Gln Glu Arg Phe Arg Met Ile Tyr Leu Glu Thr Leu Leu Ala
    50                  55                  60

Lys Glu Lys Lys Ser Tyr Asp Arg
65                  70

<210> SEQ ID NO 3
<211> LENGTH: 72
<212> TYPE: PRT
<213> ORGANISM: Artificial Sequence
<220> FEATURE:
<223> OTHER INFORMATION: synthetic construct; mutant Bcr coiled coil
      domain

<400> SEQUENCE: 3

Met Val Asp Pro Val Gly Phe Ala Glu Ala Trp Lys Ala Gln Phe Pro
1               5                   10                  15
```

```
Asp Ser Glu Pro Pro Arg Met Glu Leu Arg Ser Val Gly Asp Ile Glu
            20                  25                  30

Gln Glu Leu Glu Arg Ala Glu Ala Arg Ile Arg Arg Asp Glu Gln Arg
        35                  40                  45

Val Asn Gln Glu Arg Phe Arg Met Ile Tyr Leu Glu Thr Leu Leu Ala
    50                  55                  60

Lys Glu Lys Lys Ser Tyr Asp Arg
65                  70
```

```
<210> SEQ ID NO 4
<211> LENGTH: 40
<212> TYPE: PRT
<213> ORGANISM: Artificial Sequence
<220> FEATURE:
<223> OTHER INFORMATION: synthetic construct; mutant Bcr coiled coil
      domain

<400> SEQUENCE: 4

Val Gly Asp Ile Glu Gln Glu Leu Glu Arg Cys Lys Ala Ser Ile Arg
1               5                   10                  15

Arg Leu Glu Gln Glu Val Asn Gln Glu Arg Phe Arg Met Ile Tyr Leu
            20                  25                  30

Gln Thr Leu Leu Ala Lys Glu Lys
        35                  40

<210> SEQ ID NO 5
<211> LENGTH: 40
<212> TYPE: PRT
<213> ORGANISM: Artificial Sequence
<220> FEATURE:
<223> OTHER INFORMATION: synthetic construct; mutant Bcr coiled coil
      domain

<400> SEQUENCE: 5

Val Gly Asp Ile Glu Gln Glu Leu Glu Arg Ala Lys Ala Arg Ile Arg
1               5                   10                  15

Arg Asp Glu Gln Arg Val Asn Gln Glu Arg Phe Arg Met Ile Tyr Leu
            20                  25                  30

Glu Thr Leu Leu Ala Lys Glu Lys
        35                  40

<210> SEQ ID NO 6
<211> LENGTH: 40
<212> TYPE: PRT
<213> ORGANISM: Artificial Sequence
<220> FEATURE:
<223> OTHER INFORMATION: synthetic construct; mutant Bcr coiled coil
      domain

<400> SEQUENCE: 6

Val Gly Asp Ile Glu Gln Glu Leu Glu Arg Ala Glu Ala Arg Ile Arg
1               5                   10                  15

Arg Asp Glu Gln Arg Val Asn Gln Glu Arg Phe Arg Met Ile Tyr Leu
            20                  25                  30

Glu Thr Leu Leu Ala Lys Glu Lys
        35                  40

<210> SEQ ID NO 7
<211> LENGTH: 72
<212> TYPE: PRT
<213> ORGANISM: Artificial Sequence
<220> FEATURE:
<223> OTHER INFORMATION: synthetic construct; mutant Bcr coiled coil
```

```
            domain
<220> FEATURE:
<221> NAME/KEY: MISC_FEATURE
<222> LOCATION: (32)..(32)
<223> OTHER INFORMATION: Xaa can be Glu, Lys, Arg, or His
<220> FEATURE:
<221> NAME/KEY: MISC_FEATURE
<222> LOCATION: (38)..(38)
<223> OTHER INFORMATION: Xaa can be Cys, Gly, Ala, or Val
<220> FEATURE:
<221> NAME/KEY: MISC_FEATURE
<222> LOCATION: (39)..(39)
<223> OTHER INFORMATION: Xaa can be Lys, Glu, Asp, Gln, or Asn
<220> FEATURE:
<221> NAME/KEY: MISC_FEATURE
<222> LOCATION: (41)..(41)
<223> OTHER INFORMATION: Xaa can be Ser, Arg, His, or Lys
<220> FEATURE:
<221> NAME/KEY: MISC_FEATURE
<222> LOCATION: (45)..(45)
<223> OTHER INFORMATION: Xaa can be Leu, Glu, Asp, Gln, or Asn
<220> FEATURE:
<221> NAME/KEY: MISC_FEATURE
<222> LOCATION: (46)..(46)
<223> OTHER INFORMATION: Xaa can be Glu, Lys, Arg, or His
<220> FEATURE:
<221> NAME/KEY: MISC_FEATURE
<222> LOCATION: (48)..(48)
<223> OTHER INFORMATION: Xaa can be Glu, Arg, His, or Lys
<220> FEATURE:
<221> NAME/KEY: MISC_FEATURE
<222> LOCATION: (60)..(60)
<223> OTHER INFORMATION: Xaa can be Gln, Glu, Asp, or Asn

<400> SEQUENCE: 7

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Xaa
                20                  25                  30

Gln Glu Leu Glu Arg Xaa Xaa Ala Xaa Ile Arg Arg Xaa Xaa Gln Xaa
            35                  40                  45

Val Asn Gln Glu Arg Phe Arg Met Ile Tyr Leu Xaa Thr Leu Leu Ala
        50                  55                  60

Lys Glu Lys Lys Ser Tyr Asp Arg
65                  70

<210> SEQ ID NO 8
<211> LENGTH: 41
<212> TYPE: PRT
<213> ORGANISM: Artificial Sequence
<220> FEATURE:
<223> OTHER INFORMATION: synthetic construct; mutant Bcr coiled coil
      domain
<220> FEATURE:
<221> NAME/KEY: MISC_FEATURE
<222> LOCATION: (5)..(5)
<223> OTHER INFORMATION: Xaa can be Glu, Lys, Arg, or His
<220> FEATURE:
<221> NAME/KEY: MISC_FEATURE
<222> LOCATION: (12)..(12)
<223> OTHER INFORMATION: Xaa can be Cys, Gly, Ala, or Val
<220> FEATURE:
<221> NAME/KEY: MISC_FEATURE
<222> LOCATION: (13)..(13)
<223> OTHER INFORMATION: Xaa can be Lys, Glu, Asp, Gln, or Asn
<220> FEATURE:
<221> NAME/KEY: MISC_FEATURE
<222> LOCATION: (15)..(15)
<223> OTHER INFORMATION: Xaa can be Ser, Arg, His, or Lys
<220> FEATURE:
<221> NAME/KEY: MISC_FEATURE
<222> LOCATION: (19)..(19)
<223> OTHER INFORMATION: Xaa can be Leu, Glu, Asp Gln, or Asn
```

```
<220> FEATURE:
<221> NAME/KEY: MISC_FEATURE
<222> LOCATION: (20)..(20)
<223> OTHER INFORMATION: Xaa can be Glu, Lys, Arg, or His
<220> FEATURE:
<221> NAME/KEY: MISC_FEATURE
<222> LOCATION: (22)..(22)
<223> OTHER INFORMATION: Xaa can be Glu, Arg, His, or Lys
<220> FEATURE:
<221> NAME/KEY: MISC_FEATURE
<222> LOCATION: (34)..(34)
<223> OTHER INFORMATION: Xaa can be Gln, Glu, Asp, or Asn

<400> SEQUENCE: 8

Val Gly Asp Ile Xaa Glu Gln Glu Leu Glu Arg Xaa Xaa Ala Xaa Ile
1               5                   10                  15

Arg Arg Xaa Xaa Gln Xaa Val Asn Gln Glu Arg Phe Arg Met Ile Tyr
            20                  25                  30

Leu Xaa Thr Leu Leu Ala Lys Glu Lys
        35                  40

<210> SEQ ID NO 9
<211> LENGTH: 9
<212> TYPE: PRT
<213> ORGANISM: Artificial Sequence
<220> FEATURE:
<223> OTHER INFORMATION: synthetic construct; cell penetrating peptide

<400> SEQUENCE: 9

Cys Ala Tyr His Arg Leu Arg Arg Cys
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic construct; cell penetrating peptide

<400> SEQUENCE: 10

Cys Gly Phe Tyr Trp Leu Arg Ser Cys
1               5

<210> SEQ ID NO 11
<211> LENGTH: 11
<212> TYPE: PRT
<213> ORGANISM: Artificial Sequence
<220> FEATURE:
<223> OTHER INFORMATION: synthetic construct; cell penetrating peptide

<400> SEQUENCE: 11

Tyr Gly Arg Lys Lys Arg Arg Gln Arg Arg Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetic construct; cell penetrating peptide

<400> SEQUENCE: 12

Gly Arg Lys Lys Arg Arg Gln Arg Arg Arg Pro Pro Gln
1               5                   10

<210> SEQ ID NO 13
<211> LENGTH: 14
```

```
<212> TYPE: PRT
<213> ORGANISM: Artificial Sequence
<220> FEATURE:
<223> OTHER INFORMATION: synthetic construct; cell penetrating peptide

<400> SEQUENCE: 13

Pro Gly Arg Lys Lys Arg Arg Gln Arg Arg Pro Pro Gln
1               5                   10

<210> SEQ ID NO 14
<211> LENGTH: 16
<212> TYPE: PRT
<213> ORGANISM: Artificial Sequence
<220> FEATURE:
<223> OTHER INFORMATION: synthetic construct; cell penetrating peptide

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 21
<212> TYPE: PRT
<213> ORGANISM: Artificial Sequence
<220> FEATURE:
<223> OTHER INFORMATION: synthetic construct; cell penetrating peptide

<400> SEQUENCE: 15

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 16
<211> LENGTH: 27
<212> TYPE: PRT
<213> ORGANISM: Artificial Sequence
<220> FEATURE:
<223> OTHER INFORMATION: synthetic construct; cell penetrating peptide

<400> SEQUENCE: 16

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 17
<211> LENGTH: 21
<212> TYPE: PRT
<213> ORGANISM: Artificial Sequence
<220> FEATURE:
<223> OTHER INFORMATION: synthetic construct; cell penetrating peptide

<400> SEQUENCE: 17

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 18
<211> LENGTH: 18
<212> TYPE: PRT
<213> ORGANISM: Artificial Sequence
<220> FEATURE:
<223> OTHER INFORMATION: synthetic construct; cell penetrating peptide
```

```
<400> SEQUENCE: 18

Val Arg Leu Pro Pro Val Arg Leu Pro Pro Val Arg Leu Pro
1               5                   10                  15

Pro Pro

<210> SEQ ID NO 19
<211> LENGTH: 18
<212> TYPE: PRT
<213> ORGANISM: Artificial Sequence
<220> FEATURE:
<223> OTHER INFORMATION: synthetic construct; cell penetrating peptide

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 8
<212> TYPE: PRT
<213> ORGANISM: Artificial Sequence
<220> FEATURE:
<223> OTHER INFORMATION: synthetic construct; cell penetrating peptide

<400> SEQUENCE: 20

Arg Arg Arg Arg Arg Arg Arg Arg
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic construct; cell penetrating peptide

<400> SEQUENCE: 21

Arg Arg Arg Arg Arg Arg Arg Arg Arg
1               5

<210> SEQ ID NO 22
<211> LENGTH: 10
<212> TYPE: PRT
<213> ORGANISM: Artificial Sequence
<220> FEATURE:
<223> OTHER INFORMATION: synthetic construct; cell penetrating peptide

<400> SEQUENCE: 22

Arg Arg Arg Arg Arg Arg Arg Arg Arg Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: synthetic construct; cell penetrating peptide

<400> SEQUENCE: 23

Arg Arg Arg Arg Arg Arg Arg Arg Arg Arg Arg
1               5                   10
```